United States Patent
Chen et al.

(10) Patent No.: US 10,519,133 B2
(45) Date of Patent: Dec. 31, 2019

(54) VINYL COMPOUNDS AS FGFR AND VEGFR INHIBITORS

(71) Applicants: MEDSHINE DISCOVERY INC., Nanjing, Jiangsu (CN); HARBIN ZHENBAO PHARMACEUTICAL CO., LTD., Heilongjiang (CN)

(72) Inventors: Shuhui Chen, Shanghai (CN); Zhengxia Chen, Shanghai (CN); Meibi Dai, Shanghai (CN); Cheng Xie, Shanghai (CN); Peng Li, Shanghai (CN); Yang Zhang, Shanghai (CN); Guibai Liang, Shanghai (CN); Qiang Wang, Shanghai (CN); Jiangpeng Liao, Shanghai (CN); Fei Sun, Shanghai (CN); Guoping Hu, Shanghai (CN); Jian Li, Shanghai (CN)

(73) Assignees: MEDSHINE DISCOVERY INC., Nanjing, Jiangsu (CN); HARBIN ZHENBAO PHARMACEUTICAL CO., LTD., Heilongjiang (CN)

( * ) Notice: Subject to any disclaimer, the term of this patent is extended or adjusted under 35 U.S.C. 154(b) by 0 days.

(21) Appl. No.: 15/750,704

(22) PCT Filed: Aug. 3, 2016

(86) PCT No.: PCT/CN2016/092989
§ 371 (c)(1),
(2) Date: Feb. 6, 2018

(87) PCT Pub. No.: WO2017/024968
PCT Pub. Date: Feb. 16, 2017

(65) Prior Publication Data
US 2018/0222886 A1    Aug. 9, 2018

(30) Foreign Application Priority Data

Aug. 7, 2015 (CN) .......................... 2015 1 0484124
Dec. 9, 2015 (CN) .......................... 2015 1 0908082

(51) Int. Cl.
| | | |
|---|---|---|
| *C07D 401/14* | (2006.01) |
| *C07D 405/14* | (2006.01) |
| *C07D 401/12* | (2006.01) |
| *C07D 413/14* | (2006.01) |
| *A61P 35/00* | (2006.01) |
| *C07D 403/02* | (2006.01) |
| *C07D 403/14* | (2006.01) |
| *A61K 31/416* | (2006.01) |
| *A61K 31/395* | (2006.01) |
| *C07D 235/02* | (2006.01) |
| *C07D 401/02* | (2006.01) |

(52) U.S. Cl.
CPC .......... *C07D 401/14* (2013.01); *A61K 31/395* (2013.01); *A61K 31/416* (2013.01); *A61P 35/00* (2018.01); *C07D 235/02* (2013.01); *C07D 401/02* (2013.01); *C07D 401/12* (2013.01); *C07D 403/02* (2013.01); *C07D 403/14* (2013.01); *C07D 405/14* (2013.01); *C07D 413/14* (2013.01)

(58) Field of Classification Search
CPC ..... A61K 31/395; A61K 31/416; A61P 35/00; C07D 401/02; C07D 401/14; C07D 235/02; C07D 403/02; C07D 405/14; C07D 413/14; C07D 401/12; C07D 403/14
See application file for complete search history.

(56) References Cited

U.S. PATENT DOCUMENTS

| | | | |
|---|---|---|---|
| 6,897,231 B2 * | 5/2005 | Bhagwat ............... | C07D 231/56 514/403 |
| 7,429,609 B2 | 9/2008 | Ohi et al. | |
| 2003/0207883 A1 | 11/2003 | Renhowe et al. | |
| 2006/0058366 A1 | 3/2006 | Kanai et al. | |

FOREIGN PATENT DOCUMENTS

| | | |
|---|---|---|
| CN | 1656079 A | 8/2005 |
| WO | 2001053268 A2 | 7/2001 |
| WO | 200210137 A2 * | 2/2002 |
| WO | WO-02/10137 A2 | 2/2002 |
| WO | WO-2002/022598 A1 | 3/2002 |
| WO | WO-2003/101968 A1 | 12/2003 |

OTHER PUBLICATIONS

Extended European Search Report issued in EP 16834592.4 dated Sep. 14, 2018.
Partial European Search Report issued in related EP Application No. 16834592.4 dated Jun. 22, 2018.
Sep. 26, 2016 International Search Report issued in International Patent Application No. PCT/CN2016//092989.
Sep. 26, 2016 Written Opinion of the International Searching Authority issued in International Patent Application No. PCT/CN2016//092989.

(Continued)

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

FGFR and VEGFR inhibitors are provided, and compounds represented by formula (1) or formula (II) as FGFR and VEGFR inhibitors, pharmaceutically acceptable salts or tautomers thereof are specifically disclosed.

16 Claims, No Drawings

(56) References Cited

OTHER PUBLICATIONS

Priority Application CN 201510484124.6 filed on Aug. 7, 2015 (withdrawn without publication).
Priority Application CN 201510908082.4 filed on Dec. 9, 2015 (withdrawn without publication).
Berge et al., "Pharmaceutical Salts", Journal of Pharmaceutical Science 66: 1-19 (1977).
Remington: The Science and Practice of Pharmacy, 21st Ed., Lippincott, Williams & Wilkins (2005).
H Maehr,—"A proposed new convention for graphic presentation of molecular geometry and topography."—J. Chem. Ed., 1985, 62:114-120.
Blanchard. S. et.al., "Synthesis and Evaluation of Alkenyl Indazoles as Selecetive Aurora Kinase Inhibitors", Bioorganic&Medcinal Chemistry Letters, vol. 20, Mar. 7, 2010, pp. 2443-2447.
Liu, Y. et al., "The Discovery of Orally Bioavailable Tyrosine Threonine Kinase(TTK) Inhibitors: 3-(4-(heterocycly)phenyl-1H)-indazole-5-carboxamides as Anticancer Agents", Journal of Medicinal Chemistry,. vol. 58, No. 7, Mar. 12, 2015, pp. 3366-3392.

\* cited by examiner

VINYL COMPOUNDS AS FGFR AND VEGFR INHIBITORS

CROSS-REFERENCE TO RELATED APPLICATIONS

This application is a National Stage of International Application No. PCT/CN2016/092989, filed on Aug. 3, 2016, and published in Chinese as WO2017/024968 A1 on Feb. 16, 2017. This application claims the priority to Chinese Patent Application Nos. 201510484124.6, filed on Aug. 7, 2015, and 201510908082.4, filed Dec. 9, 2015. The entire disclosures of the above applications are incorporated herein by reference.

FIELD

The present disclosure relates to FGFR and VEGFR inhibitors, in particular to compounds represented by formula (I), pharmaceutically acceptable salts or tautomers thereof as FGFR and VEGFR inhibitors.

BACKGROUND

This section provides background information related to the present disclosure which is not necessarily prior art.

Fibroblast growth factor (FGF) has been recognized as an important mediator of many physiological processes such as developmental morphogenesis and angiogenesis. The fibroblast growth factor receptor (FGFR) family is composed of four members (FGFR1-FGFR4), which are glycoprotein composed of extracellular immunoglobulin (Ig)-like domain, hydrophobic transmembrane domain, and the cytoplasmic part including tyrosine kinase domain. FGF binding leads to dimerization of FGFR, followed by activation of receptor autophosphorylation and downstream signaling pathways. Receptor activation is sufficient to regain and activate specific downstream signaling partners involved in the diverse process of regulation such as cell growth, cell metabolism and cell survival. Therefore, the FGF/FGFR signaling pathway has a multi-effect effect in many biological processes that are critical for tumor cell proliferation, migration, invasion and angiogenesis.

Vinyl indazoles are known in the field of cancer treatment, see WO 0210137 and WO 2003101968. FGFR inhibitors are also known in this art, see WO 2002022598.

SUMMARY

This section provides a general summary of the disclosure, and is not a comprehensive disclosure of its full scope or all of its features.

The present disclosure provides a compound represented by formula (I) or formula (II), a pharmaceutically acceptable salt or a tautomer thereof,

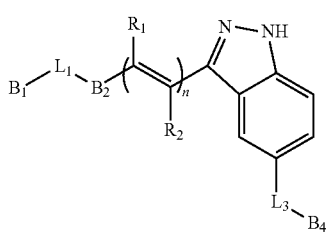

(I)

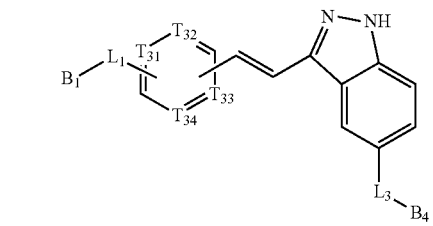

(II)

wherein, one of $R_1$ and $R_2$ is selected from the group consisting of F, Cl, Br, I, CN, OH and $NH_2$, and the other is selected from the group consisting of H, F, Cl, Br, I, CN, OH and $NH_2$;

$B_1$ is selected from the group consisting of

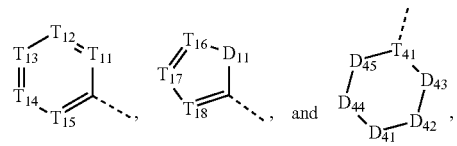

wherein, 0 to 2 of $T_{11-15}$ are selected from N and the rest are selected from C(R);

0 to 2 of $T_{16-18}$ are selected from N and the rest are selected from C(R);

$D_{11}$ is selected from the group consisting of —C(R)(R)—, —C(=O)N(R)—, —N(R)—, —C(=NR)—, —S(=O)$_2$N(R)—, —S(=O)N(R)—, —O—, —S—, —C(=O)O—, —C(=O)—, —C(=S)—, —S(=O)—, —S(=O)$_2$— or —N(R)C(=O)N(R)—;

$T_{41}$ is selected from N or C(R);

$D_{41}$ is selected from the group consisting of —C(R)(R)—, —C(=O)N(R)—, —N(R)—, —C(=NR)—, —S(=O)$_2$N(R)—, —S(=O)N(R)—, —O—, —S—, —C(=O)O—, —C(=O)—, —C(=S)—, —S(=O)—, —S(=O)$_2$— or —N(R)C(=O)N(R)—;

0 to 2 of $D_{42-45}$ are each independently selected from the group consisting of a single bond, —[C(R)(R)]$_{1-3}$—, —C(=O)N(R)—, —N(R)—, —C(=NR)—, —S(=O)$_2$N(R)—, —S(=O)N(R)—, —O—, —S—, —C(=O)O—, —C(=O)—, —C(=S)—, —S(=O)—, —S(=O)$_2$— or —N(R)C(=O)N(R)—, the rest are selected —C(R)(R)—;

optionally, any two of $D_{41-45}$ are connected to the same atom or atom group to form a 3-6 membered ring;

$L_1$ and $L_3$ are each independently selected from the group consisting of —(CRR)$_{0-3}$—, —(CRR)$_{0-3}$—C(=O)N(R)—(CRR)$_{0-3}$—, —(CRR)$_{0-3}$—N(R)—(CRR)$_{0-3}$—, —(CRR)$_{0-3}$—C(=NR)—(CRR)$_{0-3}$—, —(CRR)$_{0-3}$—S(=O)$_2$N(R)—(CRR)$_{0-3}$—, —(CRR)$_{0-3}$—S(=O)N(R)—(CRR)$_{0-3}$—, —(CRR)$_{0-3}$—O—(CRR)$_{0-3}$—, —(CRR)$_{0-3}$—S—(CRR)$_{0-3}$—, —(CRR)$_{0-3}$—C(=O)O—(CRR)$_{0-3}$—, —(CRR)$_{0-3}$—C(=O)—(CRR)$_{0-3}$—, —(CRR)$_{0-3}$—C(=S)—(CRR)$_{0-3}$—, —(CRR)$_{0-3}$—S(=O)—(CRR)$_{0-3}$—, —(CRR)$_{0-3}$—S(=O)$_2$—(CRR)$_{0-3}$— or —(CRR)$_{0-3}$—N(R)C(=O)N(R)—(CRR)$_{0-3}$—;

$B_2$ is selected from a 5- to 10-membered aryl or heteroaryl which is optionally substituted with R;

$B_4$ is selected from a 5- to 6-membered aryl or heteroaryl and a 5- to 6-membered cycloalkyl or heterocycloalkyl, the 5- to 6-membered aryl or heteroaryl and the 5- to 6-membered cycloalkyl or heterocycloalkyl is optionally substituted with R;

$T_{31-34}$ are each independently selected from N or C(R);

optionally, any two of $T_{31-34}$ are connected to the same atom or atom group to form a 3-6 membered ring;

n is 0 or 1, and when n is 0, the defined structural unit represents a single bond for linkage;

R is selected from the group consisting of H, F, Cl, Br, I, CN, OH, SH, $NH_2$, CHO, COOH, $C(=O)NH_2$, $S(=O)NH_2$, $S(=O)_2NH_2$, or selected from a $C_{1-12}$ alkyl or heteroalkyl, a $C_{3-12}$ cyclocarbyl or heterocyclocarbyl and $C_{1-12}$ alkyl or heteroalkyl which is substituted with $C_{3-12}$ cyclocarbyl or heterocyclocarbyl; the $C_{1-12}$ alkyl or heteroalkyl or the $C_{3-12}$ cyclocarbyl or heterocyclocarbyl is optionally substituted with R';

R' is selected from the group consisting of F, Cl, Br, I, CN, OH, SH, $NH_2$, CHO, COOH, $C(=O)NH_2$, $S(=O)NH_2$, $S(=O)_2NH_2$, =NH, =O, =S, or selected from the group optionally substituted with R" consisting of $NHC(=O)CH_3$, $C_{1-12}$ alkyl, $C_{1-12}$ alkylamino, N,N-di($C_{1-12}$ alkyl)amino, $C_{1-12}$ alkoxy, $C_{1-12}$ alkanoyl, $C_{1-12}$ alkoxycarbonyl, $C_{1-12}$ alkylsulfonyl, $C_{1-12}$ alkylsulfinyl, 3- to 12-membered cycloalkyl, 3- to 12-membered cycloalkylamino, 3- to 12-membered heterocycloalkylamino, 3- to 12-membered cycloalkyloxy, 3- to 12-membered cycloalkylacyl, 3- to 12-membered cycloalkyloxycarbonyl, 3- to 12-membered cycloalkyl sulfonyl, 3- to 12-cycloalkylsulfinyl, 5- to 12-membered aryl or heteroaryl, 5 to 12-membered aralkyl or heteroaralkyl;

R" is selected from the group consisting of F, Cl, Br, I, CN, OH, $N(CH_3)_2$, $NH(CH_3)$, $NH_2$, CHO, COOH, $C(=O)NH_2$, $S(=O)NH_2$, $S(=O)_2NH_2$, =NH, =O, =S, trihalomethyl, dihalomethyl, monohalomethyl, aminomethyl, hydroxymethyl, methyl, methoxy, formyl, methoxycarbonyl, methanesulfonyl, methylsulfinyl;

"hetero" represents a heteroatom or heteroatom group selected from the group consisting of —C(=O)N(R)—, —C(=NR)—, —S(=O)$_2$N(R)—, —S(=O)N(R)—, —O—, —S—, =O, =S, —C(=O)O—, —C(=O)—, —S(=O)—, —S(=O)$_2$— and/or —N(R)C(=O)N(R)—;

in each of the above cases, the number of R, R', R", heteroatoms or heteroatom groups is independently selected from 0, 1, 2 or 3;

and the compound represented by formula (I) does not include

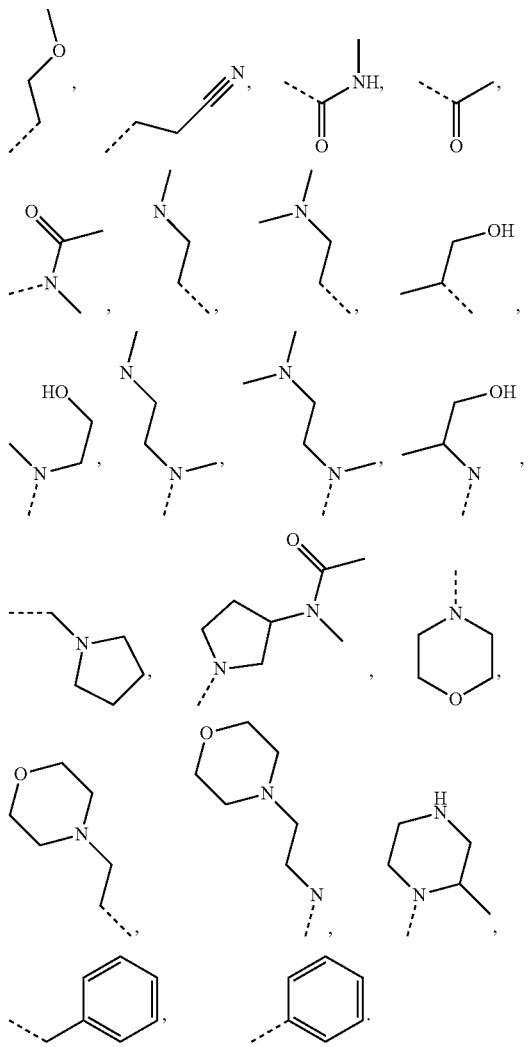

and

In some embodiments of the present disclosure, R is selected from the group consisting of H, F, Cl, Br, I, OH, $NH_2$, CN, hydroxymethyl, hydroxyethyl, carboxypropyl, carboxymethyl, methoxy, ethoxy, propoxy, methyl, ethyl, propyl, isopropyl, monohalomethyl, dihalomethyl, trihalomethyl, methylamino, dimethylamino, In some embodiments of the present disclosure, any two of $D_{41-45}$ or $T_{31-34}$ are connected together to the same atom or atom group to form a benzene ring.

In some embodiments of the present disclosure, $B_1$ is selected from the group consisting of H, F,

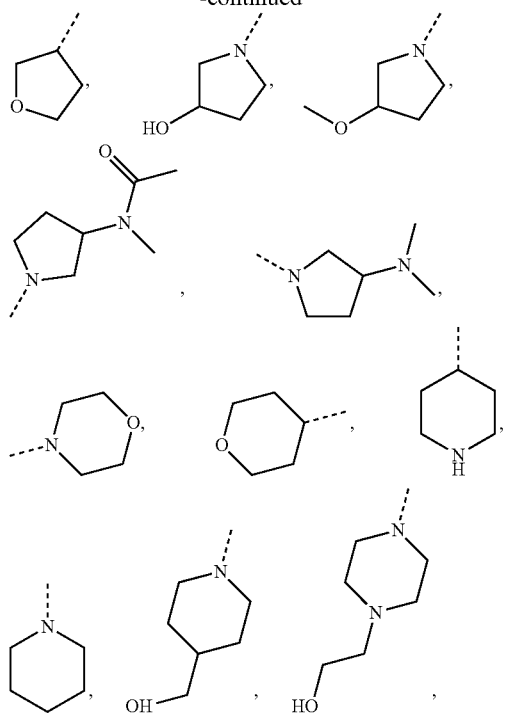
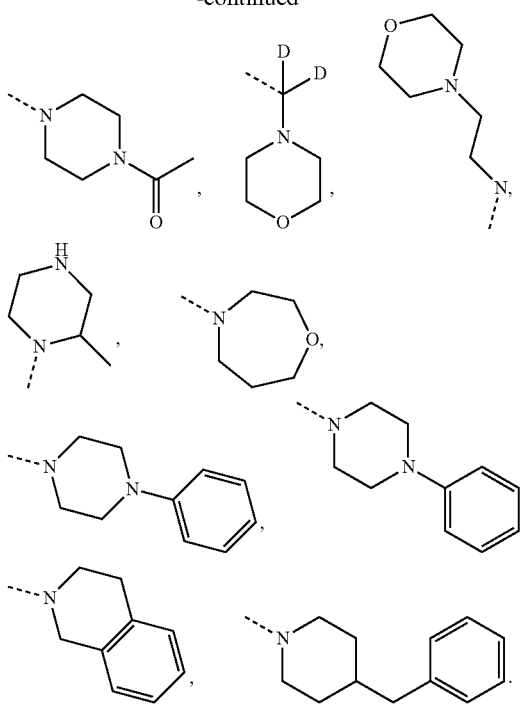
In some embodiments of the present disclosure, $L_1$ and $L_3$ are each independently selected from the group consisting of a single bond, NH,
, $CH_2$, $CH_2CH_2$,
, O, C(=O),

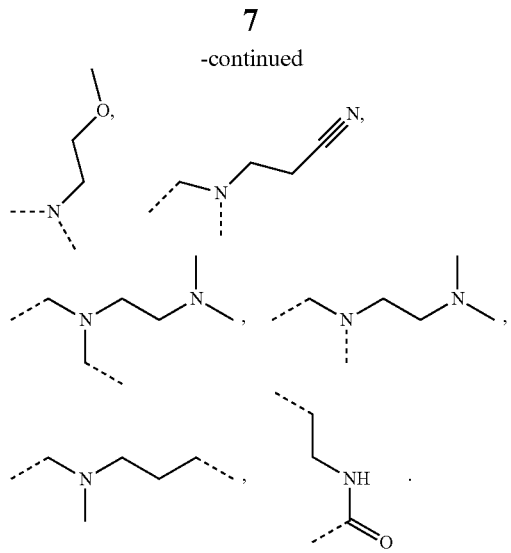

In some embodiments of the present disclosure, $B_2$ is selected from the group consisting of

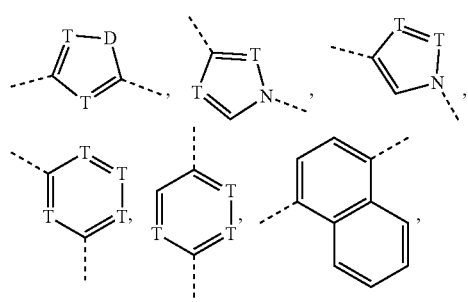

wherein, T is N or C(R); D is selected from the group consisting of —C(R)(R)—, —C(=O)N(R)—, —N(R)—, —C(=NR)—, —S(=O)$_2$N(R)—, —S(=O)N(R)—, —O—, —S—, —C(=O)O—, —C(=O)—, —C(=S)—, —S(=O)—, —S(=O)$_2$— or —N(R)C(=O)N(R)—.

In some embodiments of the present disclosure, $B_2$ is selected from the group consisting of

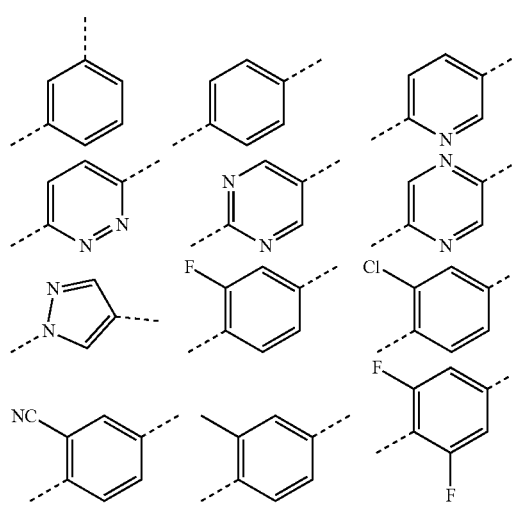

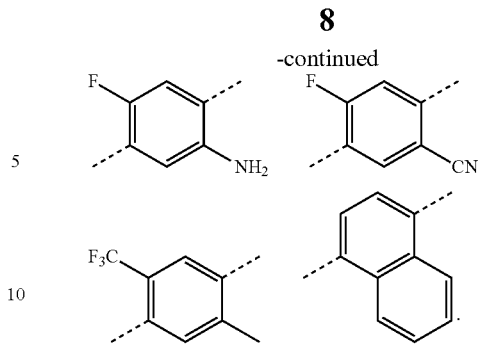

In some embodiments of the present disclosure, $B_4$ is selected from the group consisting of phenyl, pyridyl, imidazolyl, furyl, thiazolyl, piperidinyl, piperazinyl and morpholinyl, and each of which is optionally substituted with 1, 2 or 3 R.

In some embodiments of the present disclosure, $B_4$ is selected from the group consisting of

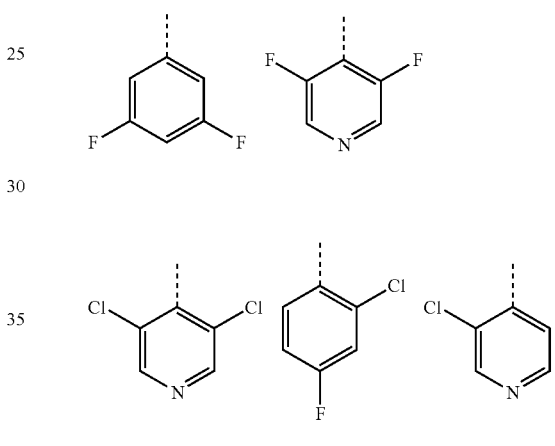

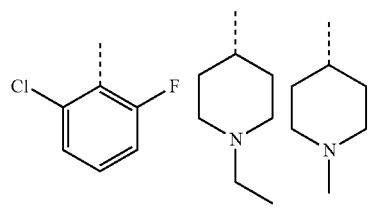

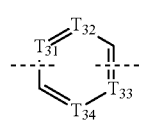

In some embodiments of the present disclosure, the structure unit

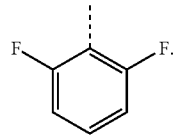

is selected from the group consisting of
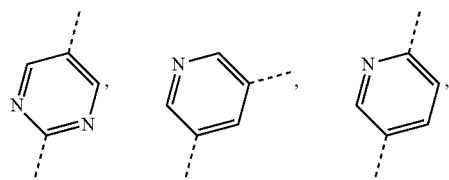
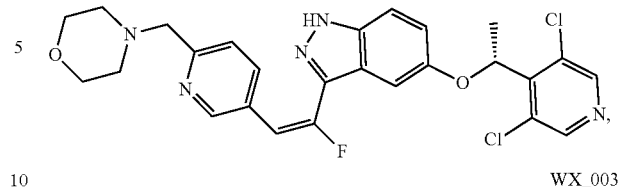
WX_002
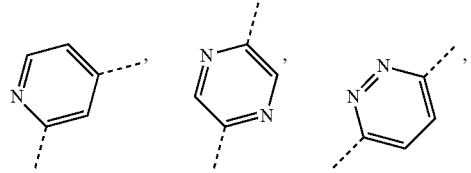
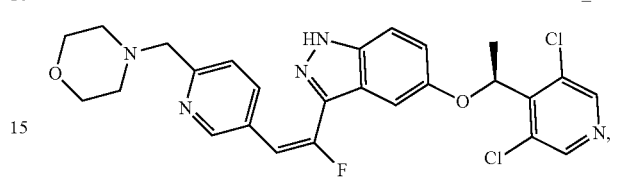
WX_003
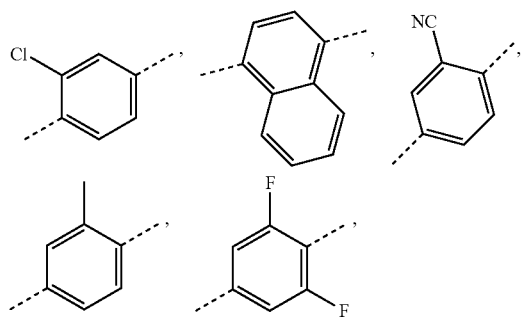
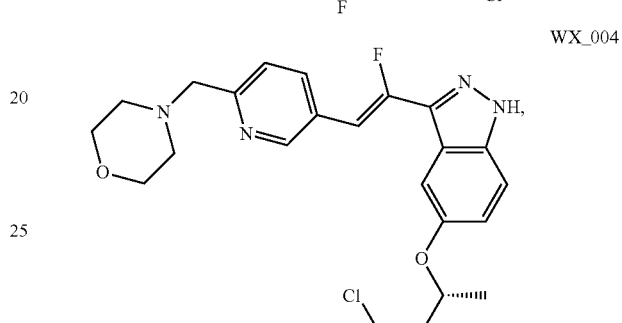
WX_004
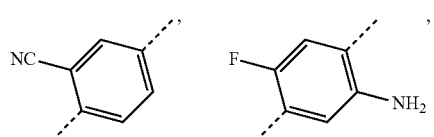
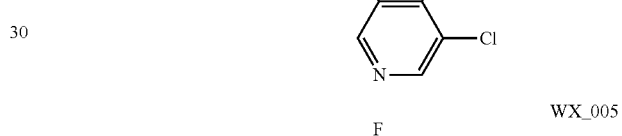
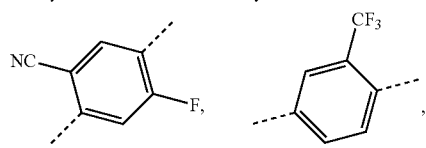
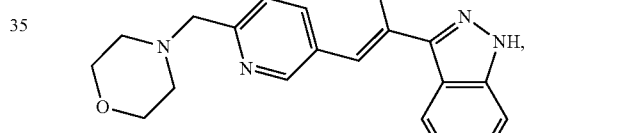
WX_005
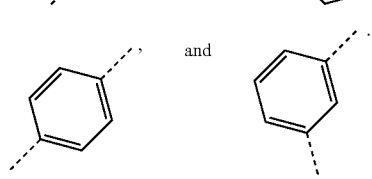 and
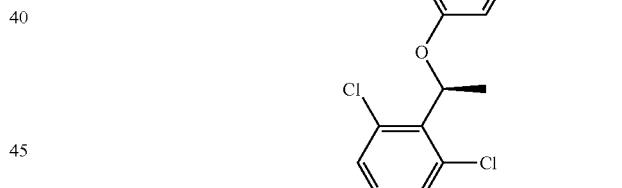
In some embodiments of the present disclosure, the compound is selected from the group consisting of
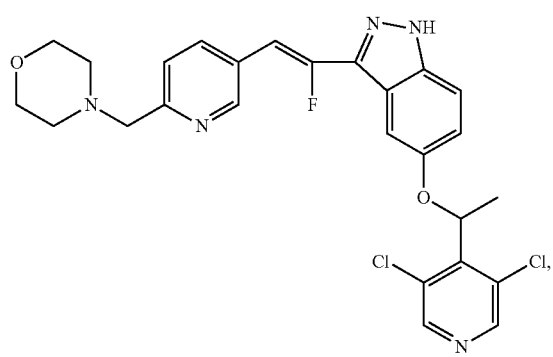
WX_001
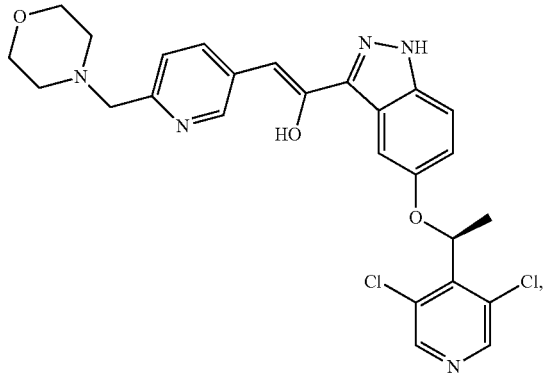
WX_006

-continued
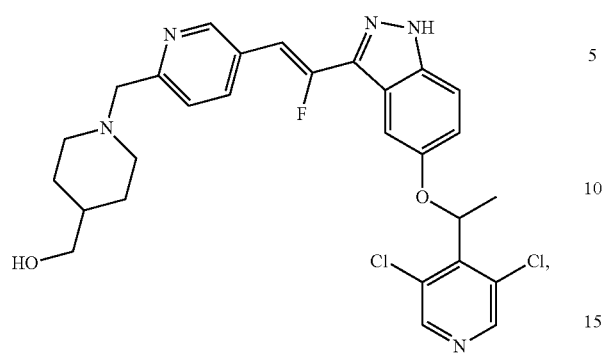
WX_009
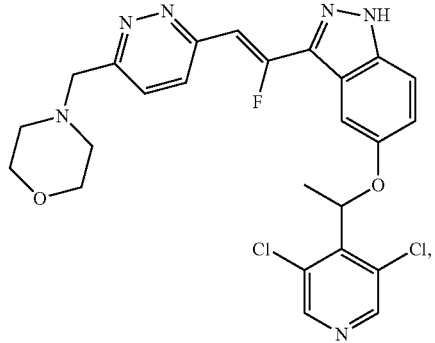
WX_013
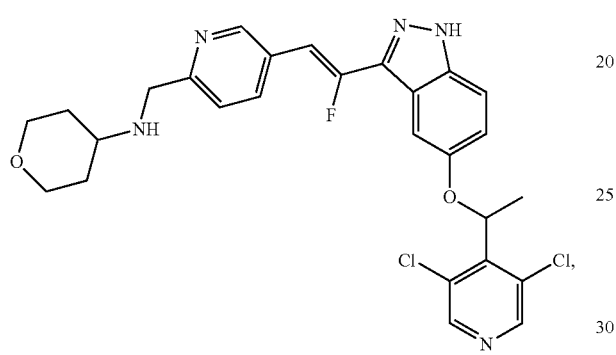
WX_010
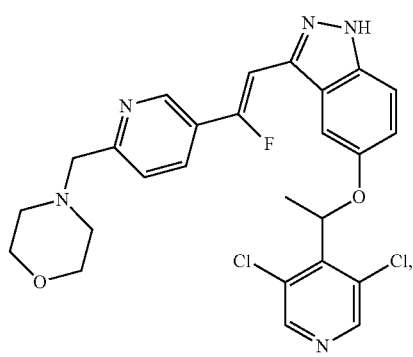
WX_016
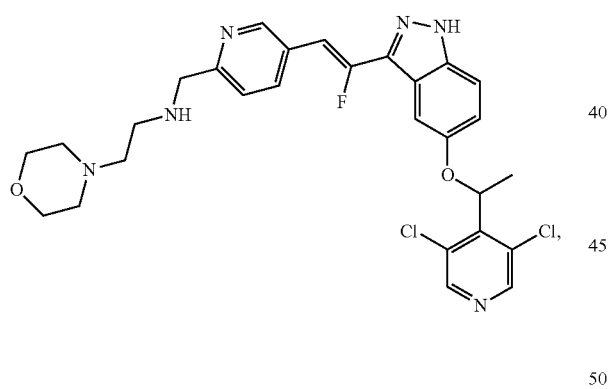
WX_011
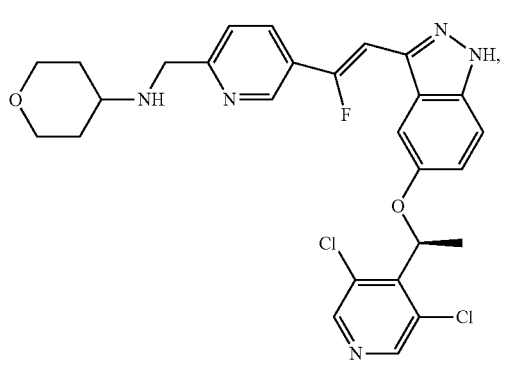
WX_017
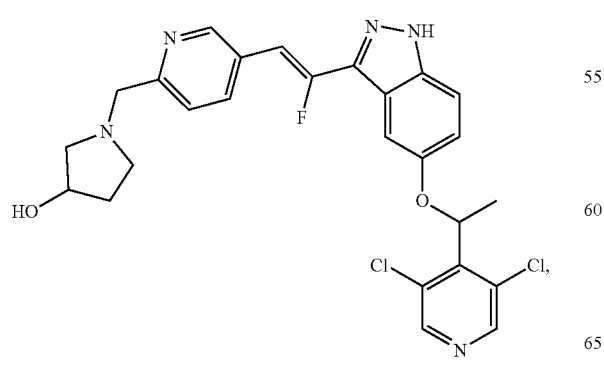
WX_012
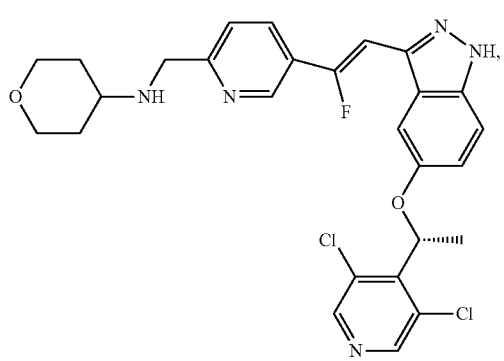
WX_018

-continued
WX_018b
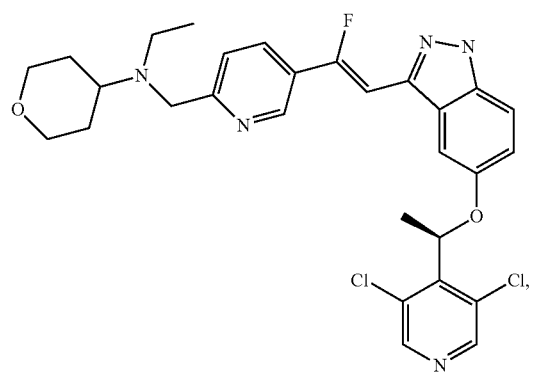
WX_021
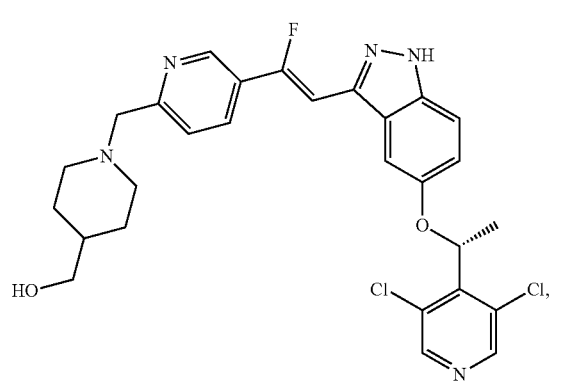
WX_022
WX_023
-continued
WX_026
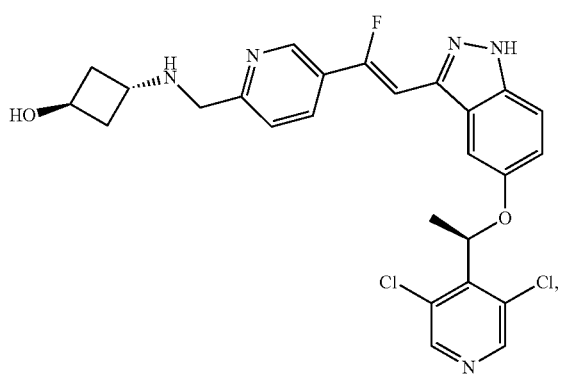
WX_027
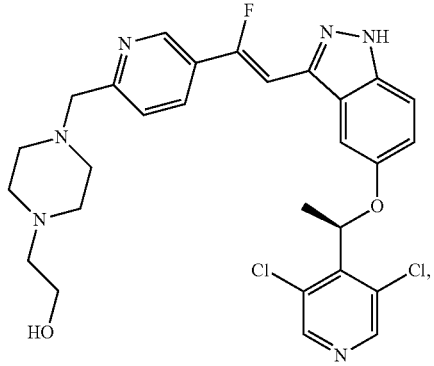
WX_029
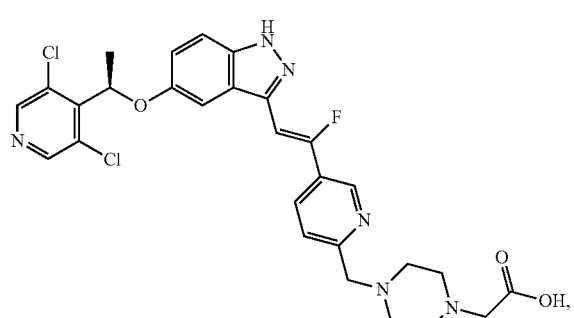
WX_030
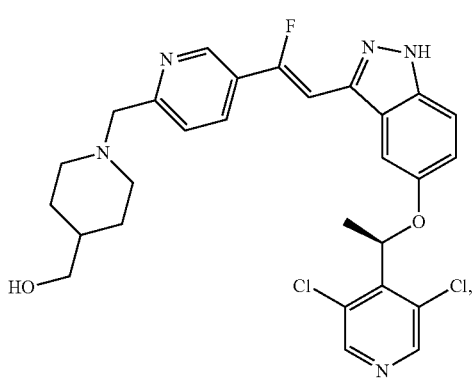
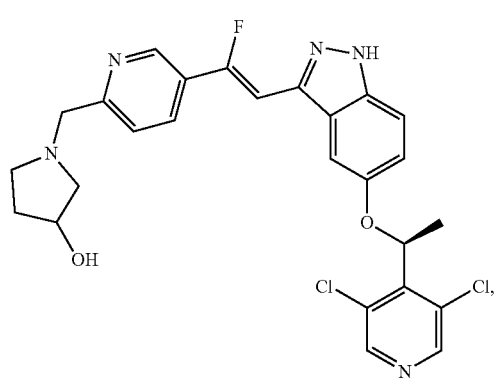

WX_031
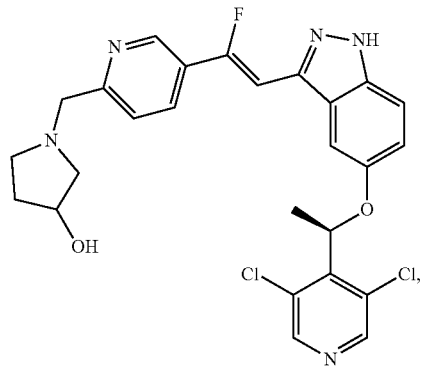
WX_032
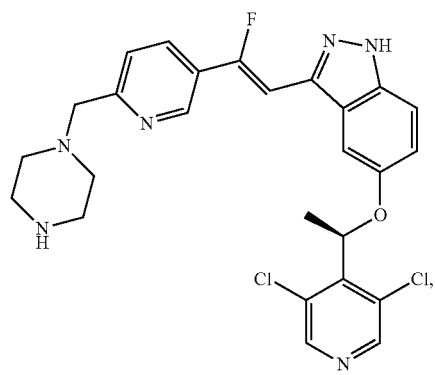
WX_033
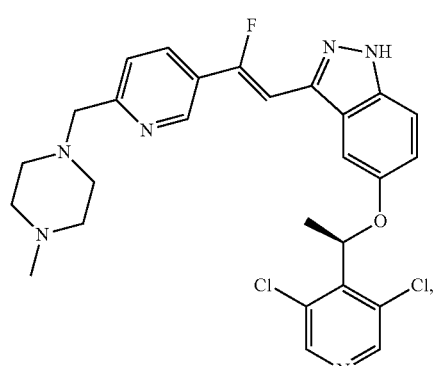
WX_034
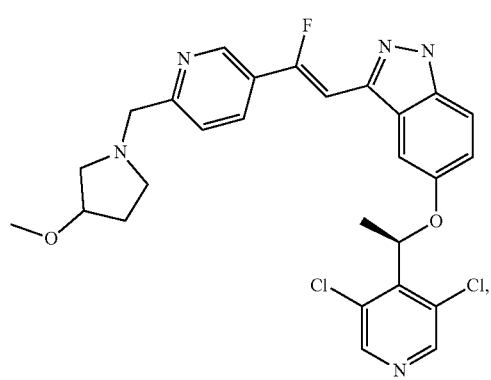
WX_036
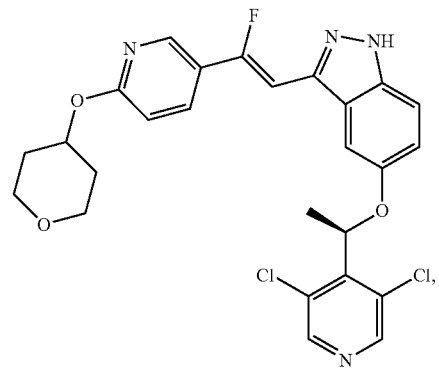
WX_037
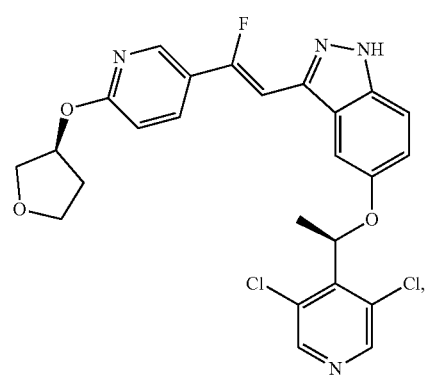
WX_038
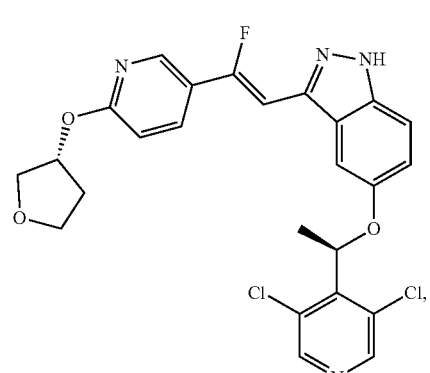
WX_041
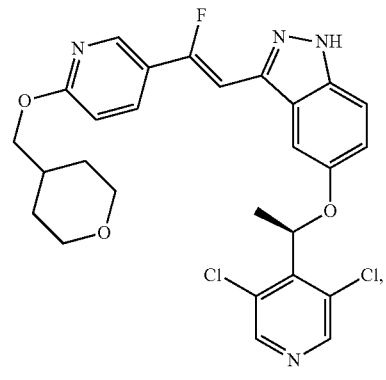

WX_043
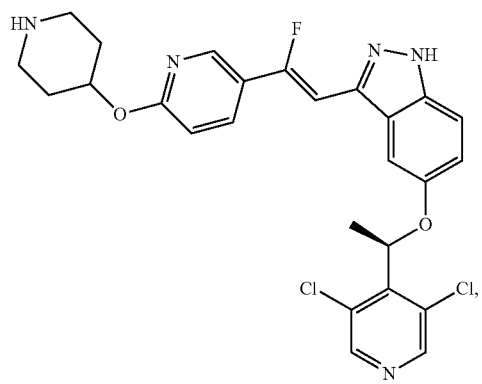
WX_044
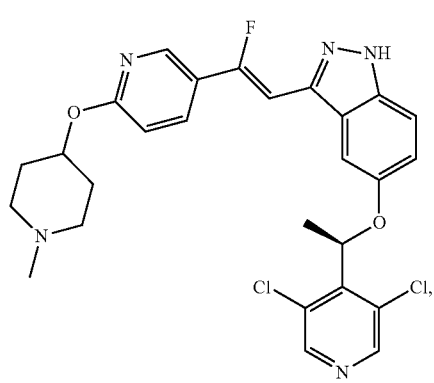
WX_045
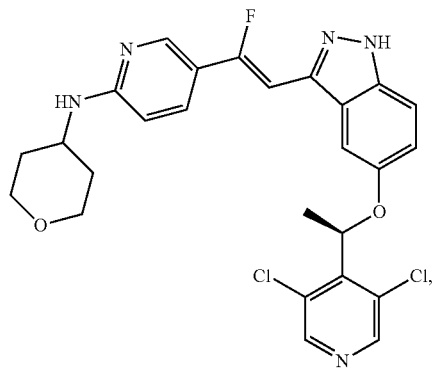
WX_047
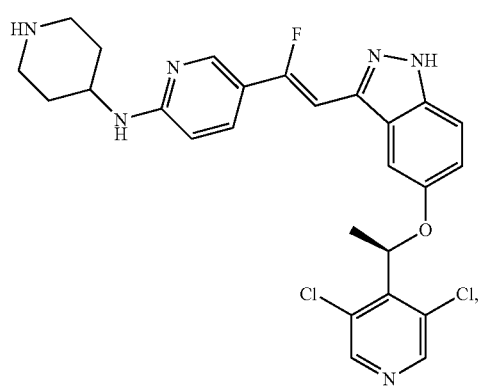
WX_048
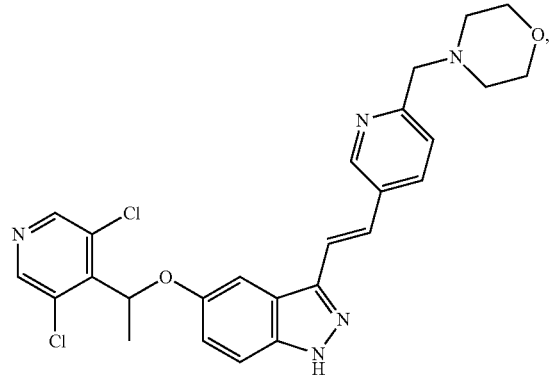
WX_049
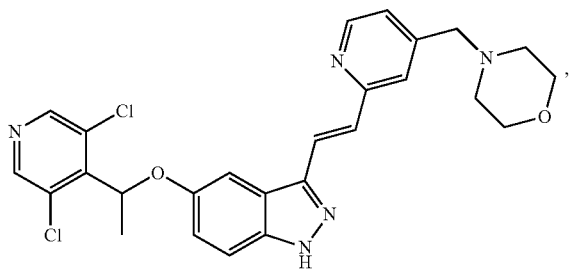
WX_050
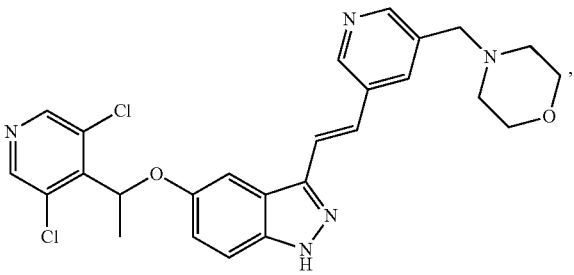
WX_051
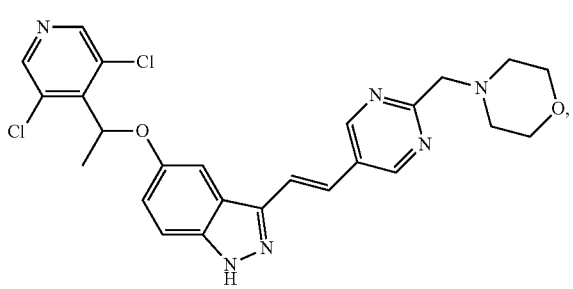

19
-continued
WX_052
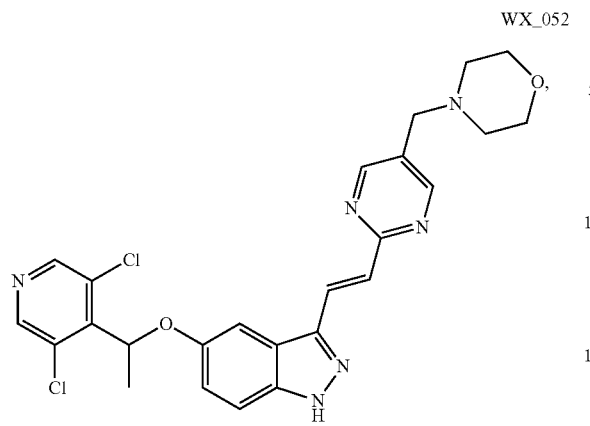
WX_053
WX_054
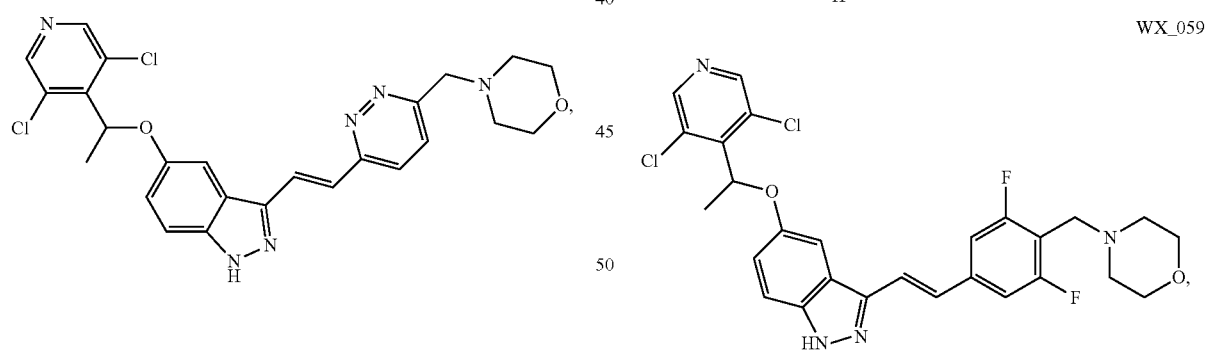
WX_055
20
-continued
WX_056
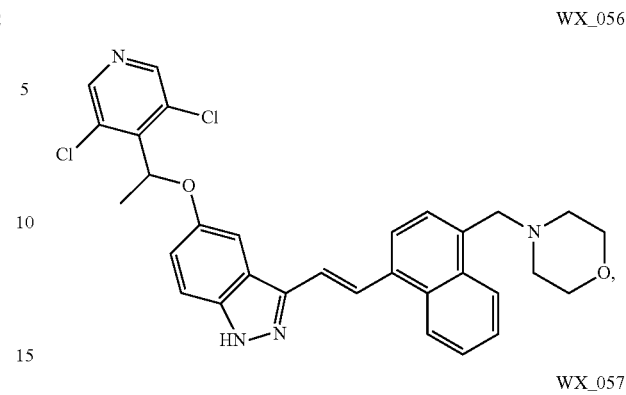
WX_057
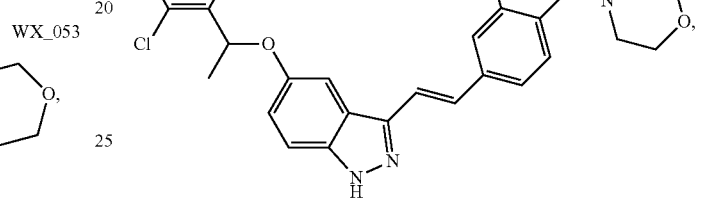
WX_058
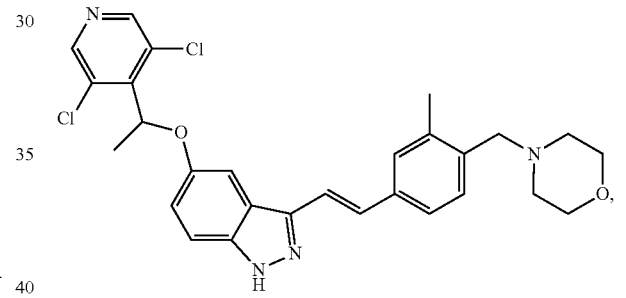
WX_059
WX_060
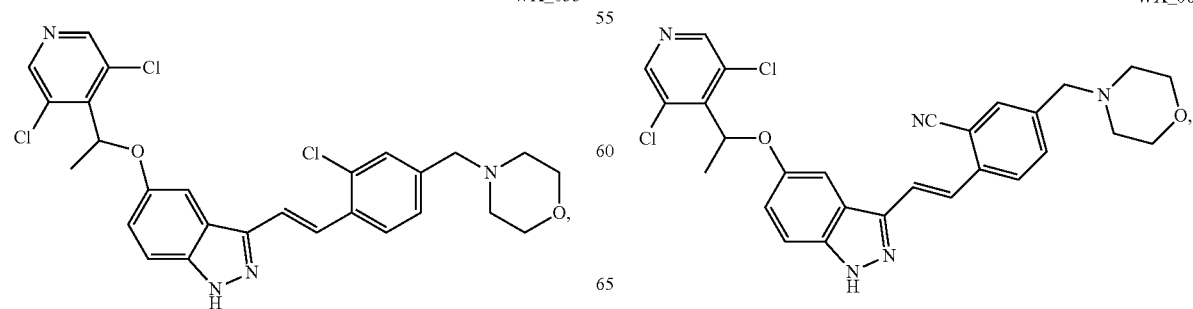

-continued
WX_061
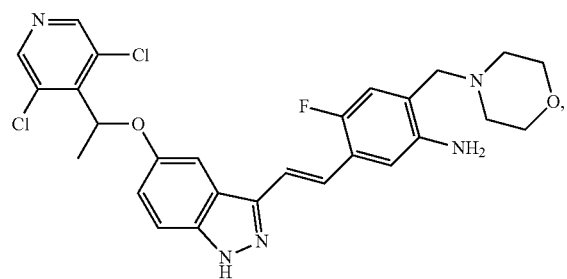
WX_062
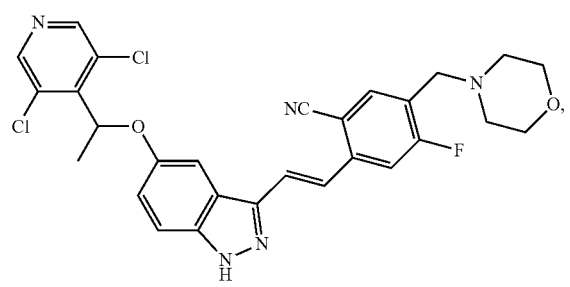
WX_063
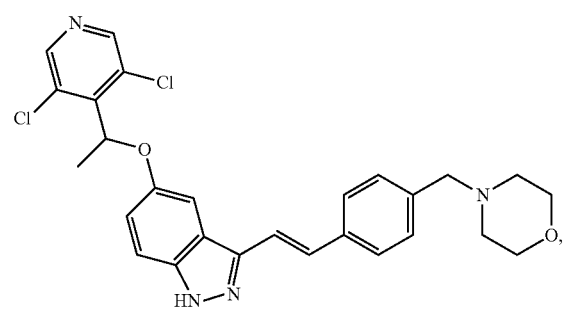
WX_064
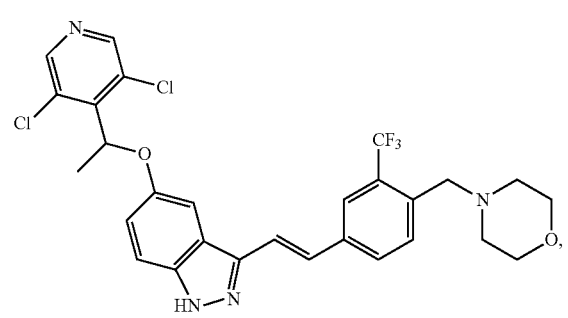
WX_065
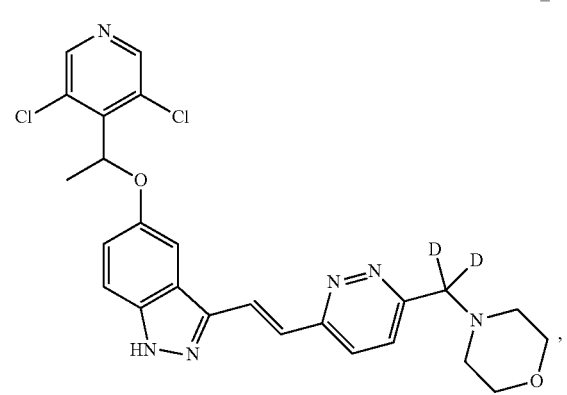
-continued
WX_066
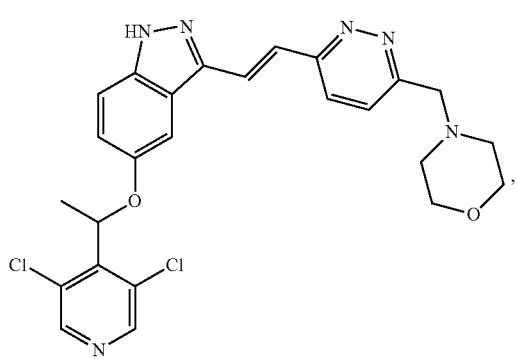
WX_067
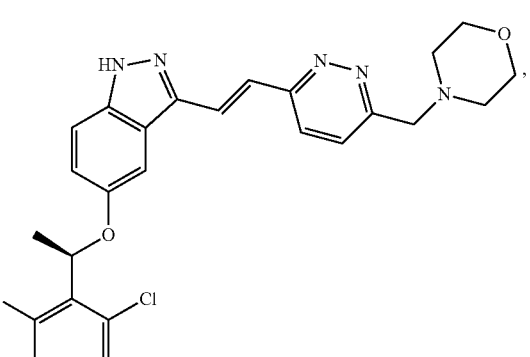
WX_068
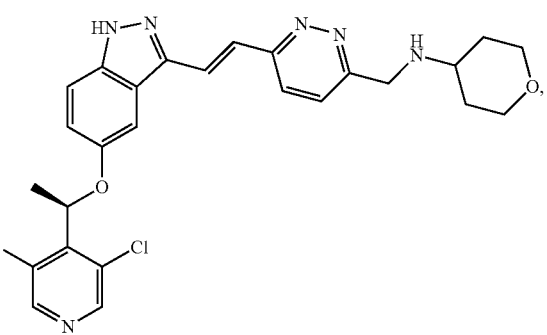
WX_069
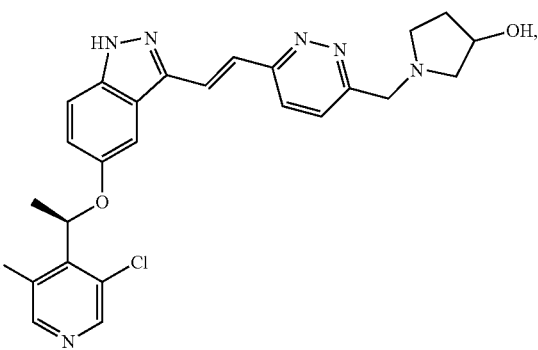

-continued
WX_070
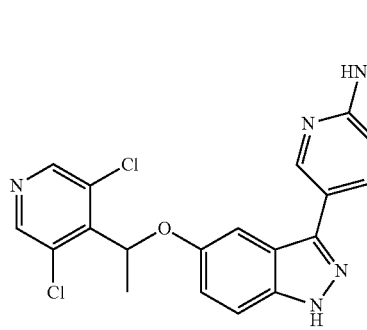
WX_076
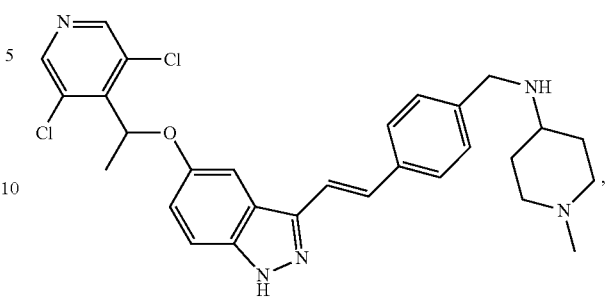
WX_071
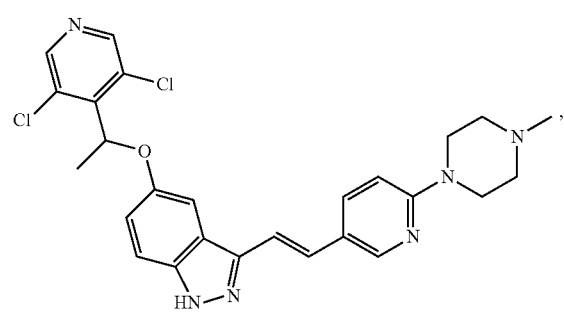
WX_078
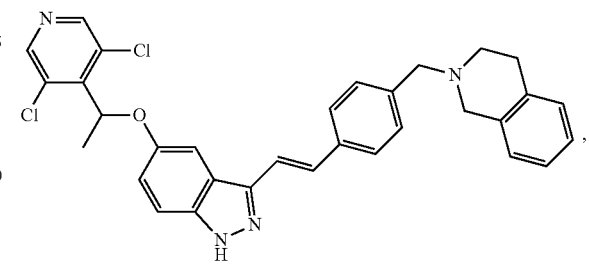
WX_072
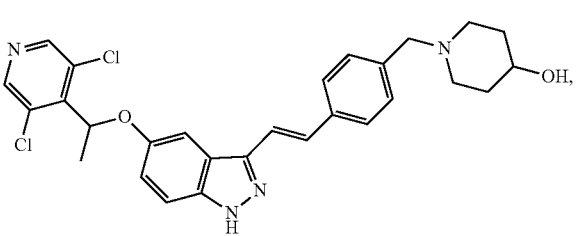
WX_080
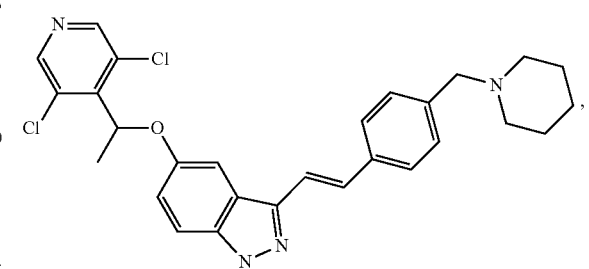
WX_073
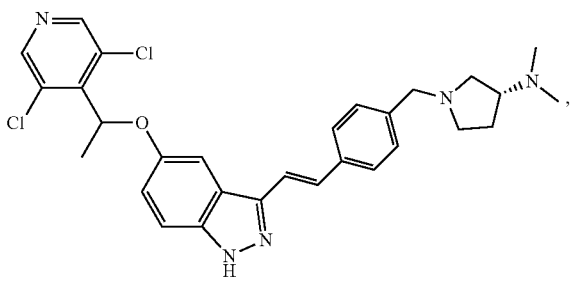
WX_081
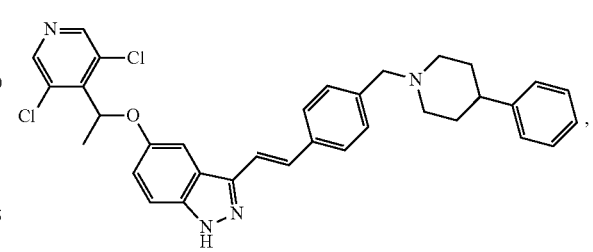
WX_074
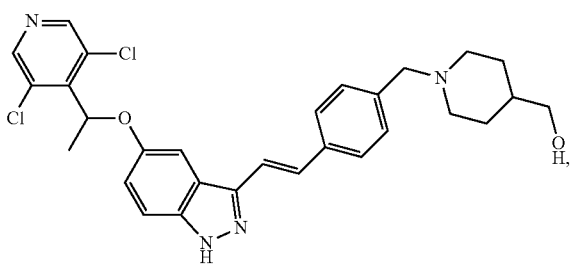
WX_082

WX_083
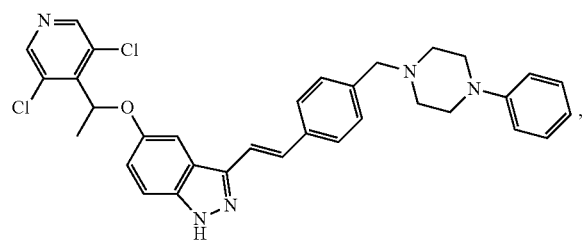
WX_086
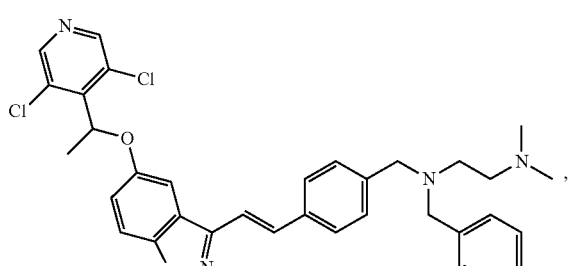
WX_087
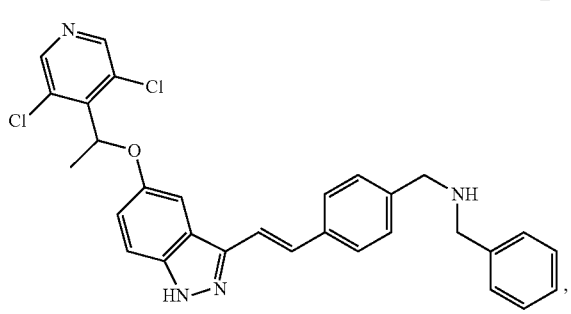
WX_088
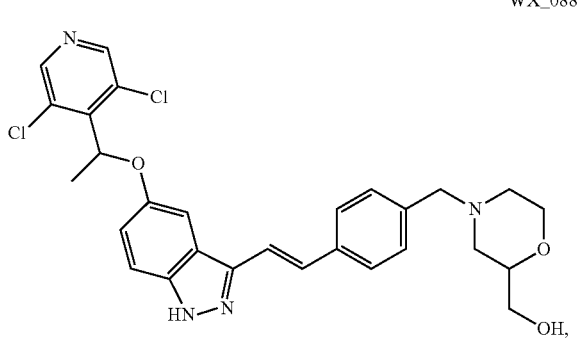
WX_089
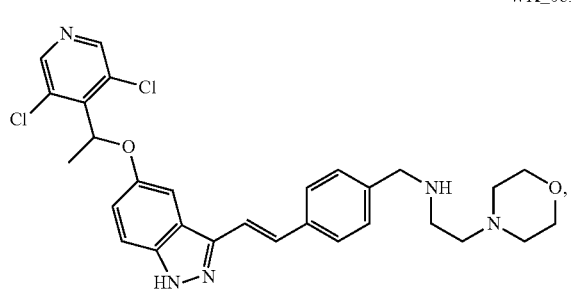
WX_090
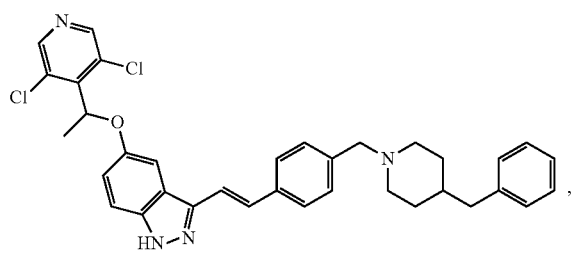
WX_091
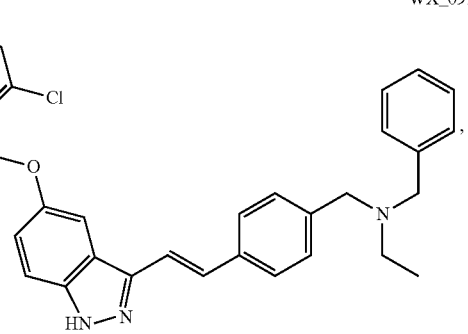
WX_093
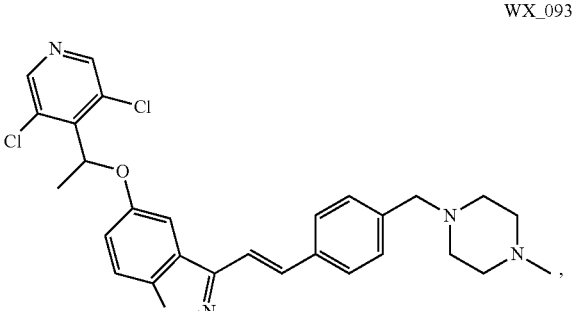
WX_094
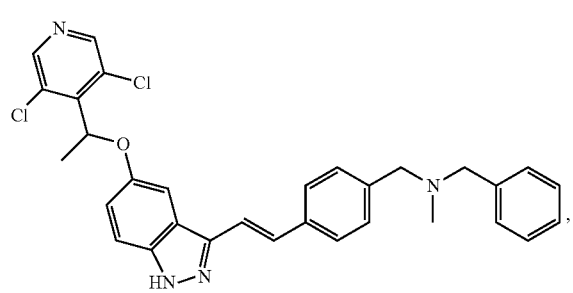
WX_095
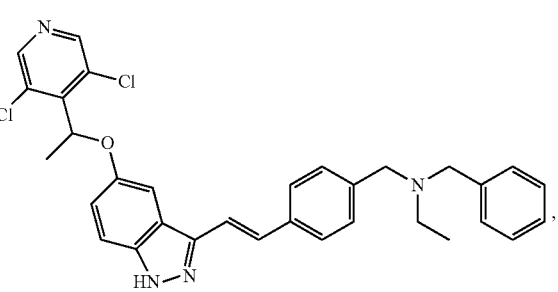

WX_097
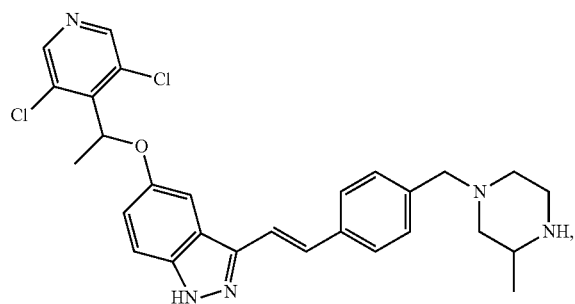
WX_099
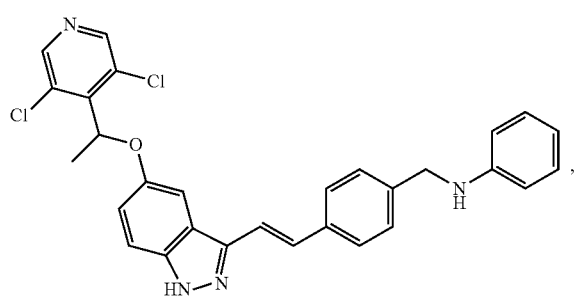
WX_100
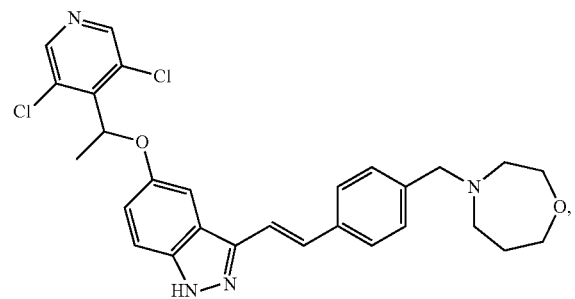
WX_101
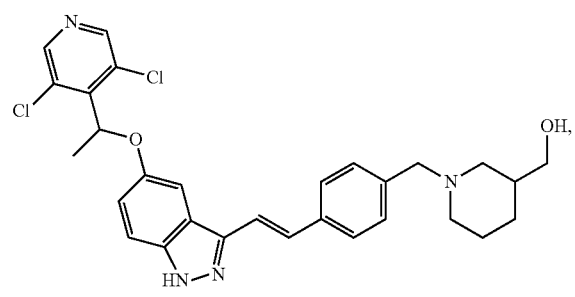
WX_102
WX_103
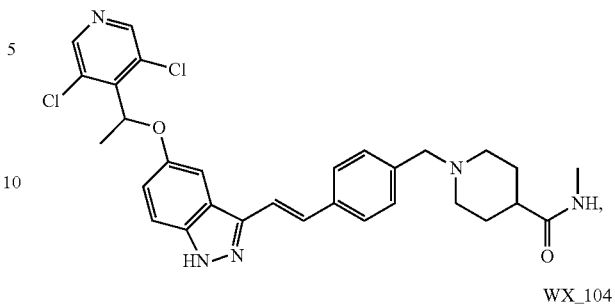
WX_104

WX_106
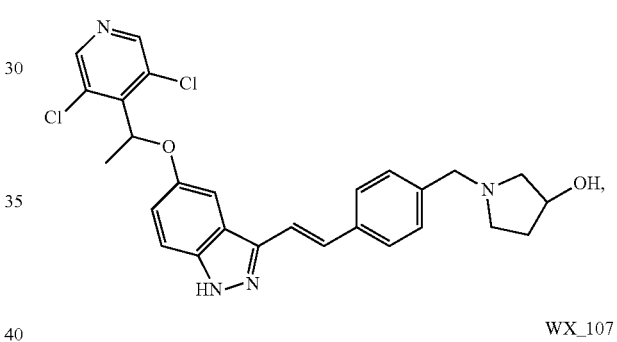
WX_107
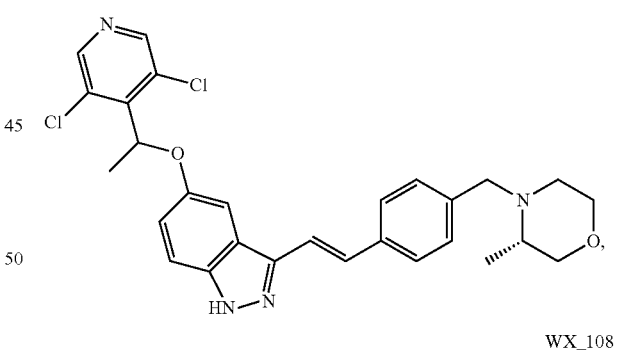
WX_108
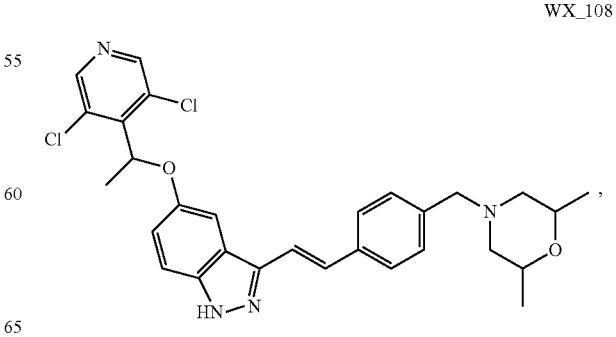

WX_109
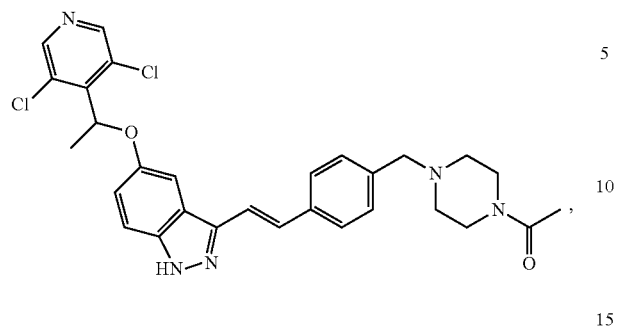
WX_112
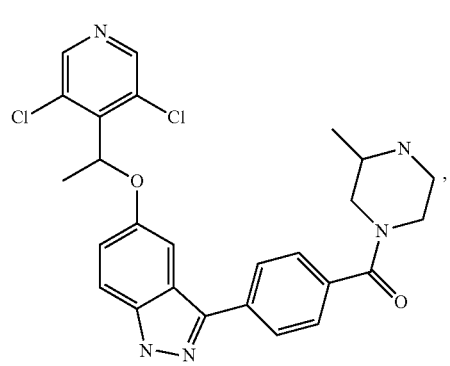
WX_113
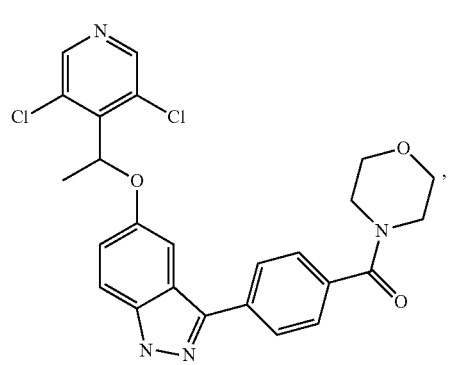
WX_114
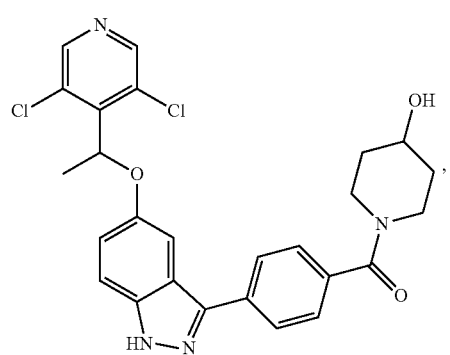
WX_115
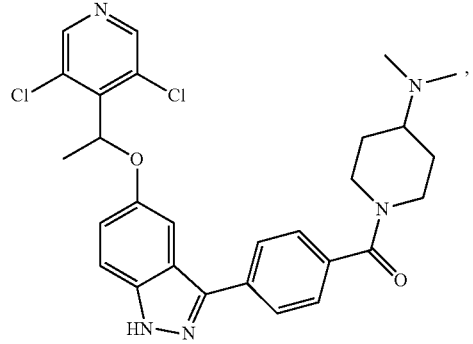
WX_116
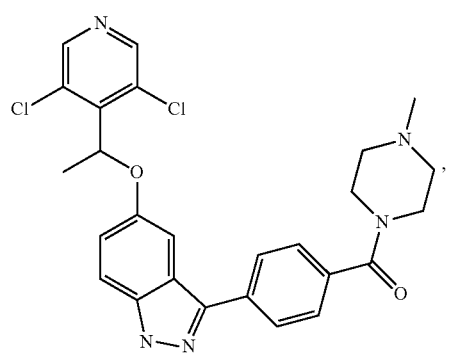
WX_117
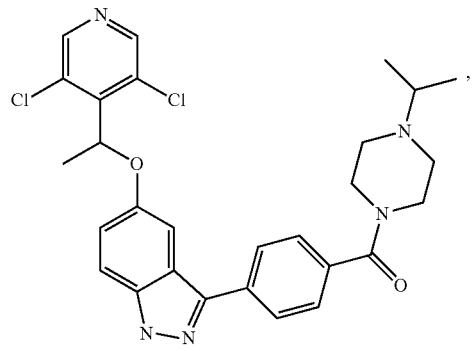
WX_119
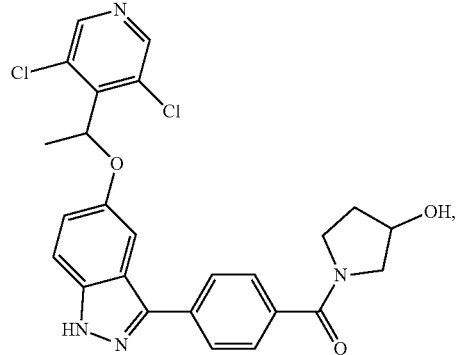

-continued
WX_120
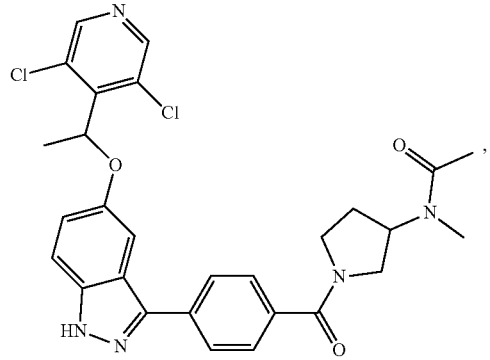
WX_127
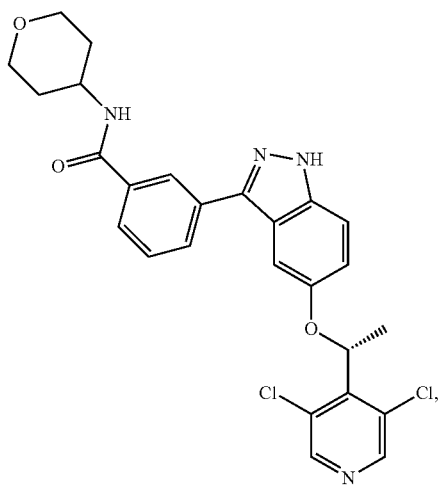
WX_121
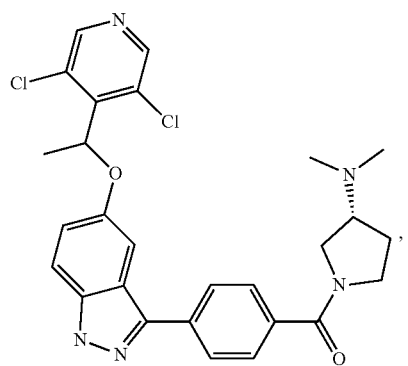
WX_129
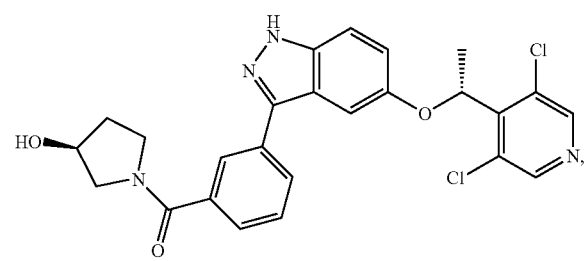
WX_125
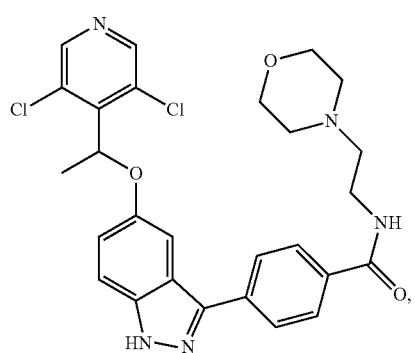
WX_130
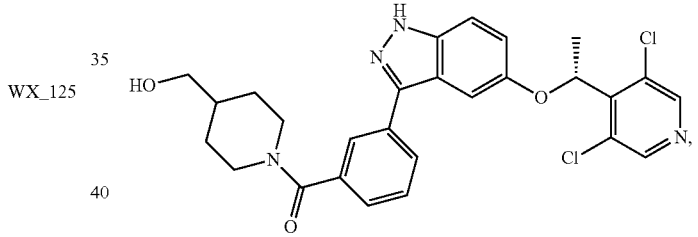
WX_132
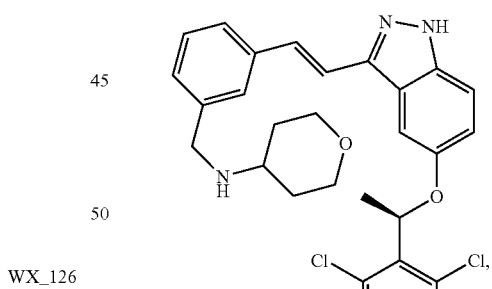
WX_126
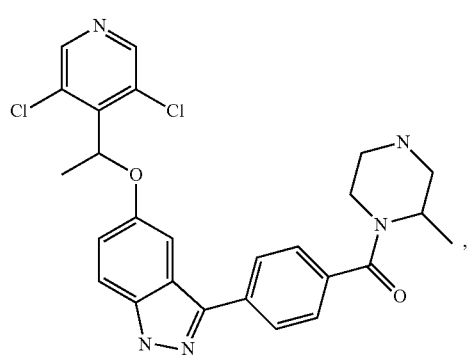
WX_134
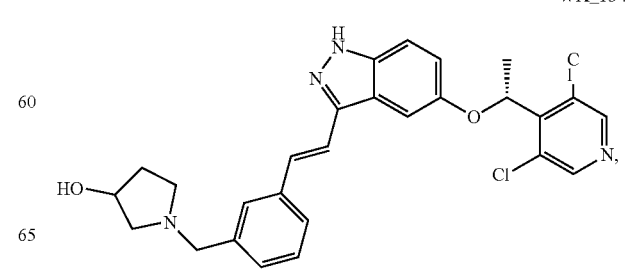

-continued
WX_135
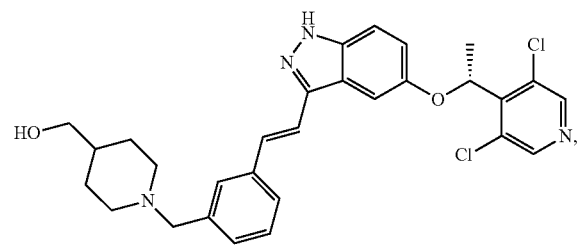
WX_137
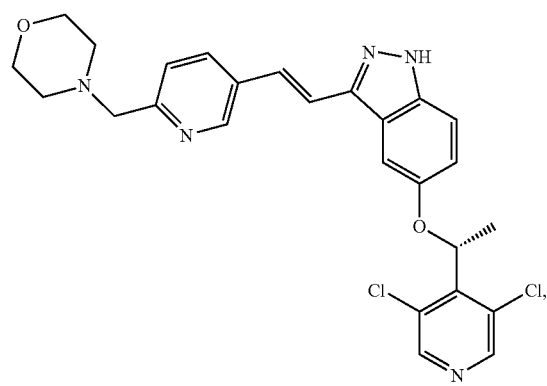
WX_138
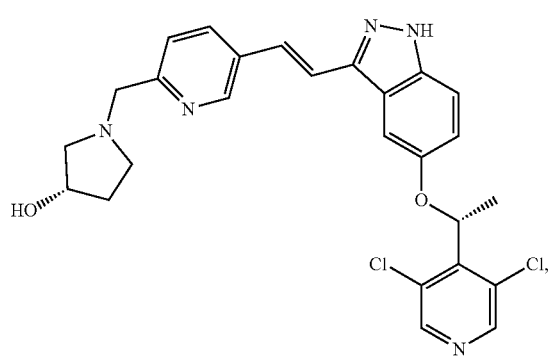
WX_140
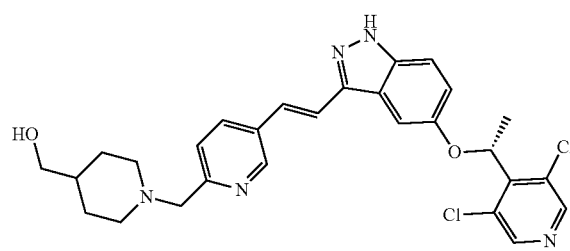
-continued
WX_142
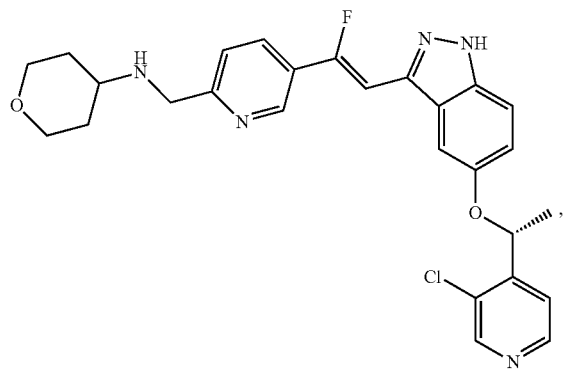
WX_143
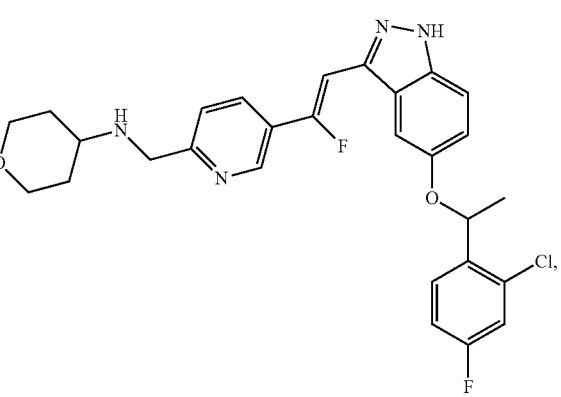
WX_144
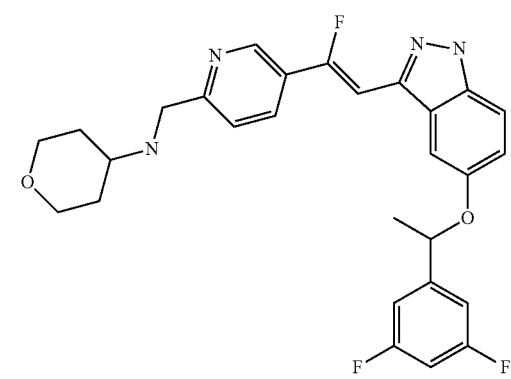
WX_145
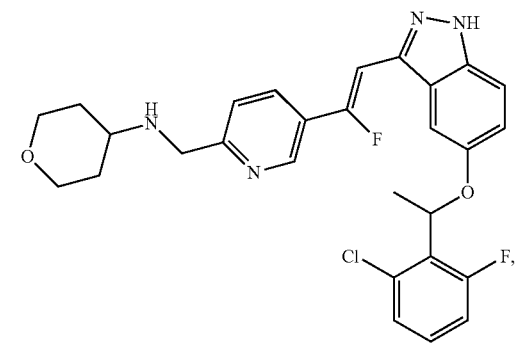

-continued

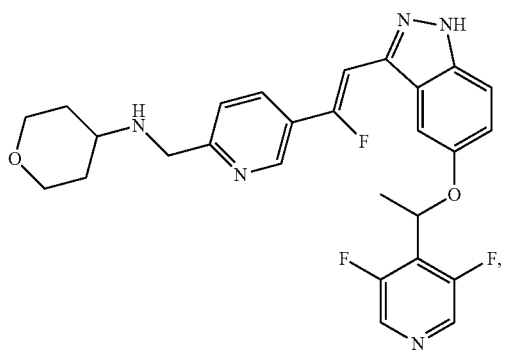
WX_146

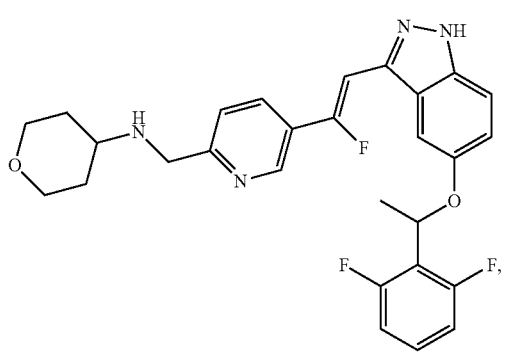
WX_147

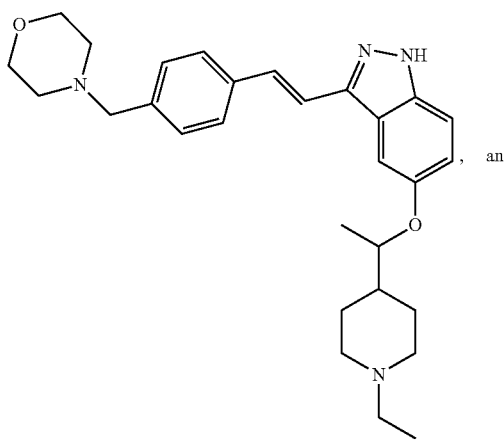
WX_148

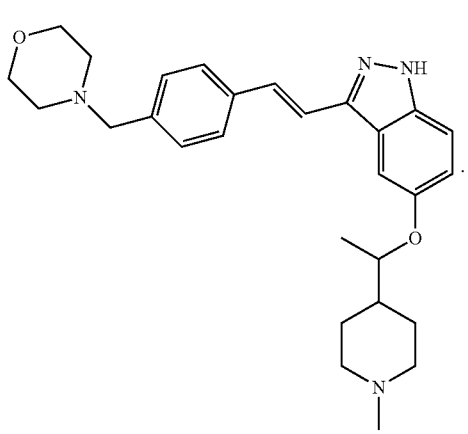
WX_149

The present disclosure also provides a process for preparing the compound represented by formula (I), comprising:

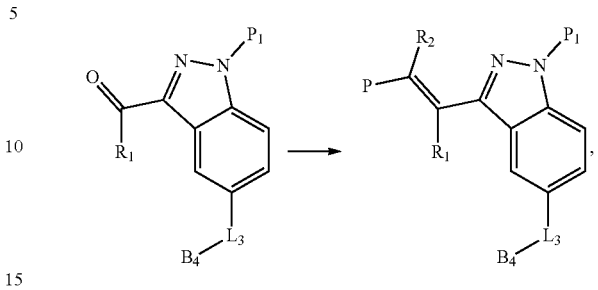

wherein, P is selected from halogen, OH, $NH_2$ and CN; $P_1$ is an amino protecting group, specifically THP; and other variables are as defined above.

In some embodiments of the present disclosure, the process for preparing the compound represented by formula (I), comprising

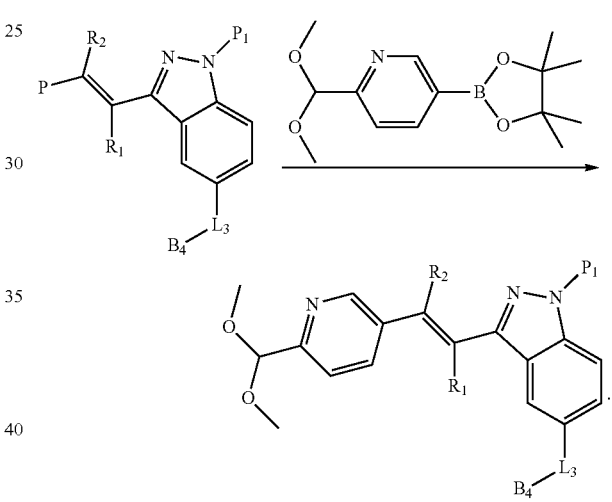

The present disclosure further provides a pharmaceutical composition comprising a therapeutically effective amount of the compound, the pharmaceutically acceptable salt or the tautomer thereof, and a pharmaceutically acceptable carrier.

The present disclosure further provides a use of the compound, the pharmaceutically acceptable salt or the tautomer thereof, or the pharmaceutical composition in the manufacture of a medicament for the treatment of cancer.

Definition and Description

Unless otherwise stated, the following terms and phrases used herein are intended to have the following meanings. A particular term or phrase should not be considered as indefinite or unclear but should be understood in the ordinary sense in the absence of any special definition. When a trade name appears in this article, it is intended to refer to its corresponding product or its active ingredient.

$C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$.

C$_{1-12}$ alkyl or heteroalkyl, C$_{3-12}$ cyclo or heterocycloalkyl, C$_{1-12}$ alkyl or heteroalkyl which is substituted with C$_{3-12}$ cyclohydrocarbyl or heterocyclohydrocarbyl include, but are not limited to, C$_{1-12}$ alkyl, C$_{1-12}$ alkylamino, N,N-di(C$_{1-12}$ alkyl)amino, C$_{1-12}$ alkoxy, C$_{1-12}$ alkanoyl, C$_{1-12}$ alkoxycarbonyl, C$_{1-12}$ alkylsulfonyl, C$_{1-12}$ alkylsulfinyl, C$_{3-12}$ cycloalkyl, C$_{3-12}$ cycloalkylamino, C$_{3-12}$ heterocycloalkyl amino, C$_{3-12}$ cycloalkyloxy, C$_{3-12}$ cycloalkylacyl, C$_{3-12}$ cycloalkyloxycarbonyl, C$_{3-12}$ cycloalkylsulfonyl, C$_{3-12}$ cycloalkylsulfinyl, 5- to 12-membered aryl or heteroaryl, 5- to 12-membered aralkyl or heteroaryl alkyl;

methyl, ethyl, n-propyl, isopropyl, —CH$_2$C(CH$_3$)(CH$_3$)(OH), cyclopropyl, cyclobutyl, propylmethylene, cyclopropionyl, benzyloxy, trifluoromethyl, aminomethyl, hydroxymethyl, methoxy, formyl, methoxycarbonyl, methanesulfonyl, methyl sulfinyl, ethoxy, acetyl, ethanesulfonyl, ethoxycarbonyl, dimethylamino, diethylamino, dimethylaminocarbonyl, diethylaminocarbonyl;

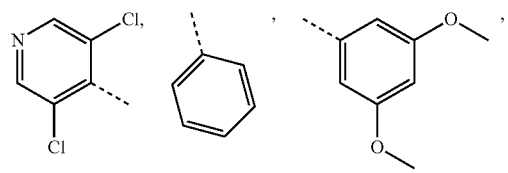

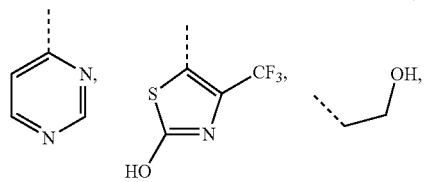

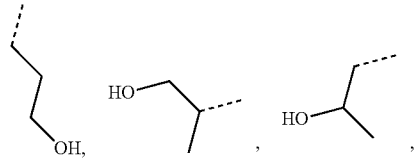

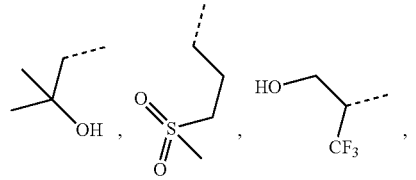

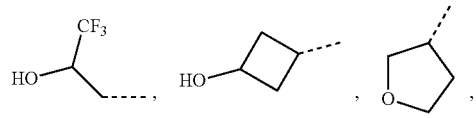

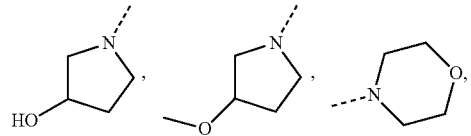

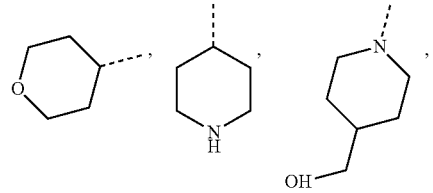

-continued

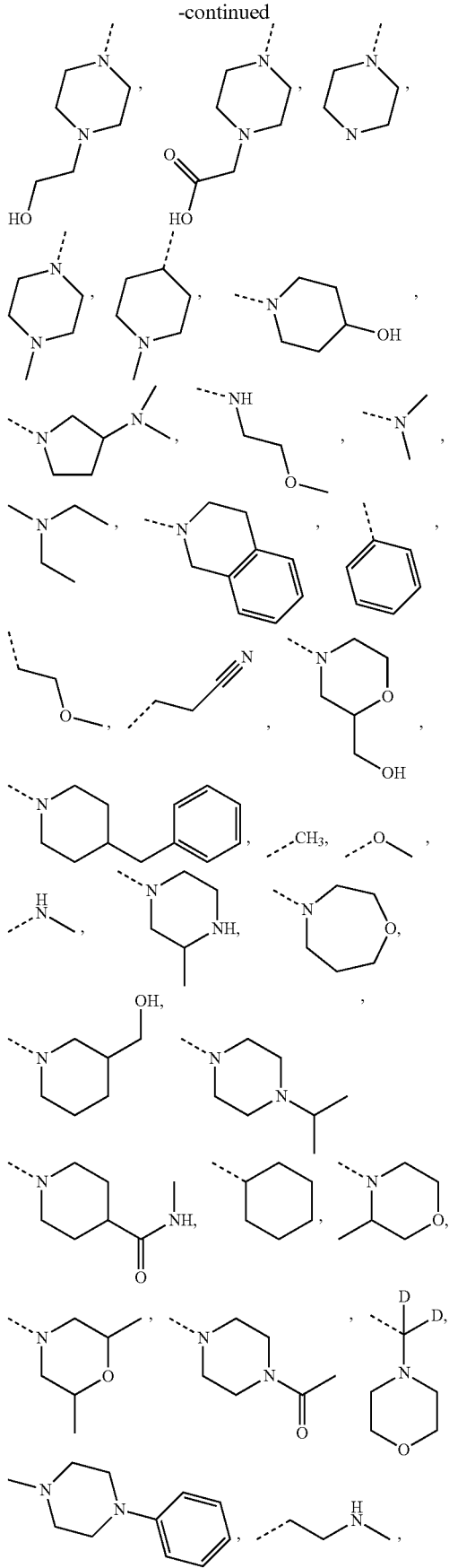

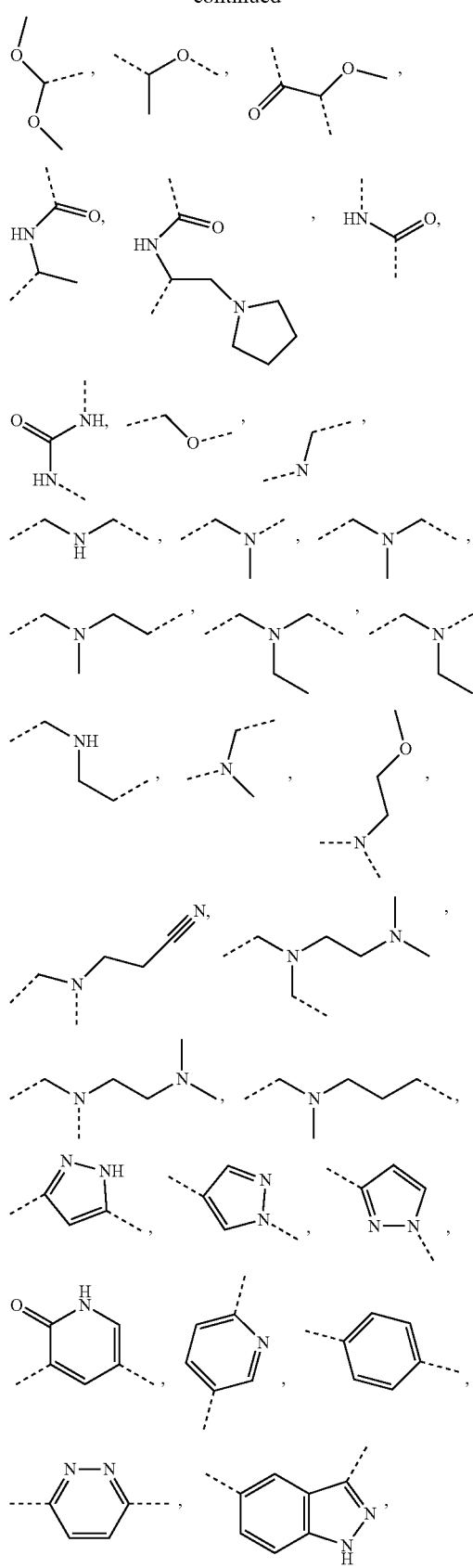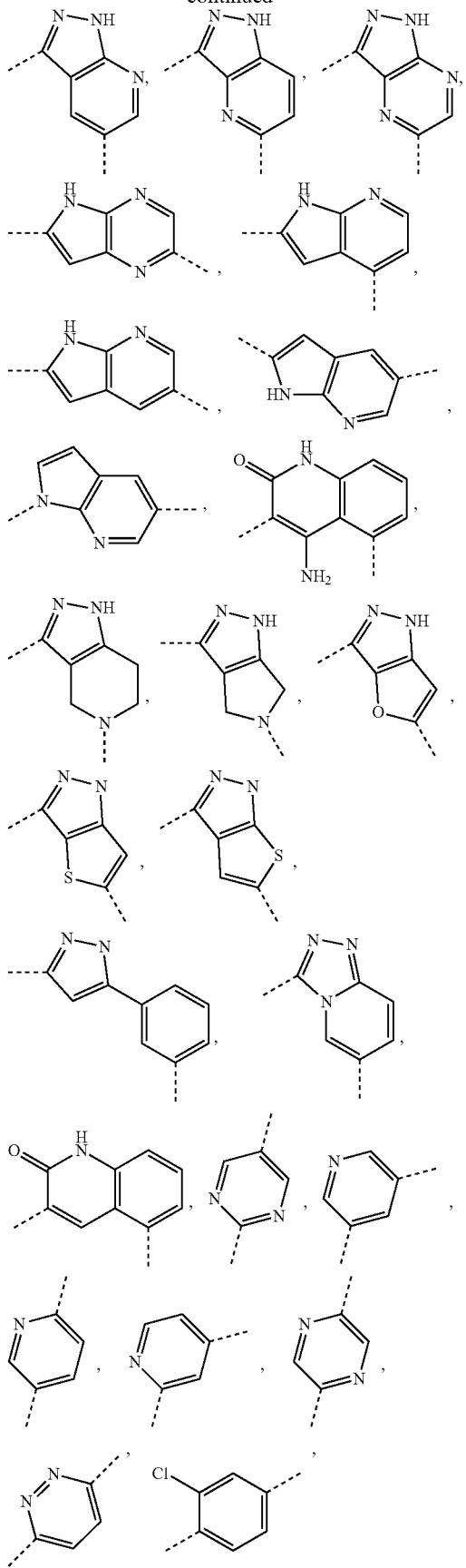

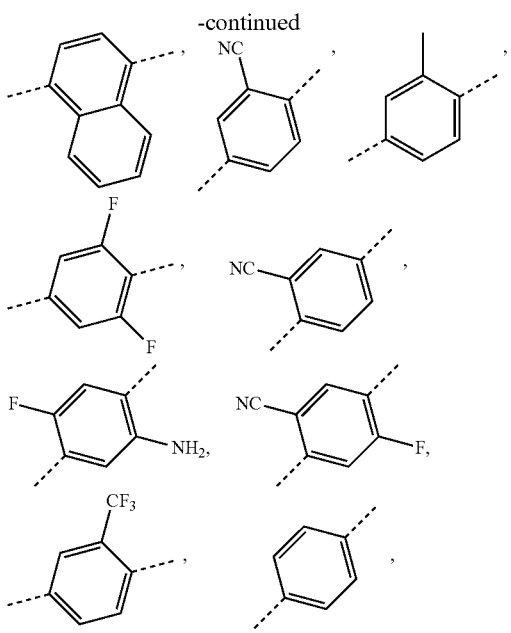

and phenyl, thiazolyl, biphenyl, naphthyl, cyclopentyl, furyl, 3-pyrrolinyl, pyrrolidinyl, 1,3-oxycyclopentyl, pyrazolyl, 2-pyrazolinyl, pyrazolidinyl, imidazolyl, oxazolyl, thiazolyl, 1,2,3-oxazolyl, 1,2,3-triazolyl, 1,2,4-triazolyl, 1,3,4-thiadiazolyl, 4H-pyranyl, pyridyl, piperidinyl, 1,4-dioxane, morpholinyl, pyridazinyl, pyrimidinyl, pyrazinyl, piperazinyl, 1,3,5-trithianyl, 1,3,5-triazinyl, benzofuranyl, benzothienyl, indolyl, benzimidazolyl, benzothiazolyl, purinyl, quinolinyl, isoquinolinyl, cinnolinyl or quinoxalinyl;

the term "pharmaceutically acceptable" as used herein, pertains to those compounds, materials, compositions and/or dosage forms that are, within the scope of sound medical judgment, suitable for use in contact with the tissues of humans and animals, without excessive toxicity, irritation, allergic reaction or other problems or complications, commensurate with a reasonable benefit/risk ratio.

The term "pharmaceutically acceptable salt" refers to a salt of the compound of the present disclosure prepared from a compound with particular substituent of the present disclosure and a relatively non-toxic acid or base. When the compound of the present disclosure contains a relatively acidic functional group, the base addition salt can be obtained by contacting a sufficient amount of base with a neutral form of such compound in pure solution or a suitable inert solvent. Pharmaceutically acceptable base addition salts include sodium, potassium, calcium, ammonium, organic ammonium or magnesium salts or similar salts. When the compound of the present disclosure contains a relatively basic functional group, the acid addition salt can be obtained by contacting a sufficient amount of acid with a neutral form of such compound in pure solution or a suitable inert solvent. Examples of pharmaceutically acceptable acid addition salts include inorganic acid salts, wherein the inorganic acid includes, for example, hydrochloric acid, hydrobromic acid, nitric acid, carbonic acid, bicarbonate, phosphoric acid, monohydrogenphosphate, dihydrogenphosphate, sulfuric acid, hydrogensulfate, hydroiodic acid, phosphorous acid and the like; and organic acid salts, wherein the organic acid includes, for example, formic acid, acetic acid, trifluoroacetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid and the like; and also include salts of amino acids such as arginine and the like, and salts of organic acids such as glucuronic acid (see Berge et al., "Pharmaceutical Salts", Journal of Pharmaceutical Science 66: 1-19 (1977)). Certain specific compounds of the present disclosure contain both basic and acidic functional groups so that they can be converted to any of the base or acid addition salts.

Preferably, the salt is contacted with a base or an acid in a conventional manner and the parent compound is then isolated, thereby regenerating the neutral form of the compound. The parent form of a compound differs from its various salt forms in certain physical properties, such as different solubility in polar solvents.

As used herein, "pharmaceutically acceptable salt" pertains to derivatives of the compound of the present disclosure wherein the parent compound is modified by salt formation with an acid or a base. Examples of pharmaceutically acceptable salts include, but are not limited to, inorganic or organic acid salt of an alkali group such as amino, acid radical such as alkali or organic salt of carboxylic acid, and the like. Pharmaceutically acceptable salts include the conventional nontoxic salts or quaternary ammonium salts of the parent compound, for example salts of non-toxic inorganic or organic acids. The conventional non-toxic salts include, but are not limited to, those derived from inorganic acids and organic acids, and the inorganic acids and organic acids are selected from 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodic acid, hydroxy, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic, propionic acid, salicylic acid, stearic acid, sub-acetic acid, succinic acid, sulfamic acid, sulfanilic acid, sulfuric acid, tannin, tartaric acid and p-toluenesulfonic acid.

Pharmaceutically acceptable salts of the present disclosure can be synthesized from the parent compound containing an acid radical or a base radical by conventional chemical methods. In general, such salts are prepared by reacting these compounds in the form of a free acid or base with a stoichiometric amount of appropriate base or acid in water or an organic solvent or a mixture thereof. In general, non-aqueous media such as ether, ethyl acetate, ethanol, isopropanol or acetonitrile etc. are preferred.

In addition to the salt form, the compounds provided herein also exist as prodrug forms. Prodrugs of the compounds described herein are readily converted to the compounds of the present disclosure by chemical changes under physiological conditions. In addition, prodrugs can be converted to the compounds of the present disclosure by chemical or biochemical methods in vivo environment.

Certain compounds of the present disclosure may exist in unsolvated as well as solvated forms, including hydrated forms. In general, solvated forms are comparable to unsolvated forms, both of which are included within the scope of the present disclosure.

Certain compounds of the present disclosure may have asymmetric carbon atoms (optical centers) or double bonds.

Racemates, diastereomers, geometric isomers, and individual isomers thereof are included within the scope of this disclosure.

Schematic illustrations of racemates, ambiscalemic and scalemic or enantiopure compounds herein are from Maehr, J. Chem. Ed. 1985, 62: 114-120. Unless otherwise specified, the absolute configuration of a stereocenter is expressed in terms of ⬈ ⬈ the wedge key, and the wavy line ⬈ refers to the relative configuration.

When the compounds described herein contain olefinic double bonds or other geometric asymmetric centers, they include the E, Z geometric isomers unless otherwise specified. Likewise, all tautomeric forms are included within the scope of the present disclosure.

The compounds of the present disclosure may exist in specific geometric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, and their racemic mixtures and other mixtures, such as enantiomer or diastereomer enriched mixtures, all of which are within the scope of the present disclosure. Additional asymmetric carbon atoms may be present in alkyl and other substituents. All such isomers and mixtures thereof are included within the scope of the present disclosure.

Optically active (R)- and (S)-isomers as well as D- and L-isomers may be prepared by chiral synthesis or chiral reagents or other conventional techniques. One enantiomer of the compound of the present disclosure, if desired, can be prepared by asymmetric synthesis or derivatization with a chiral auxiliary, wherein the resulting mixture of diastereomers is separated and the ancillary groups cleave to provide the pure desired enantiomer. Alternatively, when the molecule contains a basic functional group (such as an amino group) or an acidic functional group (such as a carboxyl group), it forms a diastereoisomeric salt with a suitable optically active acid or base, then diastereoisomeric resolution is performed by conventional methods well known in the art and the pure enantiomer is recovered. In addition, the separation of enantiomers and diastereomers is generally accomplished by chromatographic method employing a chiral stationary phase and optionally in combination with chemical derivatization (e.g., the formation of an amine formate from an amino group).

The compounds of the present disclosure may contain atomic isotopes in an unnatural proportion at one or more than one atoms that make up the compound. For example, the compounds may be labeled with a radioisotope such as tritium ($^3$H), iodine-125 ($^{125}$I) or C-14 ($^{14}$C). The conversion of all isotopic compositions of the compounds of the present disclosure, whether radioactive or not, is included in the scope of the present disclosure.

The term "pharmaceutically acceptable carrier" refers to any agent or carrier medium that is capable of delivering an effective amount of an active agent of the present disclosure, does not interfere with the biological activity of the active agent and has no toxic side effects on the host or the patient. Representative carriers include water, oils, vegetables and minerals, cream bases, lotion bases, ointment bases and the like. These bases include suspending agents, tackifiers, transdermal enhancers and the like. Their formulations are well known to those skilled in the art of cosmetics or topical medicines. For additional information on carriers, reference may be made to Remington: The Science and Practice of Pharmacy, 21st Ed., Lippincott, Williams & Wilkins (2005), the contents of which are incorporated herein by reference.

The term "excipient" generally refers to the carriers, diluents and/or vehicles required to formulate an effective pharmaceutical composition.

For pharmaceutical or pharmacologically active agents, the term "effective amount" or "therapeutically effective amount" refers to a sufficient amount of a non-toxic drug or agent that achieves the desired effect. For oral dosage forms in the present disclosure, an "effective amount" of an active substance in a composition means the amount required to achieve the desired effect when used in combination with another active substance in the composition. The determination of the effective amount will vary from person to person, depending on the age and general condition of the recipient, but also on the specific active substance, and the appropriate effective amount in each case can be determined by one skilled in the art according to routine experimentation.

The term "active ingredient," "therapeutic agent," "active substance," or "active agent" refers to a chemical entity that is effective in treating disorder, disease, or condition of a subject.

The term "substituted" means that any one or more than one hydrogen atoms on a specific atom has been substituted with a substituent, including deuterium and the variants of hydrogen, as long as the valence of the specific atom is normal and the substituted compound is stable. When the substituent is a ketonic group (i.e. =O), it means that two hydrogen atoms are substituted. Ketonic substitution does not occur on aromatic groups. The term "optionally substituted" means that may or may not be substituted, and unless otherwise specified, the kind and number of the substituents may be arbitrary on the basis that they are chemically achievable.

When any variable (e.g. R) occurs more than once in the composition or structure of the compound, its definition in each case is independent. Thus, for example, if a group is substituted with 0-2 R, the group may optionally be substituted with up to two R, and in each case R has its own individual options. In addition, a combination of substituents and/or variants thereof is only permitted if such combination results in a stable compound.

When a bond of a substituent can be cross-linked to two atoms on one ring, such substituent can be bonded to any atom on this ring. When a listed substituent is not specified by which atom it is attached to the compound included in the general chemical structural formula but not specifically mentioned, such substituent may be bonded by any of its atoms. A combination of substituents and/or variants thereof is only permitted if such combination results in a stable compound. For example, the structural unit

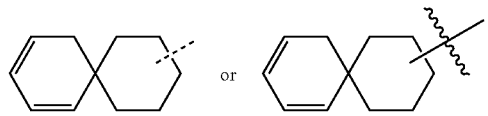

means that it can be substituted at any position on cyclohexyl or cyclohexadien.

When the number of a linking group is 0, such as —(CRR)$_0$—, this means that the linking group is a single bond.

When one of the variables is selected as a single bond, it means that the two groups are attached directly. For example, when L represents a single bond in A-L-Z, the structure is actually A-Z.

Unless otherwise specified, the term "halo" or "halogen" denotes a fluorine, chlorine, bromine or iodine, as such or as part of another substituent. In addition, the term "haloalkyl" is intended to include monohaloalkyl and polyhaloalkyl. For example, the term "halo($C_1$-$C_4$)alkyl" is intended to include but not limited to trifluoromethyl, 2,2,2-trifluoroethyl, 4-chlorobutyl and 3-bromopropyl and the like.

Examples of haloalkyl include, but are not limited to, trifluoromethyl, trichloromethyl, pentafluoroethyl, and pentachloroethyl. "Alkoxy" represents the above alkyl with specified number of carbon atoms attached through an oxygen bridge. $C_{1-6}$ alkoxy includes $C_1$, $C_2$, $C_3$, $C_4$, $C_5$ and $C_6$ alkoxy. Examples of alkoxy include, but are not limited to, methoxy, ethoxy, n-propoxy, iso-propoxy, n-butoxy, sec-butoxy, tert-butoxy, n-pentoxy and S-pentoxy. "Cycloalkyl" includes saturated cyclic groups such as cyclopropyl, cyclobutyl or cyclopentyl. 3-7 Cycloalkyl includes $C_3$, $C_4$, $C_5$, $C_6$ and $C_7$ cycloalkyl. "Alkenyl" includes hydrocarbon chains in a linear or branched configuration in which one or more than one carbon-carbon double bonds, such as vinyl and propenyl, are present at any stable site on the chain.

The term "halo" or "halogen" refers to fluorine, chlorine, bromine and iodine.

Unless otherwise specified, the term "hetero" means a heteroatom or a heteroatom group (i.e. an atom group containing a heteroatom), including atoms other than carbon (C) and hydrogen (H), as well as atom groups containing such heteroatoms, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —C(=NH)—, —S(=O)$_2$N(H)— or —S(=O)N(H)—.

Unless otherwise specified, "ring" refers to substituted or unsubstituted cycloalkyl, heterocycloalkyl, cycloalkenyl, heterocycloalkenyl, cycloalkynyl, heterocycloalkynyl, aryl, or heteroaryl. The so-called rings include monocyclic rings, bicyclic rings, spiro rings, fused ring or bridged rings. The number of atoms in a ring is usually defined as the member number of ring. For example, "5- to 7-membered ring" means that there are 5 to 7 atoms arranging in a circle. Unless otherwise specified, the ring optionally contains 1 to 3 heteroatoms. Thus, "5- to 7-membered ring" includes, for example, phenylpyridine and piperidinyl; on the other hand, the term "5- to 7-membered heterocycloalkyl ring" includes pyridyl and piperidinyl, but excludes phenyl. The term "ring" also includes ring systems containing at least one ring, each ring of which independently conforms to the above definition.

Unless otherwise specified, the term "heterocycle" or "heterocyclyl" means a stable monocyclic, bicyclic or tricyclic ring containing heteroatoms or heteroatom groups, which may be saturated, partially unsaturated or unsaturated (aromatic) containing carbon atoms and 1, 2, 3 or 4 heteroatoms in the ring independently selected from N, O and S, wherein any of the above heterocycles can be fused to a benzene ring to form a bicyclic ring. Nitrogen and sulfur heteroatoms may optionally be oxidized (i.e. NO and S(O)$_p$, p is 1 or 2). The nitrogen atom may be substituted or unsubstituted (i.e. N or NR, where R is H or other substituents that have been defined herein). The heterocycle can be attached to the pendant group of any heteroatom or carbon atom to form a stable structure. If the compound produced is stable, the heterocycle described herein may undergo substitution at the carbon or nitrogen position. The nitrogen atom in the heterocycle is optionally quaternized. A preferred embodiment is that when the total number of S and O atoms in the heterocycle exceeds 1, the heteroatoms are not adjacent to each other. Another preferred embodiment is that the total number of S and O atoms in the heterocycle does not exceed 1. As used herein, the term "aromatic heterocyclic group" or "heteroaryl" means a stable 5-, 6-, 7-membered monocyclic or bicyclic ring or 7-, 8-, 9-, or 10-membered bicyclic heterocyclyl aromatic ring, which contains carbon atoms and 1, 2, 3 or 4 heteroatoms in the ring independently selected from N, O and S. The nitrogen atom may be substituted or unsubstituted (i.e. N or NR, where R is H or other substituents that have been defined herein). Nitrogen and sulfur heteroatoms may optionally be oxidized (i.e. NO and S(O)$_p$, p is 1 or 2). It is worth noting that the total number of S and O atoms on the aromatic heterocycle does not exceed 1. Bridged rings are also included in the definition of heterocycle. A bridged ring forms when one or more than one atoms (i.e. C, O, N, or S) connect two non-adjacent carbon atoms or nitrogen atoms. Preferred bridged rings include, but are not limited to, one carbon atom, two carbon atoms, one nitrogen atom, two nitrogen atoms, and one carbon-nitrogen group. It is worth noting that a bridge always converts a monocyclic ring to a tricyclic ring. In a bridged ring, the substituents on the ring can also appear on the bridge.

Examples of heterocyclic compounds include, but are not limited to, acridinyl, azocinyl, benzimidazolyl, benzofuranyl, benzothiofuryl, benzothiophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolialkenyl, indolinyl, indolizinyl, indolyl, 3H-indolyl, iso-benzofuranyl, isoindolyl, isoindolinyl, isoquinolinyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, prazinyl, pyrazolidinyl, pyrazolyl, pyridazinyl, pyridoxazole, pyridimidazole, pyridothiazole, pyridyl, pyrrolidinyl, pyrrolinyl, 2H-pyrrolyl, pyrrolyl, quinazolinyl, quinolyl, 4H-quinolyl, quinoxalinyl, quinuclidinyl, tetrahydrofuranyl, tetrahydroisoquinolinyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrene, thiazolyl, isothiazolylthienyl, thienyl, thienoxazolyl, thienothiazolyl, thienoimidazolyl, triazinyl, 1,2,3-triazolyl, 1,2,4-triazolyl, 1,2,5-triazolyl, 1,3,4-triazolyl and xanthenyl, also include fused ring and spiro compounds.

Unless otherwise specified, the term "hydrocarbyl" or its subordinate concept (such as alkyl, alkenyl, alkynyl, phenyl, etc.) as such or as part of another substituent denotes a linear, branched or cyclic hydrocarbon radical, or combination thereof, which may be fully saturated, mono- or polyunsaturated, may be mono-substituted, di-substituted or polysubstituted, may include divalent or polyvalent radicals, with specified number of carbon atoms (for example $C_1$-$C_{10}$ represents 1 to 10 carbons). "Hydrocarbyl" includes, but is not limited to, aliphatic hydrocarbyl and aromatic hydrocarbyl, wherein, the aliphatic hydrocarby includes chain structure and cyclic structure, specific examples of which include, but are not limited to, alkyl, alkenyl, alkynyl, the aromatic hydrocarbyl includes but is not limited to 6- to 12-membered aromatic hydrocarbyl such as benzene, naphthalene and the like. In some embodiments, the term "alkyl" means a straight or branched radical or combination thereof, which may be fully saturated, mono- or polyunsaturated, and may include divalent and multivalent radicals. Examples of saturated hydrocarbon radicals include but are not limited to methyl, ethyl, n-propyl, isopropyl, n-butyl, t-butyl, isobutyl, secbutyl, isobutyl, cyclohexyl, (cyclohexyl)methyl, cyclopropylmethyl, and homologs or isomers of n-pentyl, n-hexyl, n-heptyl, n-octyl and the like. Unsaturated alkyl has one or more than one double or triple bonds and examples include, but are not limited to, vinyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butynyl, and more advanced homologues and isomers.

Unless otherwise specified, the term "heterohydrocarbyl" or its subordinate concept (such as heteroalkyl, heteroalkenyl, heteroalkynyl, heteroaryl, etc.) as such or in combination with another term denotes a stable linear, branched or cyclic hydrocarbon radical or combination thereof, with a certain number of carbon atoms and at least one heteroatom. In some embodiments, the term "heteroalkyl" as such or in combination with another term denotes a stable linear, branched hydrocarbon radical or combination thereof, with a certain number of carbon atoms and at least one heteroatom. In an exemplary embodiment, the heteroatoms are selected from the group consisting of B, O, N and S, wherein the nitrogen and sulfur atoms are optionally oxidized and the nitrogen heteroatoms are optionally quaternized. The heteroatoms B, O, N and S may be located at any internal position of the heterohydrocarbyl (including the position of the hydrocarbyl at which it is attached to the rest of the molecule). Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—(O)—$CH_3$, —$CH_2$—$CH_2$—, —S(O)—$CH_3$, —$CH_2$—$CH_2$—S (O)$_2$—$CH_3$, —CH=CH—O—$CH_3$, —$CH_2$—CH=N—$OCH_3$ and —CH=CH—N($CH_3$)—$CH_3$. Up to two heteroatoms may be consecutive, for example, —$CH_2$—NH—$OCH_3$.

The terms "alkoxy", "alkylamino" and "alkylthio" (or thioalkoxy) are the customary expressions and refer to those alkyl groups which are attached to the rest of the molecule through an oxygen atom, an amino group or a sulfur atom, respectively.

Unless otherwise specified, the terms "cyclohydrocarbyl", "heterocyclohydrocarbyl" or subordinate concept thereof (such as aryl, heteroaryl, cycloalkyl, heterocycloalkyl, cycloalkenyl, heterocycloalkenyl, cycloalkynyl, heterocycloalkynyl, etc.), as such or in combination with other terms, stand for cyclized "hydrocarbyl", "heterohydrocarbyl", respectively. In addition, as for heterohydrocarbyl or heterocyclohydrocarbyl (such as heteroalkyl, heterocycloalkyl), the heteroatom may occupy the position at which the heterocycle is attached to the rest of the molecule. Examples of cycloalkyl include, but are not limited to, cyclopentyl, cyclohexyl, 1-cyclohexenyl, 3-cyclohexenyl, cycloheptyl and the like. Non-limiting examples of heterocyclyl include 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuran indol-3-yl, tetrahydrothiophen-2-yl, tetrahydrothiophen-3-yl, 1-piperazinyl and 2-piperazinyl.

Unless otherwise specified, the term "aryl" means a polyunsaturated aromatic hydrocarbon substituent which may be mono-, di- or polysubstituted, may be monocyclic or polycyclic (preferably from 1 to 3 rings), and are fused together or covalently linked. The term "heteroaryl" refers to an aryl (or ring) containing one to four heteroatoms. In one illustrative example, the heteroatoms are selected from B, N, O and S, wherein the nitrogen and sulfur atoms are optionally oxidized and the nitrogen atoms are optionally quaternized. Heteroaryl can be attached to the rest of the molecule via heteroatoms. Non-limiting examples of aryl or heteroaryl include phenyl, 1-naphthyl, 2-naphthyl, 4-biphenyl, 1-pyrrolyl, 2-pyrrolyl, 3-pyrrolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. Any one of the above aryl and heteroaryl cyclic substituents is selected from acceptable substituents described below.

For the sake of simplicity, aryl when used in conjunction with other terms (e.g. aryloxy, arylthio, arylalkyl) includes aryl and heteroaryl rings as defined above. Thus, the term "aralkyl" is intended to include those radicals in which an aryl is attached to an alkyl (e.g. benzyl, phenethyl, pyridylmethyl and the like), including those alkyl groups in which a carbon atom (such as methylene) has been replaced by an atom such as an oxygen atom, for example, phenoxymethyl, 2-pyridyloxymethyl 3-(1-naphthyloxy)propyl and the like.

The term "leaving group" refers to a functional group or atom that can be substituted by another functional group or atom by a substitution reaction (e.g. an affinity substitution reaction). For example, representative leaving groups include triflates; chloro, bromo, iodo; sulfonate groups, such as mesylate, tosylate, brosylate, p-toluenesulfonate and the like; acyloxy groups, such as acetoxy, trifluoroacetoxy and the like.

The term "protecting group" includes, but is not limited to, "amino protecting group," "hydroxy protecting group," or "thiol protecting group". The term "amino protecting group" refers to a protecting group suitable for preventing side reactions on the amino nitrogen. Representative amino protecting groups include, but are not limited to, formyl; acyl such as alkanoyl (such as acetyl, trichloroacetyl or trifluoroacetyl); alkoxycarbonyl such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for preventing side reactions with hydroxyl groups. Representative hydroxyl protecting groups include, but are not limited to, alkyl, such as methyl, ethyl and t-butyl; acyl, such as alkanoyl (such as acetyl); arylmethyl, such as benzyl (Bn), p-methoxybenzyl (PMB), 9-fluorenylmethyl (Fm) and diphenylmethyl (benzhydryl, DPM); silyl, such as trimethylsilyl (TMS) and tert-butyldimethylsilyl (TBS) and the like.

The compounds of the present disclosure can be prepared by a variety of synthetic methods well known to those skilled in the art including the specific embodiments listed below, their combinations with other chemical synthesis methods, and the equivalent alternatives well known to those skilled in the art, preferred embodiments include, but are not limited to, embodiments of the present disclosure.

All solvents used in the present disclosure are commercially available and can be used without further purification. The reaction is generally carried out in an anhydrous solvent under an inert atmosphere of nitrogen. Proton NMR data was recorded on a Bruker Avance III 400 (400 MHz) spectrometer and the chemical shifts were reported as (ppm) of the tetramethylsilane at low field. Mass spectra was determined on an Agilent 1200 Series Plus 6110 (& 1956 A). The LC/MS or Shimadzu MS contains one DAD: SPD-M20 A (LC) and Shimadzu Micromass 2020 detector. The mass spectrometer is equipped with an electrospray ionization source (ESI) operating in positive or negative mode.

The following abbreviations are used herein: aq stands for aqueous; HATU stands for 2-(7-azobenzotriazole)-N,N,N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, an amine protecting group; BOC stands for t-butylcarbonyl, an amine protecting group; HOAc stands for acetic acid; NaCNBH$_3$ stands for sodium cyanoborohydride; r.t. stands for room temperature; O/N stands for overnight; THF stands for tetrahydrofuran; THP stands for tetrahydropyran; Novozyme 435 stands for Novozymes lipase; Boc$_2$O stands for di-tert-butyldicarbonate; TFA stands for trifluoroacetic acid; DIPEA stands for diisopropyl ethylamine; SOCl$_2$ stands for thionyl chloride; CS$_2$ stands for carbon disulfide; TsOH stands for p-toluenesulfonic acid; NFSI stands for N-fluoro-N-(phenylsulfonyl)benzenesulfonamide; NCS stands for 1-chloropyrrolidine-2,5-dione; n-Bu$_4$NF stands for tetrabutylammonium fluoride; iPrOH stands for 2-propanol; dppf stands for 1,1'-bis(diphenylphosphino)ferrocene; TBSCl stands for t-butyldimethylchlorosilane; NIS stands for N-iodosuccinimide; TBAF stands for tetrabutylammonium fluoride; MSCl stands for methanesulfonyl chloride; LDA stands for lithium diisopropylamide; TEA stands for triethylamine; DAST stands for diethylaminosulfur trifluoride; SFC stands for supercritical liquid chromatography; NBS stands for N-bromosuccinimide; TMSA stands for trimethylsilylacetylene; DMAP stands for 4-dimethylamino pyridine; DCE stands for 1,2-dichloroethane; MW stands for microwave reaction; AIBN stands for azobisisobutyronitrile; POT stands for tri-o-methyltriphenylphosphine; DTBPF stands for 1,1'-bis(di-tert-butylphosphino)ferrocene; mp stands for melting point.

Compounds are named manually or with ChemDraw® software, and commercial compounds are available under Supplier Directory Name.

Further areas of applicability will become apparent from the description provided herein. The description and specific examples in this summary are intended for purposes of illustration only and are not intended to limit the scope of the present disclosure.

DETAILED DESCRIPTION

The following examples further illustrate the present disclosure, but the present disclosure is not limited thereto.

Scheme A

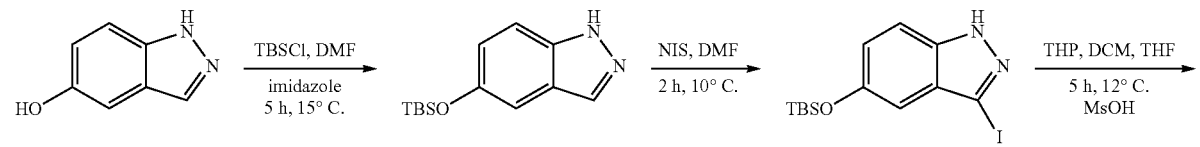

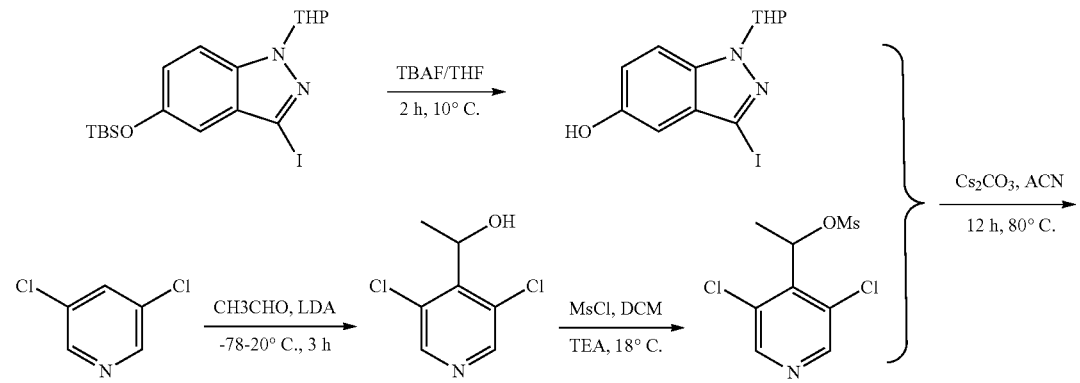

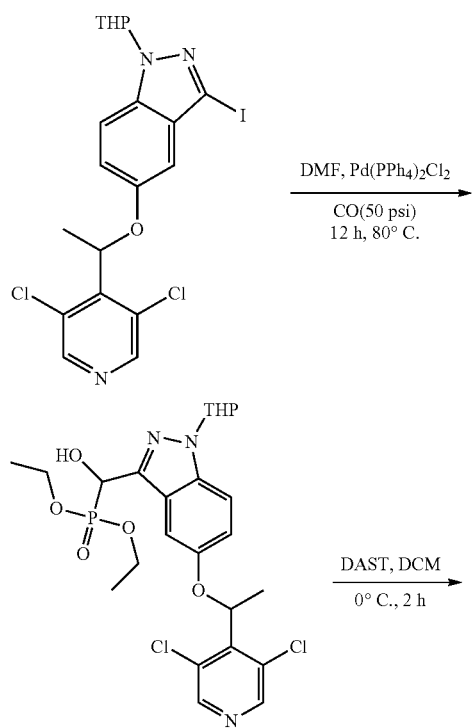
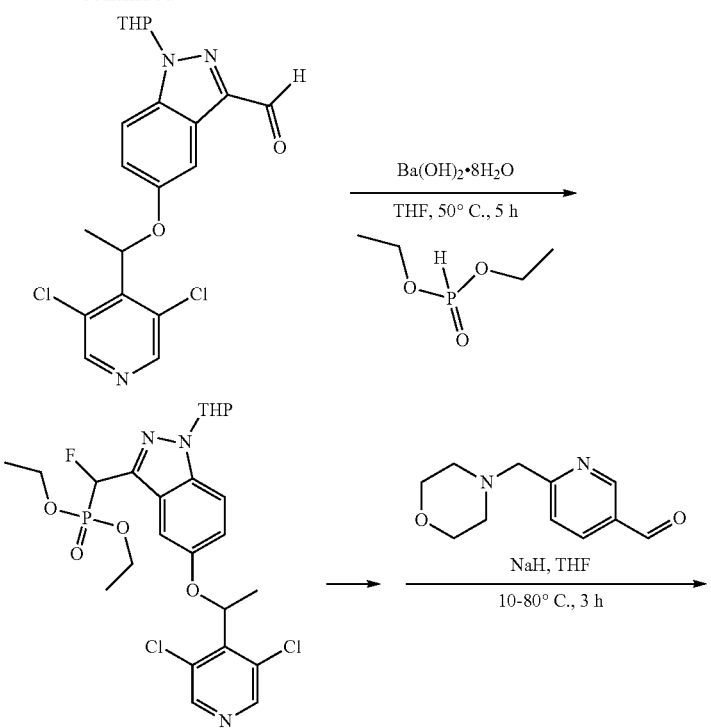
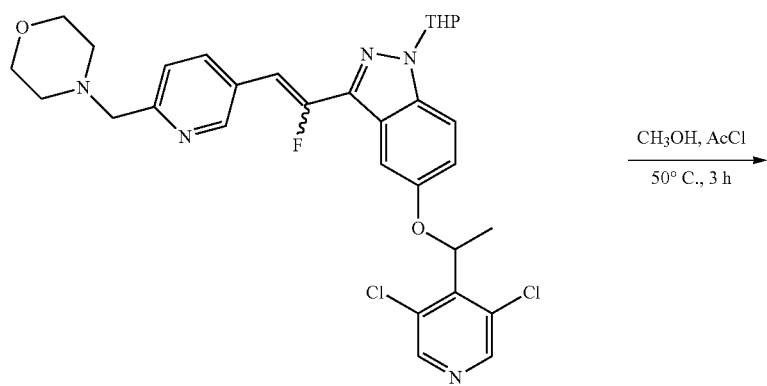
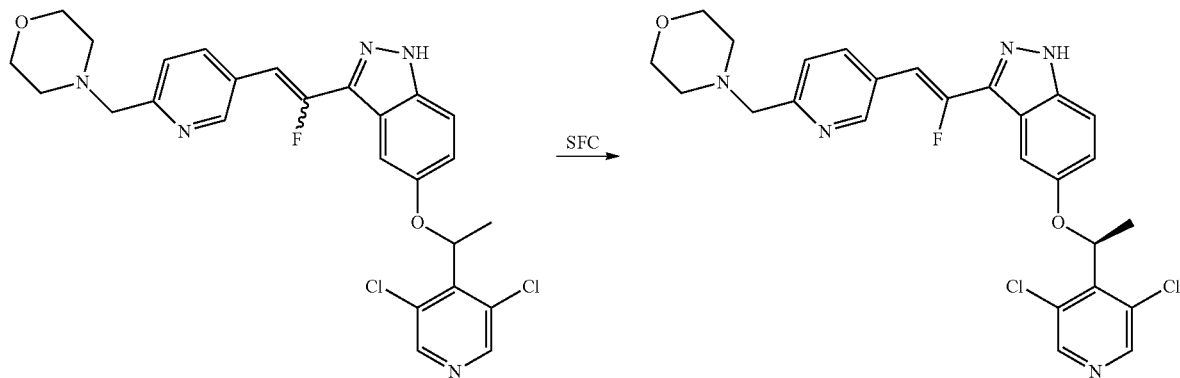

-continued

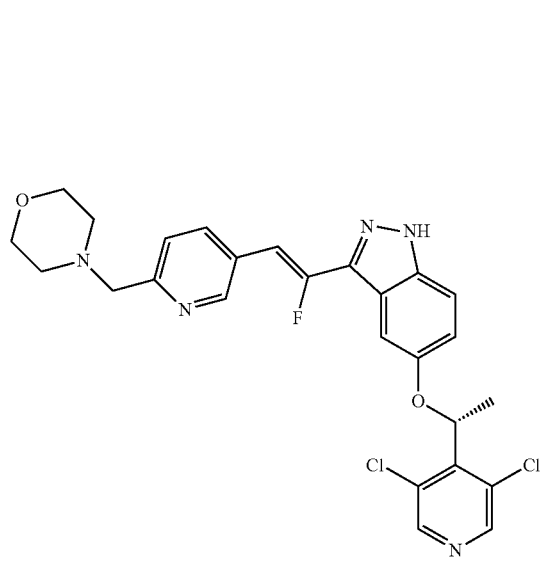

3

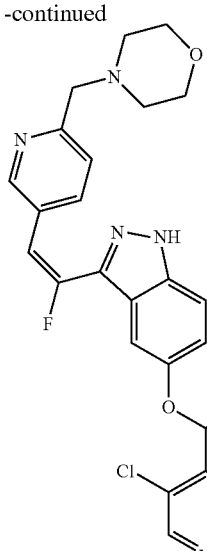

4

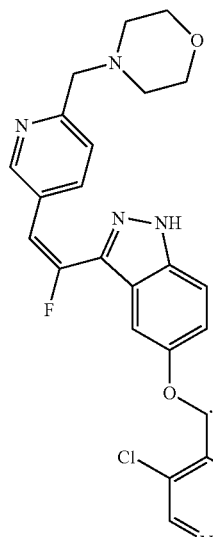

5

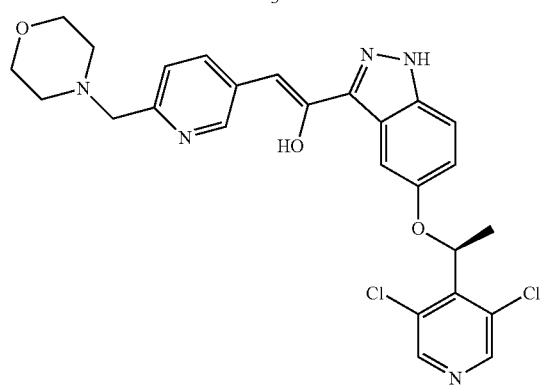

6

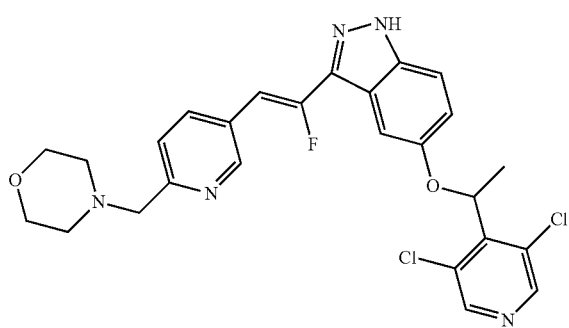 [SMILES: CC(Oc1ccc2[nH]nc(/C(F)=C/c3ccc(CN4CCOCC4)nc3)c2c1)c1c(Cl)cncc1Cl]

Example 1A

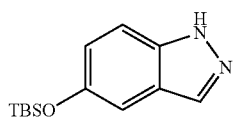

TBSCl (90 g, 0.6 mol) was added in batches to a solution of 1-hydro-indazole-5-hydroxy (54 g, 0.4 mol) and imidazole (40 g, 0.6 mol) in DMF (1 L) at room temperature. After the addition, the reaction solution was stirred at 15° C. for 5 hours. The final reaction solution was diluted with 3 L water, extracted with ethyl acetate (0.8 L×3), and the organic phases were combined, washed with water (0.8 L×3), dried over anhydrous sodium sulfate, filtered and evaporated. The residue was purified by flash silica gel column chromatography to give the title compound (90 g, yield 90%). LCMS (ESI) m/z: 249 [M+1]$^+$.

Example 1B

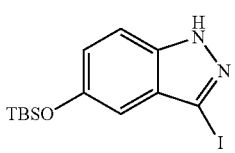 [SMILES: CC(C)(C)[Si](C)(C)Oc1ccc2[nH]nc(I)c2c1]

NIS (88 g, 0.4 mol) was added in batches to a solution of Example 1A (90 g, 0.36 mol) in dichloromethane (1.2 L) at 10° C. The reaction solution was stirred at 10° C. for 2 hours. The reaction was quenched with 10% sodium sulfite solution (plus volume) and the organic layer was washed with saturated brine (300 mL×2), the combined organic phases were dried over anhydrous sodium sulfate, filtered and evaporated. The residue was purified by flash silica gel column chromatography to give the title compound (125 g, yield 92%). LCMS (ESI) m/z: 375 [M+1]$^+$.

Example 1C

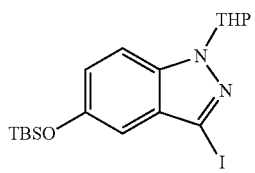

Example 1B was dissolved in a mixed solvent of dichloromethane (1 L) and tetrahydrofuran (0.4 L), then methanesulfonic acid (6.0 g, 60 mmol) was added and finally 3,4-tetrahydro-2-hydro-pyran (124.2 g, 0.92 mol) was added in batches to the reaction solution. After the addition, the mixture was stirred for 5 hours at 12° C. Upon completion of the reaction, the reaction solution was diluted with dichloromethane (500 mL) and washed with saturated sodium bicarbonate solution (300 mL). The organic layer was washed again with saturated brine and dried over anhydrous sodium sulfate, filtered and evaporated to dryness. The residue was purified by flash silica gel column chromatography to give the title compound (132 g, yield 93.6%). LCMS (ESI) m/z: 459 [M+1]$^+$.

Example 1D

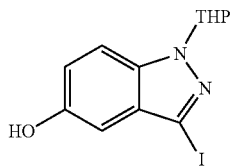

A solution of tetrabutylammonium fluoride in tetrahydrofuran (0.35 L, 0.35 mol, 1 mol/L) was added in one batch to a solution of Example 1C (132 g, 0.29 mol) in tetrahydrofuran (1.4 L) at 10° C. The mixed solution was stirred at 10° C. for 2 hours. The reaction mixture was poured into 1.5 L ice water and stirred for 20 minutes. The aqueous phase was extracted with ethyl acetate (400 mL×3) and the combined organic phase was washed with saturated brine (200 mL×2) and dried over anhydrous sodium sulfate, filtered and evaporated. The residue was purified by flash silica gel column chromatography to give the title compound (64 g, yield 65%). LCMS (ESI) m/z: 345 [M+1]$^+$.

Example 1E

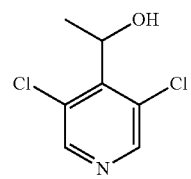

LDA (242 mL, 484 mmol, 2.0 mol/L) was added dropwise to a solution of 3,5-dichloropyridine (58.8 g, 404 mmol) in tetrahydrofuran (600 mL) under the protection of nitrogen at −78° C. After the addition, the reaction was further stirred for an hour under the atmosphere of nitrogen at −78° C. And then, anhydrous acetaldehyde (35.5 g, 808 mmol) was added to the reaction solution in batches. After the addition, the reaction solution was heated to room temperature 20° C. and stirred for another 2 hours. The reaction was quenched by the addition of saturated ammonium chloride (200 mL) and then extracted with ethyl acetate (400 mL×3). The organic phases were combined and dried over anhydrous sodium sulfate, filtered and the filtrate was concentrated to give a residue that was purified by flash silica gel column chromatography to give the title compound (51 g, yield 66%). $^1$H NMR (400 MHz, METHANOL-d$_4$) ppm: 8.43 (s, 2H), 5.53 (t, J=6 Hz, 1H), 3.12 (d, J=6 Hz, 1H), 1.64 (d, J=6.8 Hz, 3H).

Example 1F

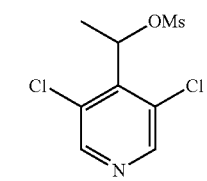

MsCl (32 g, 0.28 mol) was added in batches to a solution of a mixture of Example 1E (36 g, 0.91 mol) and triethylamine (21 g, 0.21 mol) in dichloromethane (1 L) at 0° C. The reaction was stirred at 0° C. for 3 hours and then quenched with water (100 mL) in an ice bath and stirred for 1 hour. After layering, the organic phase was washed with saturated sodium bicarbonate solution (200 mL×3) and brine (200 mL), then dried over anhydrous sodium sulfate, filtered and the filtrate was concentrated to give a residue that was purified by flash silica gel column chromatography to give the title compound (pale yellow, 50 g, yield 98%).

Example 1G

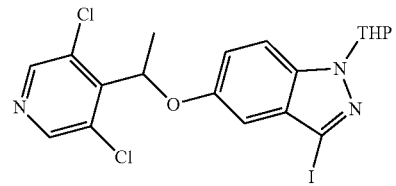

A mixture of Example 1D (35 g, 0.1 mol), Example 1F (33 g, 0.12 mol) and cesium carbonate (66 g, 0.2 mol) in acetonitrile (1.5 L) was reacted at 90° C. for 12 hours. After being cooled to the room temperature, the reaction mixture was filtered and the filtrate was evaporated to dryness to give the crude compound. The residue was purified by flash silica gel column chromatography to give the title compound (35 g, yield 85%). LCMS (ESI) m/z: 518 [M+1]$^+$. $^1$H NMR (400 MHz, METHANOL-d$_4$) ppm 8.44 (s, 2H), 7.46 (dd, J=2.8, 8.8 Hz, 1H), 7.17 (dd, J=2.4, 9.2 Hz, 1H), 6.71 (s, 1H), 6.08 (d, J=6.8 Hz, 1H), 5.6~45.59 (m, 1H), 4.0~13.97 (m, 1H), 3.73~3.69 (m, 1H), 2.48~2.47 (m, 1H), 2.13~2.11 (m, 2H), 1.83 (d, J=6.8 Hz, 3H), 1.75~1.64 (m, 3H).

Example 1H

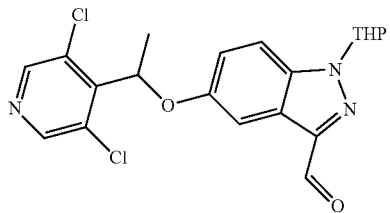

Pd(PPh$_3$)$_2$Cl$_2$ (1.36 g, 2 mmol) and sodium formate (6 g, 58 mmol) were added to a solution of Example 1G (10 g, 19.3 mmol) in DMF (300 mL) at room temperature under nitrogen. The hydrogen in the hydrogenation bottle was then replaced with carbon monoxide gas to fill the bottle with carbon monoxide gas. The reaction solution was stirred under carbon monoxide (50 psi) at 80° C. for 12 hours. The reaction solution was filtered and the filtrate was concentrated to give a residue. The residue was purified by flash silica gel column chromatography to give the title compound (7.2 g, yield 89%). LCMS (ESI) m/z: 420 [M+1]$^+$.

Example 1I

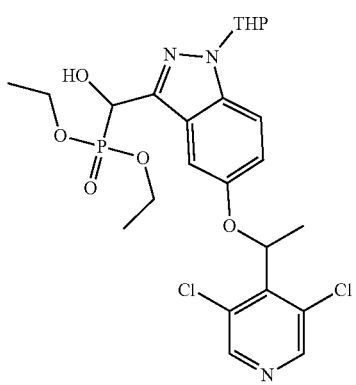

A solution of a mixture of Example 1H (7.2 g, 17.1 mmol), diethyl phosphite (5.4 mL, 51.4 mmol) and barium hydroxide octahydrate (2.7 g, 8.6 mmol) in tetrahydrofuran (130 mL) was heated to 50° C. and reacted for 5 hours. TLC test showed that the starting material disappeared and the reaction was complete. The reaction solution was filtered and the filtrate was concentrated to give a residue. The residue was purified by flash silica gel column chromatog-raphy to give the title compound (as a colorless oily liquid, 5.5 g, yield 58%). LCMS (ESI) m/z: 558 [M+1]$^+$.

Example 1J

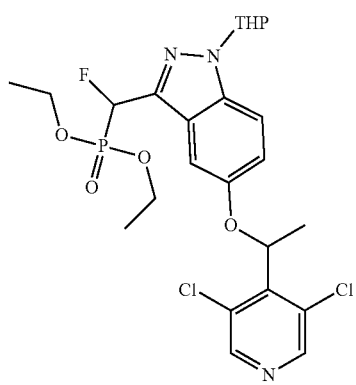

DAST (3.7 mL, 29.7 mmol) was slowly added dropwise to a solution of Example 1I (5.5 g, 9.9 mmol) in dichloroethane (100 mL) in an ice bath under the protection of nitrogen. After the addition, the reaction was stirred under nitrogen at 0° C. for 2 hours. TLC test showed that all the starting materials disappeared and a new main point was generated. The reaction solution was quenched with water (10 ml) in an ice bath, and then stirred for 10 minutes. After layering, the organic phase was washed successively with saturated sodium bicarbonate (20 mL×2) and brine (20 mL) and dried over anhydrous sodium sulphate and finally filtered and evaporated. The residue was purified by flash silica gel column chromatography to give the title compound (as a yellow oil, 2.7 g, yield 50%). LCMS (ESI) m/z: 560 [M+1]$^+$.

Example 1K

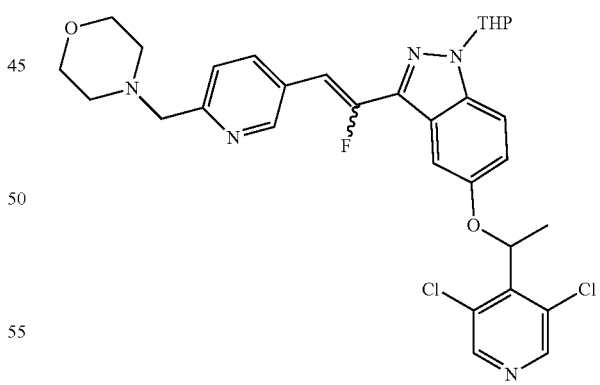

Sodium hydride (60% content) (0.63 g, 3.0 mmol) was added in batches to a solution of Example 1J (1.42 g, 2.5 mmol) in tetrahydrofuran (15 mL) at 10° C. under the protection of nitrogen. After the addition, the reaction solution was stirred at 10° C. for 30 minutes. 6-(Morpholinomethyl)-3-aldehyde pyridine (0.63 g, 3.0 mmol) was added to the stirred reaction solution, and the reaction solution was then heated to 80° C. and reacted for 3 hours. TLC showed the reaction was complete. After the reaction solution was cooled to room temperature, the reaction was quenched with water (2 ml), and stirred at room temperature for ten minutes, then extracted with ethyl acetate (10 ml×3). The organic phases are combined and washed with brine, dried over anhydrous sodium sulfate, filtered and evaporated to dryness. The residue was purified by flash silica gel column chromatography to give the title compound (as a yellow oil, 0.28 g mixture 1K (cis 1Ka and trans 1 Kb), yield 54%). LCMS (ESI) m/z: 612 [M+1]⁺.

Example 1L

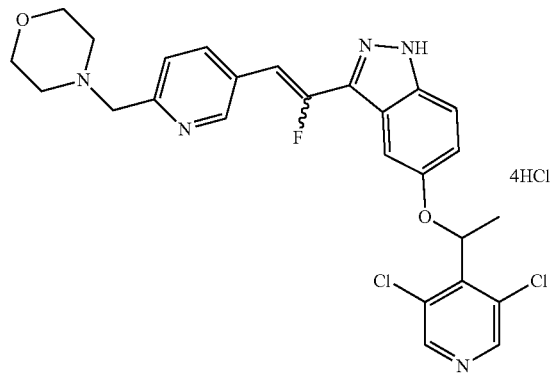 [SMILES: CC(Oc1ccc2[nH]nc(C(F)=Cc3ccc(CN4CCOCC4)nc3)c2c1)c1c(Cl)cncc1Cl]

Acetyl chloride (3 ml) was slowly added dropwise to methanol (12 ml) at 0° C. The reaction solution was then stirred at room temperature for 15 minutes. Example 1K (800 mg, 1.3 mmol) was added to the stirred reaction solution. The reaction solution was heated to 40° C. and stirred for 3 hours. LCMS showed the reaction was complete. The reaction solution was evaporated to dryness directly to give compound 1L (racemate) LCMS (ESI) m/z: 528. [M+1]⁺.

Example 2

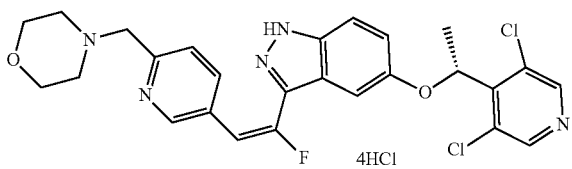 [SMILES: C[C@@H](Oc1ccc2[nH]nc(/C(F)=C\c3ccc(CN4CCOCC4)nc3)c2c1)c1c(Cl)cncc1Cl]

Example 1L was separated by SFC (with the following SFC separation conditions: Column: Chiralpak AD-3 50*4.6 mm I.D., 3 um Mobile phase: Ethanol (0.05% DEA)-CO₂ 5% to 40% Rate: 4 mL/min, Wavelength: 254 nm) to give Example 2, Example 3, Example 4, Example 5, and by-product Example 6.

Example 2: LCMS (ESI) m/z: 528.4[M+1]⁺. ¹H NMR (400 MHz, METHANOL-d₄) ppm 8.81 (s, 1H), 8.49 (s, 2H), 8.10 (d, 1H), 7.65-7.43 (m, 2H), 7.17 (d, J=7.3 Hz, 1H), 6.84 (m, 1H), 6.77-6.63 (m, 1H), 6.01 (m, 1H), 4.54 (s, 2H), 4.02-3.87 (m, 4H), 3.31 (m, 4H), 1.84 (d, 3H).

Example 3

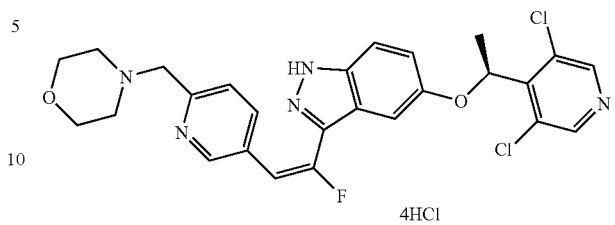

This example was prepared by the method as described in Example 2. LCMS (ESI) m/z: 528.4[M+1]⁺. ¹H NMR (400 MHz, DMSO-d₆) ppm 8.65 (s, 1H), 8.55 (s, 2H), 7.96 (d, J=8.0 Hz, 1H), 7.56 (d, J=9.0 Hz, 1H), 7.46 (d, J=8.3 Hz, 1H), 7.14 (dd, J=2.3, 9.0 Hz, 1H), 6.84 (s, 1H), 6.78 (s, 2H), 5.94 (q, J=6.4 Hz, 1H), 4.44 (s, 2H), 3.83 (m, 4H), 3.22 (m, 4H), 1.71 (d, J=6.5 Hz, 3H).

Example 4

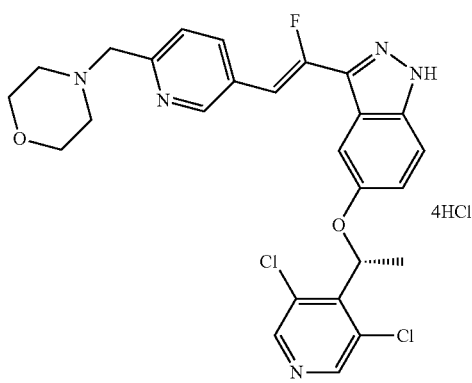 [SMILES: C[C@@H](Oc1ccc2[nH]nc(/C(F)=C/c3ccc(CN4CCOCC4)nc3)c2c1)c1c(Cl)cncc1Cl]

This example was prepared by the method as described in Example 2. LCMS (ESI) m/z: 528.4 [M+1]⁺.

¹H NMR (400 MHz, DMSO-d₆) ppm 8.94 (s, 1H), 8.60 (s, 2H), 8.21 (d, J=8.3 Hz, 1H), 7.71-7.52 (m, 2H), 7.23-7.12 (m, 2H), 6.80-6.65 (m, 1H), 6.14 (q, J=6.5 Hz, 1H), 4.54 (s, 2H), 3.88 (m, 4H), 3.31 (m, 4H), 1.77 (d, J=6.5 Hz, 3H).

Example 5

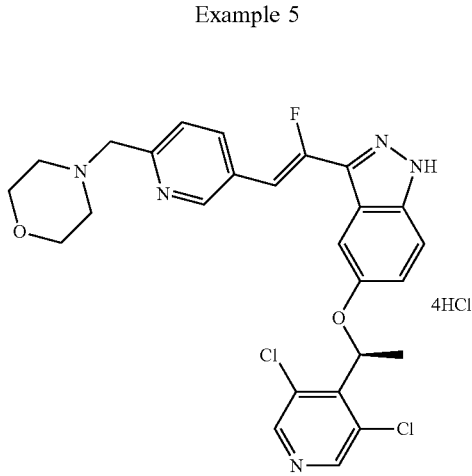

This example was prepared by the method as described in Example 2. LCMS (ESI) m/z: 528.4[M+1]+.

$^1$H NMR (400 MHz, METHANOL-$d_4$) ppm 8.98 (s, 1H), 8.52 (s, 2H), 8.36 (d, J=7.5 Hz, 1H), 7.78 (d, J=8.3 Hz, 1H), 7.51 (d, J=8.8 Hz, 1H), 7.26-7.14 (m, 2H), 6.74-6.60 (m, 1H), 6.18 (q, J=6.5 Hz, 1H), 4.63 (s, 2H), 3.99 (m, 4H), 3.46 (m, 4H), 1.83 (d, J=6.5 Hz, 3H).

Example 6

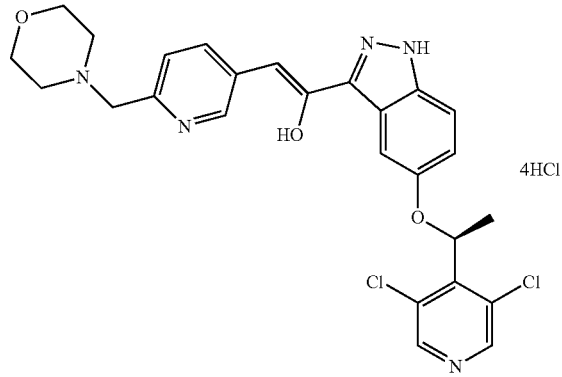 [SMILES: C[C@H](Oc1ccc2[nH]nc(/C(O)=C/c3ccc(CN4CCOCC4)nc3)c2c1)c1c(Cl)cncc1Cl]

4HCl

This example was prepared by the method as described in Example 2. LCMS (ESI) m/z: 526.4[M+1]+.

$^1$H NMR (400 MHz, METHANOL-$d_4$) ppm 8.92 (s, 1H), 8.49 (s, 2H), 8.41 (d, J=7.3 Hz, 1H), 8.11 (d, J=7.8 Hz, 1H), 7.55 (d, J=9.0 Hz, 1H), 7.43 (d, J=2.0 Hz, 1H), 7.19 (dd, J=2.0, 9.0 Hz, 1H), 6.10 (q, J=6.5 Hz, 1H), 4.74 (d, J=7.8 Hz, 4H), 3.99 (br. s., 4H), 3.47 (br. s., 4H), 1.79 (d, J=6.8 Hz, 3H).

Scheme B

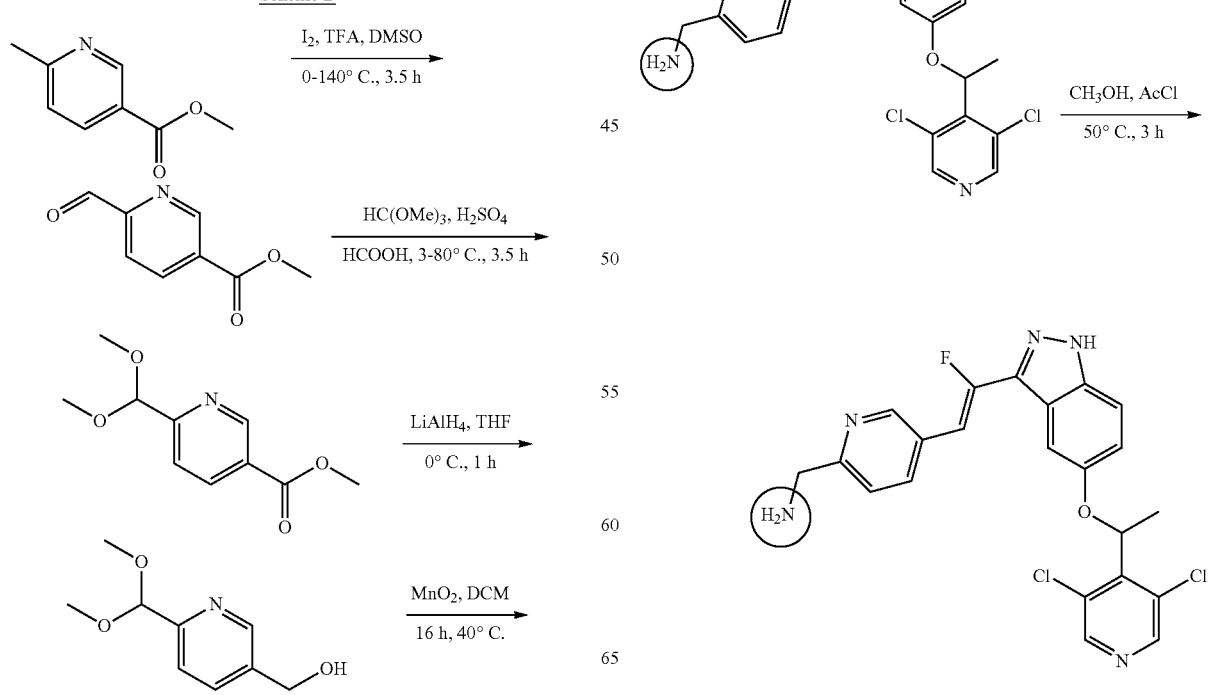

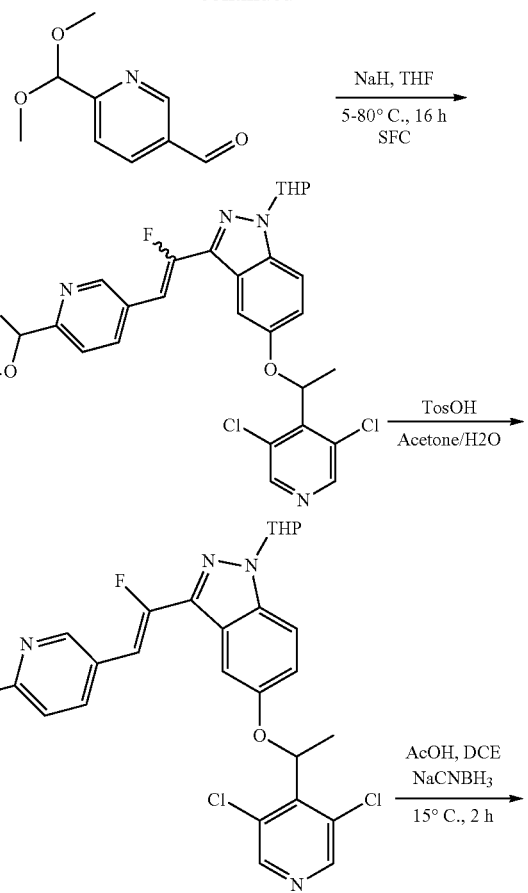

Example 7 (Reference Example)

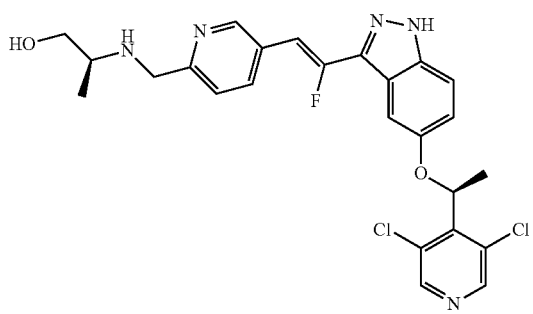

4HCl

Example 7A

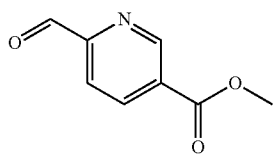

Iodine (33.5 g, 0.13 mmol) and trifluoroacetic acid (35.3 ml, 0.4 mmol) were added to a solution of methyl 6-carboxylate-1-picoline (20 g, 0.13 mol) in N,N-dimethylsulfoxide (200 ml) at 0° C. and the mixture was stirred for 1 hour and then heated to 140° C. and stirred for 2.5 hours. After being cooled to 0° C., the reaction was quenched with saturated sodium thiosulfate solution (30 ml) and stirred for 30 minutes. The aqueous layer was extracted with ethyl acetate (150 ml×3) and the organic layers were combined and washed with brine (50 ml×2), dried over anhydrous sodium sulfate, filtered, concentrated in vacuo and the residue was purified by flash silica gel column chromatography to give the title compound (8 g, yield 37%). $^1$H NMR (400 MHz, CHLOROFORM-d) ppm: 10.14 (s, 1H), 9.36 (s, 1H), 8.47 (dd, J=1.3, 8.0 Hz, 1H), 8.03 (d, J=8.0 Hz, 1H), 4.05-3.94 (s, 3H).

Example 7B

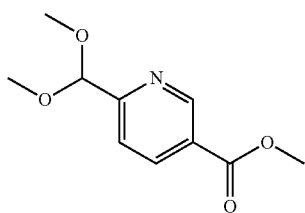

Formic acid (40 ml) was slowly added dropwise to a solution of Example 7A (20 g, 120 mmol) in trimethyl orthoformate (400 ml) at 0° C. and stirred at this temperature for 30 minutes before concentrated sulfuric acid (1.2 ml) was added dropwise. After the addition, the reaction solution was heated to 50° C. and stirred for 30 minutes and then cooled to 25° C. and stirred for another 3 hours. The mixture was cooled to room temperature and added to water (100 ml). The aqueous layer was extracted with ethyl acetate (200 ml×3). The organic phases were combined, washed with saturated brine (100 ml×2), dried over anhydrous sodium sulfate, filtered, and concentrated in vacuo to give the title compound as a brown oil (25 g, yield 98.8%) which was used directly in the next step.

Example 7C

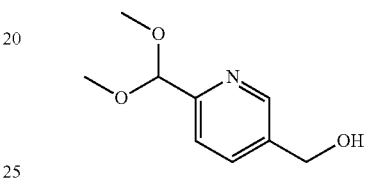

Lithium aluminum hydride (4.4 g, 114 mmol) was added in batches to a solution of Example 7B (8 g, 38 mmol) in tetrahydrofuran (120 mL) at 0° C. under the protection of nitrogen, after the addition, the reaction solution was stirred for 1 hour at this temperature. The reaction was quenched with water (4.4 mL), 15% sodium hydroxide (4.4 mL) followed by water (13.2 mL), stirred for 30 minutes, filtered and concentrated in vacuo to give the title compound as a yellow oil (5 g, yield 71%) which was used directly in the next step.

Example 7D

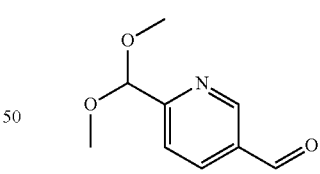

Manganese dioxide (19 g, 216 mmol) was added to a solution of Example 7C (5 g, 27 mmol) in dichloromethane (120 mL), and then the reaction solution was heated to 40° C. and stirred for 16 hours. After being cooled to room temperature, the mixture was filtered and concentrated in vacuo. The residue was purified by flash silica gel column chromatography to give the title compound (2.62 g, yield 52.4%) as a yellow oil. $^1$H NMR (400 MHz, CHLOROFORM-d) ppm 10.1 (s, 1H), 9.04-9.13 (m, 1H), 8.22 (dd, J=2.01, 8.03 Hz, 1H), 7.75 (d, J=8.03 Hz, 1H), 5.44 (s, 1H), 3.43 (s, 6H).

Example 7E

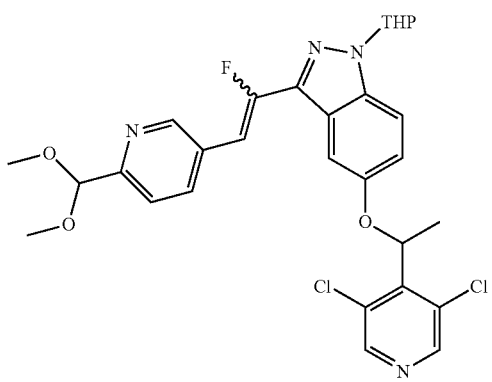

Sodium hydride (600 mg, 60%, 14.5 mmol) was added in batches to a solution of Example 7D (2.7 g, 5 mmol) in tetrahydrofuran (80 mL) at 5° C. under the protection of nitrogen. After the addition, the reaction solution was stirred for 30 minutes at this temperature and added with Example 1J (2 g, 10.6 mmol), followed by being heated to 70° C. and stirred for 16 hours. After being cooled to room temperature, the mixture was poured into ice water (50 ml). The aqueous layer was extracted with ethyl acetate (40 ml×3). The organic phases were combined, washed with saturated brine (20 ml×2), dried over anhydrous sodium sulfate, filtered and concentrated in vacuo. The residue was purified by column chromatography to give the title compound (1.35 g, yield 48%) as a colorless oil.

The mixture was resolved by chiral HPLC to give cis and trans isomers, chiral column: Chiralcel OD-3 150×4.6 mm ID, 3 um, mobile phase: ethanol (0.05% DEA) —CO$_2$, 5% to 40%, Flow rate: 2.5 mL/min, wavelength: 220 nm.

Example 7F

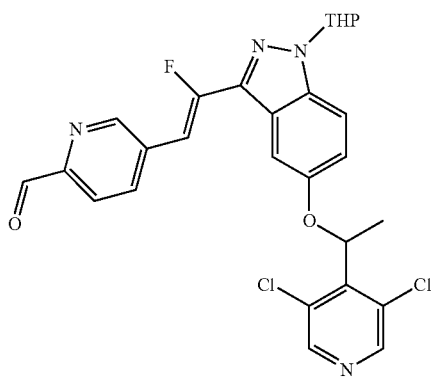

A mixed solution of Example 7E (0.2 g, 0.34 mmol) and p-benzenesulfonic acid monohydrate (12 mg, 0.068 mmol) in water (8 ml) and acetone (10 ml) was stirred at 50° C. for 3 hours. After cooling, the aqueous layer was extracted with dichloromethane (4 mL×3), and the organic layers were combined and washed with brine (4 mL×2), dried over anhydrous sodium sulfate, filtered and concentrated in vacuo to give the title compound (140 mg, yield 76%) which was used directly in the next step. LCMS (ESI) m/z: 541.4 [M+1]$^+$.

Example 7G

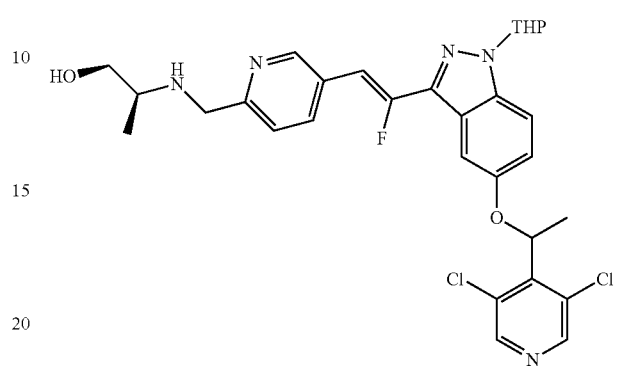

Acetic acid (9 mg, 147.77 mmol) was added dropwise to a mixed solution of Example 7F (70 mg, 130 μmol) and (S)—2-aminopropan-1-ol (29 mg, 390 μmol) in 1,2-dichloroethane (1 mL), and the mixture was stirred at 20° C. for 30 minutes after the addition. Sodium cyanoborohydride (24 mg, 390 μmol) was slowly added and the mixture was stirred for 2 hours at 20° C. The reaction was quenched with water (1 mL). The aqueous layer was extracted with dichloromethane (5 mL×3), and the organic layers were combined and washed with brine (3 mL×2), dried over anhydrous sodium sulfate, filtered and concentrated in vacuo. The residue was separated and purified by preparative HPLC (HCl) to give the title compound (3 mg, yield 3.32%). LCMS (ESI) m/z: 600.1 [M+1]$^+$. $^1$H NMR (400 MHz, METHANOL-d$_4$) ppm 8.94 (s, 1H), 8.49 (s, 2H), 8.36-8.30 (m, 1H), 7.69 (dd, J=8.8, 18.8 Hz, 2H), 7.25-7.15 (m, 2H), 6.78-6.64 (m, 1H), 6.17 (q, J=6.5 Hz, 1H), 5.86-5.76 (m, 1H), 4.59-4.45 (m, 2H), 4.03-3.88 (m, 2H), 3.85-3.75 (m, 1H), 3.69 (dd, J=6.0, 12.0 Hz, 1H), 3.56-3.47 (m, 1H), 2.56-2.40 (m, 1H), 2.18-2.08 (m, 1H), 2.02 (d, J=13.3 Hz, 1H), 1.83 (d, J=6.5 Hz, 3H), 1.73-1.62 (m, 2H), 1.42 (d, J=6.8 Hz, 3H).

Example 7H

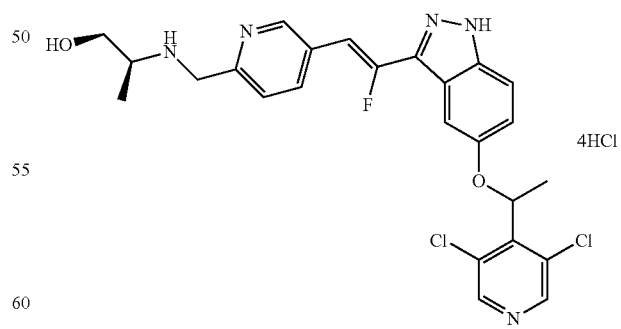

This example was prepared by the method as described in Example 1L. LCMS (ESI) m/z: 516.1 [M+1]$^+$. $^1$H NMR (400 MHz, DMSO-d$_6$) ppm 8.89 (br. s., 1H), 8.58 (s, 2H), 8.17 (d, J=8.53 Hz, 1H), 7.51-7.66 (m, 2H), 7.27 (s, 1H), 7.01 (s, 1H), 6.63-6.76 (m, 2H), 6.13 (d, J=6.78 Hz, 1H), 4.38 (br. s., 2H), 3.68 (d, J=15.81 Hz, 2H), 2.66 (br. s., 1H), 1.76 (d, J=6.53 Hz, 3H), 1.25 (d, J=6.53 Hz, 3H).

Example 9

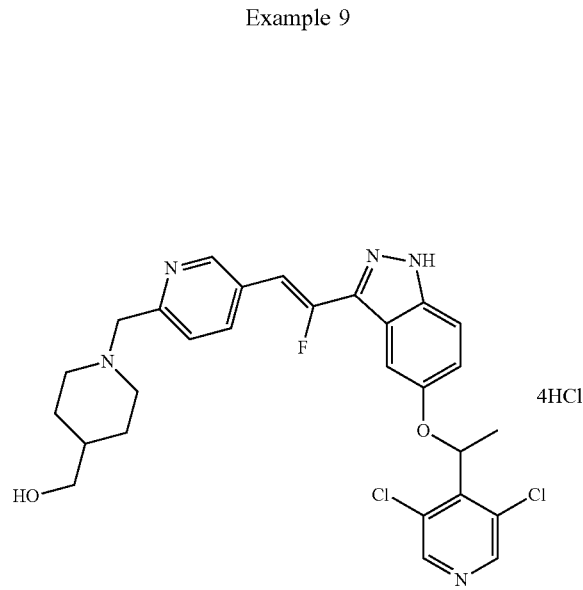

This example was prepared by the method as described in Example 7. LCMS (ESI) m/z: 556.1 [M+1]+. ¹H NMR (400 MHz, METHANOL-d₄) ppm 8.93 (s, 1H), 8.49 (s, 2H), 8.23 (d, J=6.27 Hz, 1H), 7.45-7.66 (m, 2H), 7.10-7.26 (m, 2H), 6.53-6.70 (m, 1H), 6.12-6.22 (m, 1H), 4.50 (br. s., 2H), 3.49 (br. s., 2H), 3.17 (br. s., 2H), 2.03 (d, J=12.80 Hz, 2H), 1.83 (d, J=6.53 Hz, 3H), 1.59 (br. s., 2H), 1.29 (s, 2H).

Example 10

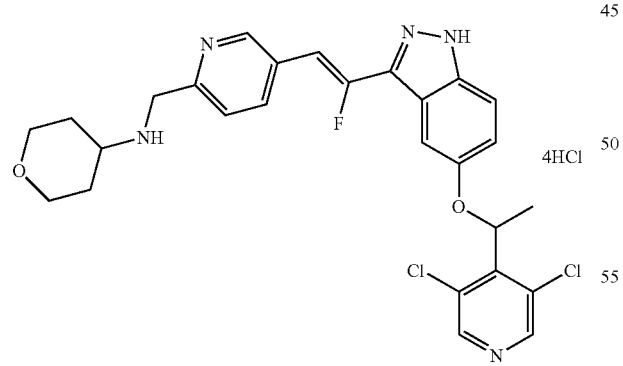

This example was prepared by the method as described in Example 7. LCMS (ESI) m/z: 542.1 [M+1]+. ¹H NMR (400 MHz, METHANOL-d₄) ppm 8.91 (s, 1H), 8.50 (s, 2H), 8.23 (d, J=8.28 Hz, 1H), 7.49-7.61 (m, 2H), 7.17-7.27 (m, 2H), 6.53-6.71 (m, 2H), 6.14-6.26 (m, 2H), 4.48 (s, 2H), 4.05-4.13 (m, 2H), 3.39-3.59 (m, 4H), 2.15 (d, J=12.05 Hz, 3H), 1.70-1.90 (m, 5H).

Example 11

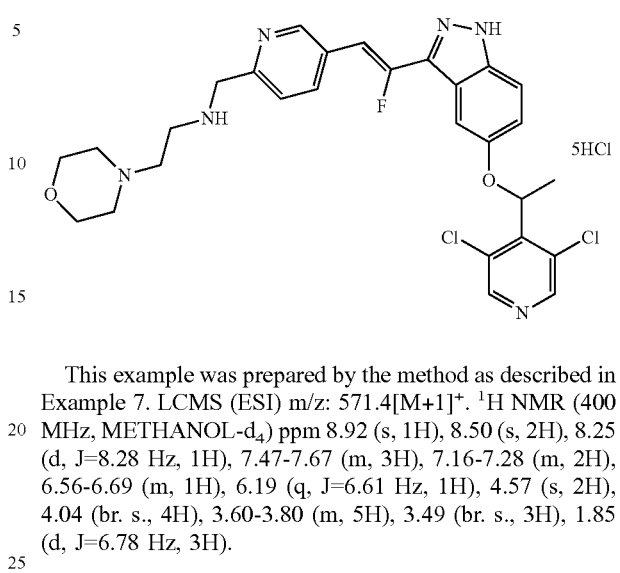

This example was prepared by the method as described in Example 7. LCMS (ESI) m/z: 571.4[M+1]+. ¹H NMR (400 MHz, METHANOL-d₄) ppm 8.92 (s, 1H), 8.50 (s, 2H), 8.25 (d, J=8.28 Hz, 1H), 7.47-7.67 (m, 3H), 7.16-7.28 (m, 2H), 6.56-6.69 (m, 1H), 6.19 (q, J=6.61 Hz, 1H), 4.57 (s, 2H), 4.04 (br. s., 4H), 3.60-3.80 (m, 5H), 3.49 (br. s., 3H), 1.85 (d, J=6.78 Hz, 3H).

Example 12

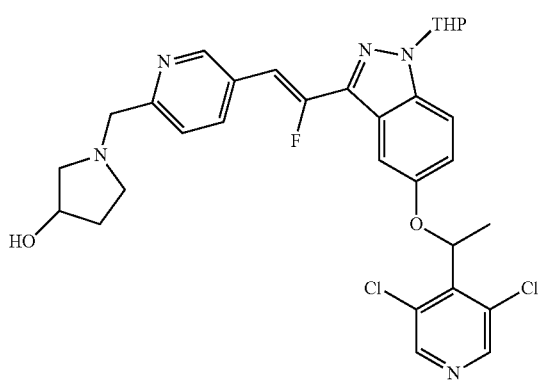

Example 12A

Acetic acid (8.87 mg, 147.77 mmol) was added dropwise to a mixed solution of Example 7F (50 mg, 90 μmol) and 3-hydroxypyrrole (23 mg, 270 μmol) in 1,2-dichloroethane (1 mL), and the mixture was stirred at 20° C. for 30 minutes after the addition. Sodium cyanoborohydride (17 mg, 270 µmol) was slowly added and stirred for 2 hours at 20° C. The reaction was quenched with water. The aqueous layer was extracted with dichloromethane (5 mL×3), and the organic layers were combined and washed with brine (3 mL×2), dried over anhydrous sodium sulfate, filtered and the filtrate was concentrated in vacuo. The residue was purified by flash silica gel column chromatography to give the title compound (29 mg, yield 53%). LCMS (ESI) m/z: 612.5 [M+1]$^+$.

Example 12 B

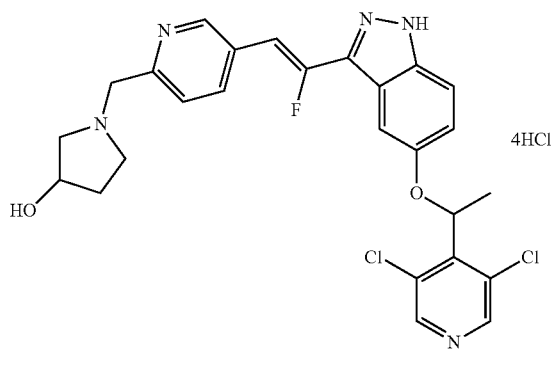 [SMILES: CC(Oc1ccc2[nH]nc(/C(F)=C/c3ccc(CN4CCC(O)C4)nc3)c2c1)c1c(Cl)cncc1Cl]

This example was prepared by the method as described in Example 7. LCMS (ESI) m/z: 528.1 [M+1]$^+$. $^1$H NMR (400 MHz, METHANOL-d$_4$) ppm 8.95 (br. s., 1H), 8.52 (br. s., 2H), 8.33 (br. s., 1H), 7.73 (d, J=4.77 Hz, 1H), 7.50 (d, J=9.03 Hz, 1H), 7.13-7.24 (m, 2H), 6.58-6.73 (m, 1H), 6.18 (d, J=6.53 Hz, 1H), 4.60-4.73 (m, 4H), 3.35 (s, 2H), 1.83 (d, J=6.27 Hz, 4H), 1.28 (s, 1H).

Scheme C

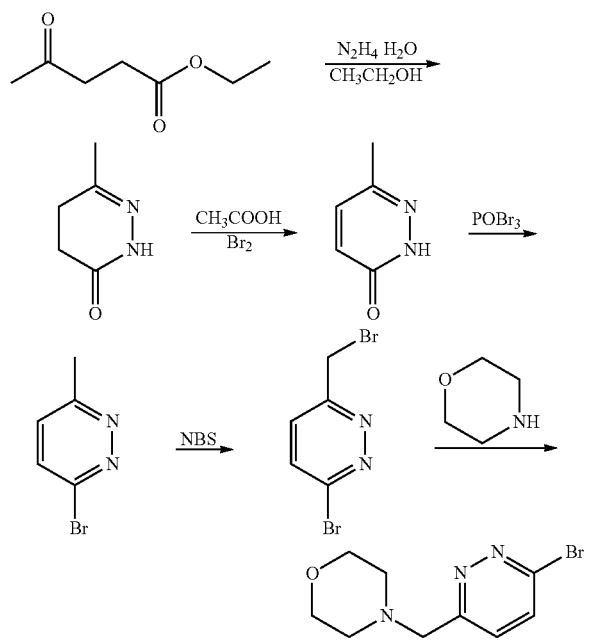

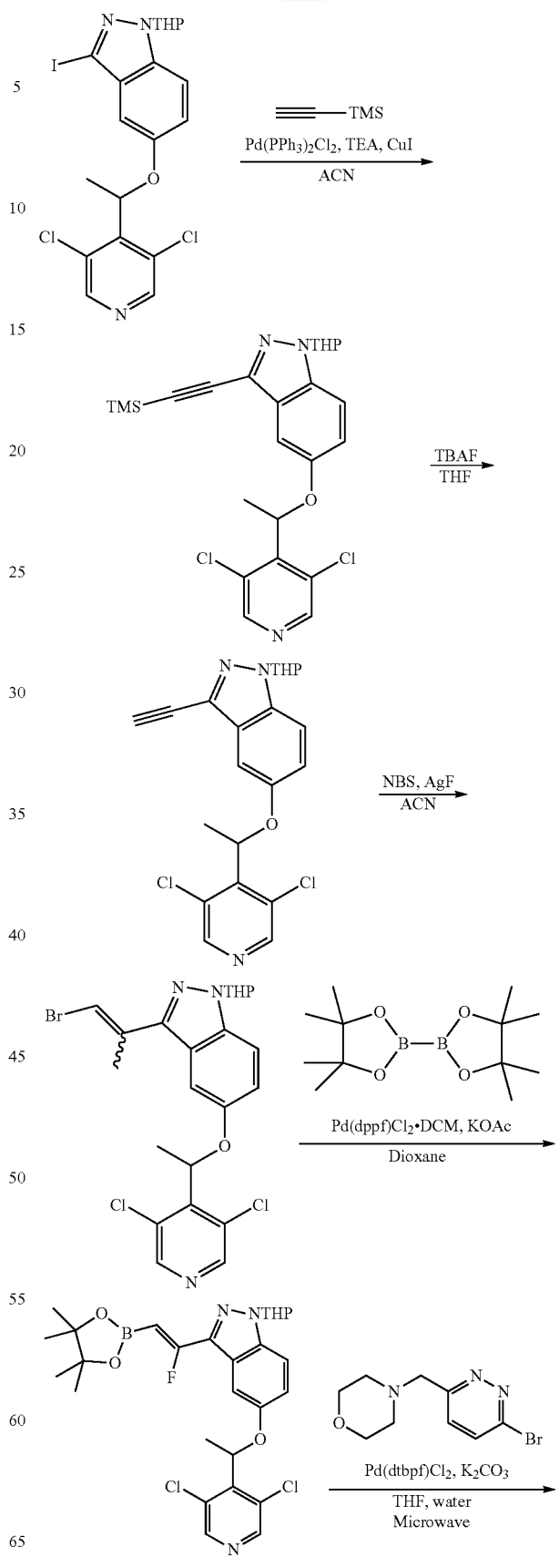

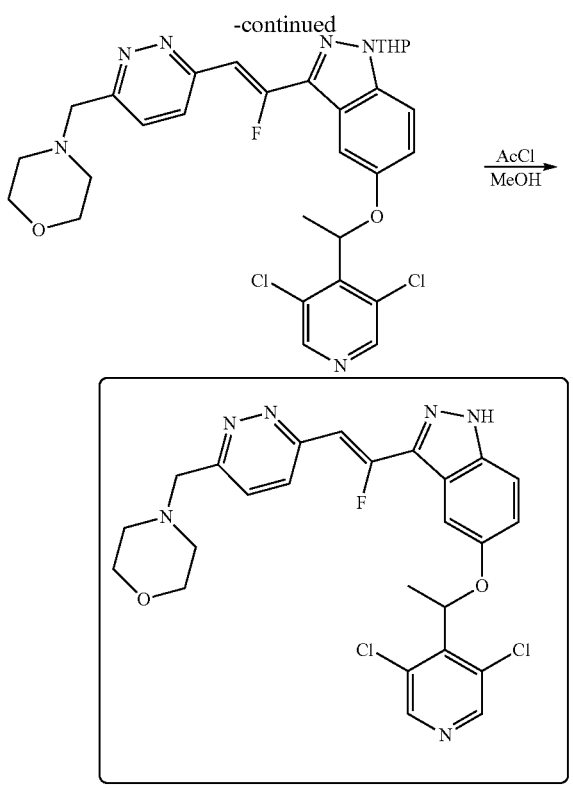

Example 13

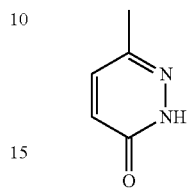

Example 13A

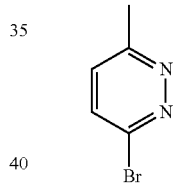

Ethyl levulinate (30 g, 208 mmol) was dissolved in ethanol (100 mL), hydrazine hydrate (15.63 g, 312 mmol, 85%) was slowly added dropwise thereto and the mixture was refluxed at 80° C. for 2 hours. After the mixture was cooled to room temperature, the target compound was precipitated from the reaction solution as 6-methyl-4,5-dihydropyridazin-3(2-hydro)-one (23 g, yield 98%) which was used directly in the next step without purification.

Example 13B

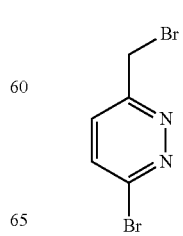

Example 13A (23 g, 205.4 mmol) was dissolved in acetic acid (100 mL) and liquid bromine (55.03 g, 348.5 mmol) was added dropwise to the above solution under vigorous stirring. The temperature during the dropwise addition did not exceed 40° C. After the addition, the mixture was reacted at 80° C. for half an hour, cooled to room temperature, filtered and the filter cake was rinsed twice with methyl tert-butyl ether to give the title compound (20 g, yield 87%) which was used directly in the next step without further purification. LCMS (ESI) m/z: 133[M+1]$^+$. $^1$HNMR (CHLOROFORM-d, Bruker Avance 400 MHz): ppm 7.36-7.39 (m, 1H), 6.69-6.89 (m, 1H), 2.22 (s, 3H).

Example 13C

A mixture of Example 13B (18 g, 163.44 mmol) and phosphorus oxybromide (93.8 g, 327.6 mmol) was stirred at 70° C. overnight. The mixture was cooled to 40° C., poured into ice-water, quenched with saturated sodium bicarbonate (20 mL) and extracted with dichloromethane (100 mL×3). The organic layers were combined, dried over anhydrous sodium sulfate, filtered and evaporated to give the title compound, 3-bromo-6-methylpyridazine (8 g, yield 31%). LCMS (ESI) m/z: 173[M+1]$^+$. $^1$H NMR (CHLOROFORM-d, Bruker Avance 400 MHz): ppm 7.86-7.88 (d, 1H, J=8 Hz), 7.52-7.54 (d, 1H, J=8 Hz), 2.55 (s, 3H).

Example 13D

Example 13C (8.0 g, 48.0 mmol) and NBS (9.44 g, 48.0 mmol) were dissolved in carbon tetrachloride (200 mL) and AIBN (1.58 g, 9.6 mmol) was added and the mixture was reacted at 80° C. for 12 hours. The mixture was filtered and concentrated. The residue was purified by flash silica gel column chromatography to give the target compound 3-bromo-6-(bromomethyl)pyridazine (2.2 g, yield 19%). LCMS (ESI) m/z: 332[M+1]$^+$. $^1$H NMR (400 MHz, CHLOROFORM-d) ppm 7.69 (d, J=8.53 Hz, 1H), 7.56 (d, J=9.04 Hz, 1H).

Example 13 E

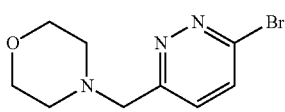 [SMILES: Brc1ccc(CN2CCOCC2)nn1]

Example 13D (2.0 g, 8.0 mmol) was dissolved in DMF (15 mL) and morpholine (1.4 g, 16 mmol) and K$_2$CO$_3$ (2.2 g, 16 mmol) were added to the solution, the mixture was reacted at 20° C. for 12 hours. The mixture was added with water (5 mL) and extracted with dichloromethane. The organic phase was concentrated and the residue was purified by flash silica gel column chromatography to give the title compound (1.46 g, yield 72%). LCMS (ESI) m/z: 258[M+1]$^+$. $^1$H NMR (400 MHz, CHLOROFORM-d) ppm 8.19 (d, J=8.53 Hz, 1H), 7.86 (d, J=8.53 Hz, 1H), 4.00 (s, 2H), 3.71-3.78 (m, 4H), 2.53-2.60 (m, 4H).

Example 13F

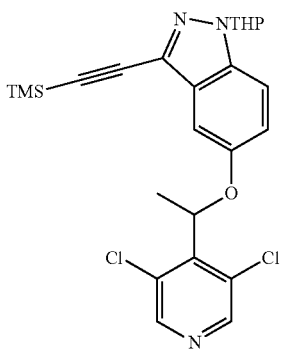

Example 1G (1 g, 1.93 mmol), Pd(PPh$_3$)$_2$Cl$_2$ (136 mg, 0.19 mmol), trimethylsilyl acetylene (227 mg, 2.32 mmol), cuprous iodide (368 mg, 0.19 mmol) and triethylamine (586 mg, 5.79 mmol) were suspended in acetonitrile (14 mL). The reaction was stirred at 80° C. for 18 hours. After cooled to room temperature, the reaction solution was filtered and the solvent was concentrated under reduced pressure to give the title compound (as a yellow liquid, 0.8 g, crude). $^1$H NMR (400 MHz, CHLOROFORM-d) ppm 8.42 (s, 1H), 7.48 (d, J=9.03 Hz, 1H), 7.12 (dd, J=2.51, 9.03 Hz, 1H), 6.91 (d, J=2.01 Hz, 1H), 6.04 (d, J=6.53 Hz, 1H), 5.58-5.68 (m, 1H), 3.95 (br. s., 1H), 3.63-3.74 (m, 1H), 2.47 (d, J=9.54 Hz, 1H), 2.11 (br. s., 1H), 2.00 (br. s., 1H), 1.81 (d, J=6.53 Hz, 3H), 1.58-1.75 (m, 3H), 0.30 (s, 9H).

Example 13G

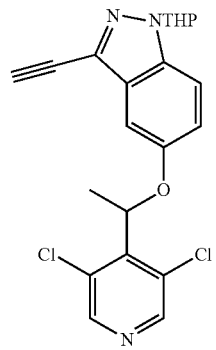

A solution of tetrabutylammonium fluoride (8.6 mL, 8.6 mmol, 1 mol/L) in tetrahydrofuran was added dropwise to a solution of Example 13F (2.8 g, 5.73 mmol) in tetrahydrofuran (30 mL). The reaction solution was stirred at 15° C. for 3 hours, followed by adding with brine (50 mL), and extracted with ethyl acetate (40 mL×3). The layers were separated and the organic phases were combined, dried over anhydrous sodium sulfate, filtered, and the solvent was evaporated to dryness under reduced pressure. The residue was purified by flash silica gel column chromatography (petroleum ether/ethyl acetate=20/1 to 10/1) to give the title compound (as a colorless oily liquid, 1 g, yield 42%). $^1$H NMR (400 MHz, CHLOROFORM-d) ppm 8.42 (s, 2H), 7.50 (dd, J=3.01, 9.03 Hz, 1H), 7.13 (dd, J=2.26, 9.29 Hz, 1H), 7.01 (d, J=2.01 Hz, 1H), 6.06 (q, J=6.69 Hz, 1H), 5.64 (ddd, J=3.01, 6.15, 8.91 Hz, 1H), 3.92-4.00 (m, 1H), 3.64-3.74 (m, 1H), 3.35 (s, 1H), 2.49 (dd, J=1.76, 8.78 Hz, 1H), 1.97-2.20 (m, 2H), 1.61-1.86 (m, 6H).

Example 13H

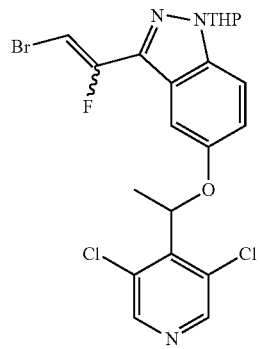

Example 13G (1 g, 2.4 mmol), silver fluoride (762 mg, 6 mmol) and NBS (470 mg, 2.64 mmol) were added to a mixed solution of acetonitrile (10 mL) and water (1 mL) in a sealing tube. The reaction was stirred at 80-90° C. for 18 hours. The progress of the reaction was monitored by TLC. After being cooled to room temperature, the reaction solution was added with brine (10 mL) and extracted with ethyl acetate (20 mL×3). The organic phase was dried over anhydrous sodium sulfate, filtered, and the solvent was evaporated to dryness in vacuo. The residue was purified by flash silica gel column chromatography (petroleum ether/ ethyl acetate=20/1 to 10/1) to give the title compound (cis-trans mixture, as a colorless oil, 200 mg, yield 16%). ¹H NMR (400 MHz, CHLOROFORM-0 ppm 8.45 (s, 2H), 7.47-7.55 (m, 1H), 7.12-7.20 (m, 1H), 7.10 (s, 1H), 6.30-6.46 (m, 1H), 6.01-6.12 (m, 1H), 5.60-5.70 (m, 1H), 3.95-4.06 (m, 1H), 3.66-3.79 (m, 1H), 2.42-2.55 (m, 1H), 2.09-2.21 (m, 1H), 1.95-2.05 (m, 1H), 1.83 (d, J=6.78 Hz, 3H), 1.62-1.79 (m, 3H).

Example 13I

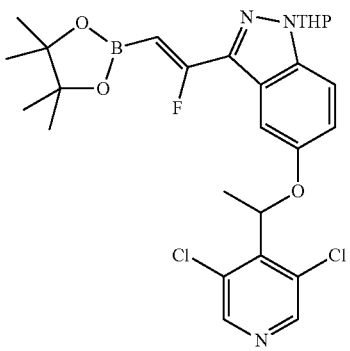

Example 13H (30 mg, 58 μmol), bispinacolatoboronate (16 mg, 64 μmol), Pd(dppf)Cl₂CH₂Cl₂ (5 mg, 6 μmol) and potassium acetate (12 mg, 120 μmol) were suspended in dioxane (1.5 mL). Under the atmosphere of nitrogen, the reaction solution was stirred at 100° C. for 18 hours. The progress of the reaction was monitored by TLC. After the reaction solution was cooled to room temperature, the solvent was removed under reduced pressure and the residue was purified by flash silica gel column chromatography (petroleum ether/ethyl acetate=10/1) to give the title compound (as a colorless oil, 10 mg, yield 30%). LCMS (ESI) m/z: 562.1 [M+1]⁺.

Example 13J

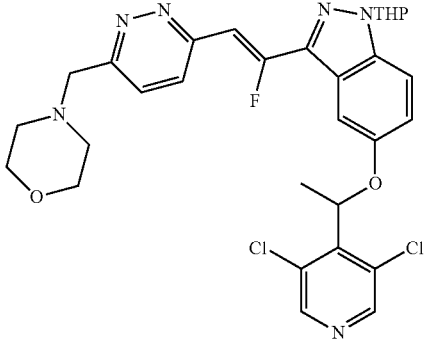

Example 13I (10 mg, 18 μmol), Example 13E (9 mg, 36 μmol), Pd(DTBPF)Cl₂ (2 mg, 3.6 μmol) and potassium carbonate (5 mg, 36 μmol) were suspended in a mixed solvent of tetrahydrofuran (1 mL) and water (0.2 mL), and reacted at 105° C. for 15 minutes under microwave conditions. After cooled to room temperature, the reaction solution was separated by preparative plate (petroleum ether/ ethyl acetate=10/1) to give the title compound (as a colorless oil, 5 mg, yield 46%). LCMS (ESI) m/z: 613.2[M+1]⁺.

Example 13K

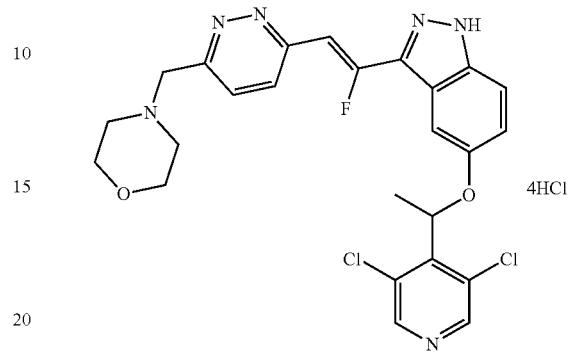

Example 13J (5 mg, 8 μmol) was dissolved in dry methanol (1 mL). The solution was then added dropwise to freshly prepared solution of acetyl chloride (0.5 mL) in dry methanol (2 mL). The reaction solution was stirred at 40° C. for 3 hours. Upon the completion of the reaction, the solvent was evaporated to give the title compound (4 mg, yield 91%). LCMS (ESI) m/z: 541.1 [M+1]⁺.

Scheme D

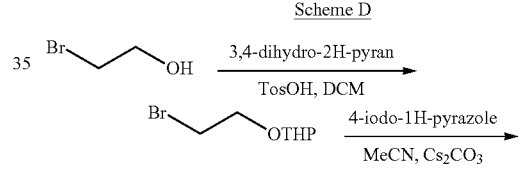

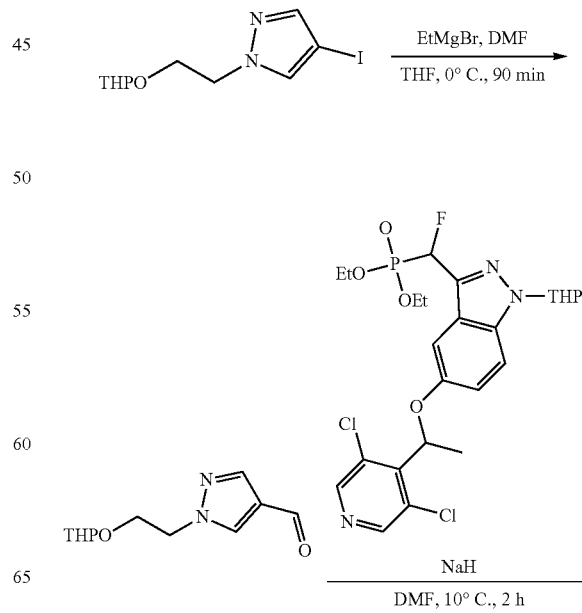

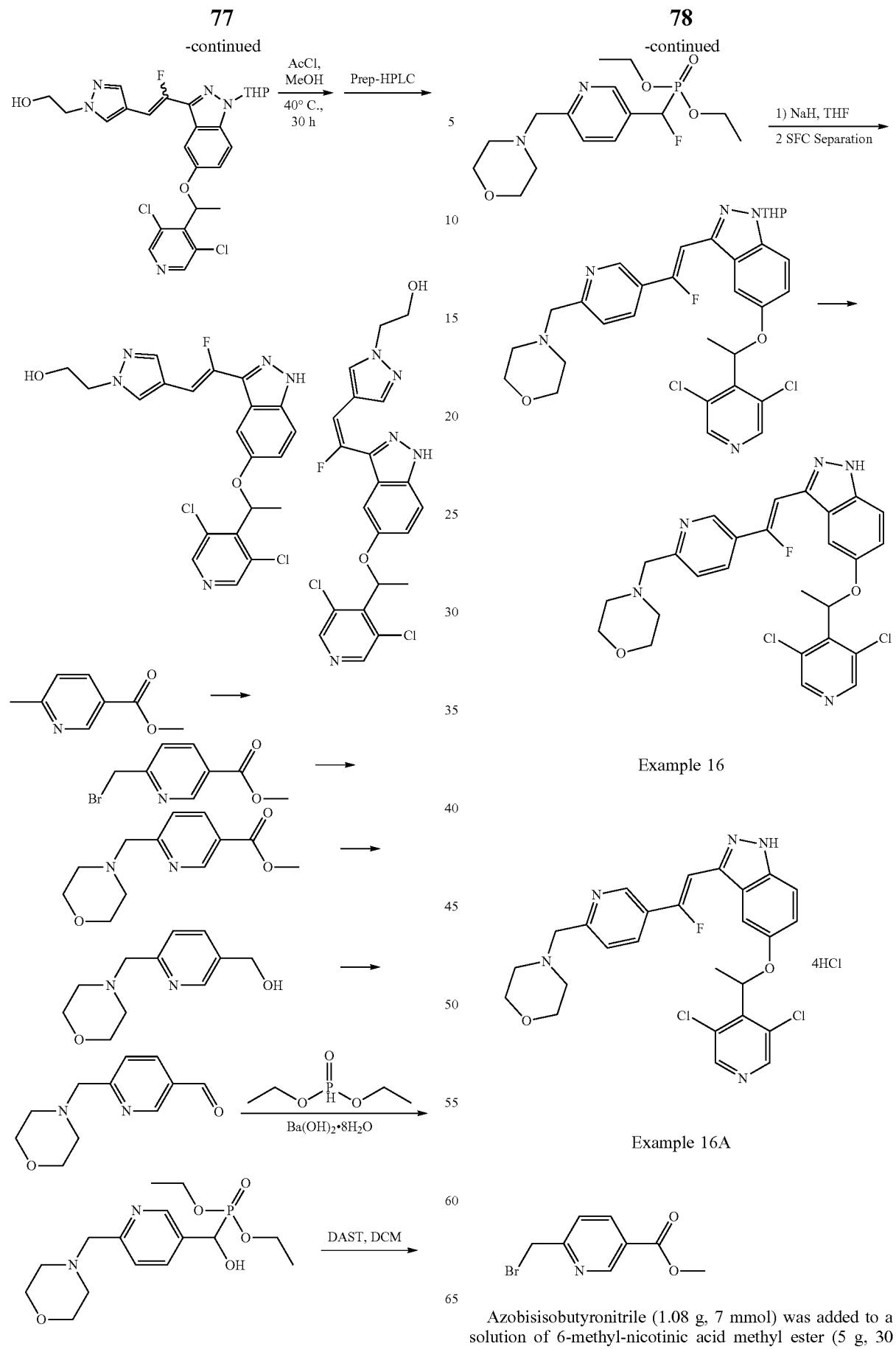
Example 16
Example 16A
Azobisisobutyronitrile (1.08 g, 7 mmol) was added to a solution of 6-methyl-nicotinic acid methyl ester (5 g, 30 mmol) and bromosuccinimide (6.48 g, 30 mmol) in carbon tetrachloride (40 mL) at room temperature under nitrogen. The reaction solution was heated to 80° C., stirred for 12 hours, and filtered while hot. The filtrate was evaporated to dryness and the residue was purified by flash silica gel column chromatography to give the title compound (1.6 g, yield 21%). ¹H NMR (400 MHz, CHLOROFORM-d) ppm 9.16 (d, J=1.00 Hz, 1H), 8.29 (dd, J=1.76, 8.03 Hz, 1H), 7.53 (d, J=8.03 Hz, 1H), 4.58 (s, 2H), 3.95 (s, 3H).

Example 16B

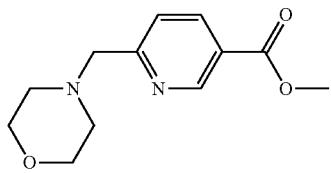 [SMILES: COC(=O)c1ccc(CN2CCOCC2)nc1]

Potassium carbonate (1.16 g, 8.4 mmol) was added in one batch to a solution of Example 16A (1.6 g, 7 mmol) in DMF (12 mL) at room temperature under nitrogen, and stirred overnight. The reaction solution was poured into ice-water (20 mL) and extracted with ethyl acetate (40 mL×3). The organic phases were combined and washed with brine (50 mL), dried over sodium sulfate, filtered and concentrated. The residue was purified by flash silica gel column chromatography to give the title compound (1 g, yield 60%). ¹H NMR (400 MHz, CHLOROFORM-d) ppm 9.15 (d, J=1.51 Hz, 1H), 8.26 (dd, J=2.01, 8.03 Hz, 1H), 7.53 (d, J=8.28 Hz, 1H), 3.94 (s, 3H), 3.68-3.78 (m, 6H), 2.46-2.55 (m, 4H).

Example 16C

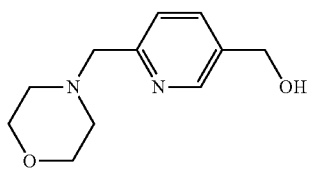 [SMILES: OCc1ccc(CN2CCOCC2)nc1]

Lithium aluminum hydride (1.08 g, 28.4 mmol) was added in batches to a solution of Example 16B (6.7 g, 28.4 mmol) in tetrahydrofuran (85 mL) at 0° C. under atmosphere of nitrogen, and stirred for 2 hours. The reaction solution was slowly added successively with water (1 mL), sodium hydroxide (1 mL, 15%) and water (3 mL), stirred for 20 minutes and filtered. The filtrate was concentrated under reduced pressure to give the title compound (48 g, yield 70%). ¹H NMR (400 MHz, CHLOROFORM-d) ppm 8.45 (s, 1H), 7.68 (dd, J=1.51, 8.03 Hz, 1H), 7.38 (d, J=8.03 Hz, 1H), 4.67 (s, 2H), 3.67-3.72 (m, 4H), 3.61 (s, 2H), 2.41-2.52 (m, 4H).

Example 16D

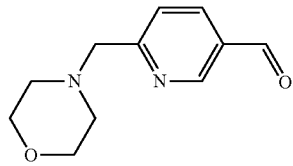

Active manganese dioxide (39 g, 449 mmol) was added in batches to a solution of Example 16C (4.06 g, 19.5 mmol) in dichloromethane (70 mL) at room temperature, and the reaction solution was heated to reflux for 16 hours. Upon the completion of the reaction, the reaction solution was filtered and the filtrate was evaporated to dryness. The residue was purified by flash silica gel column chromatography to give the title compound (1.2 g, yield 30%). ¹H NMR (400 MHz, CHLOROFORM-d) ppm 10.10 (s, 1H), 9.02 (d, J=1.00 Hz, 1H), 8.15 (dd, J=2.01, 8.03 Hz, 1H), 7.65 (d, J=8.03 Hz, 1H), 3.73-3.79 (m, 6H), 2.49-2.58 (m, 4H).

Example 16E

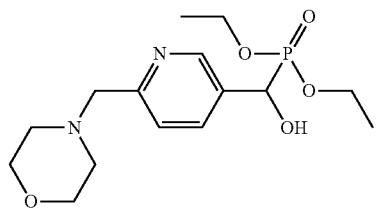 [SMILES: CCOP(=O)(OCC)C(O)c1ccc(CN2CCOCC2)nc1]

Barium hydroxide octahydrate (229 mg, 0.728 mmol) was added in one batch to a solution of Example 16D (300 mg, 1.45 mmol) and diethyl phosphite (603 mg, 4.36 mmol) in tetrahydrofuran (5 mL) at room temperature and the reaction solution was heated to 45° C. and stirred for 4 hours. Upon the completion of the reaction, the reaction solution was added with water (20 ml) and extracted with ethyl acetate (40 ml×3). The organic phases were combined and washed with brine (50 ml), dried over sodium sulfate, filtered and concentrated. The residue was purified by flash silica gel column chromatography to give the title compound (120 mg, yield 24%) as a yellow liquid. LCMS (ESI) m/z: 345.1 [M+1]⁺.

Example 16F

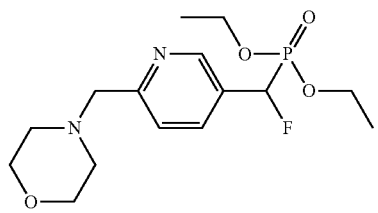 [SMILES: CCOP(=O)(OCC)C(F)c1ccc(CN2CCOCC2)nc1]

Diethylaminosulfur trifluoride (168 mg, 1.04 mmol) was slowly dropwise added to a solution of Example 16E (120 mg, 0.35 mmol) in dichloromethane (5 mL) at 0° C. After the addition, the reaction solution was stirred at 0° C. for 1 hour. Upon the completion of the reaction, the reaction solution was washed with saturated sodium bicarbonate (5 mL) and brine (5 mL), dried over sodium sulfate, filtered and concentrated. The residue was purified by flash silica gel column chromatography to give the title compound (60 mg, yield 50%) as a colorless liquid. LCMS (ESI) m/z: 347.1 [M+1]$^+$.

Example 16G

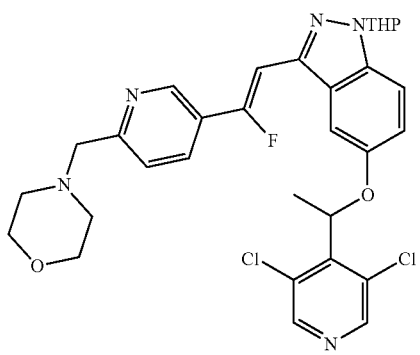

Under the protection of nitrogen and at room temperature, sodium hydride (139 mg, 60% in mineral oil, 3.46 mmol) was added in batches to a solution of Example 16F (400 mg, 1.15 mmol) in tetrahydrofuran (10 mL) and stirred for 10 minutes, and then 5-(1-(3,5-dichloropyridin-4-)ethoxy)-1-(tetrahydro-2-hydro-pyran-2-)-1H-indazol-3-carbaldehyde (485 mg, 1.15 mmol) 1H was added to above reaction solution and the mixture was stirred for 10 minutes. The reaction solution was then heated to 80° C. and stirred for 3 hours. Upon the completion of the reaction, the reaction solution was cooled to room temperature, quenched with water (10 mL) and extracted with ethyl acetate (40 mL×3). The organic phases were combined and washed with brine (50 mL), dried over sodium sulfate, filtered and concentrated. The residue was purified by flash silica gel column chromatography and then resolved by chiral HPLC to give the title compound (formula Z) (250 mg, yield 35%) and the isomer (formula E) (200 mg, yield 28%) as a yellow liquid. LCMS (ESI) m/z: 612 [M+1]$^+$.

Example 16H

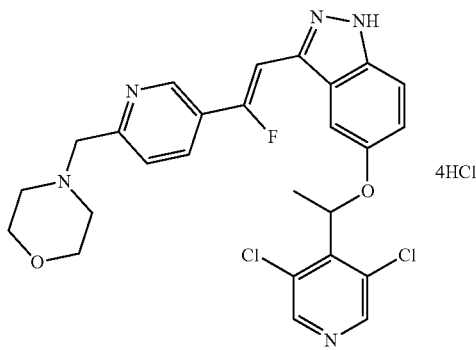 [SMILES: CC(Oc1ccc2[nH]nc(/C=C(\F)c3ccc(CN4CCOCC4)nc3)c2c1)c1c(Cl)cncc1Cl]

A freshly prepared solution of acetyl chloride (1 mL) in methanol (3 mL) was added to a solution of Example 16G (80 mg, 1.3 mmol) in methanol (1 mL) at room temperature under nitrogen. The reaction solution was stirred at 40° C. for 3 hours. The solution was removed in vacuo to give the title compound (33 mg, yield 52%). $^1$H NMR (400 MHz, METHANOL-d$_4$) ppm 9.08 (s, 1H), 8.52 (br. s., 1H), 8.26 (d, J=7.03 Hz, 1H), 7.66 (d, J=8.03 Hz, 1H), 7.48 (d, J=9.79 Hz, 1H), 7.23 (br. s., 2H), 6.92-7.08 (m, 1H), 6.12 (d, J=6.78 Hz, 1H), 4.63 (s, 2H), 4.00 (br. s., 4H), 3.47 (br. s., 4H), 1.83 (d, J=6.53 Hz, 3H).

Scheme E

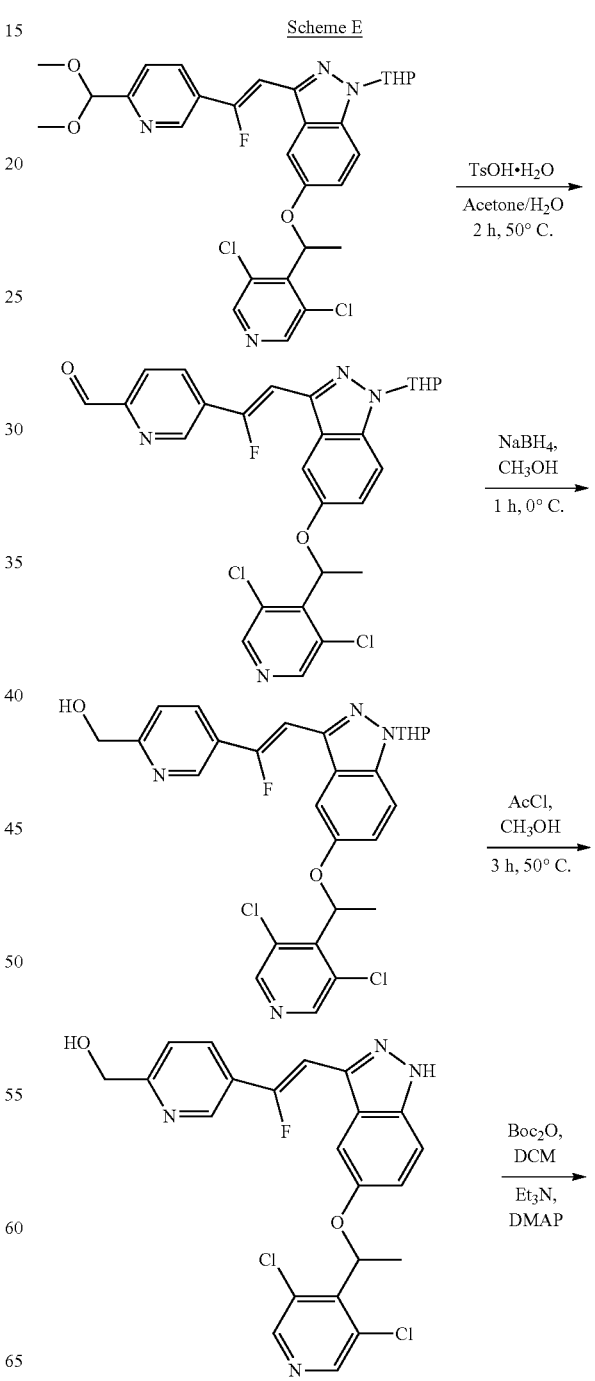

83

-continued

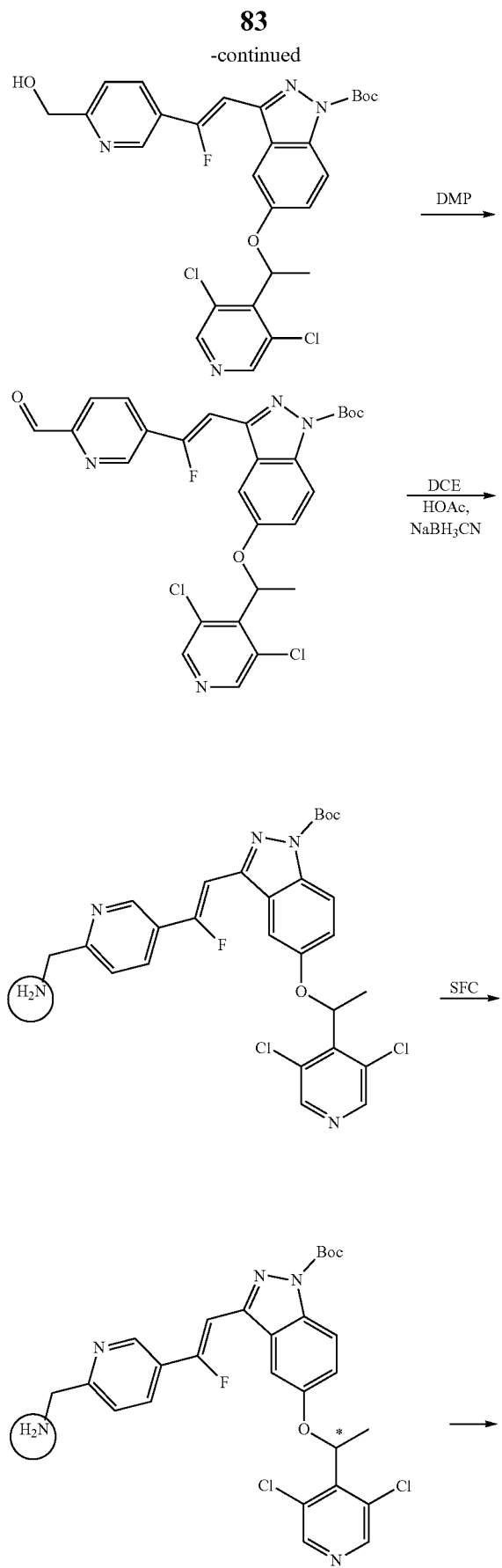

84

-continued

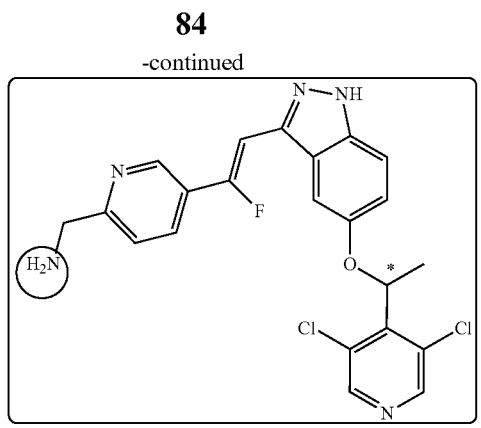

Example 17

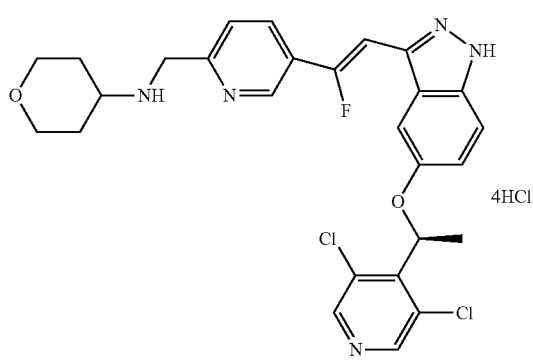 [SMILES: C[C@H](Oc1ccc2[nH]nc(/C=C(\F)c3ccc(CNC4CCOCC4)nc3)c2c1)c1c(Cl)cncc1Cl]

4HCl

Example 17A

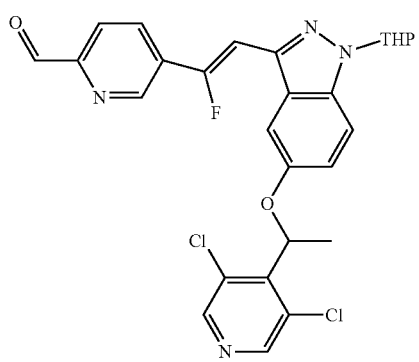

P-toluenesulfonic acid monohydrate (291 mg, 1.53 mmol) was added to a mixed solution of Example 7E (900 mg, 1.53 mmol) in acetone (4 mL) and water (4 mL) at room temperature and the reaction solution was heated to 50° C. and stirred for 10 hours. Upon the completion of the reaction, the reaction solution was added with water (4 mL) and extracted with dichloromethane (30 mL×3). The organic phases were combined, washed with saturated brine (20 mL) and dried over sodium sulfate, filtered and evaporated to give the title compound (850 mg, yield 92%). LCMS (ESI) m/z: 541 [M+1]+.

Example 17B

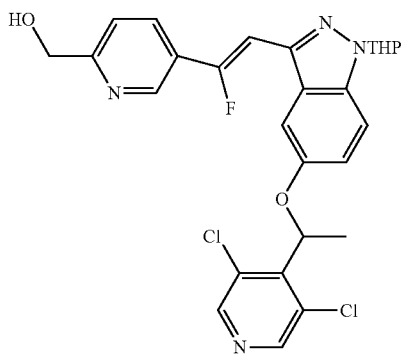

Sodium borohydride (119 mg, 3.14 mmol) was added in batches to a solution of Example 17A (850 mg, 1.57 mmol) in methanol (8 mL) and stirred for 1 hour at room temperature under nitrogen. The mixture was quenched with water (30 mL), extracted with ethyl acetate (40 mL×3) and the organic phases were combined, washed with brine (20 mL) and dried over sodium sulfate, filtered and the filtrate was evaporated to give the title compound (900 mg, crude) as a yellow liquid. LCMS (ESI) m/z: 543 [M+1]$^+$.

Example 17C

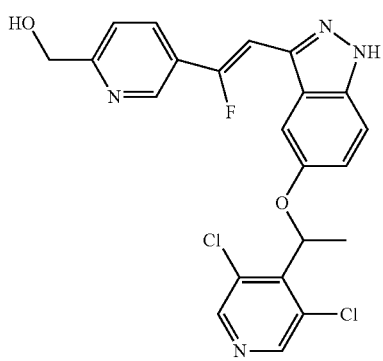 [SMILES: CC(Oc1ccc2[nH]nc(/C=C(\F)c3ccc(CO)nc3)c2c1)c1c(Cl)cncc1Cl]

A freshly prepared solution of acetyl chloride (2 mL) in methanol (6 mL) was added to a solution of Example 17B (900 mg, crude) in methanol (2 mL) at room temperature under nitrogen. The reaction solution was stirred at 40° C. and stirred for 3 hours. The solution was removed in vacuo to give the title compound (850 mg, crude). LCMS (ESI) m/z: 459 [M+1]$^+$.

Example 17D

Triethylamine (495 mg, 4.89 mmol), di-tert-butyl dicarbonate (356 mg, 1.63 mmol), DMAP (20 mg, 0.16 mmol) were added to a solution of Example 17C (748 mg, 1.63 mmol) in dichloromethane (12 mL) at room temperature under nitrogen, and the reaction solution was stirred at room temperature for 30 minutes. Upon the completion of the reaction, the reaction solution was adjusted to about pH 7 with 1M hydrochloric acid, extracted with dichloromethane (20 mL×3), the organic phases were combined and washed with brine (20 mL), dried over sodium sulfate, filtered and evaporated. The residue was purified by flash silica gel column chromatography to give the title compound (280 mg, yield 30.7%). LCMS (ESI) m/z: 559 [M+1]$^+$.

Example 17E

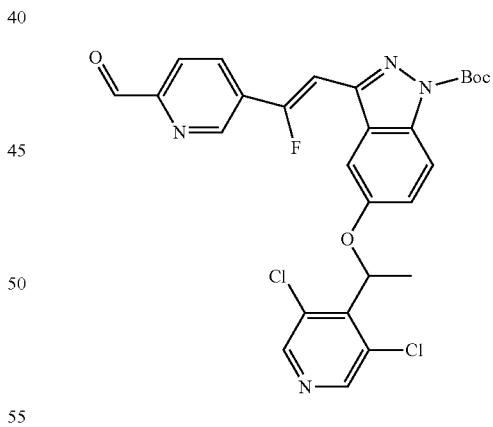

Dess-Martin reagent (318 mg, 0.75 mmol) was added in batches to a solution of Example 17D (280 mg, 0.5 mmol) in dichloromethane (6 mL) at room temperature, and the reaction solution was stirred at room temperature for 2 hours. Upon the completion of the reaction, the reaction solution was cooled in an ice-water bath, filtered and the filtrate was evaporated to give the title compound (230 mg, yield 82.4%). LCMS (ESI) m/z: 557 [M+1]$^+$.

Example 17F

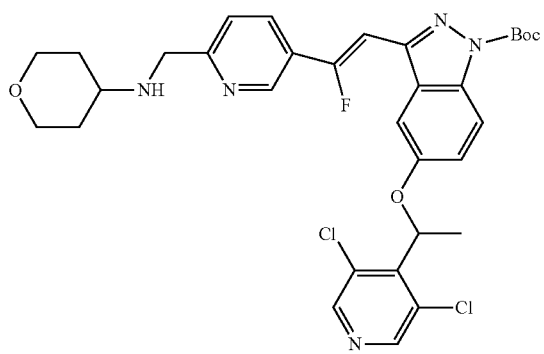 [SMILES: CC(Oc1ccc2c(c1)c(/C=C(\F)c1ccc(CNC3CCOCC3)nc1)nn2C(=O)OC(C)(C)C)c1c(Cl)cncc1Cl]

A solution of Example 17E (50 mg, 90 μmol), tetrahydro-2H-pyran-4-amine (18 mg, 180 μmol) in 1,2-dichloroethane (2.5 mL) was added with acetic acid (about 0.1 mL) to adjust pH to about 5 and the mixture was stirred for 2 hours at room temperature. Sodium cyanoborohydride (12 mg, 180 μmol) was added to the reaction solution at room temperature and stirred for 1 hour. The reaction solution was added with water (5 mL) and extracted with dichloromethane (20 mL×3). The organic phases were combined and washed with brine (20 mL), dried over sodium sulfate, filtered and evaporated. The residue was purified by flash silica gel column chromatography to give the title compound (20 mg, yield 34.7%). The sample was used for chiral column resolution to give Example 17F-R configuration (8 mg), Example 17F-S configuration (8 mg).

LCMS (ESI) m/z: 642 [M+1]$^+$.

Chiral column method: chiral column, Chiralcel OJ-H 250×4.6 mm I.D., Sum; mobile phase, methanol (0.05% DEA)-CO$_2$ 5%-40%; Flow rate, 2.35 mL/min; Wavelength, 280 nm.

Example 17G

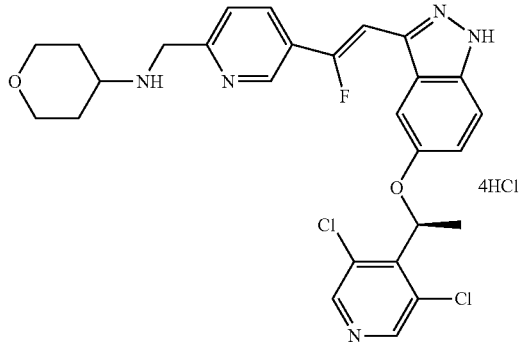 [SMILES: C[C@H](Oc1ccc2[nH]nc(/C=C(\F)c3ccc(CNC4CCOCC4)nc3)c2c1)c1c(Cl)cncc1Cl]

A freshly prepared solution of acetyl chloride (1 mL) in methanol (3 mL) was added to a solution of Example 17F-S configuration (15 mg, 23 μmol) (prepared according to the method of Example 17F, scaling up to 200 mg to give 15 mg of the 17F-S configuration product) in methanol 1 ml at room temperature under nitrogen atmosphere. The reaction was stirred at 40° C. for 3 hours. The solution was removed in vacuo to give the title compound (33 mg, yield 52%). LCMS (ESI) m/z: 542 [M+1]$^+$. $^1$H NMR (400 MHz, METHANOL-d$_4$) ppm 9.04 (s, 1H), 8.50 (br. s., 2H), 8.23 (d, J=7.03 Hz, 1H), 7.64 (d, J=8.03 Hz, 1H), 7.49 (d, J=8.53 Hz, 1H), 7.18-7.26 (m, 2H), 7.04 (s, 2H), 6.12 (q, J=6.53 Hz, 1H), 4.53 (s, 2H), 4.08 (dd, J=4.02, 11.54 Hz, 2H), 3.56-3.66 (m, 7H), 2.15 (d, J=11.04 Hz, 2H), 1.83 (d, J=6.53 Hz, 4H), 1.18 (t, J=7.03 Hz, 9H).

Example 18

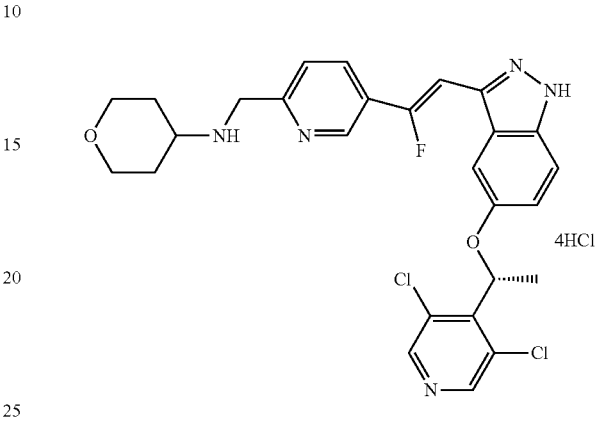

In this example, Example 17F was prepared according to such as the method of Example 17, scaling up to 200 mg, to give 15 mg of the 17F-R configuration product to give Example 18. LCMS (ESI) m/z: 542[M+1]$^+$. $^1$H NMR (400 MHz, METHANOL-d$_4$) ppm 8.95-9.12 (m, 1H), 8.44-8.59 (m, 1H), 8.25 (br. s., 1H), 7.68 (br. s., 1H), 7.51 (d, J=8.78 Hz, 1H), 7.25 (d, J=15.06 Hz, 2H), 6.91-7.10 (m, 1H), 6.13 (d, J=5.77 Hz, 1H), 4.54 (br. s., 2H), 4.07 (d, J=10.54 Hz, 2H), 3.42-3.57 (m, 3H), 2.15 (d, J=10.79 Hz, 2H), 1.83 (m, 5H).

Example 18b

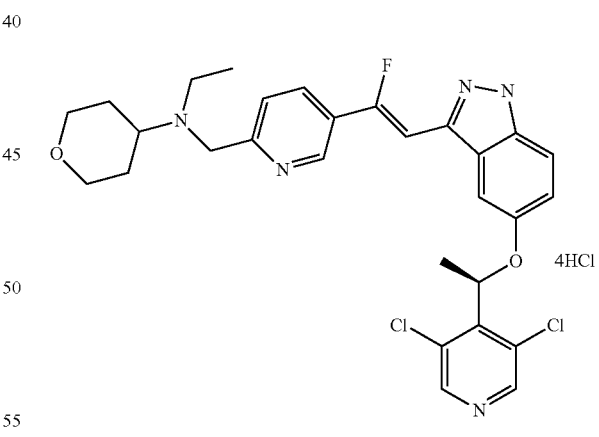

Acetic acid (2.21 mg, 38.87 μmol) was added dropwise to a mixed solution of Example 18 (15 mg, 27.68 μmol) and anhydrous acetaldehyde (5 mg, 110 μmol) in 1,2-dichloroethane (2 mL) and the mixture was stirred at 20° C. for 1 hour after the addition. Sodium cyanoborohydride (7 mg, 110 μmol) was slowly added and the mixture was stirred for 1 hour at 20° C. The reaction was quenched with water and the aqueous layer was extracted with dichloromethane (3 mL×2), the organic phases were combined and washed with brine (5 mL), dried over anhydrous sodium sulfate, filtered and concentrated in vacuo. The residue was purified by preparative column chromatography to give Example 18b (12 mg, yield 76%).

LCMS (ESI) m/z: 571 [M+1]⁺.

1H NMR (400 MHz, METHANOL-d4) 9.09 (s, 1H), 8.31 (d, J=8.03 Hz, 1H), 7.72 (d, J=8.28 Hz, 1H), 7.54 (d, J=9.03 Hz, 1H), 7.24-7.33 (m, 2H), 7.00-7.16 (m, 1H), 6.17 (q, J=6.69 Hz, 1H), 4.11 (d, J=8.53 Hz, 2H), 3.79 (t, J=11.80 Hz, 1H), 3.38-3.58 (m, 4H), 3.26-3.32 (m, 2H), 2.09 (br. s., 2H), 1.90-2.01 (m, 2H), 1.85 (d, J=6.78 Hz, 3H), 1.39 (t, J=7.15 Hz, 3H)

Example 21

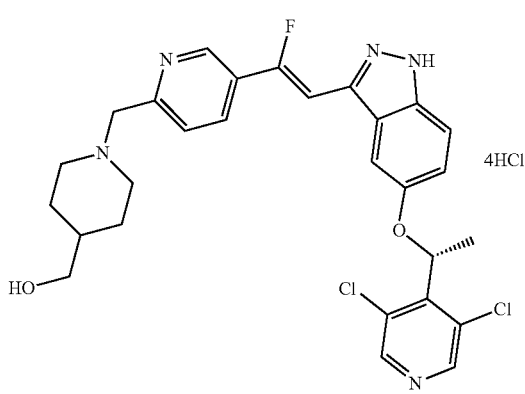 [SMILES: C[C@@H](Oc1ccc2[nH]nc(/C=C(\F)c3ccc(CN4CCC(CO)CC4)nc3)c2c1)c1c(Cl)cncc1Cl]

This example was prepared by the method as described in Example 17. LCMS (ESI) m/z: 556.1 [M+1]⁺. ¹H NMR (400 MHz, METHANOL-d₄) ppm 9.10 (br. s., 1H), 8.58 (br. s., 1H), 8.29 (br. s., 1H), 7.72 (br. s., 1H), 7.53 (d, J=8.53 Hz, 1H), 7.21-7.33 (m, 3H), 6.97-7.18 (m, 1H), 6.14 (d, J=5.52 Hz, 1H), 4.59 (br. s., 2H), 3.57-3.74 (m, 6H), 3.50 (br. s., 3H), 3.19 (br. s., 1H), 2.03 (d, J=12.55 Hz, 3H), 1.83 (d, J=5.52 Hz, 6H), 1.66 (br. s., 3H).

Example 22

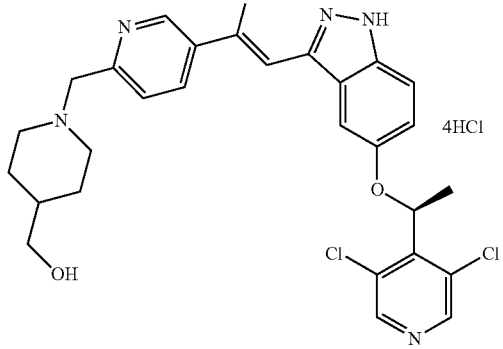

This example was prepared by the method as described in Example 17. LCMS (ESI) m/z: 556.1 [M+1]⁺. ¹H NMR (400 MHz, METHANOL-d₄) ppm 9.09 (s, 1H), 8.54 (br. s., 2H), 8.27 (d, J=7.53 Hz, 1H), 7.68 (d, J=8.03 Hz, 1H), 7.51 (d, J=9.03 Hz, 1H), 7.23-7.28 (m, 2H), 7.09 (s, 1H), 6.14 (q, J=6.53 Hz, 1H), 4.57 (br. s., 2H), 3.66 (d, J=7.03 Hz, 2H), 3.50 (br. s., 2H), 2.03 (d, J=13.55 Hz, 3H), 1.83 (d, J=6.53 Hz, 4H), 1.64 (br. s., 2H), 1.29 (br. s., 3H).

Example 23

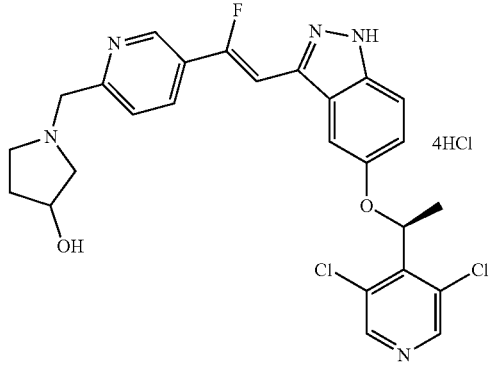 [SMILES: C[C@H](Oc1ccc2[nH]nc(/C=C(\F)c3ccc(CN4CCC(O)C4)nc3)c2c1)c1c(Cl)cncc1Cl]

This example was prepared by the method as described in Example 17. LCMS (ESI) m/z: 528.1 [M+1]⁺.

¹H NMR (400 MHz, DMSO-d₆) ppm 9.08 (s, 1H), 8.62 (s, 2H), 8.29 (d, J=6.27 Hz, 1H), 7.73 (d, J=7.78 Hz, 1H), 7.50 (d, J=9.03 Hz, 1H), 7.09-7.33 (m, 3H), 6.04 (q, J=6.53 Hz, 1H), 4.38-4.68 (m, 1H), 2.68 (br. s., 1H), 2.33 (br. s., 1H), 1.69-1.82 (m, 3H).

Scheme F

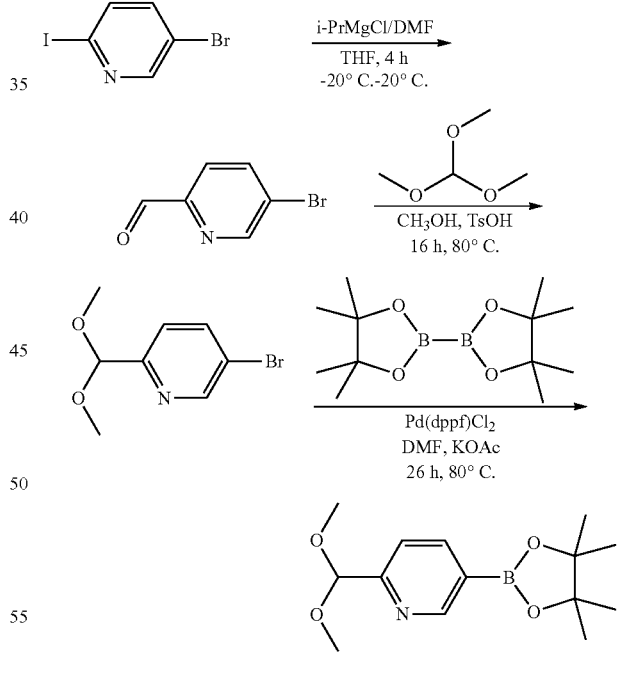

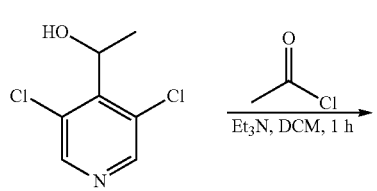

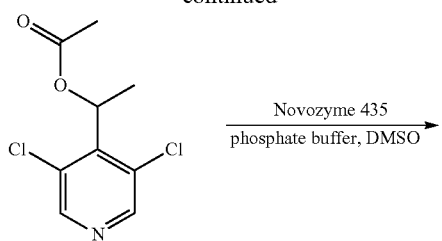
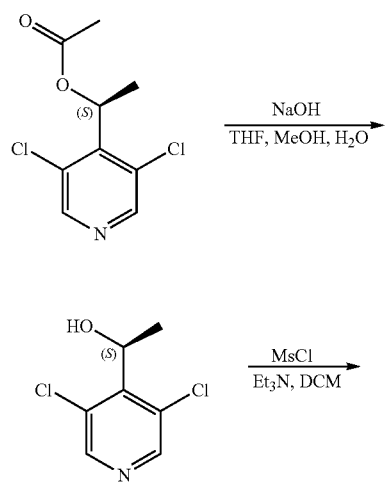
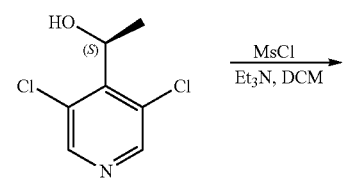
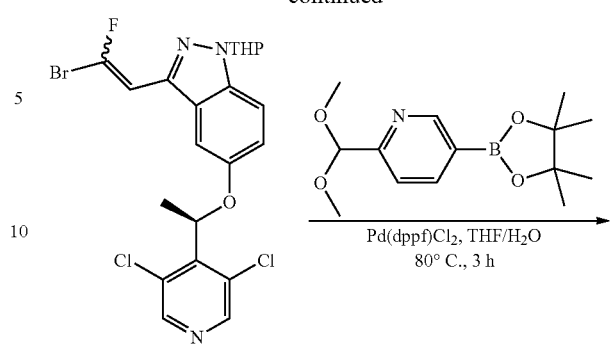
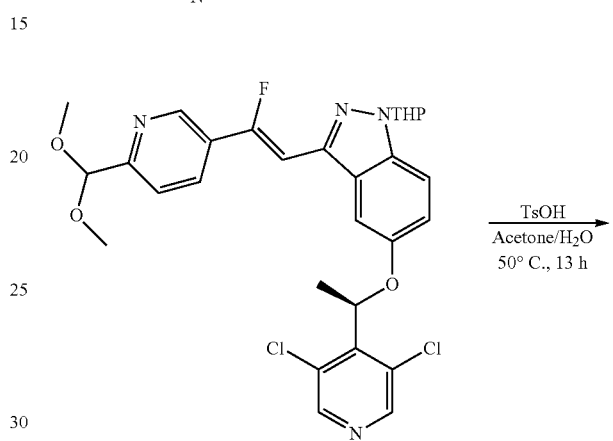
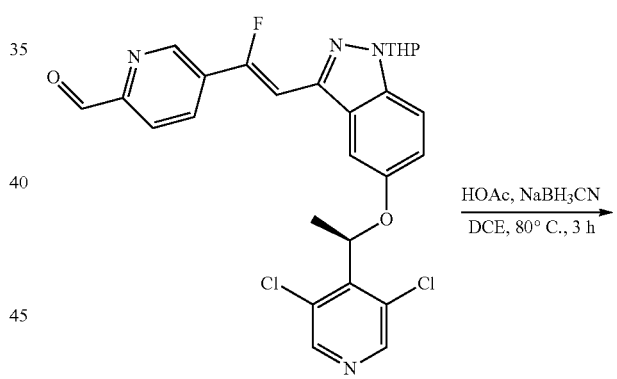
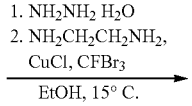
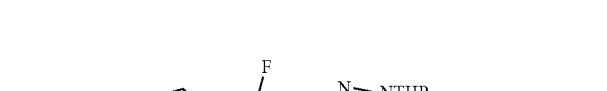
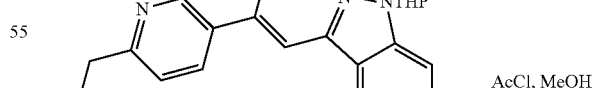
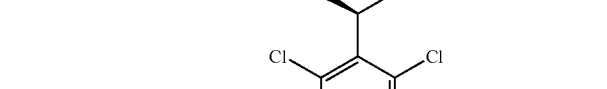
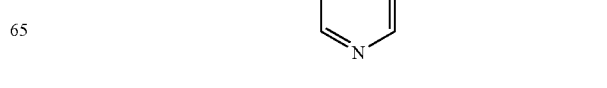

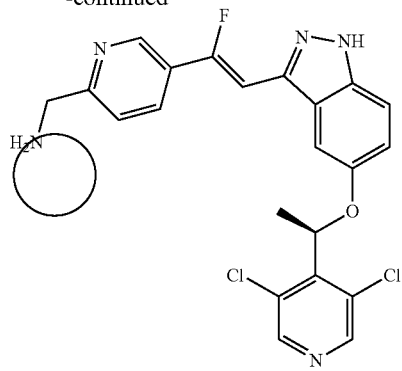

Example 24 (Reference Example)

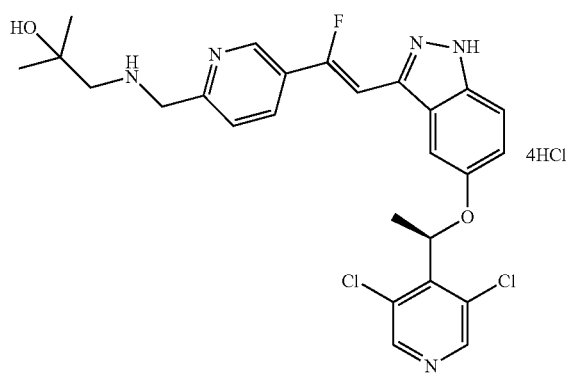 [SMILES: C[C@@H](Oc1ccc2[nH]nc(/C=C(\F)c3ccc(CNCC(C)(C)O)nc3)c2c1)c1c(Cl)cncc1Cl]

Example 24A

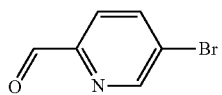

A solution of isopropylmagnesium chloride Grignard reagent (26.52 g, 257.84 mmol) in tetrahydrofuran was slowly added dropwise to a solution of 5-bromo-2-iodopyridine (61 g, 214.87 mmol) in tetrahydrofuran (700 mL) at −20° C. under nitrogen, the solution was stirred at −20° C. for 3 hours and warmed to 0° C. N,N-dimethylformamide (18.85 g, 257.84 mmol) was added dropwise in batches at 0° C. The reaction solution was warmed to 20° C. after the addition, and further stirred for 6 hours. When TLC showed the completion of the reaction, the reaction solution was added with saturated ammonium chloride (100 mL) to quench the reaction, and the aqueous layer was extracted with ethyl acetate (140 mL×3), the organic layers were combined and washed with brine (100 mL×2) and dried over anhydrous sodium sulfate, filtered and concentrated in vacuo to give the title compound (44 g) which was used directly in the next step without further purification $^1$H NMR (400 MHz, CHLOROFORM-d) ppm 10.04 (s, 1H), 8.85 (d, J=1.8 Hz, 1H), 8.03 (dd, J=1.8, 8.3 Hz, 1H), 7.86 (d, J=8.3 Hz, 1H).

Example 24B

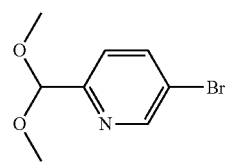

P-toluenesulfonic acid monohydrate (818.11 mg, 4.30 mmol) was added in batches to a mixed solution of Example 1A (40 g, 215.05 mmol), trimethyl orthoformate (27.38 g, 258.06 mmol) in methanol (400 mL) at 20° C. under nitrogen. After the addition, the mixture was stirred at 20° C. for 10 minutes, then heated to 70° C. and stirred for 16 hours. When TLC showed the completion of the reaction, the reaction mixture was cooled to 20° C., partially concentrated in vacuo, then poured into ice water (150 mL) and stirred for 20 minutes. The aqueous layer was extracted with ethyl acetate (100 mL×3). The combined organic phases were washed with brine (100 mL×2), dried over anhydrous sodium sulfate, filtered and concentrated in vacuo. The residue was purified by flash silica gel column chromatography to give the title compound as a yellow oil (19 g, yield 38.07%). $^1$H NMR (400 MHz, CHLOROFORM-d) ppm 8.67 (d, J=2.0 Hz, 1H), 7.86 (dd, J=2.3, 8.3 Hz, 1H), 7.46 (d, J=8.0 Hz, 1H), 3.39 (s, 6H).

Example 24C

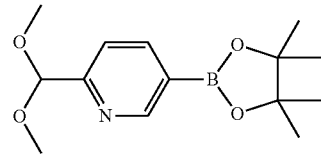 [SMILES: COC(OC)c1ccc(B2OC(C)(C)C(C)(C)O2)cn1]

Pd(dppf)Cl$_2$ (630.73 mg, 862.00 μmol) was added to a solution of Example 24B (2 g, 8.62 mmol), bispinacolatoboronate (2.85 g, 11.21 mmol), potassium acetate (2.54 g, 25.86 mmol) in dioxane (10 mL) under nitrogen atmosphere, followed by reacting at 110° C. for 2 hours. When LC-MS showed the completion of the reaction, the reaction solution was cooled to room temperature, filtered, concentrated in vacuo and the residue was purified by flash silica gel column chromatography to give the title compound as a black oil (2 g, yield 83.12%). $^1$H NMR (400 MHz, CHLOROFORM-d) ppm 8.94 (s, 1H), 8.11 (dd, J=1.4, 7.7 Hz, 1H), 7.54 (d, J=7.8 Hz, 1H), 5.40 (s, 1H), 3.39 (s, 6H), 1.35 (s, 12H).

Example 24D

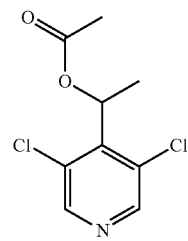

Acetyl chloride (41.99 g, 534.88 mmol) was added dropwise to a solution of 1E 1-(3,5-dichloropyridine-4-)ethanol (85.60 g, 445.74 mol), triethylamine (90.21 g, 891.47 mmol) in dichloromethane (1.5 L) at 20° C., and the mixture was stirred at 20° C. for 1 hour. When TLC showed the completion of the reaction, the solvent was evaporated under reduced pressure and the residue was purified by column chromatography to give the title compound (as a colorless oil, 57.10 g, yield 54.7%). ¹H NMR (400 MHz, CHLOROFORM-d) ppm 8.44 (s, 2H), 6.25 (q, J=6.8 Hz, 1H), 2.09 (s, 3H), 1.63 (d, J=7.2 Hz, 3H).

Example 24E

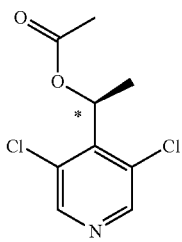

Novozymer 435 (31.78 g, 3.12×10⁴PLU) was added to a mixed solution of Example 24D (31 g, 243 mmol) in DMSO (78 mL) and 1M NaH₂PO₄/Na₂HPO₄ buffer solution (pH 7.5, 775 mL) at 20° C. After the mixture was stirred at 51° C. for 129 hours, LCMS showed that about 50% of the starting material was converted. The reaction solution was diluted with water (1 L) and extracted with ethyl acetate (1 L×5). The combined organic layer was washed with water (500 mL) and brine (500 mL×2), dried over sodium sulfate, filtered and evaporated. The residue was purified by column chromatography to give the title compound (as a colorless oil, 12.00 g, yield 77%). LCMS (ESI) m/z: 233.9 [M+1]⁺.

Example 24F

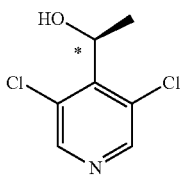

1M sodium hydroxide solution (51.26 mL, 51.26 mmol) was added dropwise to a mixed solution of Example 24E (12.00 g, 51.26 mmol) in tetrahydrofuran (50 mL) and methanol (50 mL) at 20° C. After the mixture was stirred for half an hour at 20° C., TLC showed that the reaction was completed and the reaction solution was diluted with water (30 mL) and extracted with ethyl acetate (100 mL×3). The combined organic layer was washed with brine (20 mL×2), dried over sodium sulfate and evaporated to dryness under reduced pressure to give the title compound (as a colorless oil, 7.99 g, yield 81.2%). LCMS (ESI) m/z: 191.8 [M+1]⁺.

Example 24G

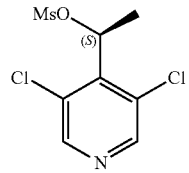

Methanesulfonyl chloride (32.21 g, 281.2 mmol) was slowly added to a mixed solution of Example 25F (18 g, 94 mmol) and triethylamine (28.45 g, 281 mmol) in dichloromethane (400 mL) at 0° C. under an ice bath. The reaction solution was stirred at room temperature for 4 hours. Upon the completion of the reaction, the reaction was quenched with water and extracted with dichloromethane (500 mL×3). The combined organic phase was dried over anhydrous sodium sulfate and evaporated to dryness. The residue was purified by column chromatography to give Example 24G (24 g, 88.9 mmol, yield 94.8%).

Example 24H

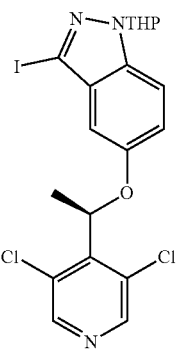

A solution of Example 24G (24 g, 88.9 mmol), Example ID (35 g, 101.7 mmol) and cesium carbonate (57.9 g, 177.7 mmol) in acetonitrile was heated to 110° C. under an oil bath under nitrogen atmosphere, and the reaction solution was stirred for 12 hours. Upon the completion of the reaction, the reaction solution was filtered and the filtrate was evaporated to dryness. The residue was subjected to column chromatography to give Example 25E as pale yellow solid (26 g, 50.2 mmol, yield 56.5%). LCMS (ESI) m/z: 518.0 [M+1]⁺. ¹H NMR (400 MHz, METHANOL-d₄) ppm 8.44 (s, 2H), 7.46 (dd, J=2.8, 8.8 Hz, 1H), 7.17 (dd, J=2.4, 9.2 Hz, 1H), 6.71 (s, 1H), 6.08 (d, J=6.8 Hz, 1H), 5.64~5.59 (m, 1H), 4.01~3.97 (m, 1H), 3.73~3.69 (m, 1H), 2.48~2.47 (m, 1H), 2.13~2.11 (m, 2H), 1.83 (d, J=6.8 Hz, 3H), 1.75~1.64 (m, 3H).

Example 24I

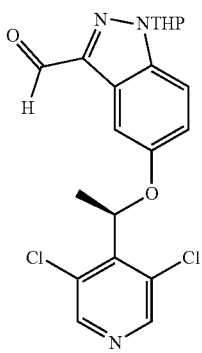

Pd(PPh$_3$)$_2$Cl$_2$ (1.63 g, 2.32 mmol) and sodium formate (9.5 g, 139.0 mmol) were added to a solution of Example 25E (24 g, 46.3 mmol) in DMF (500 mL) at room temperature under nitrogen atmosphere. The hydrogen in the hydrogenation bottle is then replaced with carbon monoxide gas to fill the bottle with carbon monoxide gas. The reaction solution was stirred to react under carbon monoxide (50 psi) at 80° C. for 12 hours. The reaction solution was then filtered and the filtrate was concentrated to dryness, the residue was subject to column chromatography to give the title compound (16 g, yield 64%). LCMS (ESI) m/z: 420.1 [M+1]$^+$.

Example 24J

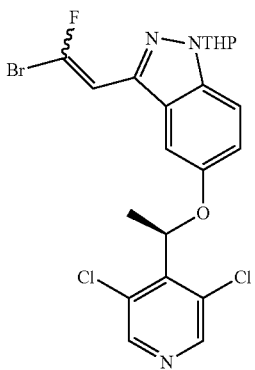

Hydrazine hydrate (2.38 g, 47.6 mmol) was added to a solution of 24F [1-(3,5-dichloro-4-pyridyl)ethoxy]-1-tetrahydropyran-2-benzofindazole-3-carbaldehyde (10 g, 23.8 mmol) in ethanol (180 mL) at 0° C., and the mixture was stirred at 20° C. for 3 hours. Ethylenediamine (2.86 g, 47.6 mmol) and cuprous chloride (2.35.6 g, 23.8 mmol) were added, and after 10 minutes, tribromofluoromethane (16.1 g, 59.6 mmol) was dropwise added slowly at 0° C. After the addition, the mixture was stirred at 20° C. for 16 hours. TLC test showed the completion of the reaction, the reaction was quenched by dropwise addition of 1 mol citric acid. The aqueous layer was extracted with ethyl acetate (50 mL×3) and the organic layers were combined and washed with brine (50 mL×2), dried over anhydrous sodium sulfate, filtered, concentrated in vacuo and the residue was purified by flash silica gel column chromatography to give the title compound as a yellow oil (6 g, yield 48.97%). $^1$H NMR (400 MHz, CHLOROFORM-d) ppm 8.41 (s, 2H), 7.46-7.43 (m, 1H), 7.13-7.10 (dd, J=2.3, 9.0 Hz, 1H), 6.98 (d, J=2.5 Hz, 1H), 6.33 (d, J=2.5 Hz, 1H), 6.25 (d, J=20 Hz 1H), 6.02 (q, J=6.7 Hz, 1H), 5.69-5.57 (m, 1H), 4.04-3.92 (m, 1H), 3.74-3.65 (m, 1H), 2.54-2.40 (m, 1H), 2.19-2.06 (m, 1H), 2.04-1.93 (m, 1H), 1.80 (d, J=6.5 Hz, 3H), 1.76-1.60 (m, 3H).

Example 24K

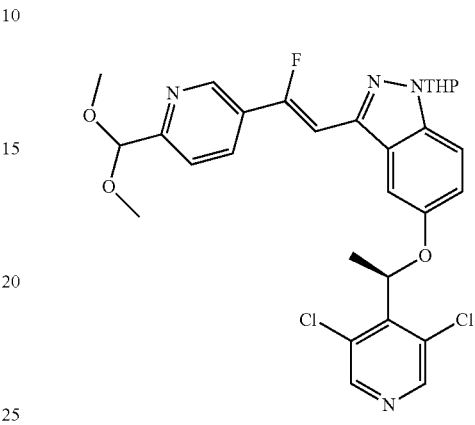

Under nitrogen, Pd(dppf)Cl$_2$ (141.95 mg, 194.00 µmol) was added to a mixed solution of Example 24C (703.99 mg, 2.52 mmol) and Example 24J (1.00 g, 1.94 mmol) in tetrahydrofuran (9 mL), and then the mixture was refluxed overnight at 80° C. with stirring. The reaction solution was cooled, filtered and concentrated in vacuo. The residue was purified by flash silica gel column chromatography to give the title compound as a yellow oil (1.0 g, yield 90%). LCMS (ESI) m/z: 587.1 [M+1]$^+$. $^1$H NMR (400 MHz, CHLOROFORM-d) ppm 8.98-8.93 (m, 1H), 8.41 (s, 2H), 7.98 (d, J=7.0 Hz, 1H), 7.64 (d, J=8.5 Hz, 1H), 7.48 (dd, J=3.8, 9.3 Hz, 1H), 7.24-7.13 (m, 2H), 6.84-6.70 (m, 1H), 6.05 (q, J=6.5 Hz, 1H), 5.68-5.61 (m, 1H), 5.44 (s, 1H), 4.03 (m, 1H), 3.72 (m., 1H), 3.49 (d, J=4.5 Hz, 1H), 3.45 (s, 6H), 2.57-2.42 (m, 1H), 2.07-1.98 (m, 2H), 1.81 (d, J=6.5 Hz, 3H), 1.78-1.70 (m, 2H).

Example 24L

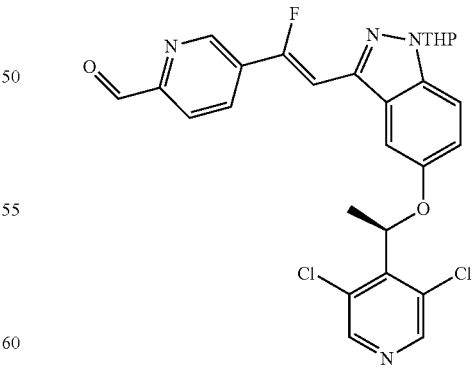

A mixed solution of Example 24K (1.00 g, 1.70 mmol) and p-benzenesulfonic acid monohydrate (19.4 mg, 1.02 mmol) in water (8 mL) and acetone (10 mL) was heated and stirred at 50° C. for 12 hours. The mixture was cooled and the aqueous layer was extracted with dichloromethane (10 mL×3), and the organic layers were combined and washed with brine (10 mL×2), dried over anhydrous sodium sulfate, filtered and concentrated in vacuo to give the title compound (940 mg, crude) which was used directly in the next step. LCMS (ESI) m/z: 541.4 [M+1]+.

Example 24M

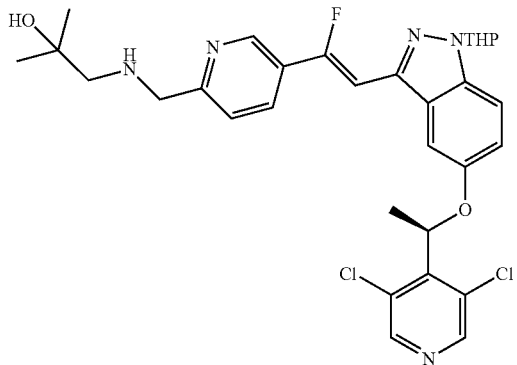

Acetic acid (8.87 mg, 147.77 μmol) was added dropwise to a mixed solution of Example 24L (80 mg, 147.77 μmol) and 1-amino-2-methylpropane-2-hydroxy (54.78 mg, 443.31 μmol) in 1,2-dichloroethane (2 mL), and the mixture was stirred at 20° C. for 30 minutes after the addition. Sodium cyanoborohydride (27.86 mg, 443.31 μmol) was added slowly and the mixture was stirred for 2 hours at 20° C. The reaction was quenched with water, and the aqueous layer was extracted with dichloromethane (5 mL×3), the organic layers were combined and washed with brine (3 mL×2), dried over anhydrous sodium sulfate, filtered and the filtrate was concentrated in vacuo. The residue was purified by flash silica gel column chromatography to give the title compound as a yellow oil (30 mg, 33%). LCMS (ESI) m/z: 613.2 [M+1]+.

Example 24N

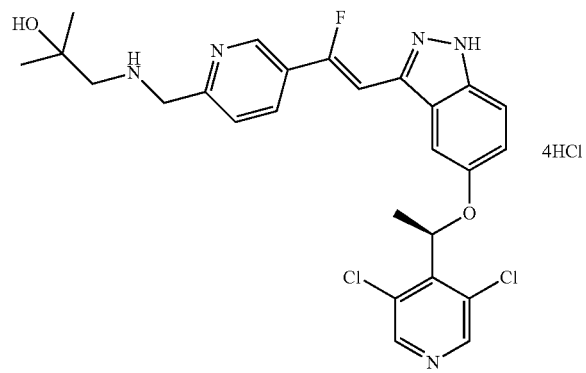 [SMILES: C[C@@H](Oc1ccc2[nH]nc(/C=C(\F)c3ccc(CNCC(C)(C)O)nc3)c2c1)c1c(Cl)cncc1Cl]

This example was prepared by the method as described in Example 24. LCMS (ESI) m/z: 529.4 [M+1]+. $^1$H NMR (400 MHz, METHANOL-$d_4$) ppm 9.09 (s, 1H), 8.55 (s, 2H), 8.32 (d, J=7.0 Hz, 1H), 7.72 (d, J=8.0 Hz, 1H), 7.56 (d, J=9.0 Hz, 1H), 7.35-7.24 (m, 2H), 7.16-7.00 (m, 1H), 6.16 (q, J=6.5 Hz, 1H), 4.57 (s, 2H), 3.16 (s, 2H), 1.84 (d, J=6.5 Hz, 3H), 1.42-1.35 (m, 6H).

Example 26

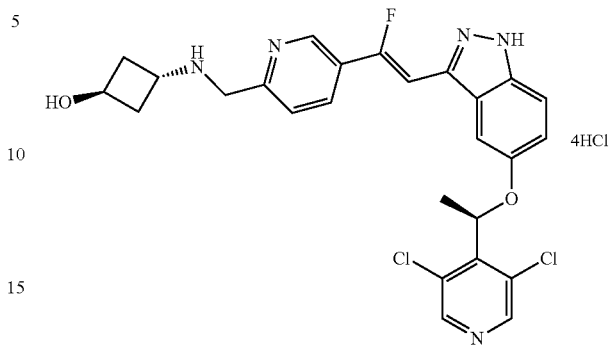

This example was prepared by the method as described in Example 24. LCMS (ESI) m/z: 529.4 [M+1]+. $^1$H NMR (400 MHz, METHANOL-$d_4$) ppm 9.04 (s, 1H), 8.51 (m, 2H), 8.23 (d, J=6.8 Hz, 1H), 7.68-7.43 (m, 1H), 7.26-7.17 (m, 2H), 7.06-6.88 (m, 2H), 6.12 (d, J=6.5 Hz, 1H), 4.55 (m, 1H), 4.40 (s, 2H), 4.08-4.01 (m, 1H), 2.61 (d, J=6.0 Hz, 2H), 2.41 (m, 2H), 1.84 (d, J=6.5 Hz, 3H).

Example 27

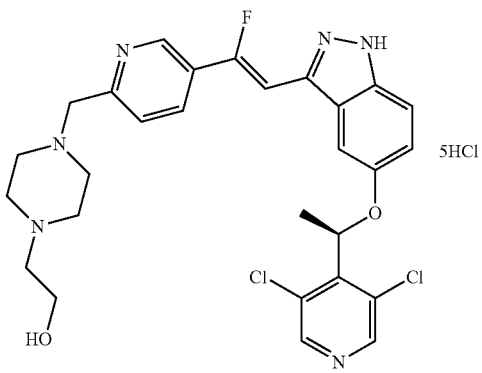 [SMILES: C[C@@H](Oc1ccc2[nH]nc(/C=C(\F)c3ccc(CN4CCN(CCO)CC4)nc3)c2c1)c1c(Cl)cncc1Cl]

Example 27A

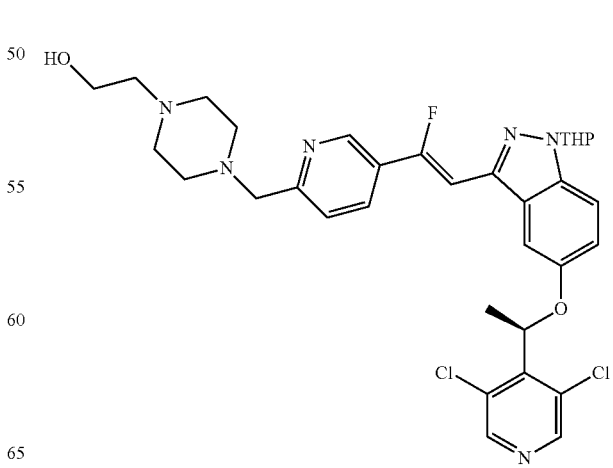

Acetic acid (8.87 mg, 147.77 μmol) was added dropwise to a mixed solution of Example 24L (80 mg, 147.77 μmol) and 2-piperazine-1-ethanol (57.71 mg, 443.31 μmol) in 1,2-dichloroethane (2 mL). After the addition, the mixture was stirred at 20° C. for 30 minutes. Sodium cyanoborohydride (27.86 mg, 443.31 μmol) was added slowly and the mixture was stirred for 2 hours at 20° C. The reaction was quenched with water and the aqueous layer was extracted with dichloromethane (5 mL×3), the organic layers were combined and washed with brine (3 mL×2), dried over anhydrous sodium sulfate, filtered and concentrated in vacuo. The residue was purified by flash silica gel column chromatography to give the title compound (30 mg, yield 30.9%). LCMS (ESI) m/z: 655.2 [M+1]$^+$.

Example 27B

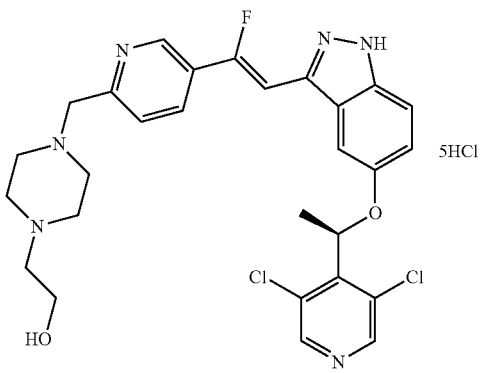 [SMILES: C[C@@H](Oc1ccc2[nH]nc(/C=C(\F)c3ccc(CN4CCN(CCO)CC4)nc3)c2c1)c1c(Cl)cncc1Cl]

A mixed solution of methanol (1 mL)/acetyl chloride (0.25 mL) was added to a solution of Example 27A (20 mg, 30.51 μmol) in methanol (1 mL) and the mixture was heated to 40° C. and stirred for 3 hours, then cooled and concentrated in vacuo to give the title compound (11.50 mg, yield 65.5%). LCMS (ESI) m/z: 571.4 [M+1]$^+$. $^1$H NMR (400 MHz, METHANOL-d$_4$) ppm: 9.07 (s, 1H), 8.58-8.49 (m, 3H), 7.92 (d, J=8.5 Hz, 1H), 7.50 (d, J=9.0 Hz, 1H), 7.27-7.20 (m, 1H), 7.18-7.06 (m, 2H), 6.14 (q, J=6.5 Hz, 1H), 4.32 (s, 2H), 3.98-3.92 (m, 2H), 3.67-3.45 (m, 4H), 3.43-3.37 (m, 2H), 3.28-3.13 (m, 4H), 1.85 (d, J=7.0 Hz, 3H).

Example 29

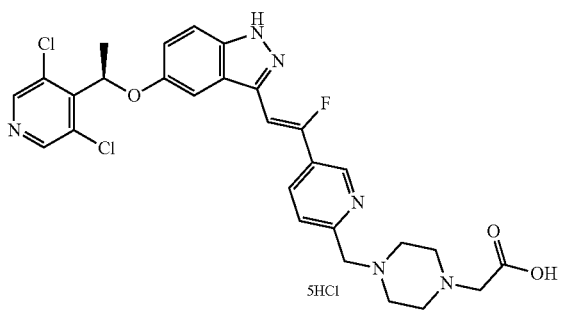 [SMILES: C[C@@H](Oc1ccc2[nH]nc(/C=C(\F)c3ccc(CN4CCN(CC(=O)O)CC4)nc3)c2c1)c1c(Cl)cncc1Cl]

Example 29A

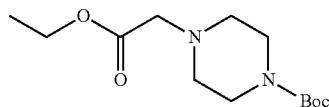 [SMILES: CCOC(=O)CN1CCN(C(=O)OC(C)(C)C)CC1]

A mixed solution of nitrogen tert-butoxycarbonylpiperidine (2 g, 10.7 mmol), ethyl bromoacetate (1.79 g, 10.7 mmol) and potassium carbonate (4.45 g, 32.2 mmol) in acetonitrile (30 mL) was heated to 90° C. and stirred to react for 16 hours. TLC showed the starting materials of the reaction disappeared. The reaction solution was filtered and the filtrate was evaporated to dryness and the residue was purified by flash silica gel column chromatography flash silica gel column chromatography to give the title compound as a colorless oil (2.1 g, 7.7 mmol). LCMS (ESI) m/z: 273.2 [M+1]$^+$.

Example 29B

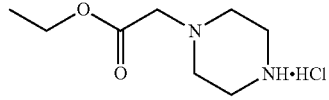

Example 29A (2.1 g, 7.7 mmol) was added to hydrochloric acid ethyl acetate (30 mL) and the reaction solution was stirred at room temperature for 16 hours. TLC showed that the reaction was complete. The reaction solution was directly evaporated to dryness to give the title compound (1.2 g, yield 90.4%) which was used directly in the next step without further purification.

Example 29C

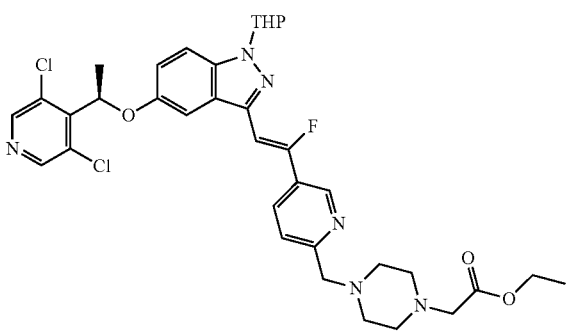

A mixed solution of Example 29B (15 mg, 87 μmol) and Example 24L (47 mg, 87 μmol) in 1,2-dichloroethane (4 mL) was stirred at room temperature for 1 hour. Sodium cyanoborohydride (5.5 mg, 87 μmol) was added to the reaction solution under an ice bath. The reaction was finally warmed to room temperature and stirred for 3 hours. The reaction was quenched with water and extracted with dichloromethane. The organic phase was dried over anhydrous sodium sulfate and evaporated to dryness. The residue was isolated by HPLC to give the title compound (30 mg, yield 49.5%). LCMS (ESI) m/z: 698.6 [M+1]$^+$.

Example 29D

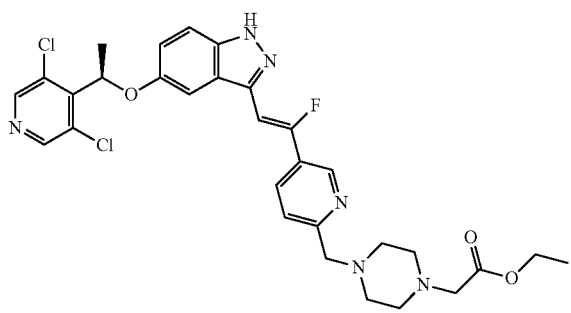 [SMILES: CCOC(=O)CN1CCN(Cc2ccc(/C(F)=C/c3n[nH]c4ccc(O[C@H](C)c5c(Cl)cncc5Cl)cc34)cn2)CC1]

Acetyl chloride (3 mL) was slowly added dropwise to methanol (8 mL) at 0° C. The reaction solution was then stirred at room temperature for 15 minutes. Example 29C (35 mg, 50 μmol) was added to the stirred reaction solution. The reaction solution was warmed to 40° C. and stirred for 3 hours. LCMS showed the reaction was complete. The reaction solution was evaporated to dryness directly to give the title compound (as a dark yellow oil, 30 mg, yield 97.5%) which was used in the next step without further purification. LCMS (ESI) m/z: 614.5 [M+1]$^+$.

Example 29E

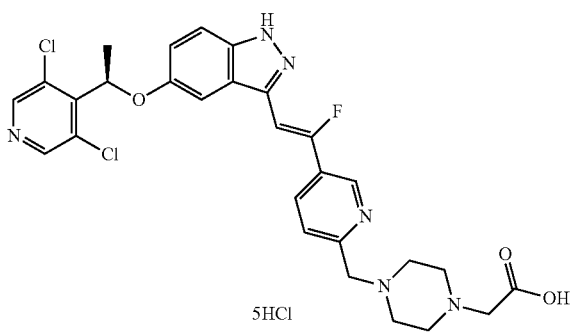 [SMILES: C[C@@H](Oc1ccc2[nH]nc(/C=C(\F)c3ccc(CN4CCN(CC(=O)O)CC4)nc3)c2c1)c1c(Cl)cncc1Cl]

Sodium hydroxide (10 mg, 245 μmol) was added in one batch to a solution of Example 29D (30 mg, 49 μmol) in a mixed solvent of tetrahydrofuran (1 mL), methanol (1 mL) and water (1 mL) at room temperature. The reaction solution was stirred at 21° C. for 16 hours. LCMS showed the reaction was complete. The reaction solution was evaporated to dryness directly, then dissolved with methanol and filtered to obtain a filtrate which was evaporated. The residue was separated by preparative chromatography to give the title compound (as a green oil, 5 mg, yield 17.5%). LCMS (ESI) m/z: 585.2 [M+1]$^+$. $^1$H NMR (400 MHz, METHANOL-d$_4$) ppm 9.11 (s, 1H), 8.87 (d, J=8 Hz, 1H), 8.53 (s, 2H), 8.00 (d, J=8.4 Hz, 1H), 7.50 (d, J=9.2 Hz, 1H), 7.24 (m, 2H), 7.18 (d, J=33.6 Hz, 1H), 6.14 (t, J=6.8 Hz, 1H), 4.40 (s, 2H), 4.21 (s, 2H), 3.65 (s, 4H), 3.3 (m, 2H), 1.84 (d, J=6.8 Hz, 3H).

Example 30

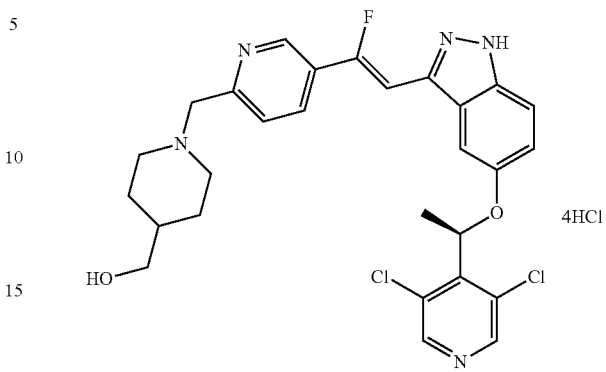

This example was prepared by the method as described in Example 24. LCMS (ESI) m/z: 556.1 [M+1]$^+$. $^1$H NMR (400 MHz, METHANOL-d$_4$) ppm 9.10 (br. s., 1H), 8.58 (br. s., 1H), 8.29 (br. s., 1H), 7.72 (br. s., 1H), 7.53 (d, J=8.53 Hz, 1H), 7.21-7.33 (m, 3H), 6.97-7.18 (m, 1H), 6.14 (d, J=5.52 Hz, 1H), 4.59 (br. s., 2H), 3.57-3.74 (m, 6H), 3.50 (br. s., 3H), 3.19 (br. s., 1H), 2.03 (d, J=12.55 Hz, 3H), 1.83 (d, J=5.52 Hz, 6H), 1.66 (br. s., 3H).

Example 31

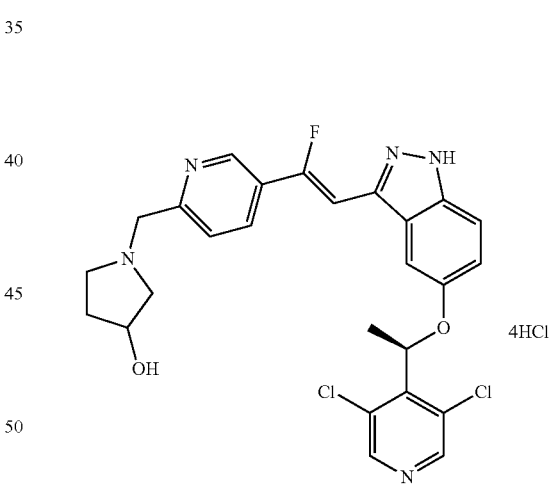

This example was prepared by the method as described in Example 24. LCMS (ESI) m/z: 528.1 [M+1]$^+$.

$^1$H NMR (400 MHz, DMSO-d$_6$) ppm 9.08 (s, 1H), 8.62 (s, 2H), 8.29 (d, J=6.27 Hz, 1H), 7.73 (d, J=7.78 Hz, 1H), 7.50 (d, J=9.03 Hz, 1H), 7.09-7.33 (m, 3H), 6.04 (q, J=6.53 Hz, 1H), 4.38-4.68 (m, 1H), 2.68 (br. s., 1H), 2.33 (br. s., 1H), 1.69-1.82 (m, 3H).

Example 32

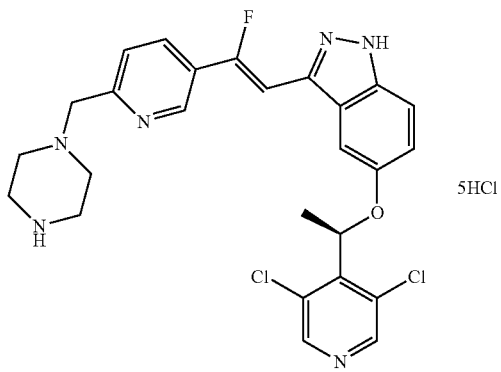 [SMILES: C[C@@H](Oc1ccc2[nH]nc(/C=C(\F)c3ccc(CN4CCNCC4)nc3)c2c1)c1c(Cl)cncc1Cl]

5HCl

This example was prepared by the method as described in Example 24. LCMS (ESI) m/z: 527.1 [M+1]$^+$.

$^1$H NMR (400 MHz, METHANOL-d$_4$) ppm 9.07 (s, 1H), 8.51 (s, 3H), 7.89 (d, J=8.4 Hz, 1H), 7.49 (d, J=8.8 Hz, 1H), 7.23-7.21 (m, 2H), 7.15 (d, J=43.2 Hz, 1H), 6.13 (q, J=6.4 Hz, 1H), 4.44 (s, 2H), 3.56-3.53 (m, 4H), 3.37 (m, 4H), 1.84 (d, J=6.4 Hz, 3H).

Example 33

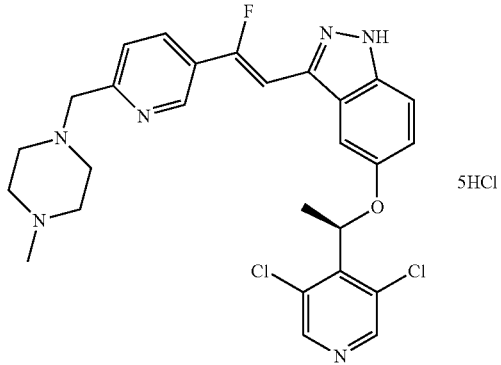 [SMILES: C[C@@H](Oc1ccc2[nH]nc(/C=C(\F)c3ccc(CN4CCN(C)CC4)nc3)c2c1)c1c(Cl)cncc1Cl]

5HCl

This example was prepared by the method as described in Example 24. LCMS (ESI) m/z: 541.1 [M+1]$^+$.

$^1$H NMR (400 MHz, METHANOL-d$_4$) ppm 9.06 (s, 1H), 8.59 (d, J=8.0 Hz, 1H), 7.95 (d, J=8.0 Hz, 1H), 7.50 (d, J=8.0 Hz, 1H), 7.25-7.21 (m, 2H), 7.14 (d, J=40 Hz, 1H), 6.14 (q, J=8.0 Hz, 1H), 4.20 (s, 2H), 3.00 (s, 3H), 1.85 (d, J=8.0 Hz, 3H).

Example 34

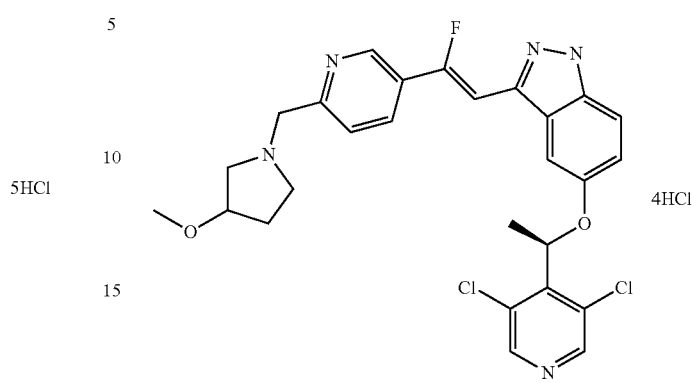

4HCl

This example was prepared by the method as described in Example 24. LCMS (ESI) m/z: 542.4 [M+1]$^+$. $^1$H NMR (400 MHz, METHANOL-d$_4$) ppm 9.04-9.14 (m, 1H), 8.53 (s, 2H), 8.26 (dd, J=2.01, 8.28 Hz, 1H), 7.65 (d, J=8.28 Hz, 1H), 7.52 (d, J=9.03 Hz, 1H), 7.21-7.32 (m, 2H), 6.15 (q, J=6.53 Hz, 1H), 4.72 (s, 2H), 4.32-4.24 (m., 1H), 3.41 (s, 3H), 1.85 (d, J=6.78 Hz, 3H).

Scheme G

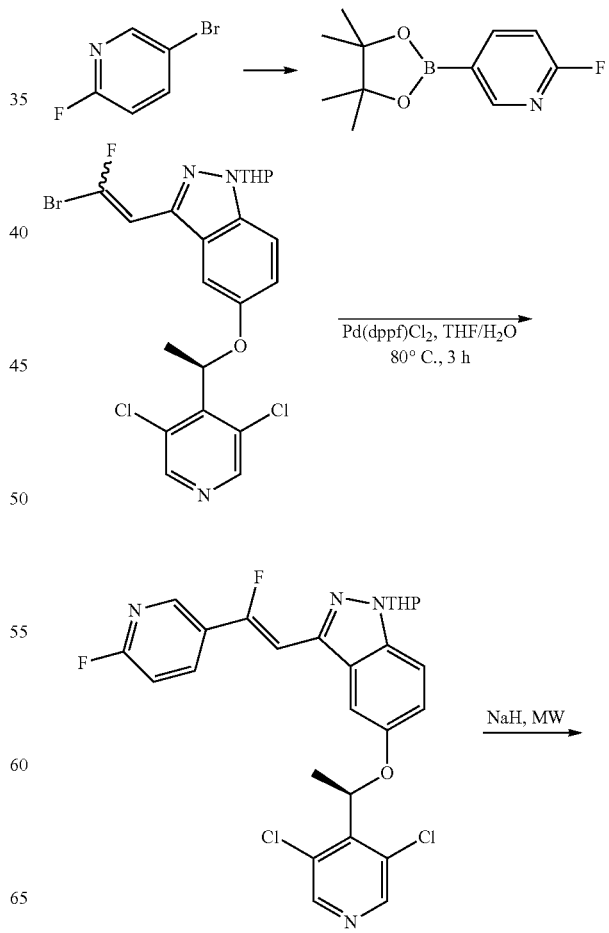

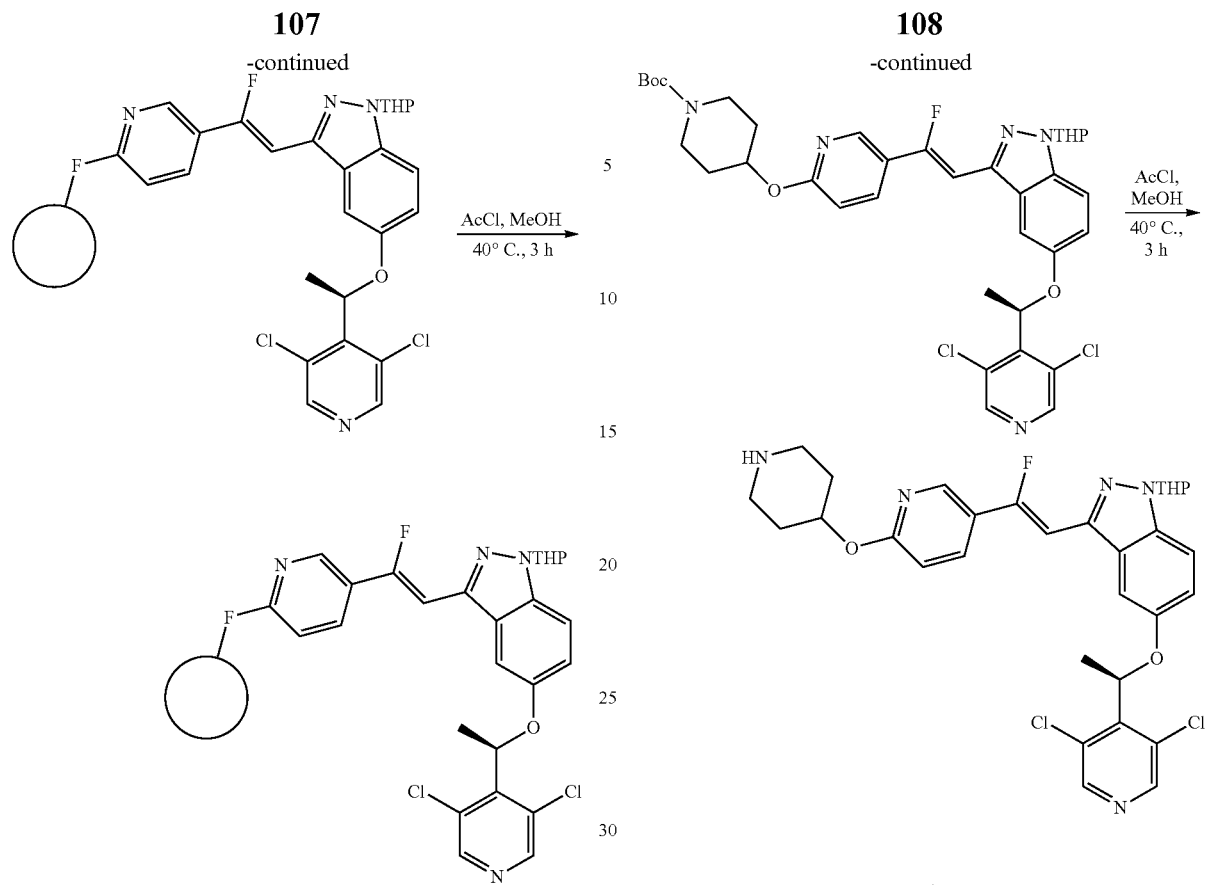
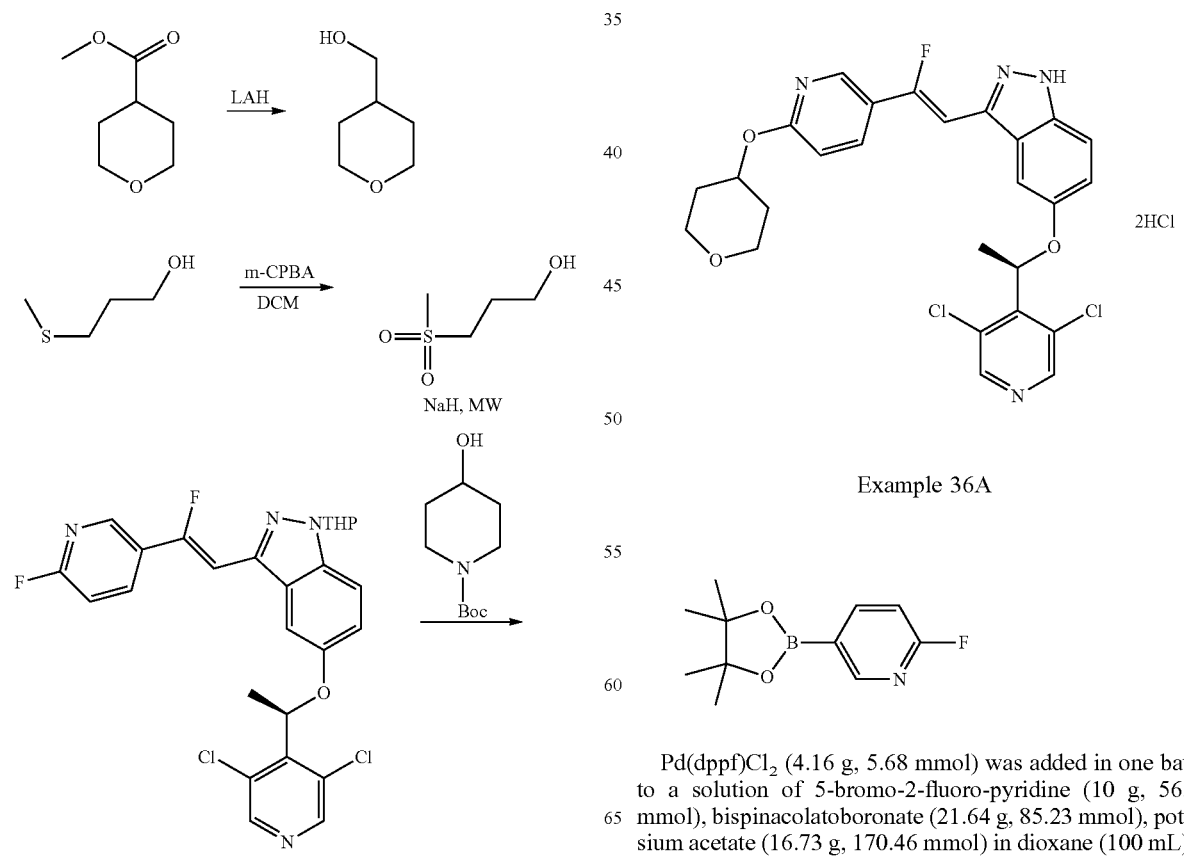
Example 36
Example 36A
Pd(dppf)Cl$_2$ (4.16 g, 5.68 mmol) was added in one batch to a solution of 5-bromo-2-fluoro-pyridine (10 g, 56.82 mmol), bispinacolatoboronate (21.64 g, 85.23 mmol), potassium acetate (16.73 g, 170.46 mmol) in dioxane (100 mL) at room temperature under nitrogen atmosphere, and the mixture was stirred for 10 minutes and heated to reflux for 6 hours. Upon the completion of the reaction, the solvent was evaporated off directly and the residue was purified by flash silica gel column chromatography to give the title compound (10.5 g, yield 82.85%). $^1$H NMR (400 MHz, CHLOROFORM-d) ppm 8.59 (s, 1H), 8.15 (dt, J=1.76, 8.41 Hz, 1H), 6.91 (dd, J=2.26, 8.28 Hz, 1H), 1.35 (s, 12H).

Example 36B

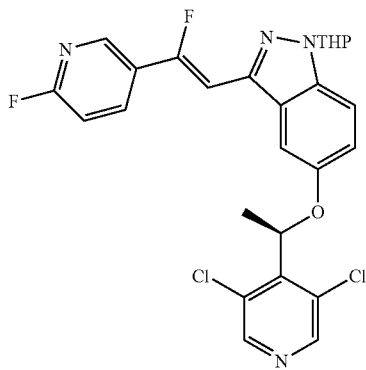

Potassium phosphate (1 mol/L, 3. ml) and Pd(dppf)Cl$_2$ (102 mg, 0.14 mmol) were added to a solution of Example 24J (720 mg, 1.40 mmol), Example 36A (311.72 mg, 1.40 mmol) in tetrahydrofuran (9 mL) at room temperature under nitrogen atmosphere and the mixture was stirred for 10 minutes, and then the reaction solution was heated to 80° C. for 6 hours with stirring. The mixture was cooled to room temperature and extracted with ethyl acetate (40 mL×3). The organic phases were combined and washed with brine (20 mL), dried over sodium sulfate, filtered and evaporated. The residue was purified by flash silica gel column chromatography to give the title compound as a colorless oil (480 mg, yield 64.52%). LCMS (ESI) m/z: 531.0 [M+1]$^+$. $^1$H NMR (400 MHz, CHLOROFORM-d) ppm 8.56 (s, 1H), 8.41 (s, 2H), 8.04 (t, J=6.78 Hz, 1H), 7.48 (dd, J=4.02, 9.03 Hz, 1H), 7.13-7.23 (m, 2H), 7.04 (dd, J=2.76, 8.78 Hz, 1H), 6.59-6.75 (m, 1H), 6.05 (q, J=6.53 Hz, 1H), 5.59-5.69 (m, 1H), 4.03 (br. s., 1H), 3.66-3.80 (m, 1H), 2.43-2.56 (m, 1H), 2.13 (br. s., 1H), 2.02 (br. s., 1H), 1.81 (d, J=6.53 Hz, 3H), 1.62-1.78 (m, 3H).

Example 36C

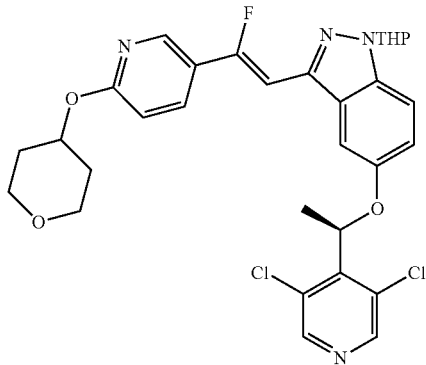

A solution of tetrahydropyran-4-ol (35 mg, 0.34 mmol) in tetrahydrofuran (2 mL) was added to the microwave tube at room temperature and sodium hydride (10 mg, 0.25 mmol) was slowly added in batches and the mixture was stirred for 10 minutes, Example 36B (45 mg, 0.085 mmol) was added and the mixture was stirred for 10 minutes. After reacting in the microwave instrument at 70° C. for 10 minutes, starting materials can still be monitored and the reaction was continued at 90° C. for 30 minutes. The reaction solution was cooled to room temperature and carefully quenched with ice water (5 mL). The organic phase was separated, washed with brine, dried over sodium sulfate, filtered and the filtrate was evaporated. The residue was purified by flash silica gel column chromatography to give the title compound as a colorless oil (35 mg, yield 67%). LCMS (ESI) m/z: 613.2 [M+1]$^+$.

Example 36D

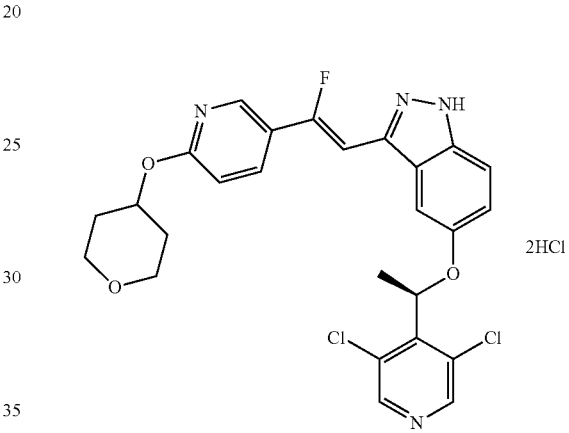

This example was prepared by the method as described in Example 24. LCMS (ESI) m/z: 529.4 [M+1]$^+$. $^1$H NMR (400 MHz, METHANOL-d$_4$) ppm 8.70 (s, 1H), 8.60-8.56 (m, 3H), 7.60 (d, J=9.29 Hz, 1H), 7.54 (d, J=6.78 Hz, 1H), 7.39 (d, J=9.03 Hz, 1H), 7.33 (br. s., 1H), 6.98-7.17 (m, 1H), 6.21 (q, J=6.19 Hz, 1H), 5.34 (br. s., 1H), 4.02 (d, J=11.54 Hz, 2H), 3.64-3.75 (m, 2H), 2.20 (d, J=11.54 Hz, 2H), 1.81-1.96 (m, 5H).

Example 37

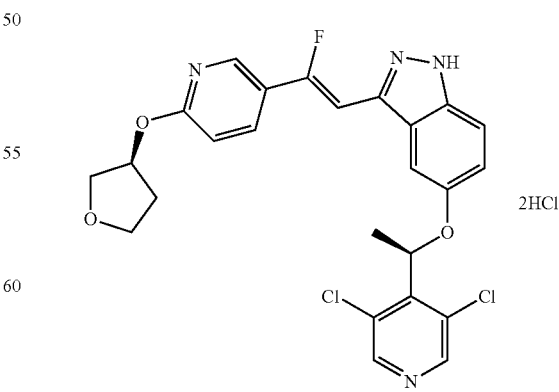

This example was prepared by the method as described in Example 36. LCMS (ESI) m/z: 516.1 [M+1]$^+$. $^1$H NMR (400 MHz, DMSO-d₆) ppm 8.89 (s, 1H), 8.58 (s, 2H), 8.16 (d, J=8.28 Hz, 1H), 7.49-7.65 (m, 3H), 7.32 (s, 3H), 7.14 (d, J=9.03 Hz, 1H), 7.06 (s, 2H), 6.62-6.77 (m, 2H), 6.13 (d, J=6.78 Hz, 1H), 4.38 (br. s., 2H), 3.61-3.71 (m, 2H), 2.62-2.70 (m, 2H), 1.75 (d, J=6.53 Hz, 3H), 1.26 (d, J=6.53 Hz, 3H).

Example 38

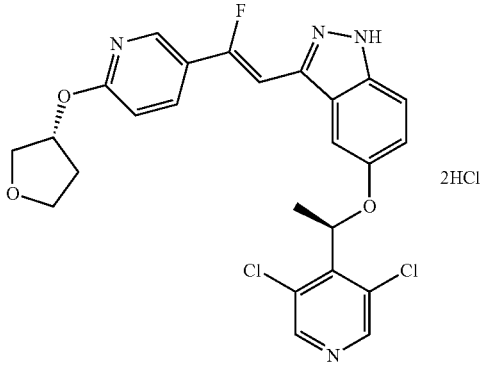 [SMILES: C[C@@H](Oc1ccc2[nH]nc(/C=C(\F)c3ccc(O[C@@H]4CCOC4)nc3)c2c1)c1c(Cl)cncc1Cl]

2HCl

This example was prepared by the method as described in Example 37. LCMS (ESI) m/z: 516.1 [M+1]⁺ ¹H NMR (400 MHz, DMSO-d6) ppm 8.89 (s, 1H), 8.58 (s, 2H), 8.16 (d, J=8.28 Hz, 1H), 7.49-7.65 (m, 3H), 7.32 (s, 3H), 7.14 (d, J=9.03 Hz, 1H), 7.06 (s, 2H), 6.62-6.77 (m, 2H), 6.13 (d, J=6.78 Hz, 1H), 4.38 (br. s., 2H), 3.61-3.71 (m, 2H), 2.62-2.70 (m, 2H), 1.75 (d, J=6.53 Hz, 3H), 1.26 (d, J=6.53 Hz, 3H).

Example 41

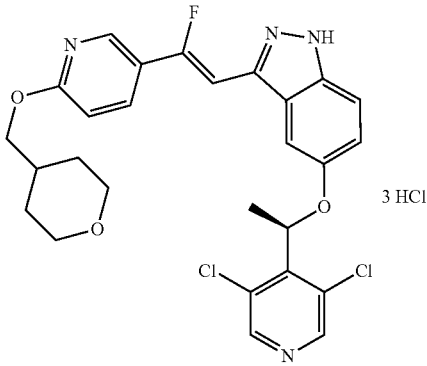 [SMILES: C[C@@H](Oc1ccc2[nH]nc(/C=C(\F)c3ccc(OCC4CCOCC4)nc3)c2c1)c1c(Cl)cncc1Cl]

3 HCl

Example 41A

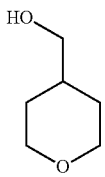

To a solution of methyl tetrahydro-2H-pyran-4-carboxylate (3 g, 21 mmol) in tetrahydrofuran (30 mL) under nitrogen atmosphere was slowly added lithium aluminum hydride (1.18 g, 31 mmol) in batches at 0° C. The reaction was stirred at 0° C. for 1 hour, then carefully quenched with H₂O (1.2 mL), NaOH (1.2 mL, 15%), H₂O (3.6 mL) successively and stirred for 20 minutes. The mixture was filtered and the filtrate was concentrated to give the title compound (2.1 g, 87% yield) as a colorless liquid. ¹H NMR (400 MHz, CHLOROFORM-d) ppm 4.00 (dd, J=4.02, 11.04 Hz, 1H), 3.51 (t, J=5.77 Hz, 1H), 3.41 (dt, J=1.76, 11.67 Hz, 1H), 1.70-1.81 (m, 1H), 1.66 (d, J=13.05 Hz, 2H), 1.27-1.40 (m, 3H).

Example 41B

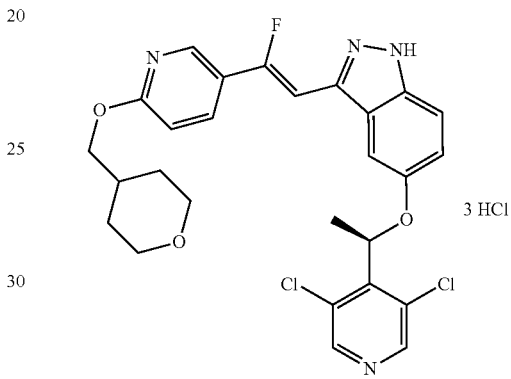

3 HCl

This example was prepared by the method as described in Example 36. LCMS (ESI) m/z: 529.4 [M+1]⁺. ¹H NMR (400 MHz, METHANOL-d₄) ppm 8.43-8.68 (m, 1H), 7.54 (d, J=9.29 Hz, 1H), 7.40 (d, J=9.03 Hz, 1H), 7.31 (dd, J=1.88, 9.16 Hz, 1H), 7.26 (s, 1H), 6.90-7.06 (m, 1H), 6.16 (q, J=6.53 Hz, 1H), 4.36 (d, J=6.53 Hz, 2H), 4.01 (dd, J=3.51, 11.29 Hz, 2H), 3.50 (t, J=10.92 Hz, 2H), 2.20 (br. s., 1H), 1.74-1.87 (m, 6H), 1.48-1.58 (m, 2H), 0.99 (d, J=5.02 Hz, 2H)

Example 43

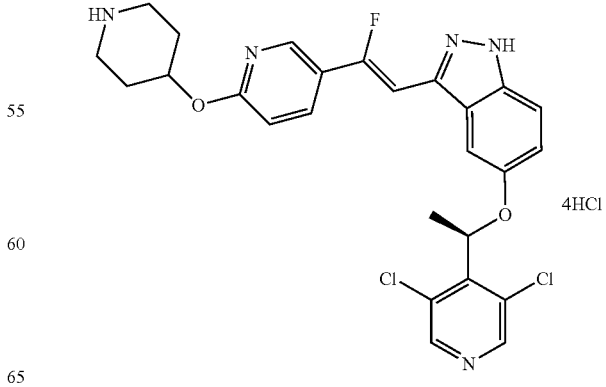

4HCl

Example 43A

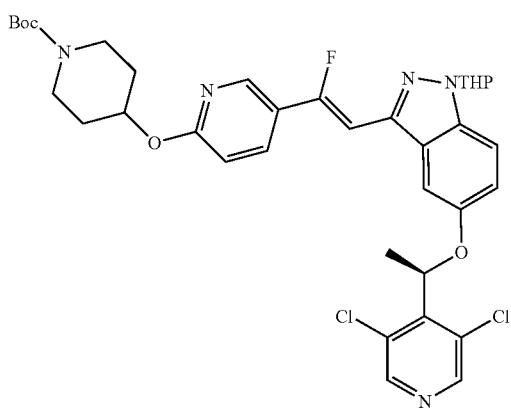

A solution of tert-butyloxycarbonyl 4-hydroxypiperidine (13.12 mg, 0.11 μmol) in tetrahydrofuran (3 mL) was added to the microwave tube at room temperature, and sodium hydride (14 mg, 0.34 mmol) was added in batches slowly and the mixture was stirred for 10 min, and then Example 36B (40 mg, 0.075 mmol) was added thereto and the mixture was stirred for 10 minutes. After reacting in a microwave instrument at 80° C. for 15 minutes, the reaction solution was cooled to room temperature and carefully quenched with ice water (5 mL), then extracted with ethyl acetate (40 mL×3). The organic phases were separated and combined, washed with brine, dried over sodium sulfate, filtered and evaporated, the residue was purified by flash silica gel column chromatography to give the title compound as a colorless oil (31 mg, yield 66%). LCMS (ESI) m/z: 712.3 [M+1]$^+$.

Example 43B

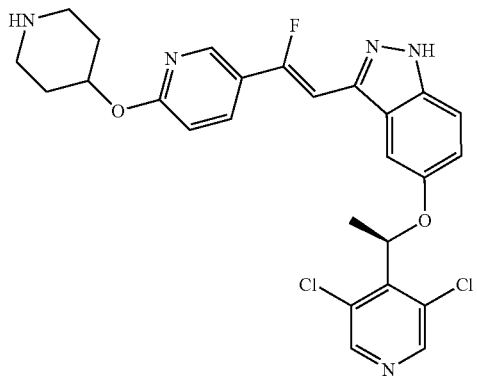

A freshly prepared solution of acetyl chloride (1 mL) in methanol (3 mL) was added to a solution of Example 43A (40 mg, 56 μmol) in methanol (1 mL) at room temperature under nitrogen atmosphere. The reaction solution was stirred at 40° C. for 3 hours. The solution was removed in vacuo to give the title compound (35 mg, yield 98%). LCMS (ESI) m/z: 528.2 [M+1]$^+$. $^1$H NMR (400 MHz, METHANOL-d$_4$) ppm 8.43-8.68 (m, 1H), 7.54 (d, J=9.29 Hz, 1H), 7.40 (d, J=9.03 Hz, 1H), 7.31 (dd, J=1.88, 9.16 Hz, 1H), 7.26 (s, 1H), 6.90-7.06 (m, 1H), 6.16 (q, J=6.53 Hz, 1H), 4.36 (d, J=6.53 Hz, 2H), 4.01 (dd, J=3.51, 11.29 Hz, 2H), 3.50 (t, J=10.92 Hz, 2H), 2.20 (br. s., 1H), 1.74-1.87 (m, 6H), 1.48-1.58 (m, 2H), 0.99 (d, J=5.02 Hz, 2H).

Example 44

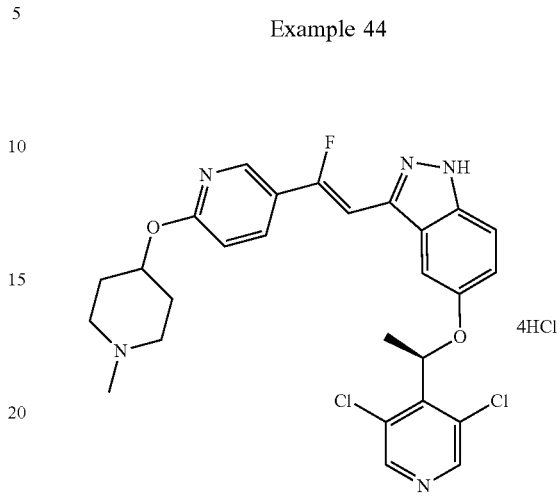

This example was prepared by the method as described in Example 36. LCMS (ESI) m/z: 529.4 [M+1]$^+$ $^1$H NMR (400 MHz, METHANOL-d$_4$) ppm 8.46-8.58 (m, 3H), 8.04-8.13 (m, 1H), 7.46 (d, J=9.03 Hz, 1H), 7.14-7.24 (m, 2H), 7.03 (d, J=8.78 Hz, 1H), 6.62-6.78 (m, 1H), 6.11 (q, J=6.53 Hz, 1H), 5.53 (br. s., 1H), 3.67 (d, J=12.80 Hz, 1H), 3.38 (s, 3H), 3.21-3.30 (m, 1H), 2.95-3.00 (m, 3H), 2.50-2.60 (m, 1H), 2.40 (d, J=15.56 Hz, 1H), 2.12-2.24 (m, 1H), 1.84 (d, J=6.78 Hz, 3H).

Scheme H

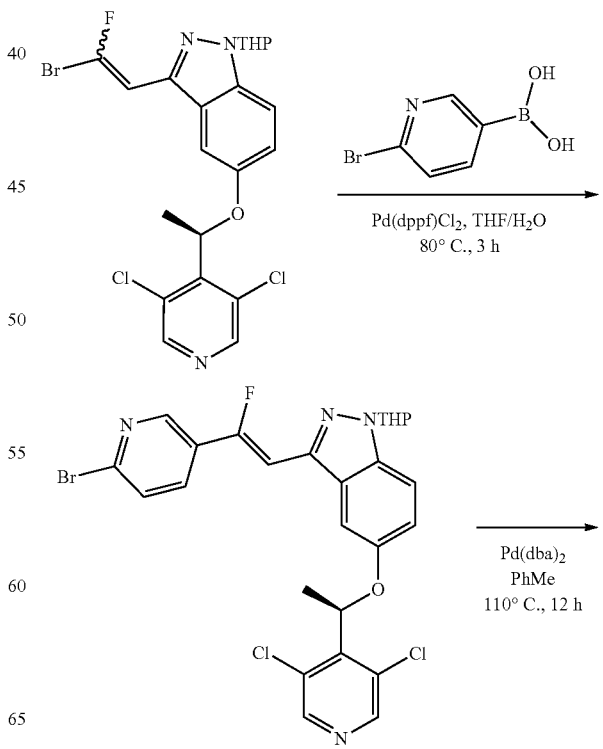

115
-continued

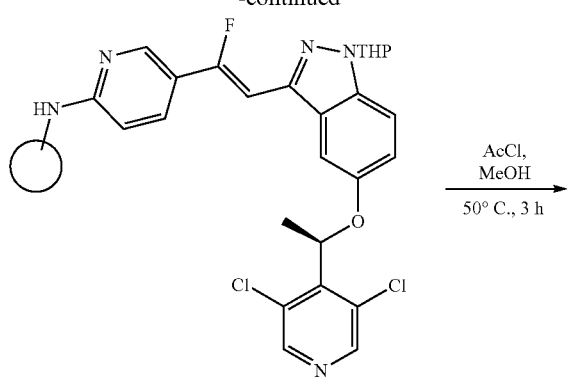

Example 45A

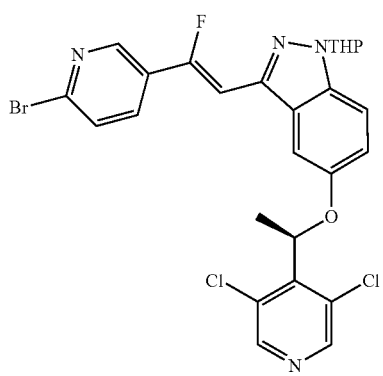

(5-Bromo-2-pyridyl)borate (70 mg, 0.35 mmol), 24 J (198.56 mg, 385.40 μmol), Pd(dppf)Cl$_2$ (28.20 mg, 38.54 μmol) and potassium phosphate (245.43 mg, 1.16 mmol) were dissolved in tetrahydrofuran (4 mL) and water (2 mL) and the mixture was reacted for 12 hours at 90° C. under nitrogen atmosphere. The reaction mixture was concentrated under reduced pressure and separated by thin layer chromatography (petroleum ether:ethyl acetate=2/1) to give the title compound (70.00 mg, 118.19 μmol, 30.67%). LCMS (ESI) m/z: 593.1 [M+1]$^+$.

Example 45B

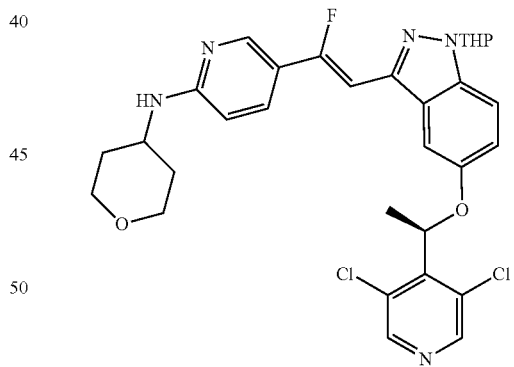

Example 45

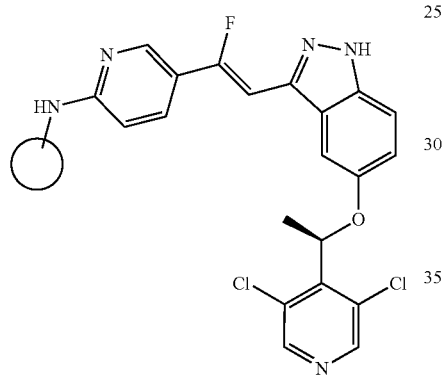

Example 45A (30.00 mg, 50.65 μmol), 4-amino-tetrahydropyran (6.15 mg, 60.78 μmol), sodium tert-butoxide (14.60 mg, 151.95 μmol) and (±)-2,2'-bis-(diphenylphosphino)-1,1'-binaphthyl (6.31 mg, 10.13 μmol) were added to toluene (2 mL) and the mixture was reacted for 12 hours at 110° C. under nitrogen atmosphere. The reaction mixture was concentrated under reduced pressure, and directly separated by HPLC to give the title compound (11.00 mg, 35.46%). LCMS (ESI) m/z: 612.1 [M+1]$^+$.

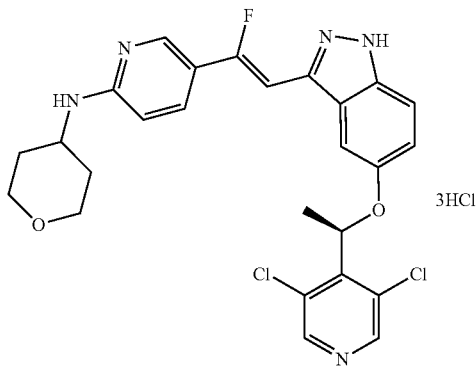 [SMILES: C[C@@H](Oc1ccc2[nH]nc(/C=C(\F)c3ccc(NC4CCOCC4)nc3)c2c1)c1c(Cl)cncc1Cl]

Example 45C

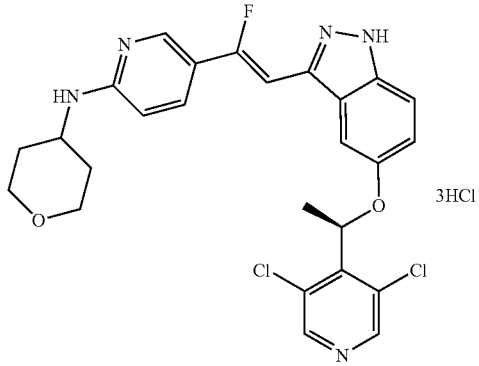

3HCl

Acetyl chloride (0.5 mL) and methanol (2 mL) were stirred at 0° C. for 30 minutes and added dropwise to a solution of Example 44B (11.00 mg, 17.96 µmol) in methanol, and the reaction mixture was stirred at 40° C. for 2 h. The reaction mixture was concentrated under reduced pressure to give the title compound (6.00 mg, 11.36 µmol, 63.22%). LCMS (ESI) m/z: 528.0 [M+1]$^+$. $^1$H NMR (400 MHz, METHANOL-d$_4$) ppm 8.59 (br. s., 2H), 8.30 (br. s., 1H), 8.13 (br. s., 1H), 7.57 (d, J=9.03 Hz, 1H), 7.34 (d, J=9.03 Hz, 1H), 7.19-7.28 (m, 2H), 6.86-7.01 (m, 1H), 6.17 (d, J=6.53 Hz, 1H), 4.07 (br. s., 1H), 4.05 (br. s., 2H), 3.64 (t, J=11.29 Hz, 2H), 2.09 (d, J=12.05 Hz, 2H), 1.82-1.89 (m, 3H), 1.74 (d, J=9.54 Hz, 2H).

Example 47

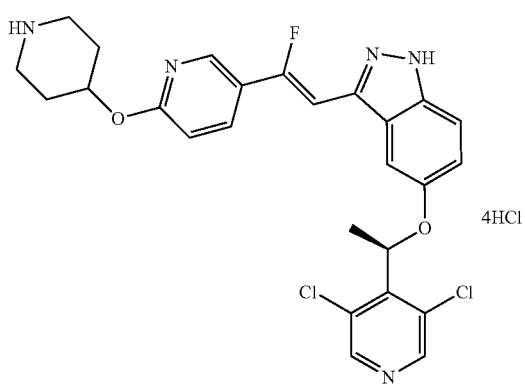 [SMILES: C[C@@H](Oc1ccc2[nH]nc(/C=C(\F)c3ccc(OC4CCNCC4)nc3)c2c1)c1c(Cl)cncc1Cl]

4HCl

This example was prepared by the method as described in Example 45. LCMS (ESI) m/z: 527.1 [M+1]$^+$ $^1$H NMR (400 MHz, METHANOL-d$_4$) ppm 8.51 (s, 1H), 8.28 (d, J=9.29 Hz, 1H), 8.11 (s, 1H), 7.51 (d, J=9.29 Hz, 1H), 7.27 (d, J=9.54 Hz, 1H), 7.21 (dd, J=2.01, 9.29 Hz, 1H), 7.14 (s, 1H), 6.71-6.87 (m, 1H), 6.04-6.16 (m, 1H), 4.06-4.20 (m, 1H), 3.59 (d, J=13.30 Hz, 2H), 3.21-3.29 (m, 2H), 2.38 (d, J=12.30 Hz, 2H).

Scheme I

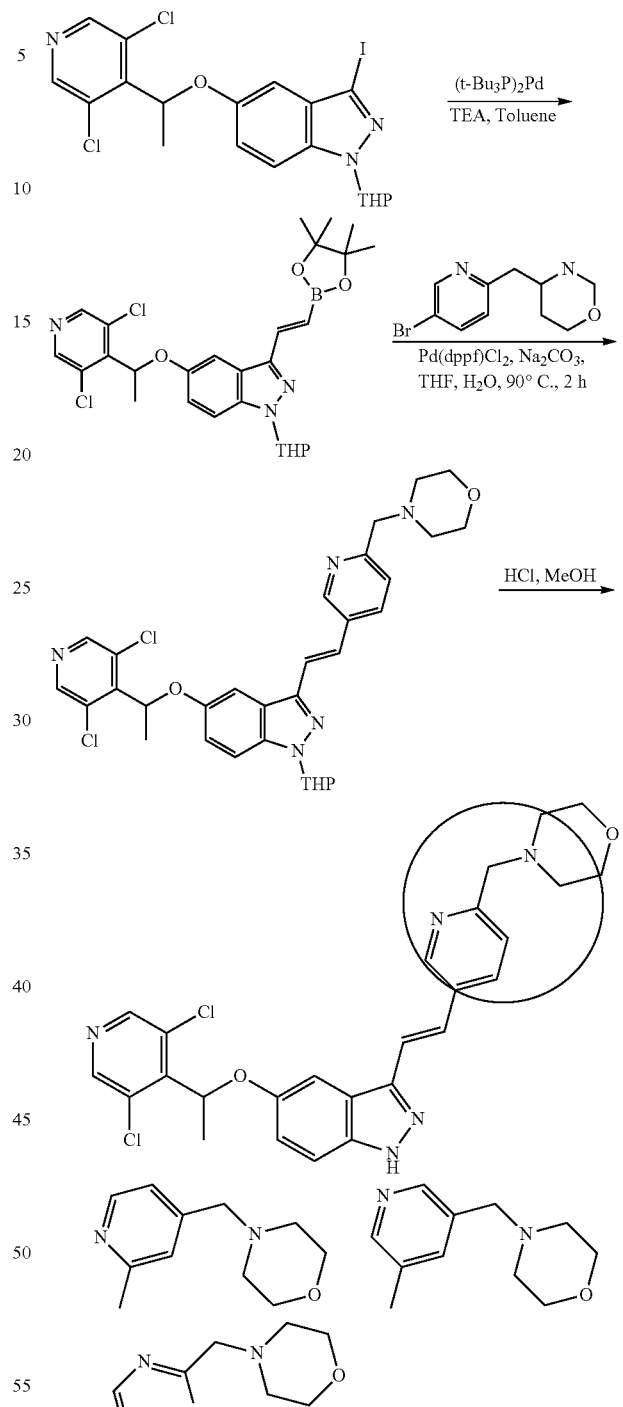

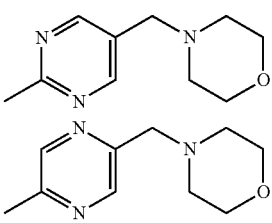

-continued

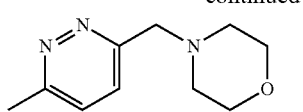

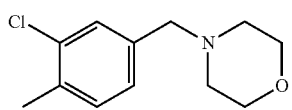

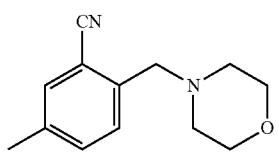

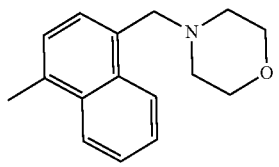

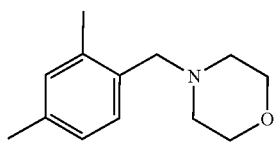

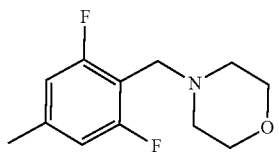

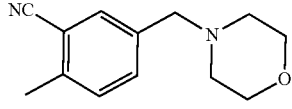

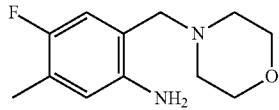

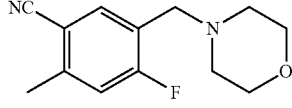

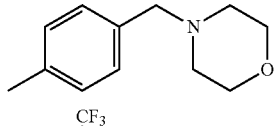

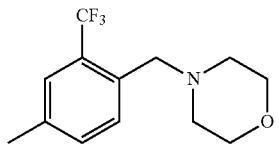

Example 48

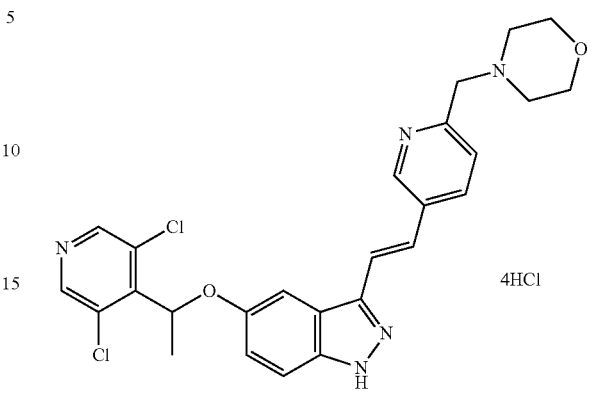

4HCl

Example 48A

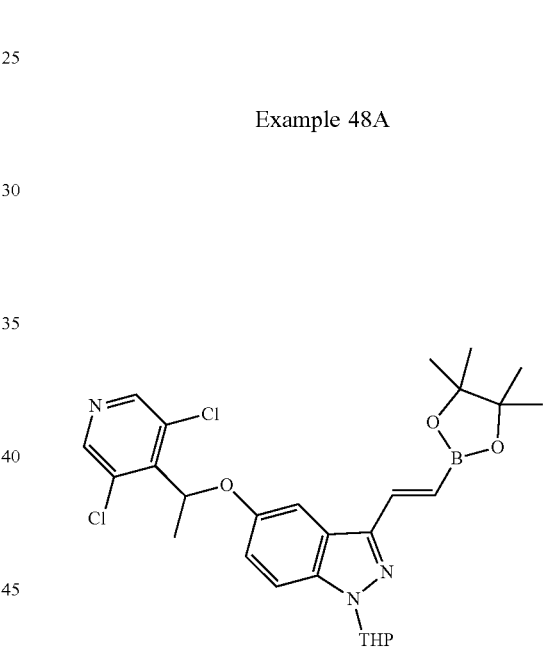

Vinyl pinacol boronate (890 mg, 5.79 mmol), Pd(t-Bu₃P)₂ (130 mg, 0.3 mmol) and triethylamine (900 mg, 8.9 mmol) were added to a solution of 1 G (1.5 g, 2.89 mmol) in toluene (10 mL) under nitrogen atmosphere, and the mixture was stirred under microwave conditions at 90° C. for 2 hours. The reaction mixture was poured into sodium bicarbonate solution (50 mL). The aqueous layer was extracted with ethyl acetate (50 mL×3), the combined organic phase was washed with brine and dried over anhydrous sodium sulfate, filtered, the filtrate was concentrated in vacuo and the residue was purified by column chromatography to give the title compound (1.2 g, yield 76%). LCMS (ESI) m/z: 544.1 [M+1]⁺.

Example 48B

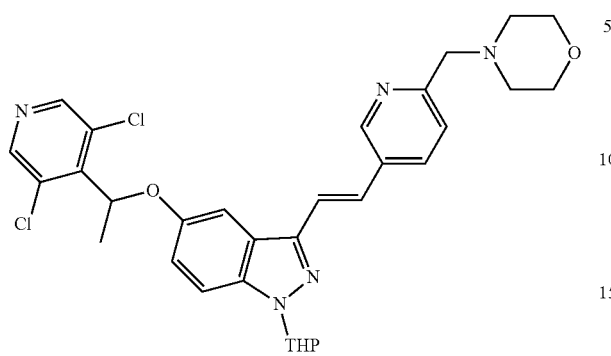

4-((5-Bromopyridin-2-yl)methyl)morpholine (60 mg, 0.23 mmol), Pd(dppf)Cl$_2$ (20 mg, 0.027 mmol) and sodium carbonate (80 mg, 0.75 mmol) were added to a solution of Example 48A (80 mg, 0.15 mmol) in tetrahydrofuran (2.5 mL) and water (0.5 mL) under nitrogen atmosphere, and the mixture was stirred under microwave at 90° C. for 1.5 hours. After being cooled to room temperature, the mixture was poured into ice-water (5 mL). The aqueous layer was extracted with ethyl acetate (10 mL×3), and the organic layers were combined, washed with brine, dried over anhydrous sodium sulfate, filtered and the filtrate was concentrated in vacuo. The residue was purified by preparative thin layer chromatography to give the title compound (50 mg, yield 57%). LCMS (ESI) m/z: 594.1 [M+1]$^+$.

Example 48C

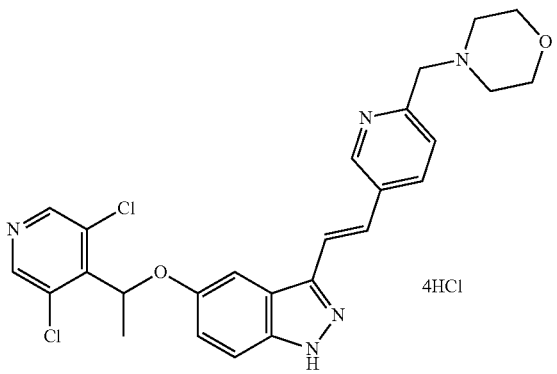 [SMILES: CC(Oc1ccc2[nH]nc(/C=C/c3ccc(CN4CCOCC4)nc3)c2c1)c1c(Cl)cncc1Cl]

Aqueous hydrochloric acid (0.6 mL) was added dropwise to a solution of Example 48B (50 mg, 0.08 mmol) in methanol (8 mL), the mixture was stirred at 28° C. for 16 hours. The mixture was basified with saturated sodium bicarbonate solution (15 mL). The aqueous layer was extracted with ethyl acetate (20 mL×3), the combined organic phase was washed with brine, dried over anhydrous sodium sulfate, filtered and the filtrate was concentrated in vacuo. The residue was purified by preparative thin layer chromatography (dichloromethane/methanol=30:1) to give the title compound (20 mg, yield 40%). LCMS (ESI) m/z: 594.1 [M+1]$^+$. $^1$HNMR (400 MHz, DMSO-d$_6$) ppm 8.94 (s, 1H), 8.60 (s, 1H), 8.27 (dd, J=8.0 &2.0 Hz, 1H), 7.65-7.69 (m, 2H), 7.49 (d, J=8.8 Hz, 1H), 7.40 (s, 1H), 7.29 (d, J=17.2 Hz, 1H), 7.11 (dd, J=9.2 &2.0 Hz, 1H), 6.18 (q, J=6.8 Hz, 1H), 4.53 (s, 2H), 3.89 (s, 4H), 3.31 (s, 4H), 1.79 (d, J=7.2 Hz, 3H).

Example 49

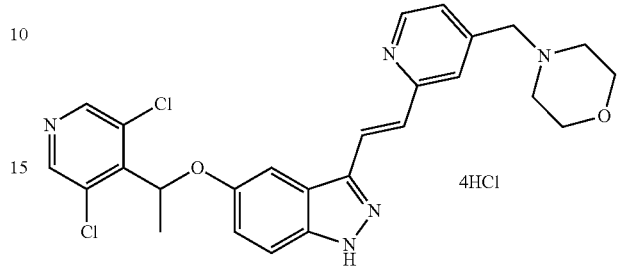

Example 49A

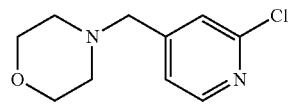 [SMILES: Clc1cc(CN2CCOCC2)ccn1]

Morpholine (1.48 g, 0.017 mol) and glacial acetic acid (0.2 mL) were added to a solution of 2-chloronicotinaldehyde (2 g, 0.014 mol) in tetrahydrofuran (40 mL) and the mixture was stirred at 20° C. for 2 hours. The mixture was added with NaBH(OAc)$_3$ (6 g, 0.028 mol) and stirred for 1 hour, then added with water (40 mL) and extracted with ethyl acetate (30 mL×3). The organic layers were combined and washed with saturated brine, dried over sodium sulfate, filtered and the solvent was evaporated off under reduced pressure to give the title compound as a colorless oil (2 g, yield 67%). $^1$H NMR (CHLOROFORM-d, Bruker Avance 400 MHz) ppm 8.30 (d, J=5.0 Hz, 1H), 7.34 (s, 1H), 7.21 (d, J=4.3 Hz, 1H), 3.79-3.65 (m, 4H), 3.48 (s, 2H), 2.52-2.36 (m, 4H).

Example 49B

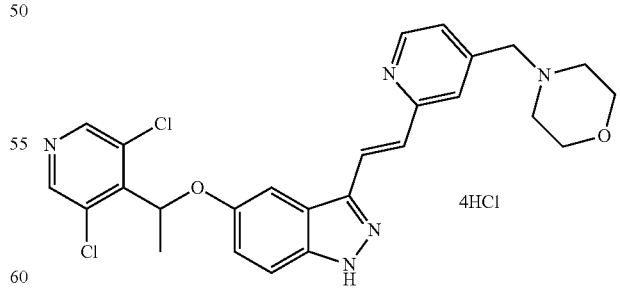

This example was prepared by the method as described in Example 48. LCMS (ESI) m/z: 510.0 [M+1]$^+$.

$^1$H NMR (DMSO-d$_6$, Bruker Avance 400 MHz): ppm 8.74 (d, J=4.8 Hz, 1H), 8.62 (s, 2H), 7.90 (d, J=16.6 Hz, 1H), 7.73 (s, 1H), 7.51 (d, J=9.0 Hz, 1H), 7.43 (d, J=4.5 Hz, 1H), 7.37-7.27 (m, 2H), 7.12 (dd, J=2.1, 8.9 Hz, 1H), 6.17 (q, J=6.4 Hz, 1H), 4.40 (br. s., 2H), 3.22 (br. s., 8H), 1.79 (d, J=6.5 Hz, 3H).

Example 50

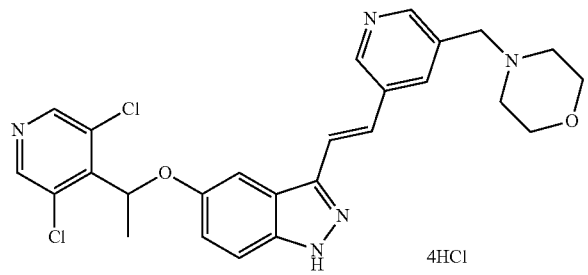 [SMILES: CC(Oc1ccc2[nH]nc(/C=C/c3cncc(CN4CCOCC4)c3)c2c1)c1c(Cl)cncc1Cl]

4HCl

Example 50A

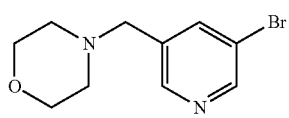 [SMILES: Brc1cncc(CN2CCOCC2)c1]

Morpholine (1.1 g, 0.013 mol) and glacial acetic acid (0.2 mL) were added to a solution of 5-bromonicotinaldehyde (2 g, 0.01 mol) in tetrahydrofuran (40 mL) and stirred at 20° C. for 2 hours. The mixture was added with NaBH(OAc)$_3$ (4.3 g, 0.02 mol) and stirred for 1 hour, then added with water (40 mL) and extracted with ethyl acetate (30 mL×3). The organic layers were combined and washed with saturated brine, dried over sodium sulfate, filtered and evaporated to dryness under reduced pressure to give the title compound (as a colorless oil, 2 g, yield 71%).

Example 50B

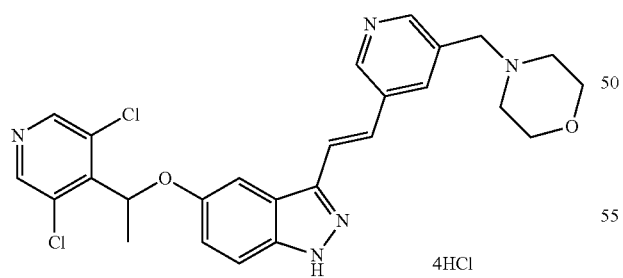

4HCl

This example was prepared by the method as described in Example 48. LCMS (ESI) m/z: 510.0 [M+1]$^+$.

$^1$H NMR (DMSO-d$_6$, Bruker Avance 400 MHz): ppm 8.91 (s, 1H), 8.60 (s, 2H), 8.28 (s, 1H), 7.62 (d, J=16.8 Hz, 1H), 7.49 (d, J=9.0 Hz, 1H), 7.40 (s, 1H), 7.30 (d, J=16.8 Hz, 1H), 7.11 (dd, J=2.1, 9.2 Hz, 1H), 6.22-6.13 (m, 1H), 4.44 (br. s., 2H), 4.02-3.62 (m, 4H), 3.27-3.13 (m, 4H), 1.79 (d, J=6.8 Hz, 3H).

Example 51

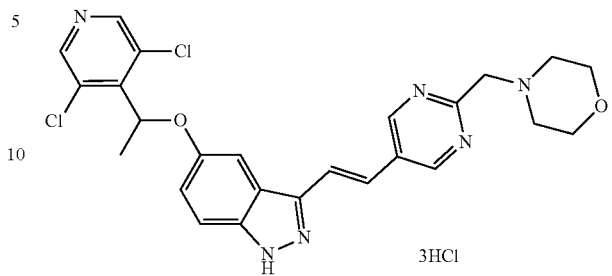

3HCl

This example was prepared by the method as described in Example 48. LCMS (ESI) m/z: 511.1 [M+1]$^+$.

$^1$H NMR (DMSO-d$_6$, Bruker Avance 400 MHz) ppm 13.35 (s, 1H), 9.24 (s, 2H), 8.60 (s, 2H), 7.83 (d, J=16.8 Hz, 1H), 7.51-7.46 (m, 2H), 7.29 (d, J=16.8, 1H), 7.11-7.09 (m, 1H), 6.20-6.16 (m, 1H), 4.72 (s, 2H), 3.93 (d, J=19.8, 4H), 3.52 (s, 4H), 1.79 (s, 3H).

Example 52

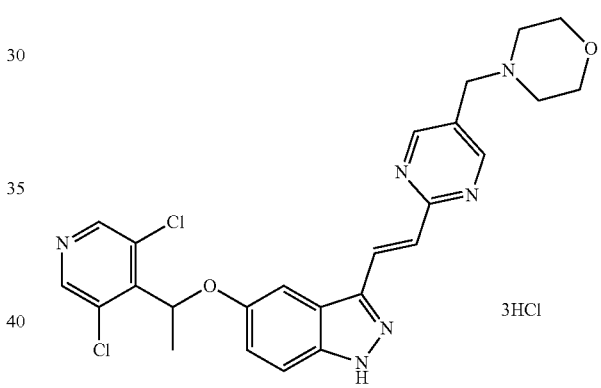

3HCl

Example 52A

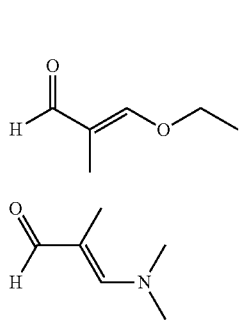

2a

2b

At 0° C., DMF (62 mL) was dropwise added slowly to vigorously stirred phosphorus oxychloride (64 mL) below 30° C. After heated to 40° C., the reaction solution was slowly added with 1,1-diethoxypropane (53 mL, 307.9 mmol) with the temperature kept between 60° C. to 70° C., and then the dark brown reaction solution was heated to 70°

C. and stirred for 2 hours. After cooled to room temperature, the mixture was poured to ice water and kept overnight, then adjusted to pH=9 with anhydrous potassium carbonate. The aqueous layer was extracted with dichloromethane, the organic layer was dried and concentrated in vacuo to give the title compound as a liquid (15 g, crude mixture).

Example 52B

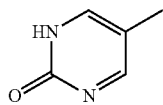

Sodium (12.2 g, 530.3 mmol) was added to absolute ethanol (200 mL) at room temperature and the mixture was stirred until sodium disappeared. Then, a solution of (E)-3-ethoxy-2-methylacrolein and (E)-3-(dimethylamino)-2-methylacrolein (15 g, 134 mmol) in ethanol (100 mL) and urea (9.6 g, 159 mmol) were added, the mixture was stirred under reflux for 2 days. The reaction solution was adjusted to pH=9 and continued to reflux overnight, and then concentrated in vacuo. The residue was purified by column chromatography to give the title compound (9 g). $^1$H NMR (400 MHz, DMSO-$d_6$) ppm 7.92-8.14 (m, 2H), 2.52 (s, 3H).

Example 52C

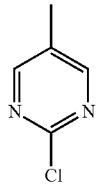

A solution of Example 52B (8.8 g, 79.9 mmol) in phosphorus oxychloride (50 mL) was stirred overnight at 90° C. The reaction solution was poured into ice water, and sodium bicarbonate solution was added, the aqueous layer was extracted with dichloromethane. The organic layer was concentrated to give the title compound (2.8 g). $^1$H NMR (400 MHz, DMSO-$d_6$) ppm 2.27 (s, 3H) 8.64 (s, 2H).

Example 52D

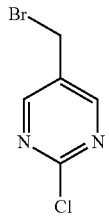

NBS (0.28 g, 1.56 mmol) and AIBN (0.05 g, 0.31 mmol) were added to a solution of Example 52C (0.2 g, 1.56 mmol) in carbon tetrachloride (10 mL) and the mixture was stirred at 80° C. for 12 hours. Water was added and the aqueous layer was extracted with dichloromethane. The organic layer was purified by preparative TLC (ethyl acetate) to give the title compound (40 mg), LCMS (ESI) m/z: 206 [M+1]$^+$.

Example 52E

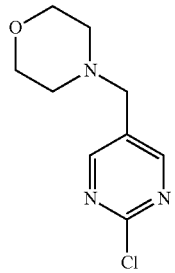

Morpholine (0.25 g, 2.9 mmol) and potassium carbonate (0.65 g, 4.8 mmol) were added to a solution of 5-(bromomethyl)-2-chloropyrimidine (0.5 g, 2.4 mmol) in DMF (5 mL), and the mixture was stirred at room temperature for 12 hours. Water was added and the aqueous layer was extracted with dichloromethane. The organic layer was purified by preparative TLC to give the title compound (330 mg), LCMS (ESI) m/z: 214 [M+1]$^+$. $^1$H NMR (400 MHz, DMSO-$d_6$) ppm 2.34-2.42 (m, 4H), 3.50-3.54 (m, 2H), 3.56 (d, J=4.52 Hz, 4H), 8.71 (s, 2H).

Example 52F

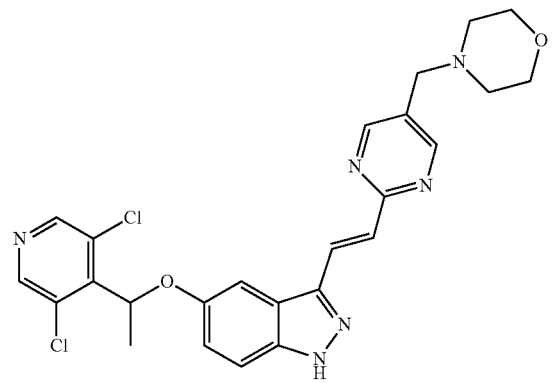 [SMILES: CC(Oc1ccc2[nH]nc(/C=C/c3ncc(CN4CCOCC4)cn3)c2c1)c1c(Cl)cncc1Cl]

This example was prepared by the method as described in Example 24K. LCMS (ESI) m/z: 511.1 [M+1]$^+$.

$^1$H NMR (DMSO-$d_6$, Bruker Avance 400 MHz) ppm 1.85 (d, J=6.62 Hz, 3H) 3.46-3.56 (m, 1H) 3.81 (t, J=12.46 Hz, 1H) 4.10 (d, J=12.13 Hz, 2H) 4.50 (s, 2H) 6.20 (d, J=6.62 Hz, 1H) 7.21 (dd, J=9.04, 1.98 Hz, 1H) 7.27 (s, 1H) 7.35 (d, J=16.32 Hz, 1H) 7.50 (d, J=9.04 Hz, 1H) 8.28 (d, J=16.32 Hz, 1H) 8.50 (s, 2H) 9.00 (s, 2H).

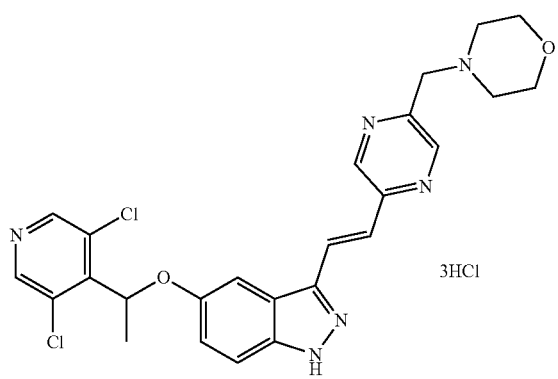 [SMILES: CC(Oc1ccc2[nH]nc(/C=C/c3cnc(CN4CCOCC4)cn3)c2c1)c1c(Cl)cncc1Cl]

This example was prepared by the method as described in Example 52. LCMS (ESI) m/z: 511.2 [M+1]+.

¹H NMR (DMSO-d₆, Bruker Avance 400 MHz) ppm 1.83 (d, J=6.39 Hz, 3H) 3.33-3.46 (m, 2H) 3.60 (d, J=9.26 Hz, 2H) 3.90 (br. s., 2H) 4.09 (d, J=11.91 Hz, 2H) 4.65 (br. s., 2H) 6.17 (d, J=6.39 Hz, 1H) 7.17-7.26 (m, 2H) 7.36 (d, J=16.10 Hz, 1H) 7.50 (d, J=9.04 Hz, 1H) 8.03 (d, J=16.32 Hz, 1H) 8.52 (br. s., 2H) 8.75-8.87 (m, 2H).

Example 54

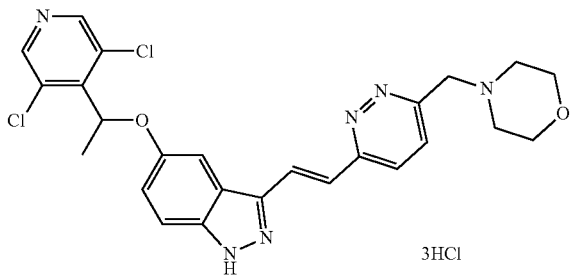 [SMILES: CC(Oc1ccc2[nH]nc(/C=C/c3ccc(CN4CCOCC4)nn3)c2c1)c1c(Cl)cncc1Cl]

This example was prepared by the method as described in Example 52. LCMS (ESI) m/z: 511.1 [M+1]+.

¹H NMR (MeOD-d₄, Bruker Avance 400 MHz) ppm 8.49 (s, 2H), 8.23 (d, J=8.4 Hz, 1H), 8.07 (d, J=16.4 Hz, 1H), 7.92 (d, J=8.8 Hz, 1H), 7.51-7.49 (m, 2H), 7.36 (s, 1H), 7.22 (d, J=2.0 Hz, 1H), 6.25-6.20 (q, 1H), 4.79 (s, 2H), 4.02 (s, 4H), 3.54 (s, 4H), 1.86 (d, J=6.4 Hz, 3H).

Example 55

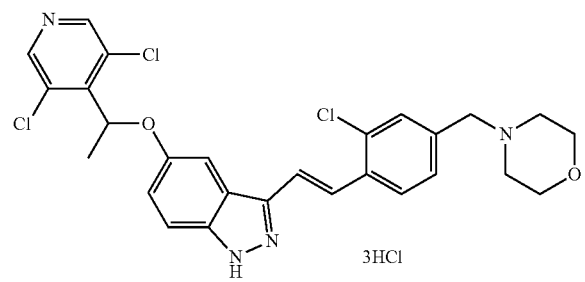 [SMILES: CC(Oc1ccc2[nH]nc(/C=C/c3ccc(CN4CCOCC4)cc3Cl)c2c1)c1c(Cl)cncc1Cl]

This example was prepared by the method as described in Example 51. LCMS (ESI) m/z: 543.1 [M+1]+. ¹H NMR (DMSO-d₆, Bruker Avance 400 MHz) ppm 1.77 (d, J=6.62 Hz, 3H) 2.33 (d, J=1.76 Hz, 4H) 3.49 (s, 2H) 3.60 (d, J=4.19 Hz, 4H) 5.97-6.26 (m, 1H) 6.99-7.19 (m, 1H) 7.26-7.38 (m, 2H) 7.39-7.60 (m, 5H) 7.89 (d, J=7.94 Hz, 1H) 8.57 (s, 2H) 13.21 (s, 1H).

Example 56

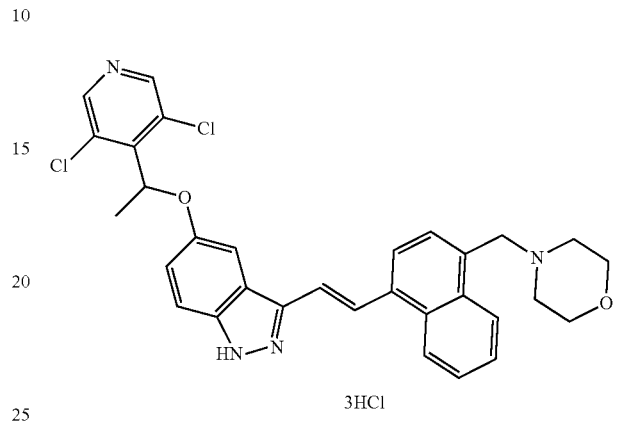

This example was prepared by the method as described in Example 51. LCMS (ESI) m/z: 559.1 [M+1]+. ¹H NMR (400 MHz, METHANOL-d₄) ppm 8.45-8.33 (m, 4H), 7.93 (d, J=9.2 Hz, 1H), 7.81 (d, J=6.4 Hz, 4H), 7.54 (d, J=8.8 Hz, 2H), 7.32-7.28 (m, 2H), 6.20 (d, J=6 Hz, 1H), 4.96 (s, 2H) 4.06 (d, J=12.4 Hz 2H) 3.85-3.80 (m, 2H) 3.48 (s, 4H), 1.84 (d, J=6.4 Hz, 3H).

Example 57

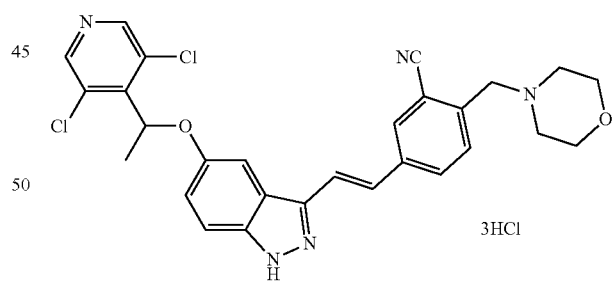

This example was prepared by the method as described in Example 51. LCMS (ESI) m/z: 577.1 [M+1]+. ¹H NMR (CD₃OD, 400 MHz): ppm 8.47 (s, 2H), 8.16 (s, 1H), 8.04 (d, J=6.8 Hz, 1H), 7.86 (d, J=8.4 Hz, 1H), 7.58 (d, J=16.8 Hz, 1H), 7.46 (d, J=9.2 Hz, 1H), 7.30 (d, J=13.6 Hz, 2H), 7.23 (d, J=31.2 Hz, 1H), 6.23-6.18 (m, 1H), 4.62 (s, 2H), 4.08 (br. s., 2H), 3.80 (br. s., 2H), 3.46 (d, J=41.6 Hz, 4H), 1.84 (d, J=6.8 Hz, 3H).

Example 58

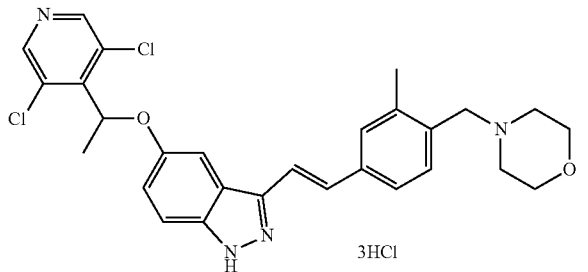 [SMILES: Cc1cc(/C=C/c2n[nH]c3ccc(OC(C)c4c(Cl)cncc4Cl)cc23)ccc1CN1CCOCC1]

This example was prepared by the method as described in Example 51. LCMS (ESI) m/z: 523.2 [M+1]⁺. ¹H NMR (DMSO-d$_6$, Bruker Avance 400 MHz) ppm 1.78 (d, J=6.62 Hz, 3H) 2.43-2.46 (m, 3H) 3.84-3.97 (m, 4H) 4.35 (br. s., 2H) 6.17 (q, J=6.62 Hz, 1H) 7.09 (dd, J=8.93, 1.87 Hz, 1H) 7.18 (d, J=16.76 Hz, 1H) 7.33 (s, 1H) 7.44-7.53 (m, 2H) 7.57 (s, 2H) 7.69 (d, J=8.38 Hz, 1H) 8.61 (s, 2H).

Example 59

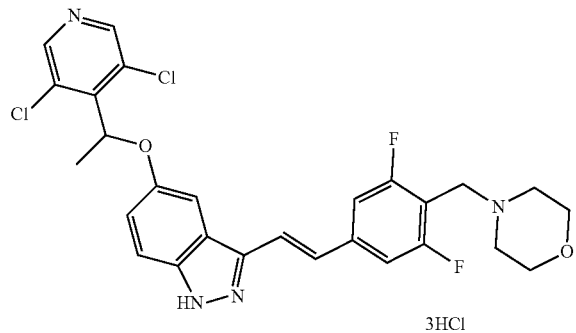 [SMILES: CC(Oc1ccc2[nH]nc(/C=C/c3cc(F)c(CN4CCOCC4)c(F)c3)c2c1)c1c(Cl)cncc1Cl]

This example was prepared by the method as described in Example 51. LCMS (ESI) m/z: 577.1 [M+1]⁺.

¹H NMR (MeOD-d$_4$, Bruker Avance 400 MHz) ppm 8.49 (s, 2H), 7.46-7.41 (m, 2H), 7.26-7.19 (m, 5H), 6.22-6.19 (m, 1H), 4.58 (s, 2H), 3.70 (t, J=4.4 Hz, 4H), 2.58 (s, 4H), 1.85 (d, J=6.8 Hz, 3H).

Example 60

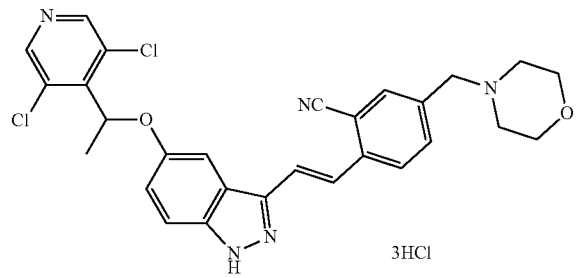 [SMILES: CC(Oc1ccc2[nH]nc(/C=C/c3ccc(CN4CCOCC4)cc3C#N)c2c1)c1c(Cl)cncc1Cl]

Example 60A

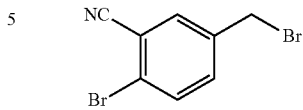

2-Bromo-5-methylbenzonitrile (0.5 g, 2.53 mmol) and NBS (404.58 mg, 2.27 mmol) were dissolved in tetrachloromethane (20 mL) and AIBN (catalytic amount) was added to the above solution. The reaction solution was refluxed for 12 hours at a range of temperature of 60° C. to 80° C. and the reaction solution was poured into water (20 mL). The organic layer was separated, washed with brine, then dried over anhydrous sodium sulfate, and concentrated under pressure to give the title compound (as a colorless liquid, 0.5 g, yield 72%).

Example 60B

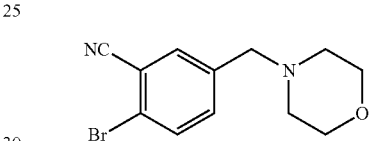

2-Bromo-(benzylbromide)benzonitrile was dissolved in methanol (20 mL). Morpholine (661.3 mg, 7.58 mmol) was added dropwise to the above solution and the reaction was stirred at room temperature for 16 hours. The pH of the reaction solution was adjusted to 2.0, the organic phase was washed with water (10 mL×3), and the pH of the organic layer was adjusted to 11. The final organic phase was extracted with dichloromethane (20 mL) for three times and the organic phase was concentrated to give the title compound (as a pale yellow oil, 350 mg, yield 49.4%). LCMS (ESI) m/z: 281.6 [M+1]⁺.

Example 60C

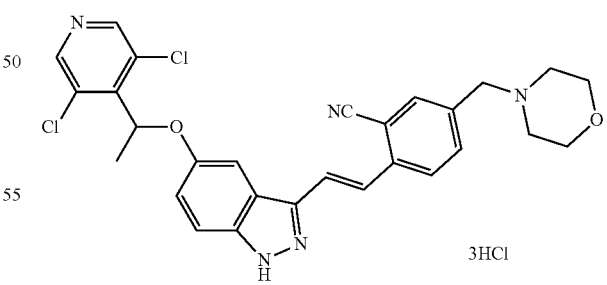

This example was prepared by the method as described in Example 51. LCMS (ESI) m/z: 534.1 [M+1]⁺.

¹H NMR (MeOD-d$_4$, Bruker Avance 400 MHz): ppm. 77 (d, J=6.39 Hz, 3H) 2.39 (br. s., 4H) 3.60 (br. s., 6H) 6.15 (d, J=6.62 Hz, 1H) 7.12 (d, J=8.82 Hz, 1H) 7.39-7.59 (m, 3H) 7.63-7.73 (m, 2H) 7.77 (s, 1H) 8.06 (d, J=8.16 Hz, 1H) 8.57 (s, 2H) 13.33 (br. s., 1H).

Example 61

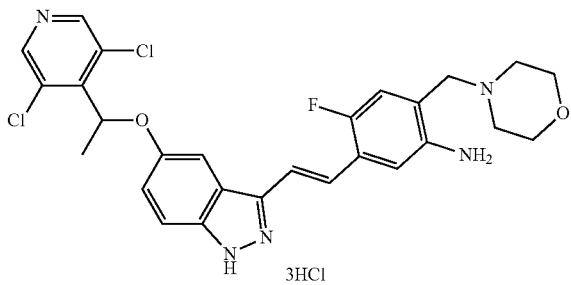 [SMILES: CC(Oc1ccc2[nH]nc(/C=C/c3cc(N)c(CN4CCOCC4)cc3F)c2c1)c1c(Cl)cncc1Cl]

Example 61A

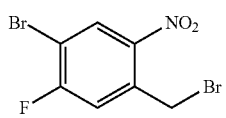

1-Bromo-2-Fluoro-4-methyl-5-nitrobenzene (2.0 g, 8.5 mmol) and NBS (1.53 g, 8.6 mmol) were dissolved in CCl$_4$ (15 mL) and AIBN (100 mg, 0.61 mmol) was added to the above solution. The reaction was refluxed for 16 hours. Water (20 mL) was added to the solution and the organic layer was separated and washed with brine, dried over anhydrous sodium sulfate and concentrated under reduced pressure to give the title compound (as a brown oil, 2.7 g, yield 50%).

Example 61B

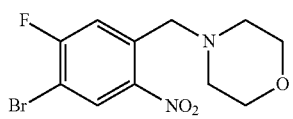

Example 61A (2.7 g, 4.3 mmol) was dissolved in methanol and morpholine (750 mg, 8.6 mmol) was slowly added dropwise at 0° C. The reaction solution was stirred at 0° C. for 4 hours. The reaction solution was diluted with water (50 mL) and extracted with dichloromethane (50 mL×2). The organic phase was dried over anhydrous sodium sulfate, filtered and concentrated under reduced pressure to give a residue. The residue was purified by column chromatography (ethyl acetate/petroleum ether=1/10 to 1/5) to give the title compound (740 mg, yield 54%). LCMS (ESI) m/z: 318.7 [M+1]$^+$.

Example 61C

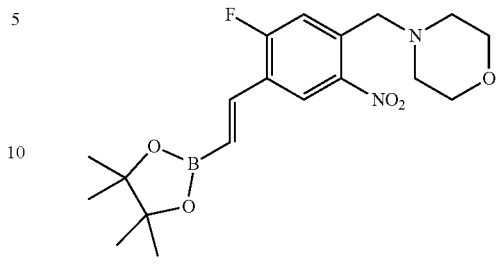

Example 61B (200 mg, 0.63 mmol) was dissolved in toluene (4 mL), and 4,4,5,5-tetramethyl-2-vinyl-1,3,2-boronic acid pinacol ester (200 mg, 1.98 mmol), Pd(t-Bu$_3$P)$_2$ (48 mg, 0.09 mmol) and Et$_3$N (200 mg, 1.98 mmol) were added to the solution under nitrogen atmosphere, and the reaction solution was stirred under microwave conditions at 80° C. for 1 hour. The reaction solution was poured into sodium bicarbonate solution (10 mL), extracted with ethyl acetate (10 mL×3), washed with brine, dried and concentrated under reduced pressure to obtain a residue which was separated by column chromatography to give the title compound (195 mg, yield 56%). LCMS (ESI) m/z: 393 [M+1]$^+$.

Example 61D

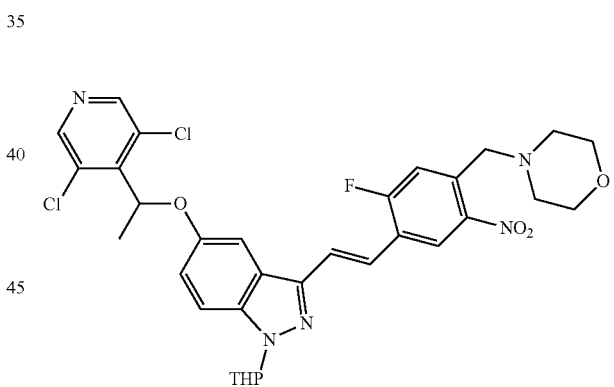

Example 61C (150 mg, 0.28 mmol) was dissolved in a mixture of tetrahydrofuran and water (5/1, 3 mL). Then, 1 G (170 mg, 0.28 mmol), Na$_2$CO$_3$ (100 mg, 0.84 mmol) and Pd(dppf)Cl$_2$ (20 mg, 0.027 mmol) were added to the above solution under nitrogen atmosphere. The reaction solution was reacted under nitrogen atmosphere at 80° C. for 1 hour under microwave conditions, and added with water (5 mL). The mixture was extracted with ethyl acetate (10 mL×3), washed with brine, dried and concentrated under reduced pressure. The resulting residue was separated by thin layer chromatography (ethyl acetate/petroleum ether=1/2) to give the title compound (220 mg, yield 96%). LCMS (ESI) m/z: 656.0 [M+1]$^+$.

Example 61E

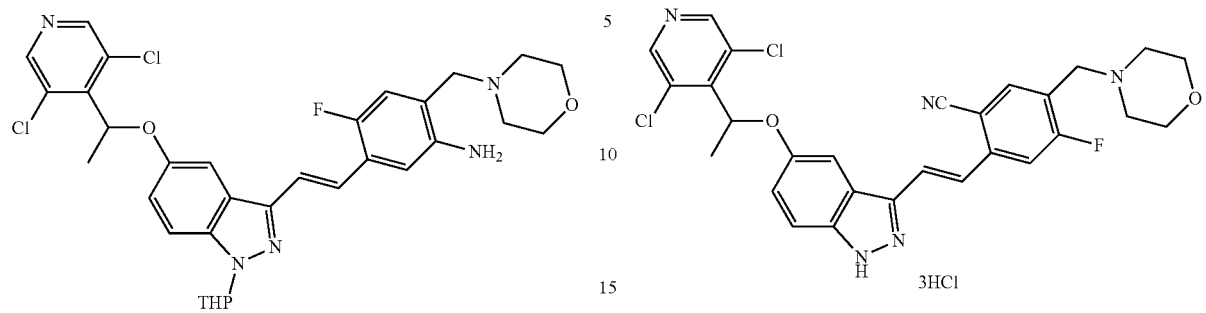

Example 61D (80 mg, 0.12 mmol) was dissolved in a mixture of ethanol (10 mL) and water (5 mL). The reduced iron powder (50 mg, 0.89 mmol), ammonium chloride (50 mg, 0.94 mmol) were added to the reaction solution, and the reaction solution was refluxed for 6 hours. The reaction was quenched with saturated sodium bicarbonate solution (10 mL) and extracted with dichloromethane (10 mL×3). The organic phase was washed with brine, dried over anhydrous sodium sulfate and concentrated under reduced pressure. The residue was separated by thin layer chromatography (methylene chloride/methanol=20/1) to give the title compound (as a pale yellow liquid, 80 mg, yield 73%). LCMS (ESI) m/z: 538.9 [M+1]$^+$.

Example 61F

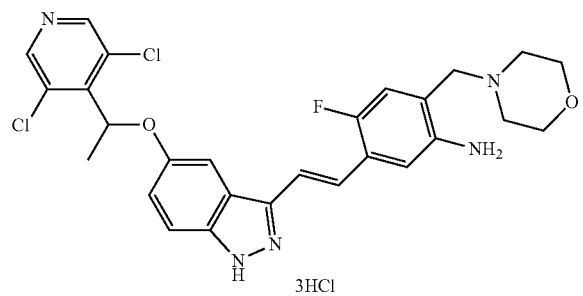 [SMILES: CC(Oc1ccc2[nH]nc(/C=C/c3cc(N)c(CN4CCOCC4)cc3F)c2c1)c1c(Cl)cncc1Cl]

Example 61E (80 mg, 0.09 mmol) was dissolved in methanol (2 mL) and then concentrated hydrochloric acid (0.1 mL) was added dropwise to the solution. The reaction solution was stirred at 30° C. for 16 hours. The reaction solution was added with saturated sodium bicarbonate (15 mL) and extracted with ethyl acetate (20 mL×3). The organic phase was concentrated under reduced pressure to give a residue. The residue was purified by thin layer chromatography (methylene chloride/methanol=10/1) to give the title compound (as a pale yellow liquid, 44 mg, yield 63%). LCMS (ESI) m/z: 542.0 [M+1]$^+$. $^1$H NMR (CDCl$_3$, Bruker Avance 400 MHz): ppm 8.44 (s, 2H), 7.37 (d, J=8.8 Hz, 1H), 7.34 (s, 2H), 7.25 (d, J=2.0 Hz, 1H), 7.16 (dd, J$_1$=2.0 Hz, J$_2$=8.8, 1H), 6.91 (d, J=6.4 Hz, 1H), 6.83 (d, J=10.4 Hz, 1H), 6.10 (q, J=6.4 Hz, 1H), 4.35 (d, J=4.8 Hz, 2H), 3.75 (s, 3H), 3.56 (s, 1H), 3.48 (s, 6H), 1.82 (d, J=6.4 Hz, 3H).

Example 62

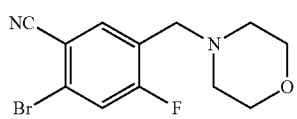 [SMILES: N#Cc1cc(CN2CCOCC2)c(F)cc1Br]

Example 62A

2-Bromo-4-fluoro-5-methylbenzonitrile (1 g, 4.67 mmol) and NBS (838 mg, 4.7 mmol) were dissolved in carbon tetrachloride (15 mL). AIBN (50 mg, 0.30 mmol) was then added to the solution. The reaction was refluxed for 16 hours. The reaction was quenched in water (20 mL), the organic phase was separated and washed with brine (40 mL). The organic phase was dried over anhydrous sodium sulphate and evaporated to give the crude title compound (as a brown oil, 1.2 g, purity 70%).

Example 62B

Morpholine (500 mg, 5.8 mmol) was added dropwise to a solution of Example 62A (1.2 g, 2.9 mmol) in methanol (40 mL) at 0° C. and the mixture was allowed to react for 4 hours. The reaction solution was diluted with water (50 mL) and extracted with dichloromethane (50 mL×2). The organic phases were collected, dried over anhydrous sodium sulfate and filtered to give a filtrate which was evaporated to dryness under increased pressure. The residue was purified by column chromatography to give the title compound (600 mg, yield 69%). LCMS (ESI) m/z: 300.6 [M+1]$^+$.

Example 62C

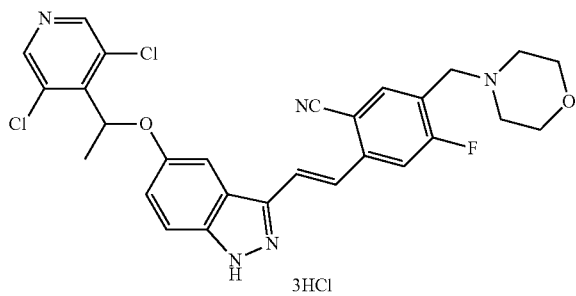 [SMILES: CC(Oc1ccc2[nH]nc(/C=C/c3cc(F)c(CN4CCOCC4)cc3C#N)c2c1)c1c(Cl)cncc1Cl]

3HCl

This example was prepared by the method as described in Example 51. LCMS (ESI) m/z: 551.9 [M+1]$^+$.

$^1$H NMR (MeOD-d$_4$, Bruker Avance 400 MHz): ppm 8.47 (s, 2H), 8.14 (d, J=6.8 Hz, 1H), 7.96 (d, J=11.2 Hz, 1H), 7.60-7.8 (m, 2H), 7.50 (d, J=9.6 Hz, 1H), 7.42 (d, J=1.6 Hz, 1H), 7.23 (dd, J$_1$=8.8 Hz, J$_2$=2.0 Hz, 1H), 6.24 (q, J=7.2 Hz, 1H), 4.52 (s, 2H), 4.09 (d, J=12.4 Hz, 2H), 3.83 (t, J=12.4 Hz, 2H), 3.50 (d, J=12 Hz, 2H), 3.35 (t, J=12.4 Hz, 2H), 1.84 (d, J=6.4 Hz, 3H).

Example 63

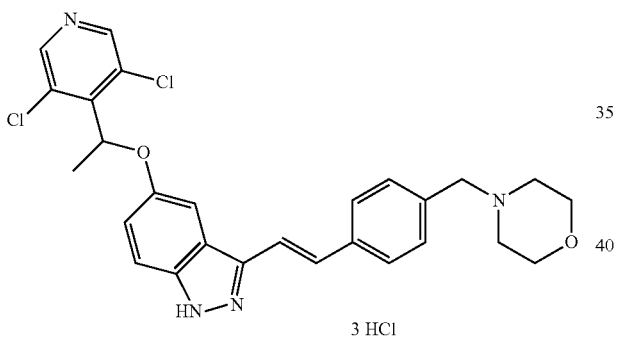

3 HCl

Example 63A

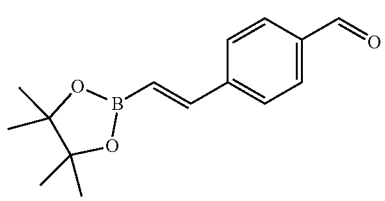 [SMILES: CC1(C)OB(/C=C/c2ccc(C=O)cc2)OC1(C)C]

Vinyl pinacol boronate (923 mg, 6 mmol), Pd(t-Bu$_3$P)$_2$ (56 mg, 0.11 mmol) and triethylamine (1.1 g, 10.9 mmol) were added to a solution of 4-bromobenzaldehyde (1 g, 5.45 mmol) in toluene (10 mL), and the mixture was stirred under nitrogen atmosphere at 80° C. for 5 hours. The mixture was poured into sodium bicarbonate solution (10 mL), the aqueous layer was extracted with ethyl acetate (10 mL×3), and the organic layers were combined and washed with brine, dried over anhydrous sodium sulfate, filtered, the filtrate was concentrated in vacuo and the residue was purified by column chromatography to give the title compound as a yellowish solid (1 g, yield 71%). $^1$HNMR (CHLOROFORM-d, Bruker Avance 400 MHz) ppm 10.01 (s, 1H), 7.86 (d, J=8.3 Hz, 2H), 7.63 (d, J=8.3 Hz, 2H), 7.43 (d, J=18.6 Hz, 1H), 6.33 (d, J=18.3 Hz, 1H), 1.33 (s, 12H).

Example 63B

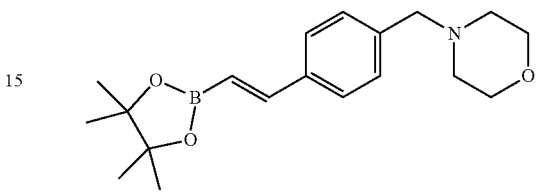

Morpholine (202 mg, 2.4 mmol), sodium cyanoborohydride (93 mg, 1.5 mmol) and glacial acetic acid (0.1 mL) were added to a solution of Example 63A (300 mg, 1.2 mmol) in dichloromethane (5 mL) and the mixture was stirred for 2 hours at 30° C. Water (5 mL) was added, the aqueous layer was extracted with dichloromethane (10 mL×3), the organic layers were combined, washed with brine, dried over anhydrous sodium sulfate, filtered and the filtrate was concentrated in vacuo. The residue was purified by preparative TLC (ethyl acetate/petroleum ether=1:10) to give the title compound as a yellowish oil (240 mg, yield 63%), LCMS (ESI) m/z: 330.1 [M+1]$^+$.

Example 63C

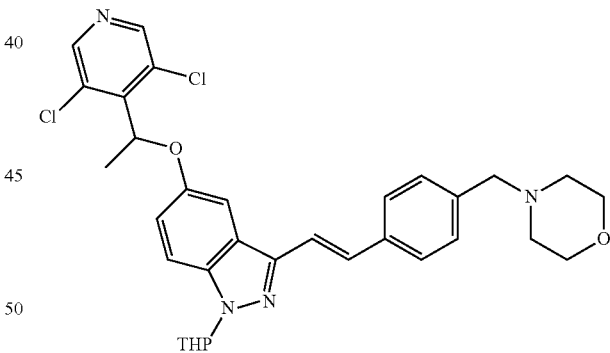

63B (96 mg, 0.29 mmol), Pd(dppf)Cl$_2$ (15 mg, 0.02 mmol) and sodium carbonate (40 mg, 0.38 mmol) were added to a solution of 1 G (100 mg, 0.19 mmol) in tetrahydrofuran (5 mL) and water (1.0 mL) under nitrogen gas atmosphere, and the mixture was stirred at 80° C. for 18 hours. After being cooled to room temperature, the mixture was poured into ice-water (5 mL). The aqueous layer was extracted with ethyl acetate (10 mL×3), the organic layers were combined and washed with brine, dried over anhydrous sodium sulfate, filtered and the filtrate was concentrated in vacuo. The residue was purified by preparative TLC (ethyl acetate/petroleum ether=1:2) to give the title compound as a yellowish oil (50 mg, yield 43%). LCMS (ESI) m/z: 593.5 [M+1]$^+$.

Example 63D

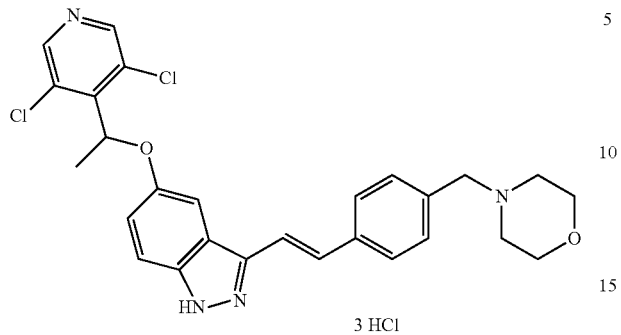

3 HCl

The aqueous hydrochloric acid (0.1 mL) was dropwise added to a solution of Example 63C (50 mg, 0.08 mmol) in methanol (2 mL) and the mixture was stirred at 30° C. for 4 hours, and then concentrated in vacuo. The residue was purified by preparative liquid chromatography to give the title compound (15 mg, yield 35%), LCMS (ESI) m/z: 501.0 [M+1]+. $^1$H NMR (DMSO-d$_6$, Bruker Avance 400 MHz) ppm 11.35 (br. s., 1H), 8.62 (s, 2H), 7.78-7.71 (m, 2H), 7.67 (d, J=8.3 Hz, 2H), 7.55-7.46 (m, 2H), 7.35 (d, J=2.0 Hz, 1H), 7.24 (d, J=16.6 Hz, 1H), 7.14-7.08 (m, 1H), 6.18 (q, J=6.8 Hz, 1H), 4.35 (d, J=4.8 Hz, 2H), 4.00-3.92 (m, 3H), 3.26 (d, J=12.0 Hz, 2H), 3.11 (d, J=12.0 Hz, 3H), 1.79 (d, J=6.5 Hz, 3H).

Example 64

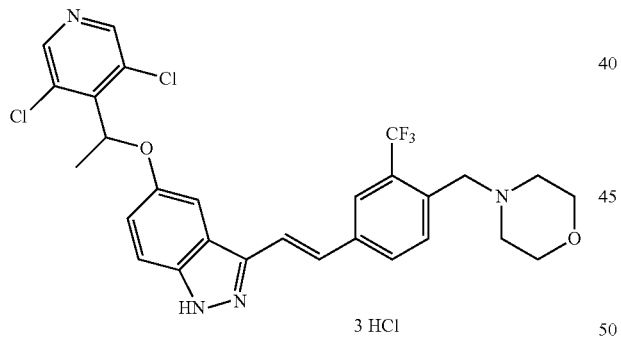

3 HCl

This example was prepared by the method as described in Example 63. LCMS (ESI) m/z: 577.1 [M+1]+.

$^1$H NMR (CDCl$_3$, Bruker Avance 400 MHz): ppm 8.46 (s, 2H), 7.84-7.80 (m, 2H), 7.72 (s, 1H), 7.44-7.37 (m, 2H), 7.22-7.16 (m, 3H), 6.12-6.06 (m, 1H), 3.73 (d, J=28.0 Hz, 6H), 2.53 (s, 4H), 1.85 (d, J=6.8 Hz, 3H).

Scheme J

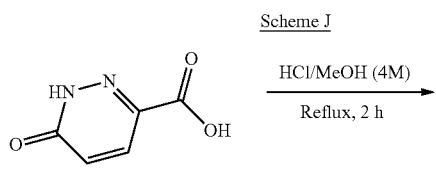

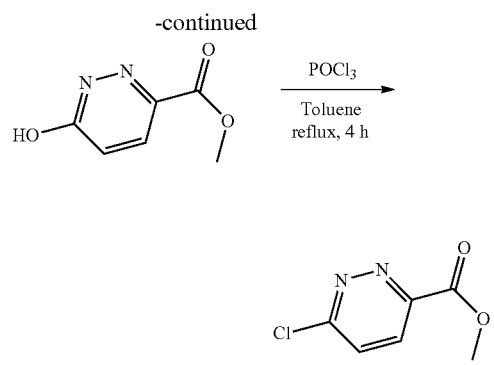

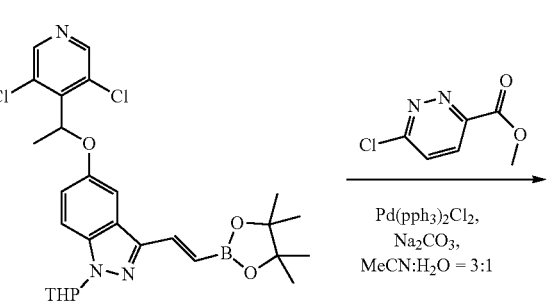

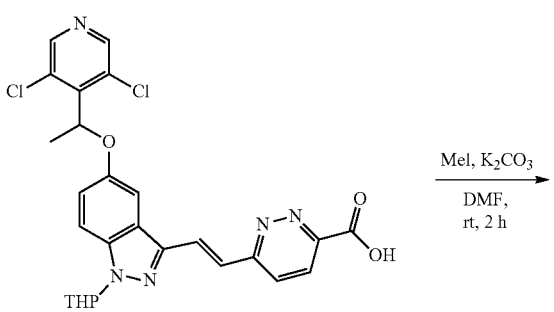

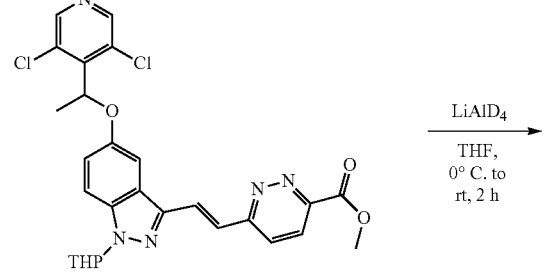

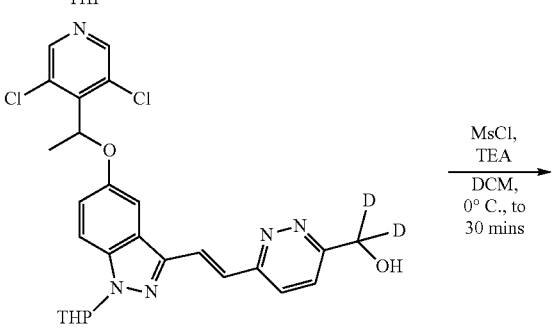

139
-continued

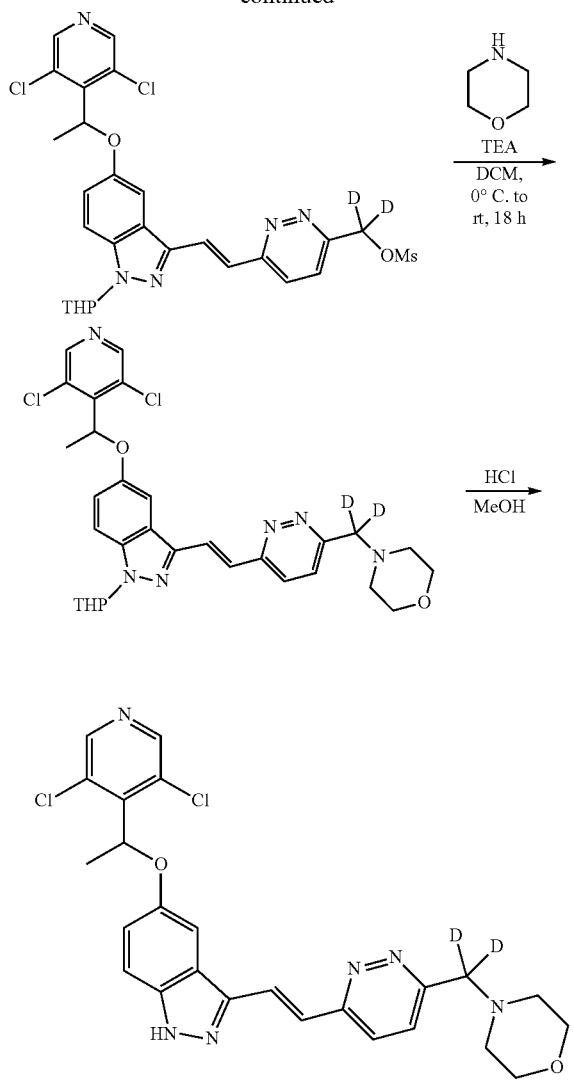

Example 65

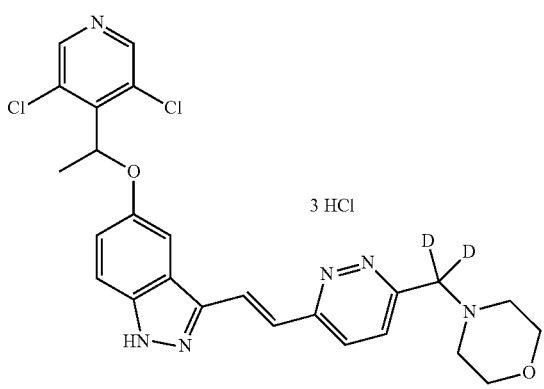 [SMILES: [2H]C([2H])(c1ccc(/C=C/c2n[nH]c3ccc(OC(C)c4c(Cl)cncc4Cl)cc23)nn1)N1CCOCC1]

140

Example 65A

HCl/MeOH solution (4M, 30 mL) was added to 6-oxo-1,6-dihydropyridazine-3-carboxylic acid (3 g, 0.02 mol) and the mixture was heated to 80° C. and stirred for 2 hours. The solvent was evaporated to dryness under reduced pressure to give the title compound (2.8 g, yield 85%). $^1$H NMR (CHLOROFORM-d, Bruker Avance 400 MHz) ppm 11.26 (br. s., 1H), 7.91 (d, J=10.0 Hz, 1H), 7.02 (d, J=10.0 Hz, 1H), 3.99 (s, 3H).

Example 65B

POCl$_3$ (5.60 g, 0.036 mol) was added to a solution of Example 65A (2.8 g, 0.018 mol) in toluene at room temperature and the mixture was heated to 120° C. and stirred for 2 hours. The solvent was evaporated to dryness, water (20 mL) was added and the mixture was extracted with ethyl acetate (15 mL×3). The combined organic layer was washed with brine, dried over sodium sulfate, filtered and the filtrate was evaporated. The residue was purified by column chromatography to give the title compound (1.5 g, yield 50%). $^1$H NMR (CHLOROFORM-d, Bruker Avance 400 MHz) ppm 8.17 (d, J=8.8 Hz, 1H), 7.68 (d, J=8.8 Hz, 1H), 4.09 (s, 3H).

Example 65C

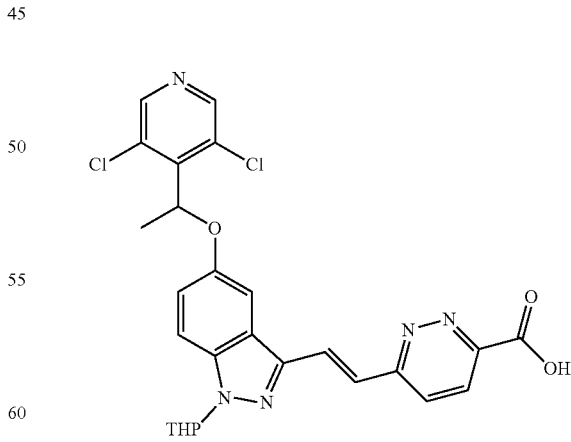

47 A (1 g, 1.93 mmol), Example 65B (400 mg, 2.32 mmol), Na$_2$CO$_3$ (307 mg, 2.9 mmol), a mixed solvent of acetonitrile/water (9 mL/3 mL) and Pd (PPh$_3$)$_2$Cl$_2$ (135 mg, 0.19 mmol) were added to the microwave reaction tube at room temperature. Then, the mixture was heated to 130° C.

and reacted for 30 minutes in the microwave reactor under nitrogen atmosphere. The reaction solution was diluted with water (10 mL) and extracted with ethyl acetate (15 mL×3). The combined organic layer was washed with saturated brine, dried over sodium sulfate, filtered and evaporated. The residue was purified by column chromatography to give the title compound (500 mg, yield 50%). LCMS (ESI) m/z: 540.0 [M+1]+.

Example 65D

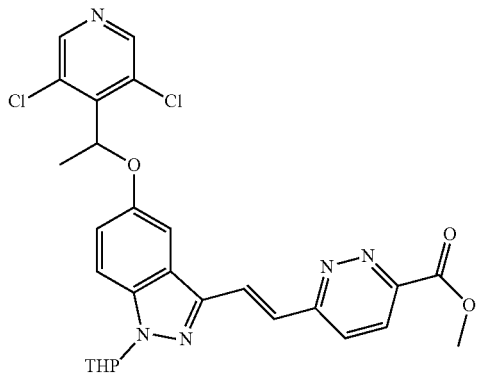

Potassium carbonate (229 mg, 1.66 mmol) was added to a solution of Example 65C (450 mg, 0.83 mmol) in DMF at room temperature and methyl iodide (118 mg, 0.83 mmol) was added dropwise. The mixture was stirred at 20° C. for 2 hours, added with water (10 mL) and extracted with ethyl acetate (15 mL×3). The combined organic layer was washed with brine, dried over sodium sulfate, filtered and the filtrate was evaporated. The residue was purified by column chromatography to give the title compound (160 mg, yield 35%). LCMS (ESI) m/z: 554.0 [M+1]+.

Example 65E

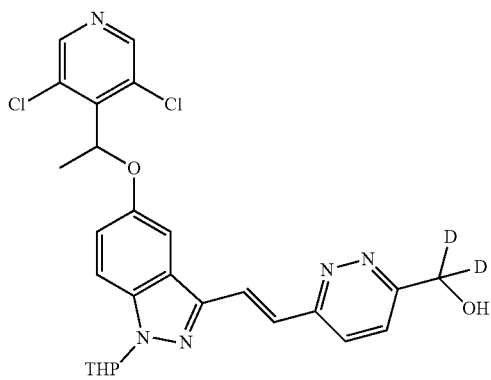

LiAlD$_4$ (24 mg, 0.58 mmol) was added to a solution of Example 65D (160 mg, 0.29 mmol) in tetrahydrofuran (5 mL) at 0° C. The mixture was stirred at 0° C. for 2 hours. The reaction was quenched with water (0.1 mL), filtered and the filtrate was evaporated to dryness under reduced pressure to give the title compound (158 mg, crude). LCMS (ESI) m/z: 528.1 [M+1]+.

Example 65F

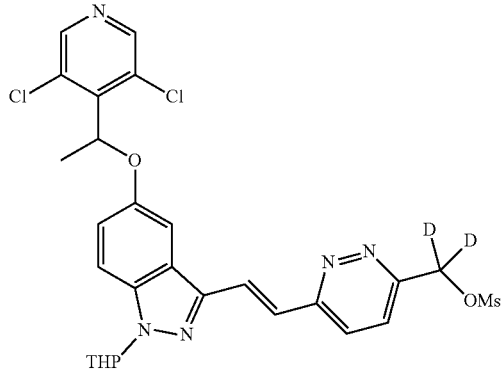

Methanesulfonyl chloride (38 mg, 0.33 mmol) was added in batches to a solution of Example 65E (158 mg, 0.30 mmol) and triethylamine (61 mg, 0.60 mmol) in dichloromethane (5 mL) at 0° C. The reaction solution was stirred at 0° C. for 1 hour, and then poured into ice water (10 mL). After layering, the organic layer was washed successively with saturated sodium bicarbonate solution (10 mL) and brine (20 mL), dried over sodium sulfate, filtered and the filtrate was evaporated. The residue was purified by column chromatography to give the title compound (84 mg, yield 46%). LCMS (ESI) m/z: 606.0[M+1]+.

Example 65G

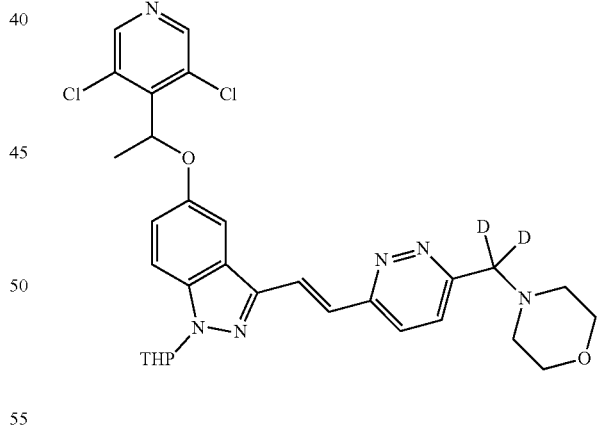

Morpholine (14.5 mg, 0.17 mmol) and triethylamine (21 mg, 0.029 mmol) were added to a solution of Example 65F (84 mg, 0.14 mmol) in dichloromethane (5 mL). The mixture wad stirred for 18 hours at 15° C., added with water (10 mL) and extracted with dichloromethane (15 mL×3). The combined organic layers were washed with brine, dried over sodium sulfate, filtered and the filtrate was evaporated. The residue was purified by column chromatography to give the title compound (40 mg, yield 49%). LCMS (ESI) m/z: 597.1 [M+1]+.

Example 65H

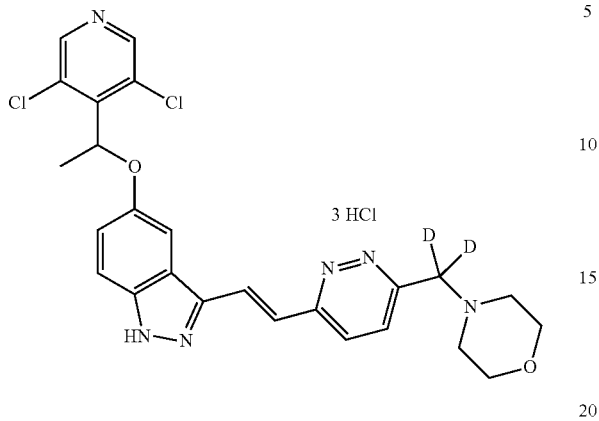

Concentrated hydrochloric acid (0.1 mL) was added dropwise to a solution of Example 65G (40 mg, 0.07 mmol) in methanol (2 mL). The mixture was heated to 50° C. and stirred for 4 hours, filtered and the filtrate was separated by preparative high performance liquid chromatography to give the title compound (26 mg, yield 76%). LCMS (ESI) m/z: 513.1 [M+1]+. $^1$H NMR (DMSO-$d_6$, Bruker Avance 400 MHz): ppm 8.60 (s, 2H), 8.21 (d, J=8.8 Hz, 1H), 8.06 (d, J=16.8 Hz, 1H), 7.84 (d, J=8.8 Hz, 1H), 7.55-7.44 (m, 2H), 7.38 (s, 1H), 7.14 (dd, J=2.3, 9.0 Hz, 1H), 6.22-6.15 (m, 1H), 3.87 (br. s., 4H), 3.34 (br. s., 4H), 1.79 (d, J=6.5 Hz, 3H).

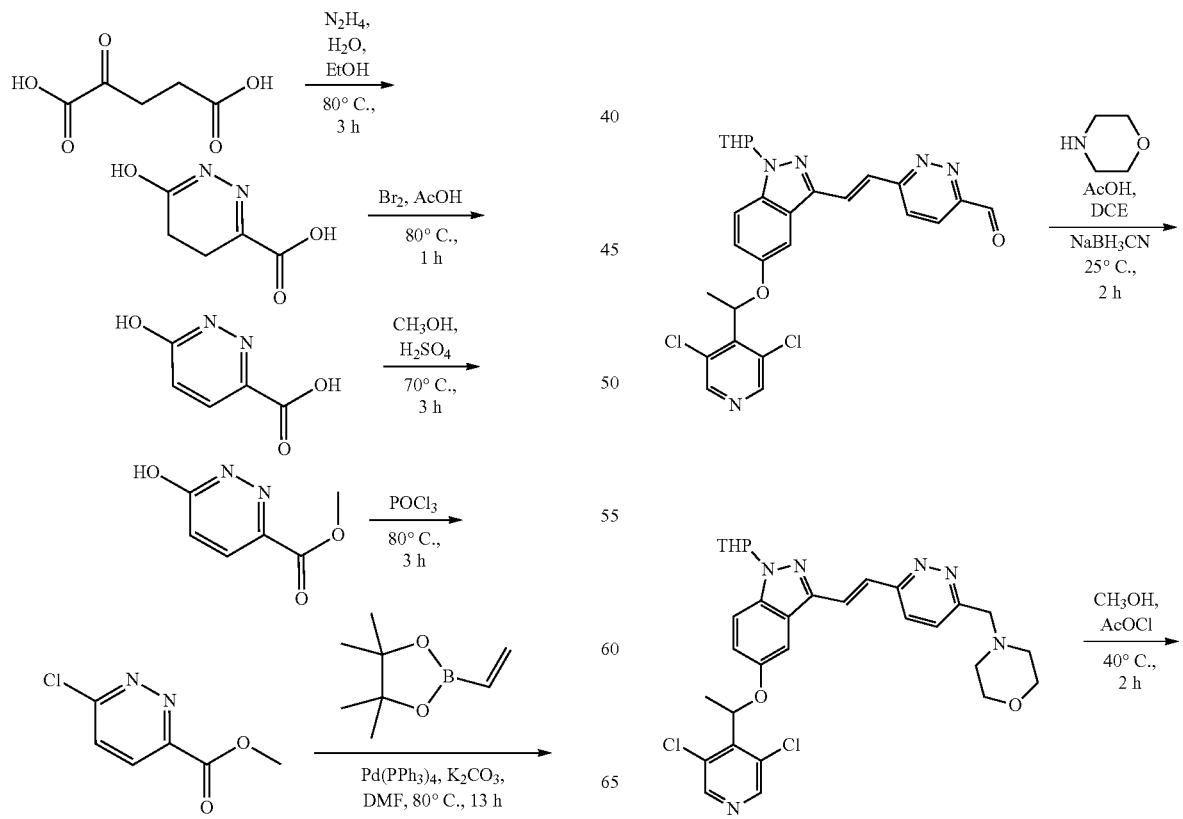

-continued

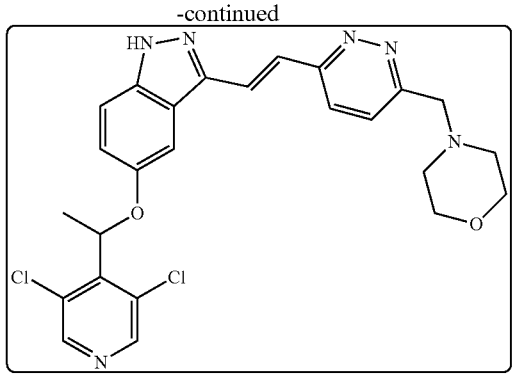

Example 66

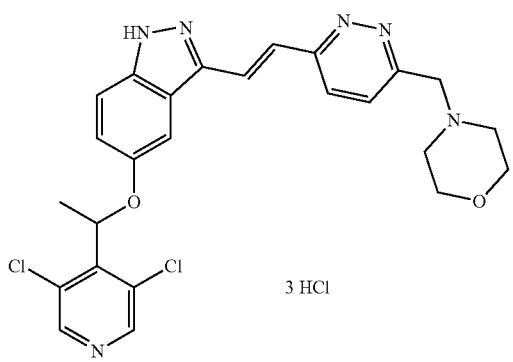 [SMILES: CC(Oc1ccc2[nH]nc(/C=C/c3ccc(CN4CCOCC4)nn3)c2c1)c1c(Cl)cncc1Cl]

3 HCl

Example 66A

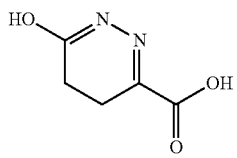

Hydrazine hydrate (6.85 g, 136.89 mmol) was added to a solution of 2-oxoglutaric acid (20 g, 136.89 mmol) in ethanol (200 mL) and the mixture was stirred at 60° C. for 3 hours, then cooled and filtered to give a portion of the title compound (12 g, crude) and the filtrate was concentrated to give the yellowish title compound (8 g, crude). $^1$H NMR (400 MHz, DMSO-d$_6$) ppm 11.17 (s, 1H), 2.78-2.68 (m, 2H), 2.45-2.36 (m, 2H).

Example 66B

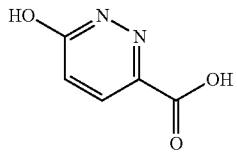

Liquid bromine (38.23 g, 239.25 mmol) was slowly added dropwise to a solution of Example 66A (20 g, 140.74 mmol) in glacial acetic acid (200 mL) at 25° C. After the addition, the mixture was heated to 80° C. and stirred for 3 hours. When TLC showed that the starting material was consumed completely, the reaction solution was cooled and filtered to give the title compound (20 g, crude). $^1$H NMR (400 MHz, DMSO-d$_6$) ppm 13.49 (s, 1H), 7.80 (d, J=9.8 Hz, 1H), 6.92 (d, J=9.8 Hz, 1H).

Example 66C

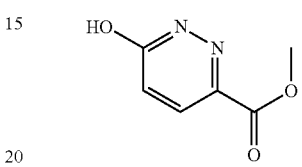

Concentrated sulfuric acid (19.9 g, 202.9 mmol) was slowly added dropwise to a solution of Example 66B (20 g, 142.76 mmol) in methanol (500 mL). After the addition, the mixture was heated to 70° C. and stirred for 2 hours. Then, the reaction solution was cooled and concentrated in vacuo, added with ice water (300 mL) and filtered, the filter cake was washed with water to give the title compound (17 g, yield 73.4%). $^1$H NMR (400 MHz, DMSO-d$_6$) ppm 13.62 (s., 1H), 7.83 (d, J=10.0 Hz, 1H), 6.97 (d, J=9.8 Hz, 1H), 3.85 (s, 3H).

Example 66D

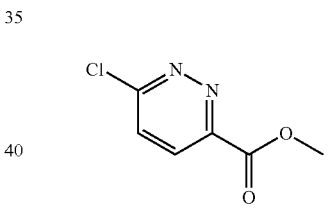

A solution of Example 66C (5 g, 32.44 mmol) in phosphorus oxychloride (60 mL) was stirred at 110° C. for 3 hours. The solution was cooled and concentrated in vacuo. The residue was slowly added to ice water (20 mL). The precipitate was filtered and the filter cake was washed with water to give pale white title compound (1.8 g, yield 32.15%). $^1$H NMR (400 MHz, DMSO-d$_6$) ppm 8.27 (d, J=9.0 Hz, 1H), 8.13 (d, J=9.0 Hz, 1H), 3.96 (s, 3H).

Example 66E

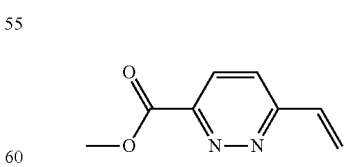

A solution of Example 65D (600 mg, 3.48 mmol), vinyl pinacol borate (803.2 mg, 5.22 mmol), potassium carbonate (961.07 mg, 6.95 mmol) and Pd(PPh$_3$)$_4$ (602.66 mg, 521.53 mmol) in DMF (8 mL) was stirred at 100° C. for 5 hours under nitrogen atmosphere. The solution was cooled, filtered and concentrated in vacuo. The residue was purified by column chromatography to give the title compound (500 mg, yield 84.02%). ¹H NMR (400 MHz, CHLOROFORM-d) ppm 8.18 (d, J=8.8 Hz, 1H), 7.72 (d, J=8.8 Hz, 1H), 7.16 (dd, J=11.0, 17.8 Hz, 1H), 6.44 (d, J=17.8 Hz, 1H), 5.85 (d, J=10.8 Hz, 1H), 4.10 (s, 3H).

Example 66F

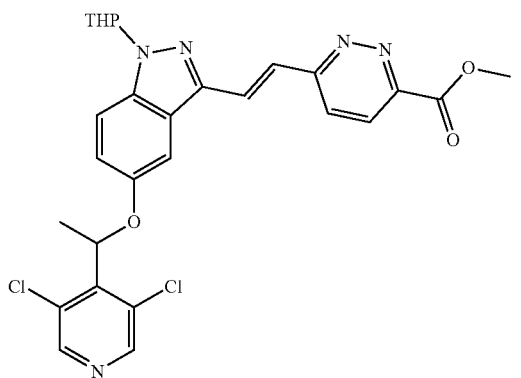

A suspension of Example 66E (200 mg, 1.22 mmol), 1 G (694.43 mg, 1.34 mmol), POT (37.08 mg, 121.83 μmol), palladium acetate (27.35 mg, 121.83 mmol) and triethylamine (369.85 mmol, 3.65 mmol) in DMF (4 mL) was stirred at 110° C. for 30 minutes under microwave conditions and nitrogen atmosphere. The suspension was cooled, filtered and the filtrate was concentrated in vacuo. The residue was purified by preparative TLC to give the yellow title compound (345 mg, yield 50%), LCMS (ESI) m/z: 554.4 [M+1]⁺. ¹H NMR (400 MHz, DMSO-d₆) ppm 8.60 (s, 2H), 8.26 (q, J=9.0 Hz, 1H), 8.13 (d, J=16.6 Hz, 1H), 7.74 (d, J=9.0 Hz, 1H), 7.59 (d, J=17.1 Hz, 1H), 7.47 (s, 1H), 7.20 (d, J=9.0 Hz, 1H), 6.23 (dd, 6.5 Hz, 1H), 5.86 (d, J=9.5 Hz, 1H), 4.00 (s, 3H), 3.87 (br. s., 1H), 3.75 (br. s., 1H), 2.68 (br. s., 1H), 2.41-2.31 (m, 2H), 2.00 (br. s., 3H), 1.81 (d, J=6.5 Hz, 3H).

Example 66G

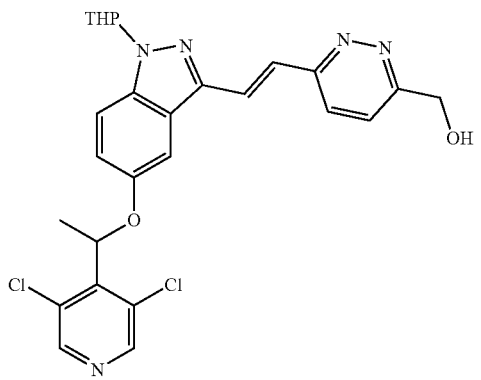

Lithium aluminum hydride (10.27 mg, 270.55 mmol) was slowly added to a solution of Example 66F (100 mg, 180.37 μmol) in tetrahydrofuran (1 mL) at 0° C. and then the mixture was stirred at this temperature for 30 minutes. The reaction was quenched with water (0.1 mL), aqueous sodium hydroxide (0.1 mL, 15%) and water (0.3 mL), filtered and the filtrate was concentrated in vacuo. The residue was purified by preparative TLC to give the title compound as a yellow oil (30 mg, 30.33%). LCMS (ESI) m/z: 526.4 [M+1]. ¹H NMR (400 MHz, METHANOL-d₄) ppm 8.51 (s, 2H), 8.08 (d, J=8.8 Hz, 1H), 7.93-7.86 (m, 2H), 7.65 (d, J=9.0 Hz, 1H), 7.54 (d, J=16.8 Hz, 1H), 7.36 (s, 1H), 7.22 (dd, J=2.1, 9.2 Hz, 1H), 6.24 (q, J=6.7 Hz, 1H), 5.79 (d, J=9.3 Hz, 1H), 4.94 (s, 2H), 3.99 (br. s., 1H), 3.81 (t, J=10.8 Hz, 1H), 3.62-3.56 (m, 1H), 2.58-2.44 (m, 1H), 2.15 (d, J=13.3 Hz, 1H), 2.05 (br. s., 1H), 1.87 (d, J=6.8 Hz, 3H), 1.76-1.62 (m, 3H).

Example 66H

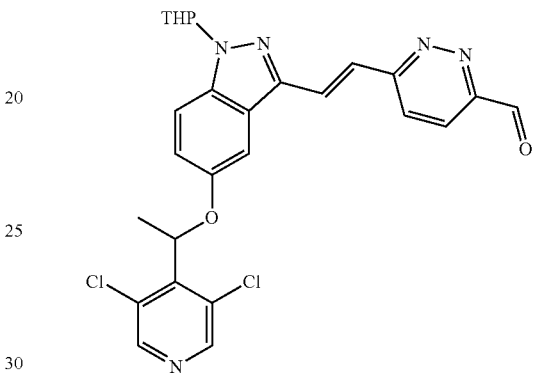

Dess-Martin oxdizer (36.26 mg, 85.48 mmol) was added to a solution of Example 66G (30 mg, 56.99 mmol) in dichloromethane (2 mL) at 0° C. and the suspension was stirred at 25° C. for 12 hours, then filtered, the filtrate was concentrated in vacuo and the residue was purified by preparative thin layer chromatography to give the title compound (25 mg, yield 81.98%), LCMS (ESI) m/z: 524.4 [M+1]⁺.

¹H NMR (400 MHz, CHLOROFORM-d) ppm 10.44 (s, 1H), 8.47 (s, 2H), 8.14-8.00 (m, 2H), 7.82 (d, J=8.8 Hz, 1H), 7.70-7.51 (m, 2H), 7.35 (s, 1H), 7.19 (dd, J=2.1, 9.2 Hz, 1H), 6.16 (q, J=6.5 Hz, 1H), 5.70 (dd, J=2.9, 8.9 Hz, 1H), 4.04 (br. s., 1H), 3.81-3.71 (m, 1H), 2.54 (d, J=9.5 Hz, 1H), 2.24-2.02 (m, 2H), 1.87 (d, J=6.5 Hz, 3H), 1.82-1.67 (m, 3H).

Example 66I

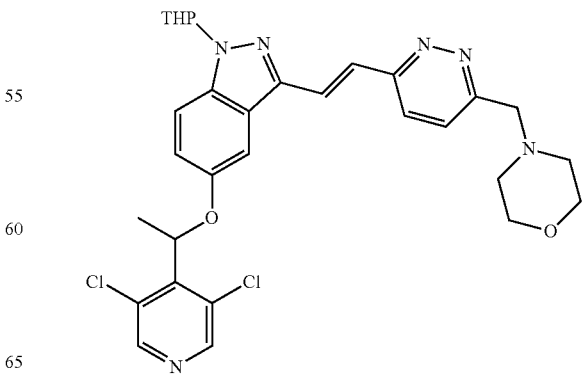

Acetic acid (3.44 mg, 57.2 μmol) was added dropwise to a mixed solution of Example 66H (30 mg, 57.21 μmol) and morpholine (15 mg, 171.63 μmol) in 1,2-dichloroethane (2 mL), and the mixture was stirred at 28° C. for 2 hours after the addition. Sodium cyanoborohydride (11 mg, 171.6 mmol) was slowly added and the mixture was stirred for 1 hour at 28° C. The reaction was quenched with water, and the aqueous layer was extracted with dichloromethane (3 mL×3), the combined organic layer was washed with brine and dried over anhydrous sodium sulfate, filtered and the filtrate was concentrated in vacuo. The residue was purified by preparative TLC to give the title compound as a yellow oil (25 mg, crude), LCMS (ESI) m/z: 594.2 [M+1]$^+$.

Example 66J

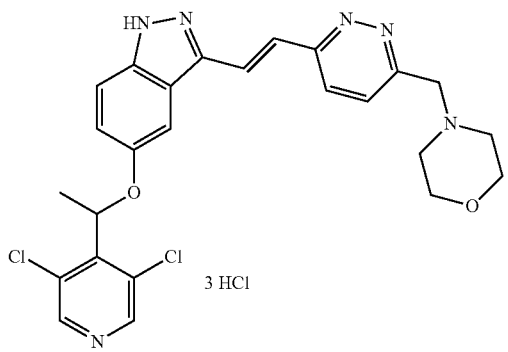 [SMILES: CC(Oc1ccc2[nH]nc(/C=C/c3ccc(CN4CCOCC4)nn3)c2c1)c1c(Cl)cncc1Cl]

3 HCl

Example 66I (25 mg, 42 μmol) was dissolved in dry methanol (1 mL) and then the solution was added dropwise to acetyl chloride (0.2 mL) in dry methanol (0.8 mL). The reaction solution was stirred at 40° C. for 1 hour, concentrated in vacuo and the residue was purified by preparative liquid chromatography to give the title compound as a yellow oil (8 mg, yield 37.26%). LCMS (ESI) m/z: 528.4 [M+1]$^+$. $^1$H NMR (400 MHz, METHANOL-d$_4$) ppm 8.59 (m, 2H), 8.20 (d, J=8.8 Hz, 1H), 8.06 (d, J=16.8 Hz, 1H), 7.88 (d, J=8.5 Hz, 1H), 7.60-7.48 (m, 2H), 7.36 (s, 1H), 7.26-7.19 (m, 1H), 6.28-6.20 (m, 1H), 4.80 (m, 2H), 4.03 (m, 4H), 3.62-3.48 (m, 4H), 1.91-1.83 (d, 3H).

Example 67

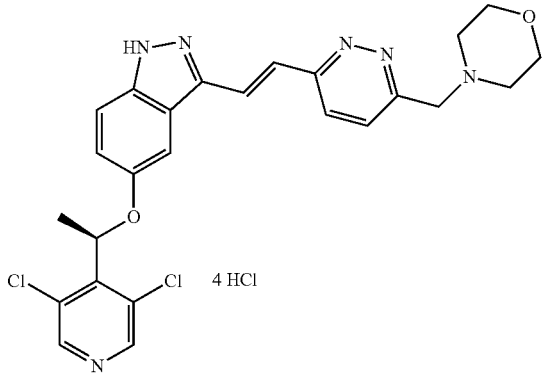 [SMILES: C[C@@H](Oc1ccc2[nH]nc(/C=C/c3ccc(CN4CCOCC4)nn3)c2c1)c1c(Cl)cncc1Cl]

4 HCl

This example was prepared by the method as described in Example 66. $^1$H NMR (400 MHz, DMSO-d$_6$) ppm 8.59 (s, 2H), 8.21 (d, J=8.8 Hz, 1H), 8.09-7.97 (m, 2H), 7.55-7.43 (m, 2H), 7.38 (d, J=1.8 Hz, 1H), 7.12 (dd, J=2.3, 9.0 Hz, 1H), 6.17 (q, J=6.5 Hz, 1H), 4.72 (s, 2H), 3.90 (m, 4H), 3.35 (m, 4H), 1.78 (d, J=6.5 Hz, 3H)

Example 68

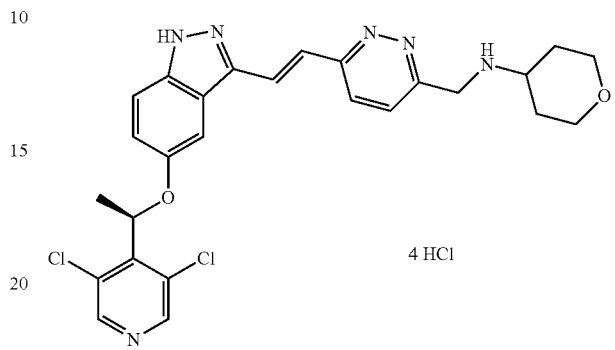

4 HCl

This example was prepared by the method as described in Example 66. $^1$H NMR (400 MHz, DMSO-d$_6$) ppm 9.50 (m, 1H), 8.59 (s, 2H), 8.20 (d, J=8.8 Hz, 1H), 8.01 (d, J=16.8 Hz, 1H), 7.84 (d, J=8.8 Hz, 1H), 7.52 (d, J=9.0 Hz, 1H), 7.46 (d, J=16.8 Hz, 1H), 7.36 (s, 1H), 7.15-7.10 (m, 1H), 6.17 (d, J=6.8 Hz, 1H), 4.58 (m, 2H), 3.95 (d, J=7.3 Hz, 1H), 2.66 (m, 2H), 2.32 (m, 2H), 2.06 (d, J=11.5 Hz, 2H), 1.78 (d, J=6.5 Hz, 3H), 1.70 (d, J=11.8 Hz, 2H)

Example 69

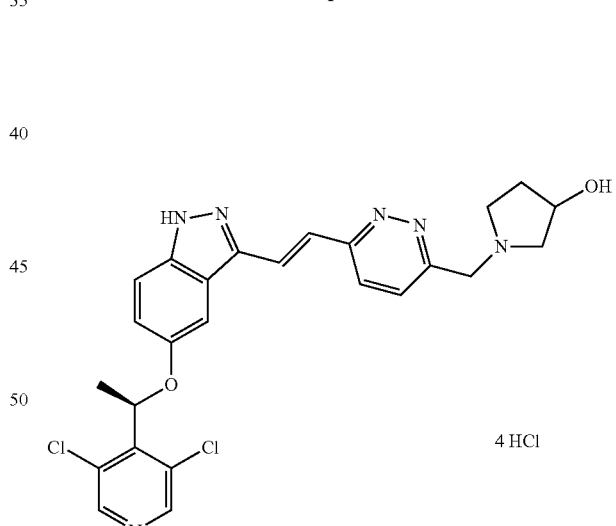

4 HCl

This example was prepared by the method as described in Example 66. $^1$H NMR (400 MHz, METHANOL-d$_4$) ppm 8.63 (d, J=9.0 Hz, 1H), 8.51 (s, 2H), 8.30 (d, J=16.6 Hz, 1H), 8.20 (d, J=9.0 Hz, 1H), 7.65 (d, J=16.6 Hz, 1H), 7.55 (d, J=9.0 Hz, 1H), 7.49 (d, J=1.8 Hz, 1H), 7.23 (dd, J=2.0, 9.0 Hz, 1H), 6.27 (q, J=6.8 Hz, 1H), 5.04-4.94 (m, 2H), 4.67 (br. s., 1H), 4.09-3.72 (m, 3H), 2.33-2.11 (m, 2H), 1.88 (d, J=6.5 Hz, 3H).

Scheme L

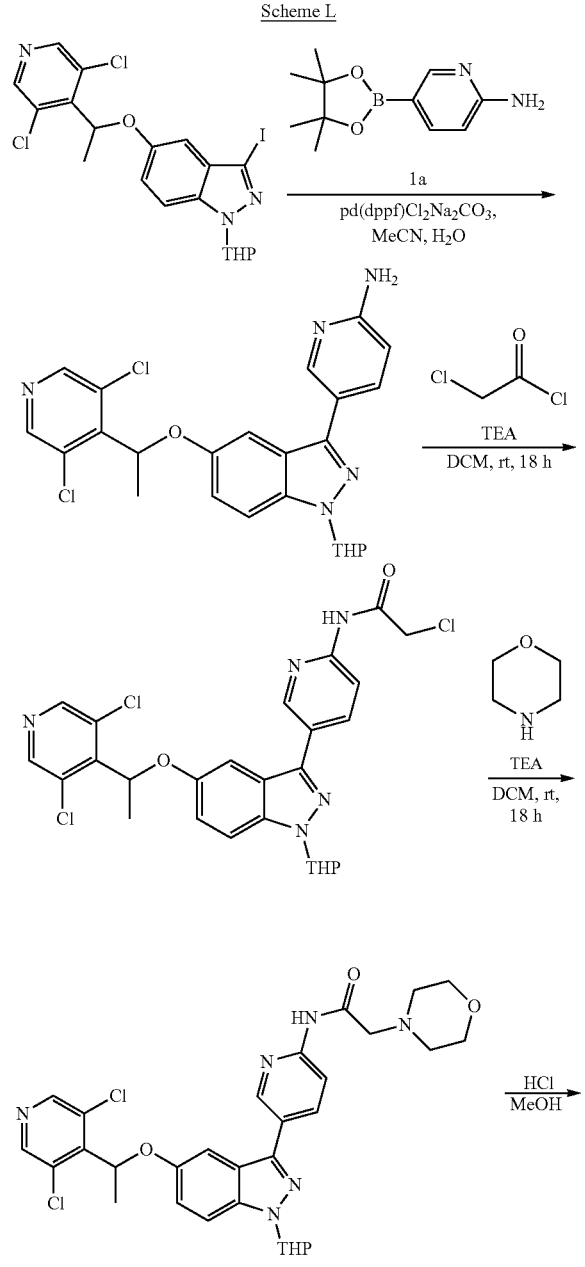

Example 70

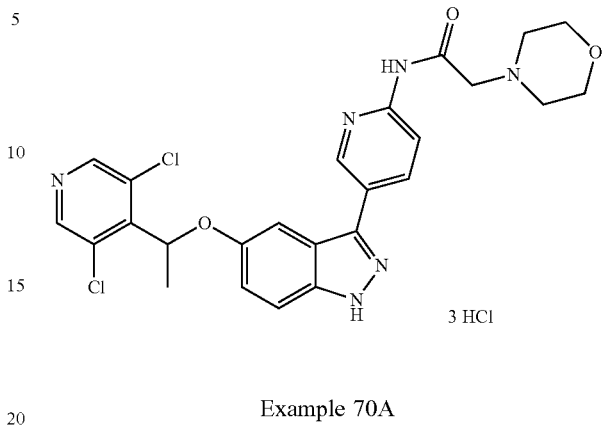

Example 70A

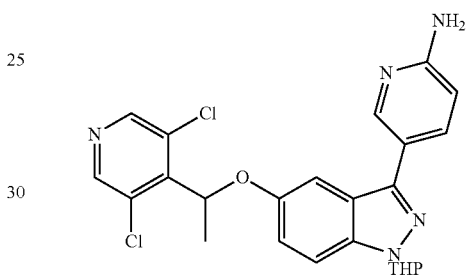

5-(4,4,5,5-Tetramethyl-1,3,2-diboricacid-2-yl)pyridin-2-amino (205 mg, 0.93 mmol), Pd(dppf)Cl$_2$ (57 mg, 0.078 mmol) and sodium carbonate (165 mg, 1.56 mmol) were added to a mixed solution of Example 1G (400 mg, 0.78 mmol) in acetonitrile (6 mL) and water (2 mL). The reaction was heated under microwave to 100° C. under nitrogen atmosphere and stirred for 15 minutes. The reaction solution was added with water (10 mL) and washed with ethyl acetate (15 mL×3) and brine, dried and the filtrate was concentrated to give a residue. The residue was purified by column chromatography to give the title compound (340 mg, yield 91%). LCMS (ESI) m/z: 483.9[M+1]$^+$.

Example 70B

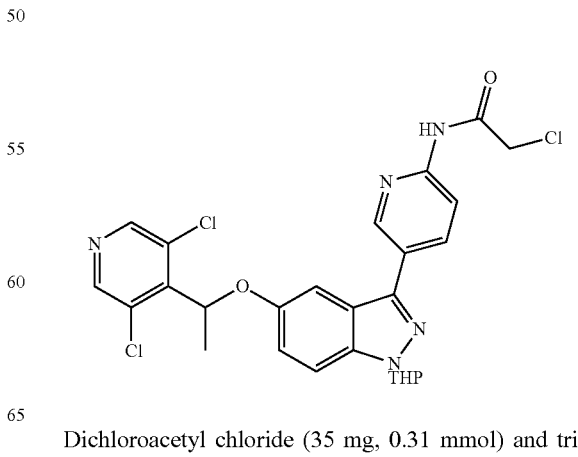

Dichloroacetyl chloride (35 mg, 0.31 mmol) and triethylamine (31 mg, 0.31 mmol) were added to a solution of Example 70A (100 mg, 0.21 mmol) in dichloromethane (5 mL). The reaction solution was stirred at 15° C. for 18 hours, added with water (10 mL), and then extracted with dichloromethane (15 mL×3), the organic phase was washed with brine, dried and the filtrate was evaporated to give a residue which was purified by column chromatography to give the title compound (as a brown oil, 73 mg, yield 63%). LCMS (ESI) m/z: 559.6[M+1]⁺.

Example 70C

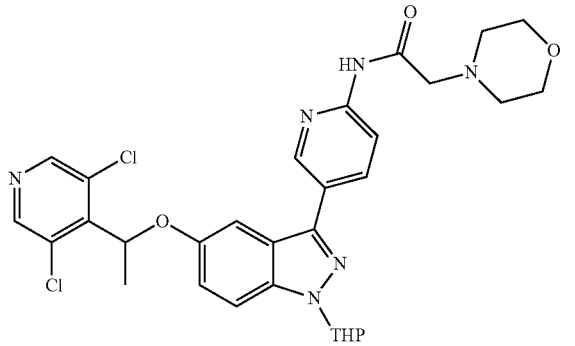

Morpholine (14 mg, 0.16 mmol) and triethylamine (20 mg, 0.20 mmol) were added to a solution of Example 70B (73 mg, 0.13 mmol) in dichloromethane (5 mL). The reaction solution was stirred at 15° C. for 18 hours, added with water (10 mL) and extracted with dichloromethane (15 mL×3), the organic phase was washed with brine, dried and the filtrate was evaporated to give a residue which was separated by thin layer chromatography to give the title compound (as a brown oil, 75 mg, yield 74%). LCMS (ESI) m/z: 611.1 [M+1]⁺.

Example 70D

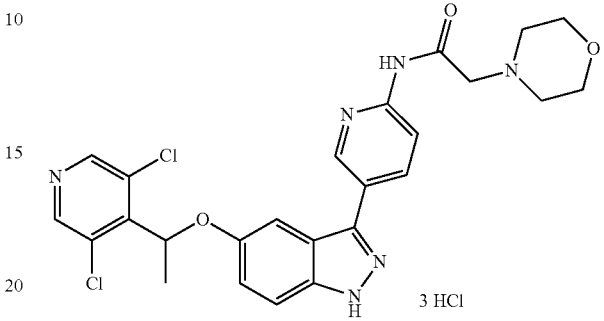

Concentrated hydrochloric acid (0.1 mL) was added dropwise to a solution of Example 70C (75 mg, 0.12 mmol) in methanol (2 mL). The reaction was stirred at 50° C. for 4 hours, filtered and the filtrate was separated by liquid chromatography to give the title compound (23 mg, yield 34%). LCMS (ESI) m/z: 510.0[M+1]⁺. $^1$H NMR (DMSO-$d_6$, Bruker Avance 400 MHz): ppm 10.18 (s, 1H), 8.76 (s, 1H), 8.58 (s, 2H), 8.27-8.18 (m, 2H), 7.51 (d, J=8.8 Hz, 1H), 7.25 (s, 1H), 7.12 (dd, J=2.0, 9.0 Hz, 1H), 6.16 (q, J=6.6 Hz, 1H), 3.73-3.60 (m, 4H), 3.25 (s, 2H), 2.57 (br. s., 4H), 1.76 (d, J=6.5 Hz, 3H).

Scheme M

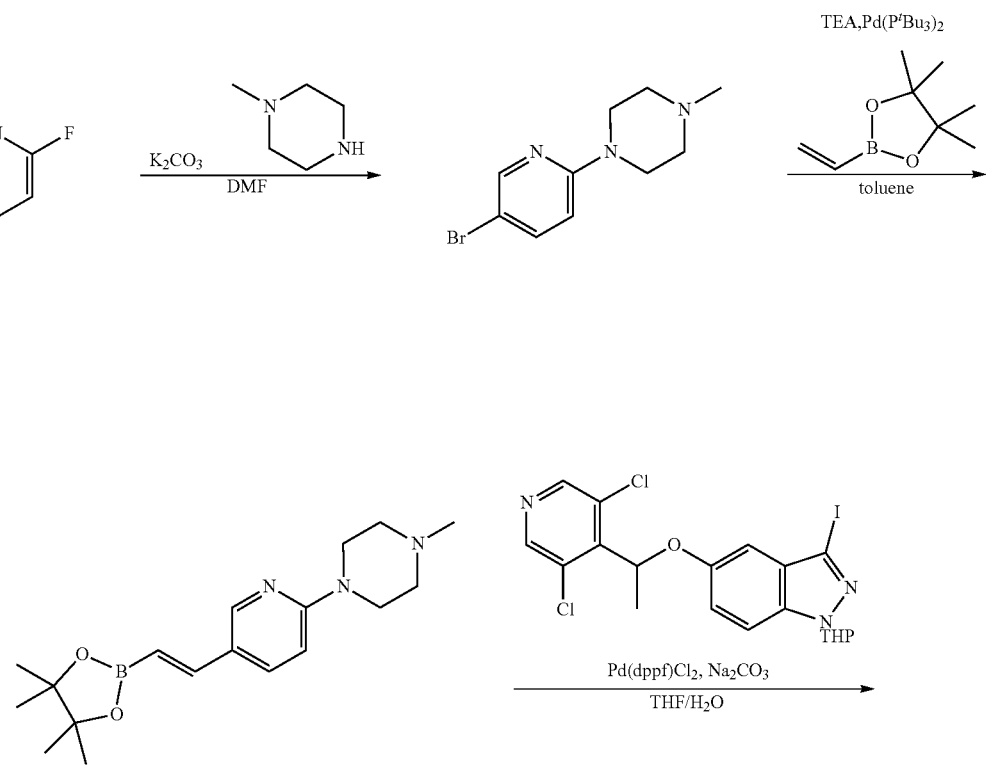

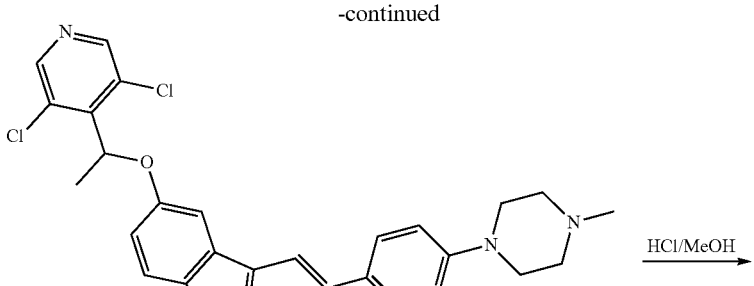

HCl/MeOH →

Example 71

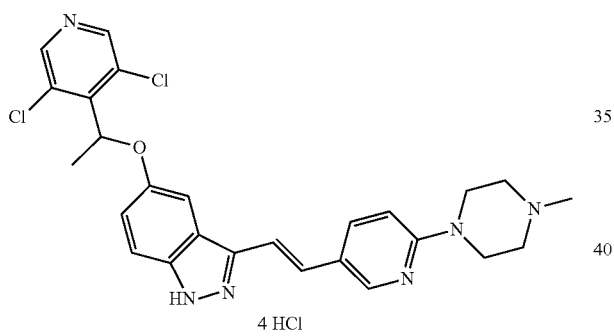

· 4 HCl

Example 71A

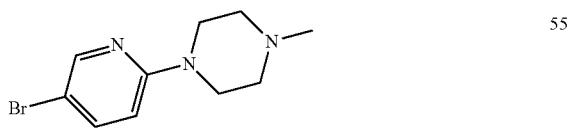

N-methylpiperazine (2.8 g, 28.4 mmol) and potassium carbonate (7.8 g, 56.8 mmol) were added to a solution of 5-bromo-2-fluoropyridine (5.0 g, 28.4 mmol) in DMF (50 mL) at 30° C. The mixture was heated to 80-90° C. and stirred for 16 hours, cooled to 33° C., added with water (50 mL) and extracted with ethyl acetate (50 mL×3). The combined organic layer was washed with water (20 mL×3), dried over sodium sulfate, filtered and the filtrate was evaporated. The residue was purified by column chromatography to give the title compound (5.3 g, yield 73%). $^1$H NMR (CDCl$_3$, Bruker Avance 400 MHz): ppm 8.21 (d, J=2.3 Hz, 1H), 7.54 (dd, J=9.0 Hz, 2.5 Hz, 1H), 6.56 (d, J=9.0 Hz, 1H), 3.57-3.52 (m, 4H), 2.55-2.50 (m, 4H), 2.36 (s, 3H).

Example 71B

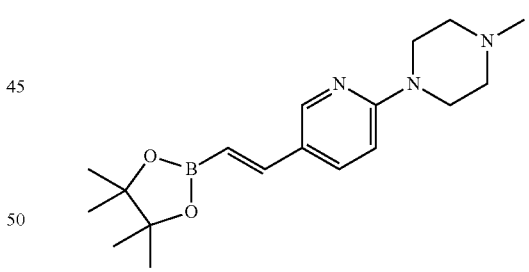

Pd(t-Bu$_3$P)$_2$ (20 mg, 0.04 mmol) was added to a solution of Example 71A (1.0 g, 3.90 mmol), 4,4,5,5-tetramethyl-2-vinyl-1,3,2-dioxaborolane (0.66 g, 4.30 mmol) and triethylamine (0.79 g, 7.80 mmol) in toluene (10 mL) at 30° C. and the mixture was degassed for 10 minutes and then protected with nitrogen. The reaction solution was heated to 80° C., stirred for 16 hours, then cooled to 35° C. and evaporated to remove the solvent under reduced pressure. The residue is purified by column chromatography to give the title compound (as a yellow oil, 370 mg, crude). LCMS (ESI) m/z: 330.0[M+1]$^+$.

Example 71C

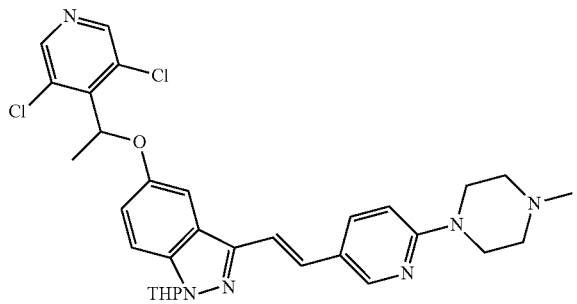

5-(1-(3,5-Dichloropyridin-4-yl)ethoxy)-3-iodo-1-(tetrahydro-2H-pyran-2-yl)-1H-indazole (79 mg, 0.15 mmol), potassium carbonate (32 mg, 0.30 mmol) and Pd(dppf)Cl$_2$ (11 mg, 0.015 mmol) were added to a mixed solution of Example 71B (50 mg, 0.15 mmol) in tetrahydrofuran/water (v/v=5/1, 5 ml) at 37° C. The mixture was degassed for 10 minutes and then protected with nitrogen. The reaction solution was heated to 75° C., stirred for 16 hours, then cooled to 30° C., added with water (10 mL) and extracted with ethyl acetate (20 mL). The organic layer was dried over sodium sulfate, filtered and evaporated. The residue was purified by preparative thin layer chromatography to give the title compound (as a yellow oil, 50 mg, crude). LCMS (ESI) m/z: 606.2 [M+1]$^+$.

Example 71D

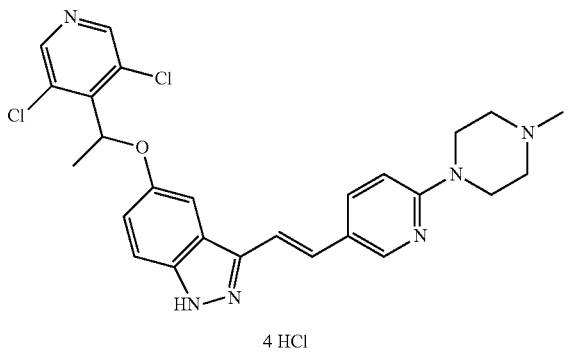 [SMILES: CC(Oc1ccc2[nH]nc(/C=C/c3ccc(N4CCN(C)CC4)nc3)c2c1)c1c(Cl)cncc1Cl]

4 HCl

Concentrated hydrochloric acid (0.2 mL) was added dropwise to a solution of Example 70C (50 mg, 0.08 mmol) in methanol (4 mL) at 0° C. The mixture was heated to 38° C. and stirred for 16 hours. The reaction solution was separated by preparative high performance liquid chromatography and recrystallized from acetonitrile to give the title compound (5.0 mg, yield 10%). $^1$H NMR (DMSO-d$_6$, Bruker Avance 400 MHz): ppm 8.61 (s, 2H), 8.36 (d, J=1.8 Hz, 1H), 8.23 (d, J=8.8 Hz, 1H), 7.47-7.36 (m, 3H), 7.26-7.16 (m, 2H), 7.08 (dd, J$_1$=9.0 Hz, J$_2$=2.0 Hz, 1H), 6.17 (q, J=6.6 Hz, 1H), 4.52 (d, J=13.6 Hz, 2H), 3.45-3.36 (m, 4H), 3.24-2.95 (m, 4H), 2.81 (d, J=2.5 Hz, 3H), 1.78 (d, J=6.5 Hz, 3H).

Scheme N

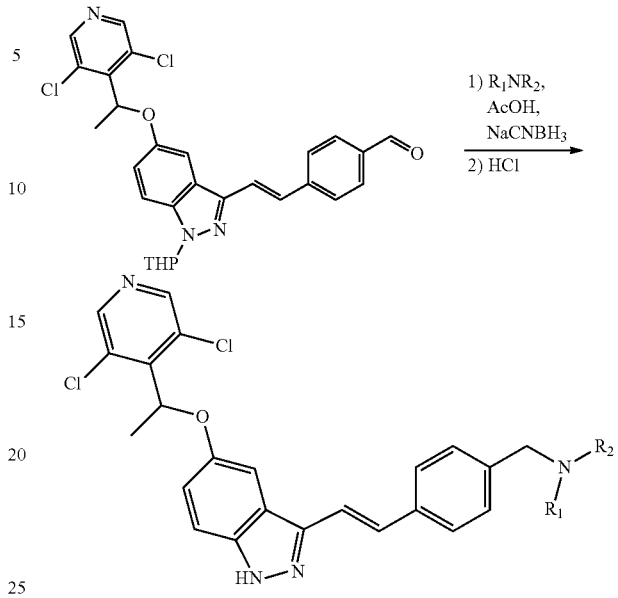

Example 72

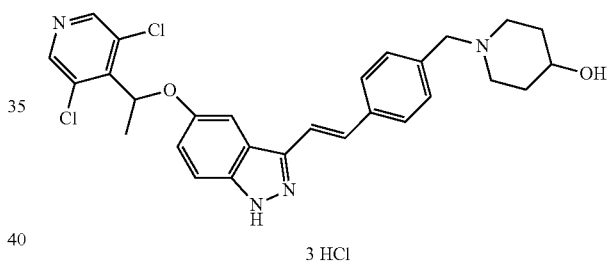

3 HCl

This example was prepared by the method as described in Example 17.

LCMS (ESI) m/z: 523.2[M+1]$^+$.

$^1$H NMR (DMSO-d$_6$, Bruker Avance 400 MHz): ppm 10.83-10.65 (m, 1H), 8.61 (s, 2H), 7.77-7.62 (m, 4H), 7.56-7.45 (m, 2H), 7.33 (s, 1H), 7.24 (d, J=16.8 Hz, 1H), 7.15-7.07 (m, 1H), 6.22-6.11 (m, 1H), 4.28 (dd, J=13.3, 4.5 Hz, 2H), 3.32 (d, J=11.5 Hz, 2H), 3.18-3.12 (m, 2H), 2.99-2.90 (m, 1H), 2.07-1.90 (m, 2H), 1.84-1.69 (m, 5H).

Example 73

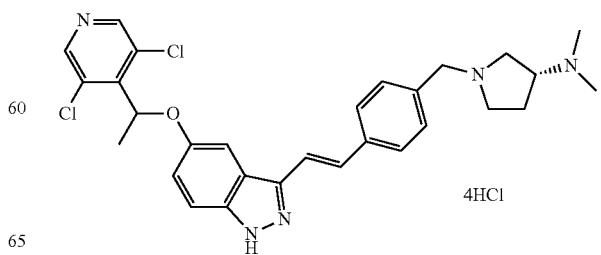

4HCl

This example was prepared by the method as described in Example 17.

LCMS (ESI) m/z: 536.3 [M+1]+.

¹H NMR (DMSO-d₆, Bruker Avance 400 MHz): ppm 12.09-11.52 (m, 1H), 8.63-8.57 (m, 2H), 7.72 (s, 4H), 7.54-7.46 (m, 2H), 7.34 (d, J=1.5 Hz, 1H), 7.24 (d, J=16.8 Hz, 1H), 7.10 (dd, J=9.0, 2.0 Hz, 1H), 6.16 (q, J=7.0 Hz, 1H), 4.58-4.40 (m, 3H), 3.46 (brs, 4H), 2.81 (brs, 6H), 2.42-2.28 (m, 1H), 1.77 (d, J=6.5 Hz, 3H).

Example 74

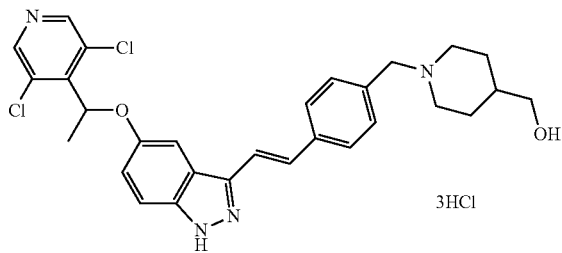 [SMILES: CC(Oc1ccc2[nH]nc(/C=C/c3ccc(CN4CCC(CO)CC4)cc3)c2c1)c1c(Cl)cncc1Cl]

This example was prepared by the method as described in Example 17.

LCMS (ESI) m/z: 537.2[M+1]+.

¹H NMR (DMSO-d₆, Bruker Avance 400 MHz): ppm 10.48 (brs, 1H), 8.61 (s, 2H), 7.73 (d, J=8.0 Hz, 2H), 7.65 (d, J=8.0 Hz, 2H), 7.54-7.46 (m, 2H), 7.34 (d, J=1.8 Hz, 1H), 7.24 (d, J=16.8 Hz, 1H), 7.11 (dd, J=8.9, 1.9 Hz, 1H), 6.17 (q, J=6.5 Hz, 1H), 4.27 (d, J=4.8 Hz, 2H), 3.38-3.26 (m, 4H), 2.91 (q, J=10.5 Hz, 2H), 1.87-1.77 (m, 5H), 1.69-1.44 (m, 3H).

Example 76

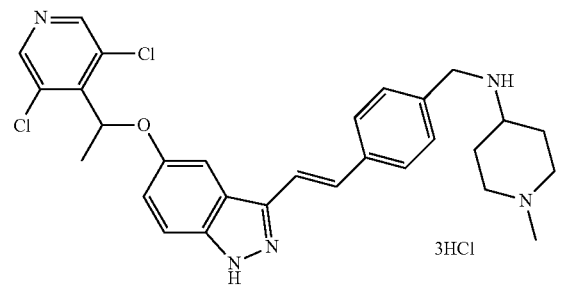 [SMILES: CC(Oc1ccc2[nH]nc(/C=C/c3ccc(CNC4CCN(C)CC4)cc3)c2c1)c1c(Cl)cncc1Cl]

This example was prepared by the method as described in Example 17.

LCMS (ESI) m/z: 536.1 [M+1]+.

¹H NMR (DMSO-d₆, Bruker Avance 400 MHz): ppm 10.80 (brs, 1H), 9.74 (brs, 1H), 8.61 (s, 2H), 7.75-7.64 (m, 4H), 7.53-7.46 (m, 2H), 7.35 (s, 1H), 7.24 (d, J=16.6 Hz, 1H), 7.10 (dd, J=9.0, 2.0 Hz, 1H), 6.18 (q, J=6.5 Hz, 1H), 4.24-4.17 (m, 2H), 3.51 (d, J=11.5 Hz, 2H), 3.31-3.25 (m, 1H), 3.02 (q, J=11.1 Hz, 2H), 2.71 (d, J=4.3 Hz, 3H), 2.40-2.33 (m, 2H), 2.16-2.02 (m, 2H), 1.78 (d, J=6.5 Hz, 3H).

Example 77 (Reference Example)

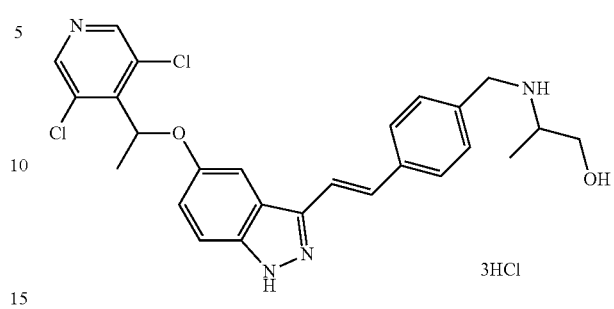

This example was prepared by the method as described in Example 17.

LCMS (ESI) m/z: 497.1 [M+1]+.

¹H NMR (DMSO-d₆, Bruker Avance 400 MHz): ppm 9.23 (brs, 1H), 9.02 (brs, 1H), 8.61 (s, 2H), 7.74-7.69 (m, 2H), 7.67-7.61 (m, 2H), 7.53-7.46 (m, 2H), 7.34 (s, 1H), 7.23 (d, J=16.8 Hz, 1H), 7.10 (dd, J=8.9, 1.9 Hz, 1H), 6.18 (q, J=6.5 Hz, 1H), 4.21 (t, J=5.3 Hz, 2H), 3.63-3.57 (m, 2H), 3.21-3.15 (m, 1H), 1.78 (d, J=6.5 Hz, 3H), 1.28 (d, J=6.5 Hz, 3H)

Example 78

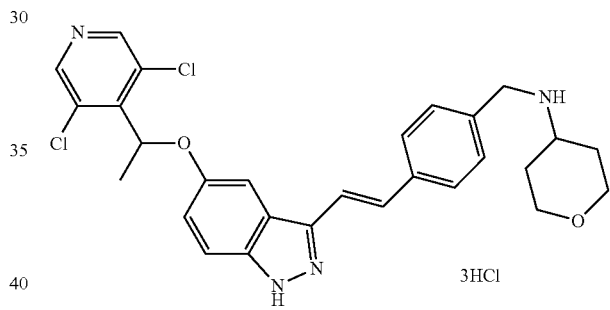

This example was prepared by the method as described in Example 17.

LCMS (ESI) m/z: 523.1 [M+1]+.

¹H NMR (DMSO-d₆, Bruker Avance 400 MHz): ppm 9.53 (brs, 2H), 8.61 (s, 2H), 7.75-7.70 (m, 2H), 7.68-7.64 (m, 2H), 7.53-7.46 (m, 2H), 7.34 (d, J=1.5 Hz, 1H), 7.24 (d, J=16.8 Hz, 1H), 7.10 (dd, J=9.0, 2.0 Hz, 1H), 6.18 (q, J=6.5 Hz, 1H), 4.17 (d, J=5.5 Hz, 4H), 3.35-3.27 (m, 3H), 2.11-2.04 (m, 2H), 1.80-1.71 (m, 5H).

Example 80

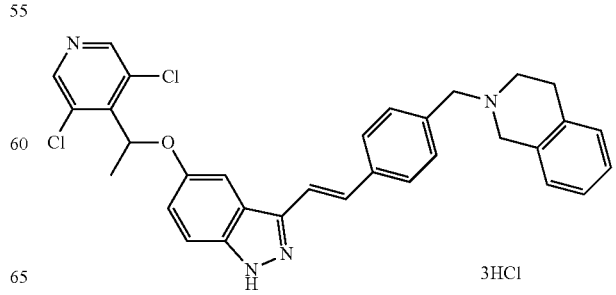

This example was prepared by the method as described in Example 17.
LCMS (ESI) m/z: 555.1 [M+1]⁺.

Example 81

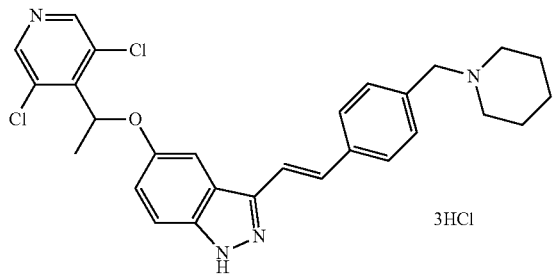 [SMILES: CC(Oc1ccc2[nH]nc(/C=C/c3ccc(CN4CCCCC4)cc3)c2c1)c1c(Cl)cncc1Cl]

3HCl

This example was prepared by the method as described in Example 17.
LCMS (ESI) m/z: 507.1 [M+1]⁺
1H NMR (400 MHz, METHANOL-$d_4$): ppm 8.60-8.47 (m, 2H), 7.83-7.76 (m, 2H), 7.68-7.63 (m, 2H), 7.61-7.55 (m, 1H), 7.52-7.43 (m, 2H), 7.41-7.34 (m, 1H), 7.33-7.30 (m, 1H), 6.29-6.21 (m, 1H), 4.37 (s, 2H), 3.56-3.47 (m, 2H), 3.10-2.98 (m, 2H), 2.04-1.93 (m, 2H), 1.88 (d, m, 6H), 1.63-1.51 (m, 1H).

Example 82

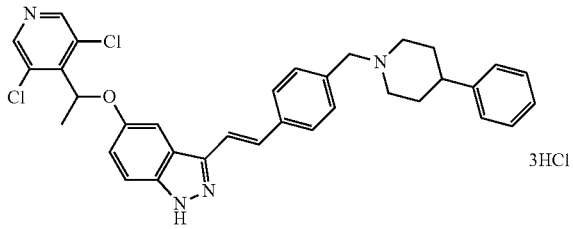 [SMILES: CC(Oc1ccc2[nH]nc(/C=C/c3ccc(CN4CCC(c5ccccc5)CC4)cc3)c2c1)c1c(Cl)cncc1Cl]

3HCl

This example was prepared by the method as described in Example 17.
LCMS (ESI) m/z: 583.1 [M+1]⁺.
¹H NMR (400 MHz, METHANOL-$d_4$): ppm 8.60-8.47 (m, 2H), 7.83-7.76 (m, 2H), 7.68-7.63 (m, 2H), 7.61-7.55 (m, 1H), 7.52-7.43 (m, 2H), 7.41-7.34 (m, 1H), 7.33-7.30 (m, 1H), 6.29-6.21 (m, 1H), 4.37 (s, 2H), 3.56-3.47 (m, 2H), 3.10-2.98 (m, 2H), 2.04-1.93 (m, 2H), 1.88 (d, m, 6H), 1.63-1.51 (m, 1H).

Example 83

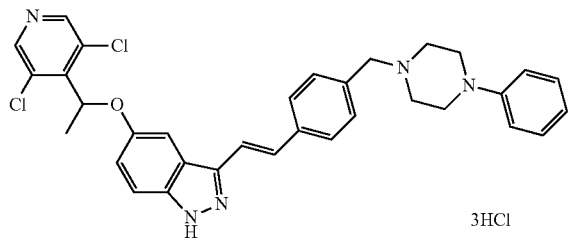 [SMILES: CC(Oc1ccc2[nH]nc(/C=C/c3ccc(CN4CCN(c5ccccc5)CC4)cc3)c2c1)c1c(Cl)cncc1Cl]

3HCl

This example was prepared by the method as described in Example 17.
LCMS (ESI) m/z: 584.1 [M+1]⁺

Example 86

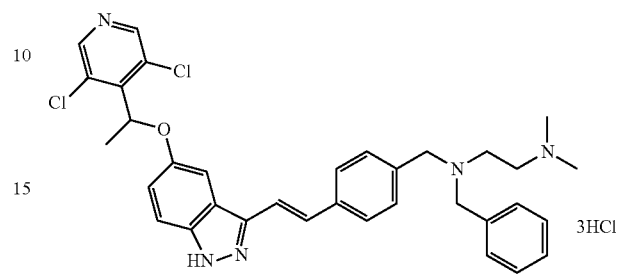

3HCl

This example was prepared by the method as described in Example 17.
LCMS (ESI) m/z: 600.2 [M+1]⁺

Example 87

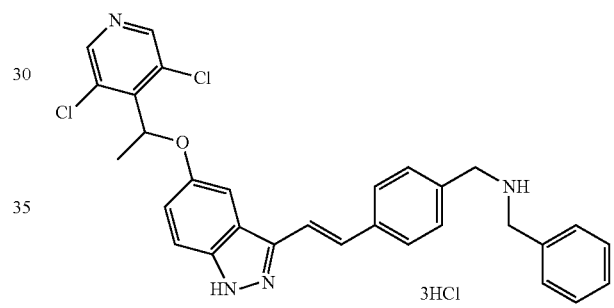

3HCl

This example was prepared by the method as described in Example 17.
LCMS (ESI) m/z: 529.1 [M+1]⁺

Example 88

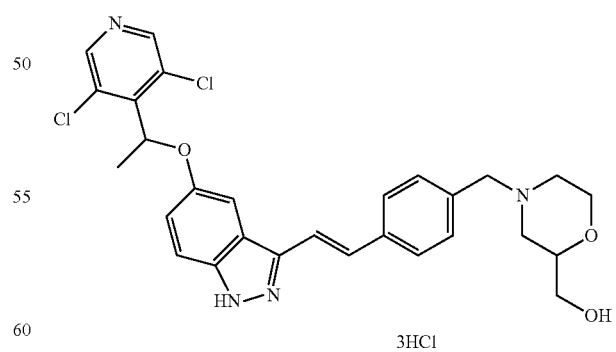

3HCl

This example was prepared by the method as described in Example 17.
LCMS (ESI) m/z: 539.1 [M+1]⁺.
¹H NMR (400 MHz, DMSO-$d_6$): ppm 11.5 (brs, 1H), 8.60 (s, 2H), 7.75-7.66 (m, 4H), 7.54-7.47 (m, 2H), 7.34 (s, 1H), 7.26-7.22 (m, 1H), 7.10 (dd, J=8.0, 1.6 Hz, 1H), 6.20-6.15 (m, 1H), 4.37 (brs, 2H), 4.01-3.99 (m, 2H), 3.41-3.48 (m, 3H), 3.38-3.28 (m, 2H), 3.06-2.91 (m, 2H), 1.78 (d, J=6.4 Hz, 3H).

Example 89

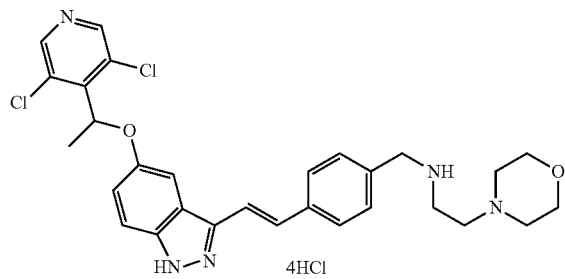 [SMILES: CC(Oc1ccc2[nH]nc(/C=C/c3ccc(CNCCN4CCOCC4)cc3)c2c1)c1c(Cl)cncc1Cl]

This example was prepared by the method as described in Example 17.

LCMS (ESI) m/z: 552.1 [M+1]$^+$.

$^1$H NMR (400 MHz, DMSO-d$_6$): ppm 11.4 (brs, 1H), 9.85 (brs, 2H), 8.61 (s, 2H), 7.73-7.66 (m, 4H), 7.53-7.47 (m, 2H), 7.35 (s, 1H), 7.26-7.22 (m, 1H), 7.11 (dd, J=8.0, 1.6 Hz, 1H), 6.20-6.15 (m, 1H), 4.23 (brs, 2H), 4.00 (brs, 2H), 3.56 (brs, 3H), 3.17 (brs, 2H), 1.76 (d, J=6.4 Hz, 3H).

Example 90

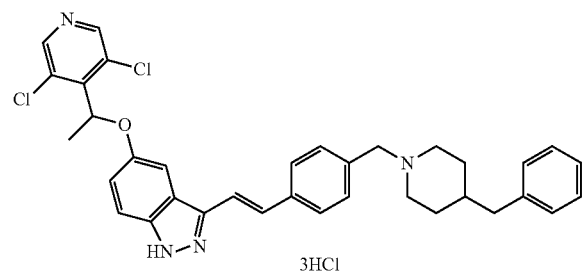 [SMILES: CC(Oc1ccc2[nH]nc(/C=C/c3ccc(CN4CCC(Cc5ccccc5)CC4)cc3)c2c1)c1c(Cl)cncc1Cl]

This example was prepared by the method as described in Example 17.

LCMS (ESI) m/z: 597.1 [M+1]$^+$

Example 91

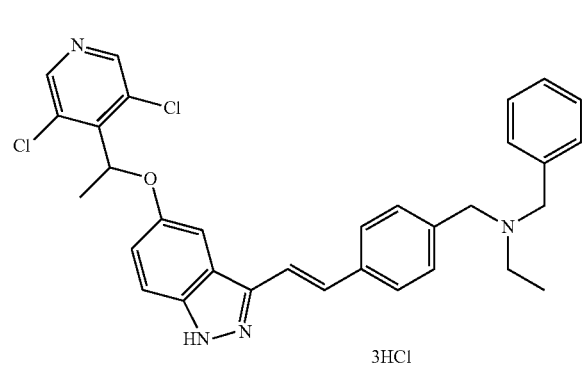 [SMILES: CCN(Cc1ccccc1)Cc1ccc(/C=C/c2n[nH]c3ccc(OC(C)c4c(Cl)cncc4Cl)cc23)cc1]

This example was prepared by the method as described in Example 17.

LCMS (ESI) m/z: 557.1 [M+1]$^+$

Example 93

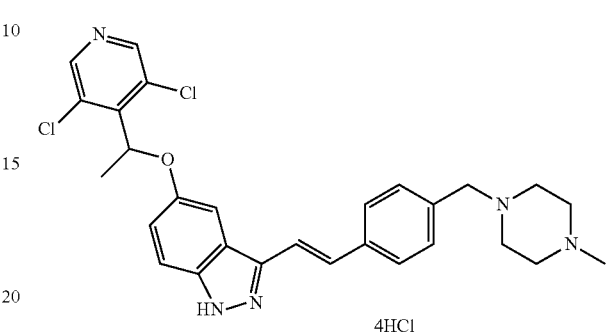

This example was prepared by the method as described in Example 17.

LCMS (ESI) m/z: 522.1 [M+1]$^+$

This example was prepared by the method as described in Example 17.

LCMS (ESI) m/z: 543.1 [M+1]$^+$

Example 95

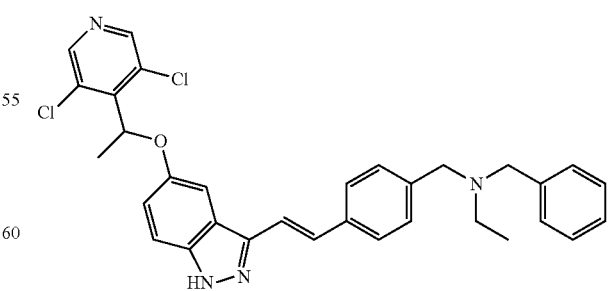

This example was prepared by the method as described in Example 17.

LCMS (ESI) m/z: 558.1 [M+1]$^+$

Example 97

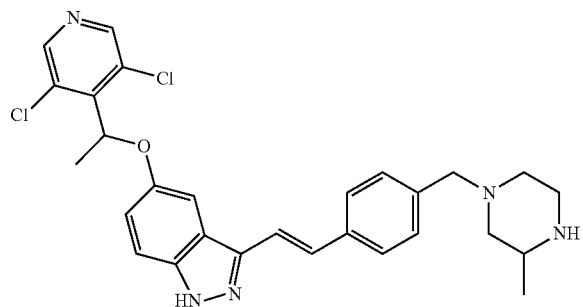 [SMILES: CC1CN(Cc2ccc(/C=C/c3n[nH]c4ccc(OC(C)c5c(Cl)cncc5Cl)cc34)cc2)CCN1]

This example was prepared by the method as described in Example 17.

LCMS (ESI) m/z: 522.1 [M+1]$^+$.

$^1$H NMR (DMSO-d$_6$, Bruker Avance 400 MHz): ppm 10.34-10.21 (m, 1H), 10.14 (brs, 1H), 8.65-8.59 (m, 2H), 7.77-7.69 (m, 4H), 7.55-7.46 (m, 2H), 7.35 (d, J=2.0 Hz, 1H), 7.24 (d, J=16.8 Hz, 1H), 7.10 (dd, J=9.0, 2.0 Hz, 1H), 6.18 (q, J=7.0 Hz, 1H), 4.41 (brs, 2H), 3.86-3.76 (m, 1H), 3.62-3.46 (m, 4H), 3.34-3.26 (m, 1H), 3.15 (t, J=12.3 Hz, 1H), 1.78 (d, J=6.5 Hz, 3H), 1.32 (d, J=6.3 Hz, 3H).

Example 99

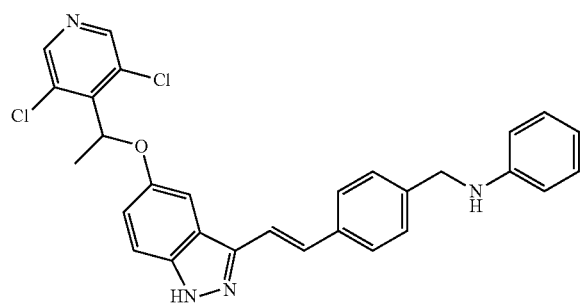 [SMILES: CC(Oc1ccc2[nH]nc(/C=C/c3ccc(CNc4ccccc4)cc3)c2c1)c1c(Cl)cncc1Cl]

This example was prepared by the method as described in Example 17.

LCMS (ESI) m/z: 514.9 [M+1]$^+$

Example 100

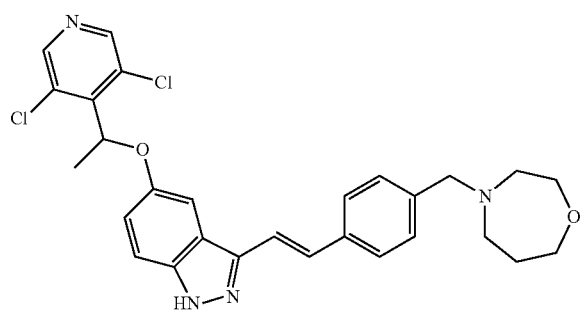 [SMILES: CC(Oc1ccc2[nH]nc(/C=C/c3ccc(CN4CCCOCC4)cc3)c2c1)c1c(Cl)cncc1Cl]

This example was prepared by the method as described in Example 17.

LCMS (ESI) m/z: 523.1 [M+1]$^+$

Example 101

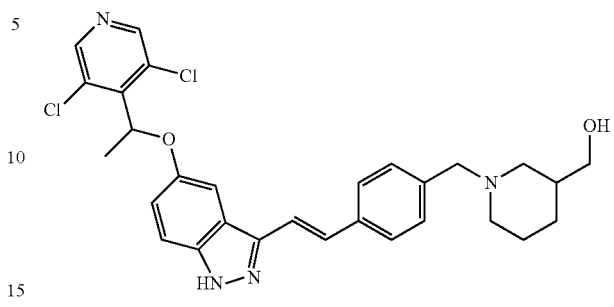

This example was prepared by the method as described in Example 17.

LCMS (ESI) m/z: 537.1 [M+1]$^+$

Example 102

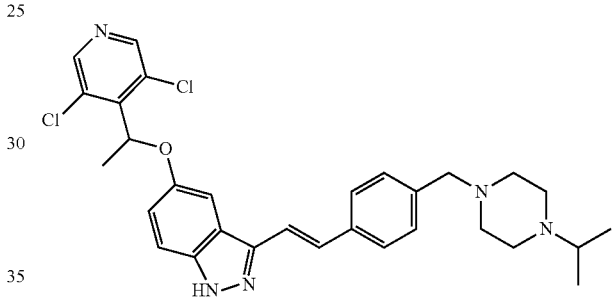

This example was prepared by the method as described in Example 17.

LCMS (ESI) m/z: 550.1 [M+1]$^+$ $^1$H NMR (DMSO-d$_6$, Bruker Avance 400 MHz): ppm 11.64 (br. s., 1H), 8.61 (s, 2H), 7.79-7.73 (m, 2H), 7.71-7.65 (m, 2H), 7.55-7.45 (m, 2H), 7.35 (d, J=1.5 Hz, 1H), 7.24 (d, J=16.8 Hz, 1H), 7.10 (dd, J=2.0, 9.0 Hz, 1H), 6.18 (q, J=6.5 Hz, 1H), 4.42 (br. s., 2H), 3.69-3.45 (m, 9H), 1.78 (d, J=6.5 Hz, 3H), 1.28 (d, J=6.0 Hz, 6H).

Example 103

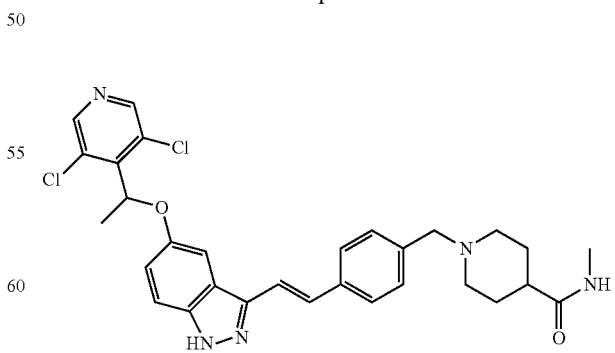

This example was prepared by the method as described in Example 17.

LCMS (ESI) m/z 564.1 [M+1]$^+$

Example 104

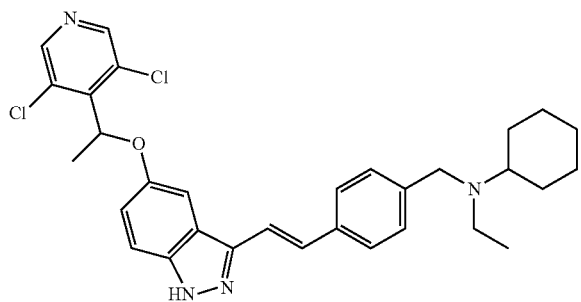 [SMILES: CCN(Cc1ccc(/C=C/c2n[nH]c3ccc(OC(C)c4c(Cl)cncc4Cl)cc23)cc1)C1CCCCC1]

This example was prepared by the method as described in Example 17.
LCMS (ESI) m/z: 549.2 [M+1]$^+$ Example 106

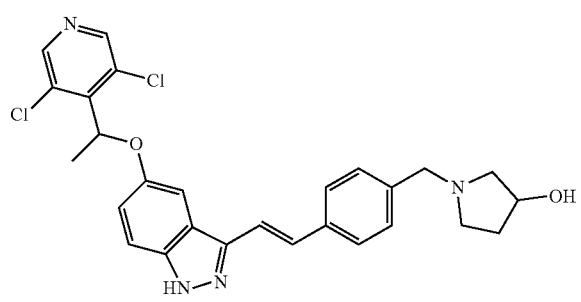 [SMILES: CC(Oc1ccc2[nH]nc(/C=C/c3ccc(CN4CCC(O)C4)cc3)c2c1)c1c(Cl)cncc1Cl]

This example was prepared by the method as described in Example 17.
LCMS (ESI) m/z: 509.0 [M+1]$^+$
$^1$H NMR (DMSO-d$_6$, Bruker Avance 400 MHz): ppm 11.56-11.41 (m, 0.5H), 11.08-10.94 (m, 0.5H), 8.61 (s, 2H), 7.76-7.64 (m, 4H), 7.54-7.45 (m, 2H), 7.35 (s, 1H), 7.24 (d, J=16.8 Hz, 1H), 7.10 (dd, J=9.0, 1.8 Hz, 1H), 6.18 (q, J=6.4 Hz, 1H), 4.47-4.32 (m, 3H), 3.55-3.39 (m, 1.5H), 3.32-3.12 (m, 2H), 3.01-2.96 (m, 0.5H), 2.34-2.26 (m, 0.5H), 2.08-1.86 (m, 1.5H), 1.78 (d, J=6.8 Hz, 3H).

Example 107

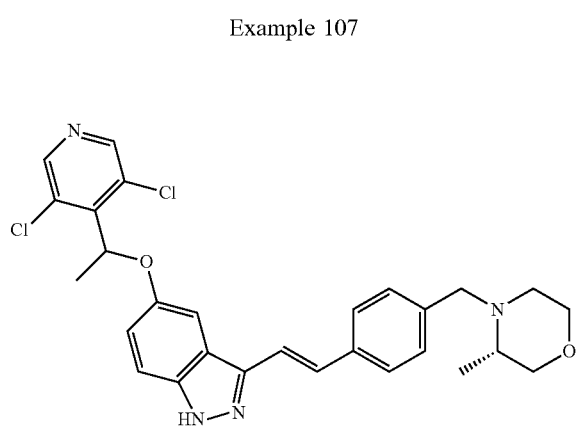

This example was prepared by the method as described in Example 17.
LCMS (ESI) m/z: 524.9 [M+1]$^+$ Example 108

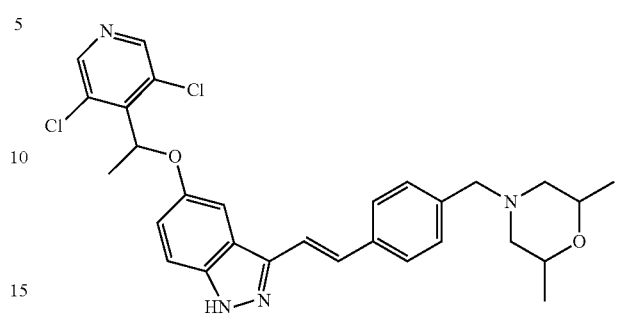

This example was prepared by the method as described in Example 17.
LCMS (ESI) m/z: 537.1 [M+1]$^+$ Example 109

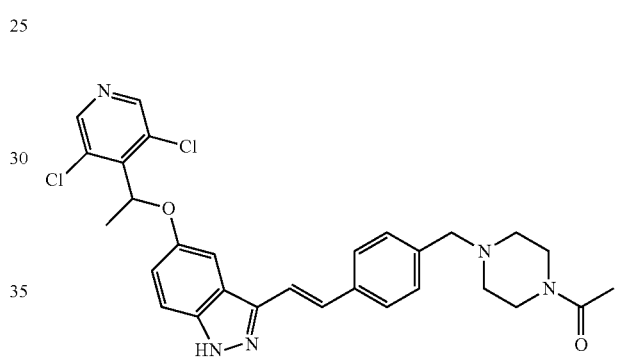

This example was prepared by the method as described in Example 17.
LCMS (ESI) m/z: 550.1 [M+1]$^+$ Scheme O

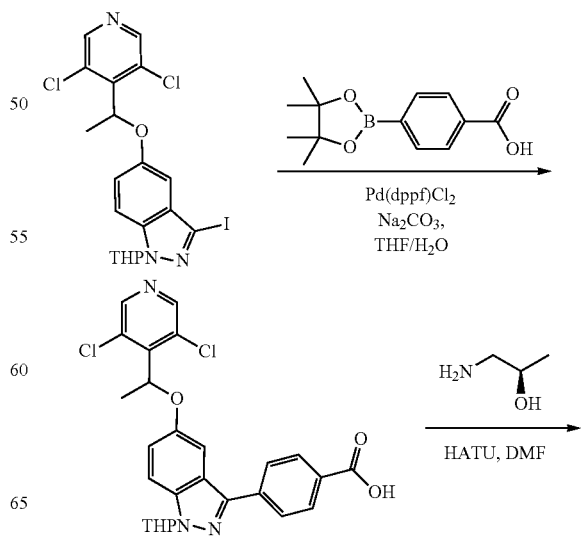

-continued

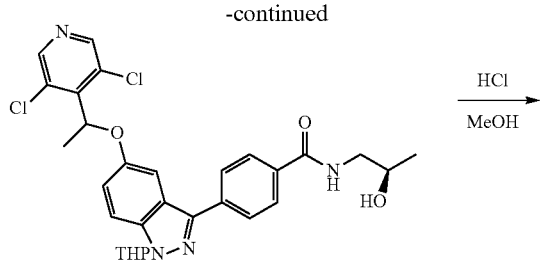

Example 111 (Reference Example)

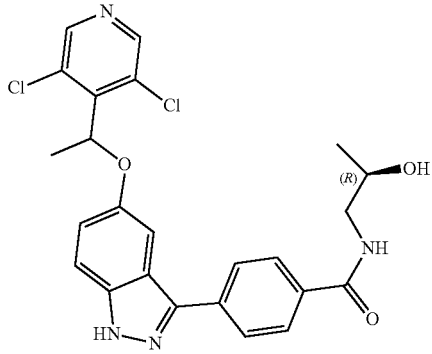

Example 111A

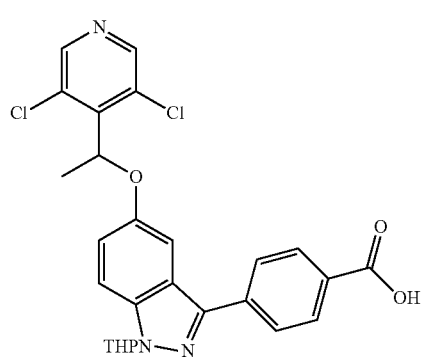

4-Carboxybenzyl boronate (84 mg, 0.50 mmol), Pd(dppf)Cl$_2$ (29 mg, 0.04 mmol) and sodium carbonate (83 mg, 0.78 mmol) were added to a mixed solution of a compound 1G (200 mg, 0.39 mmol) in tetrahydrofuran (5 mL) and water (1 mL) at room temperature under nitrogen atmosphere, and the reaction solution was heated to 80° C. for 18 hours. The reaction solution was cooled to room temperature, added with water (5 mL) and extracted with ethyl acetate (10 mL×3). The combined organic phase was washed with brine, dried, filtered and the filtrate was evaporated to dryness. The residue was purified by flash silica gel column chromatography to give the title compound (85 mg, yield 43%). LCMS (ESI) m/z: 512.0 [M+1]$^{+1}$ Example 111B

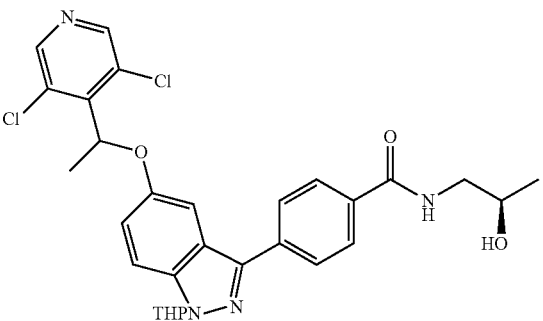

(R)-1-Aminoisopropanol (7 mg, 0.09 mmol) was added to a solution of Example 111A (40 mg, 0.08 mmol), HATU (46 mg, 0.12 mmol) and triethylamine (24 mg, 0.24 mml) in DMF (2 mL) at room temperature. The reaction solution was stirred at 30° C. for 1 hour. The reaction solution was added with water (5 mL) and extracted with ethyl acetate (10 mL×3). The organic phases were combined and washed with brine and dried. The filtrate was evaporated to dryness to give the title compound (50 mg, crude). LCMS (ESI) m/z: 569.1 [M+1]$^{+1}$ Example 111C

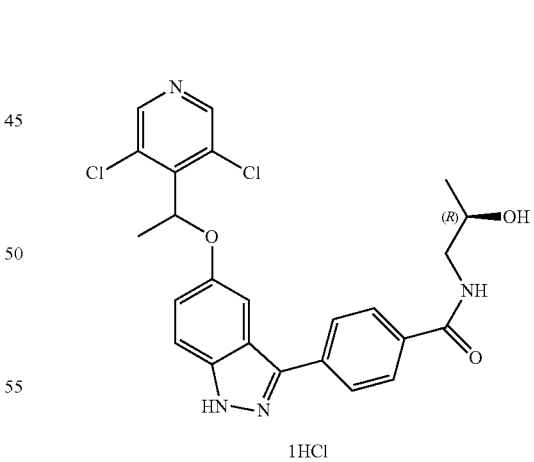

Example 111B (50 mg, 0.08 mmol) was dissolved in methanol (2 mL) and concentrated HCl (0.1 mL) was slowly added dropwise. The reaction solution was stirred at room temperature for 4 hours. The reaction solution was concentrated and purified by preparative HPLC to give the target compound (18 mg, yield 42%). LCMS (ESI) m/z: 485 [M+1]$^{+1}$ $^1$H NMR (DMSO-d$_6$, Bruker Avance 400 MHz): ppm 8.63 (s, 2H), 8.53 (t, J=5.3 Hz, 1H), 8.01 (d, J=8.3 Hz, 2H), 7.84 (d, J=8.3 Hz, 2H), 7.52 (d, J=9.0 Hz, 1H), 7.20 (d, J=1.8 Hz, 1H), 7.13 (dd, J=2.1, 8.9 Hz, 1H), 6.13 (q, J=6.5 Hz, 1H), 3.84 (td, J=6.2, 12.4 Hz, 2H), 3.32-3.18 (m, 2H), 1.77 (d, J=6.5 Hz, 3H), 1.10 (d, J=6.3 Hz, 3H).

Example 112

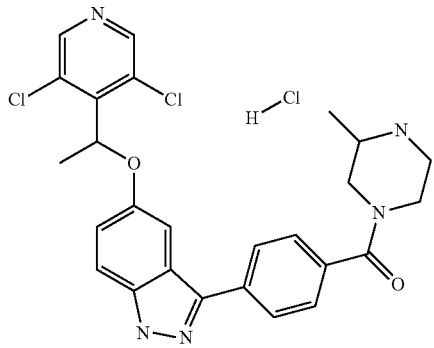

This example was prepared by the method as described in Example 111.

LCMS (ESI) m/z: 510.1 [M+1]+

$^1$H NMR (400 MHz, DMSO-d$_6$): ppm 9.64 (d, J=10.4 Hz, 1H), 9.16 (s, 2H), 8.63 (d, J=4.4 Hz, 2H), 7.82 (t, J=3.6 Hz, 2H), 7.59 (d, J=7.6 Hz, 2H), 7.52 (d, J=4.4 Hz, 1H), 7.16-7.11 (m, 2H), 6.12-6.07 (m, 1H), 4.51 (m, 1H), 4.06 (m, 1H), 3.21 (m, 3H), 3.05 (m, 2H), 1.76 (d, J=6.8 Hz, 3H), 1.39 (d, J=5.6 Hz, 3H).

Example 113

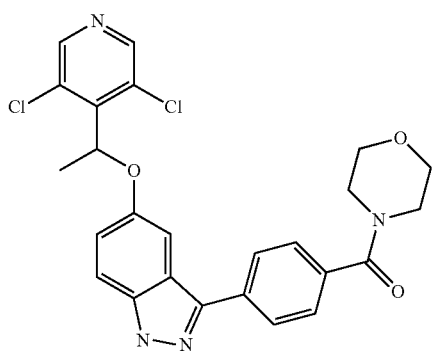 [SMILES: CC(Oc1ccc2[nH]nc(-c3ccc(C(=O)N4CCOCC4)cc3)c2c1)c1c(Cl)cncc1Cl]

This example was prepared by the method as described in Example 111.

LCMS (ESI) m/z: 497.0 [M+1]+

Example 114

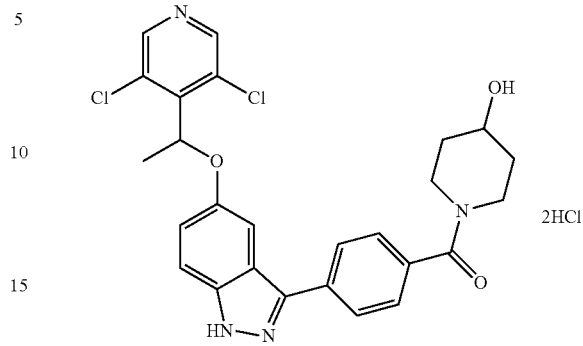

This example was prepared by the method as described in Example 111.

LCMS (ESI) m/z: 511.1 [M+1]+

$^1$H NMR (DMSO-d6, varian 400 MHz): ppm 8.60 (s, 2H), 7.77 (d, J=8.0 Hz, 3H) 7.50 (s, 1H) 7.49 (d, J=8.0 Hz, 2H), 7.13 (d, J=2 Hz, 2H), 7.11-7.08 (m, 2H), 6.07 (dd, J=6.8 Hz, J=13.6 Hz, 1H), 4.02 (s, 1H), 3.75 (m, 1H), 3.20 (s, 2H), 1.75-1.73 (m, 5H), 1.39 (s, 2H).

Example 115

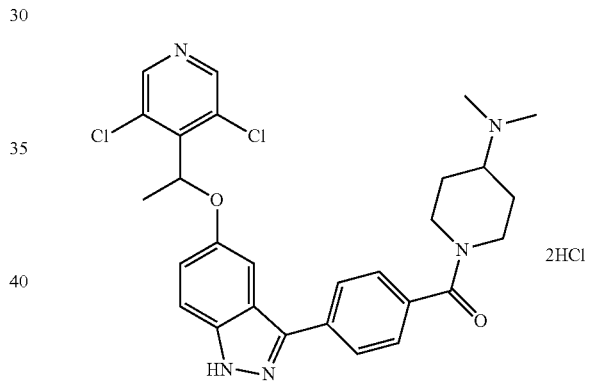

This example was prepared by the method as described in Example 111.

LCMS (ESI) m/z: 540.2 [M+1]+

Example 116

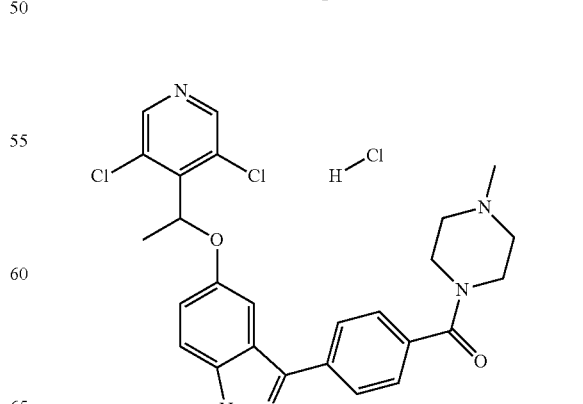

This example was prepared by the method as described in Example 111.
LCMS (ESI) m/z: 509.9 [M+1]⁺

Example 117

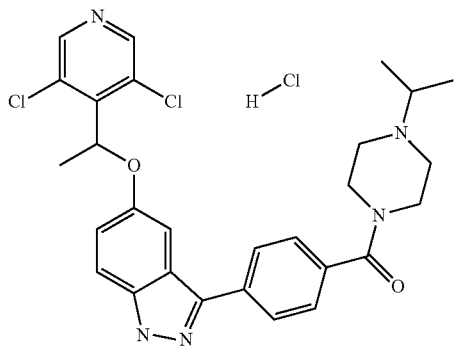 [SMILES: CC(Oc1ccc2[nH]nc(-c3ccc(C(=O)N4CCN(C(C)C)CC4)cc3)c2c1)c1c(Cl)cncc1Cl ; Cl]

This example was prepared by the method as described in Example 111. LCMS (ESI) m/z: 538.3 [M+1]⁺

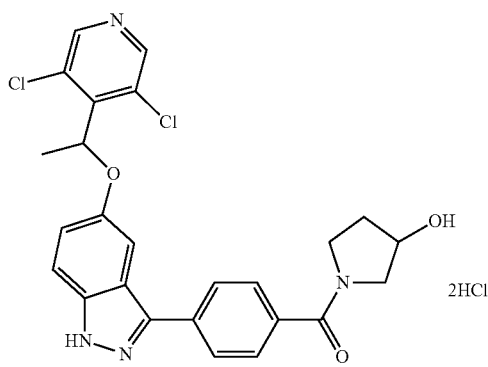 [SMILES: CC(Oc1ccc2[nH]nc(-c3ccc(C(=O)N4CCC(O)C4)cc3)c2c1)c1c(Cl)cncc1Cl]

This example was prepared by the method as described in Example 111. LCMS (ESI) m/z: 497.3 [M+1]⁺
¹H NMR (400 MHz, DMSO-$d_6$): ppm 8.63 (d, 2H), 7.80 (d, J=8, 2H), 7.65 (dd, J=3.2, J=7.6, 2H), 7.51 (d, J=9.2, 1H), 7.16 (s, 1H), 7.13 (d, J=8.8, 1H), 6.10 (t, J=2.8, 1H), 4.28 (s, 2H), 3.45-3.66 (m, 3H), 1.98-1.92 (m, 2H), 1.76 (d, J=6.4, 3H).

Example 120

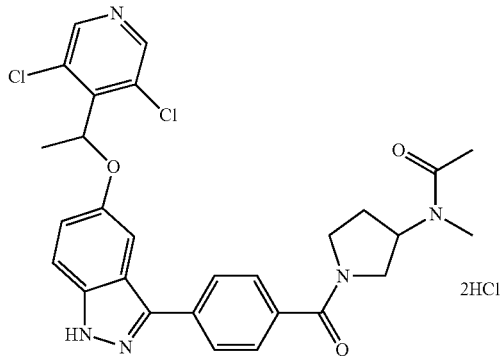 [SMILES: CC(=O)N(C)C1CCN(C(=O)c2ccc(-c3n[nH]c4ccc(OC(C)c5c(Cl)cncc5Cl)cc34)cc2)C1]

This example was prepared by the method as described in Example 111.
LCMS (ESI) m/z: 552.3 [M+1]⁺

Example 121

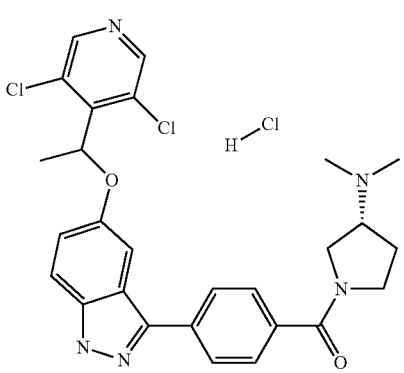 [SMILES: CC(Oc1ccc2[nH]nc(-c3ccc(C(=O)N4CC[C@@H](N(C)C)C4)cc3)c2c1)c1c(Cl)cncc1Cl ; Cl]

This example was prepared by the method as described in Example 111. LCMS (ESI) m/z: 524.2 [M+1]⁺
¹H NMR (400 MHz, DMSO-$d_6$): ppm 11.42 (s, 1H), 8.64 (s, 2H), 7.82 (d, J=7.60 Hz, 2H), 7.69 (d, J=6.80 Hz, 2H), 7.52 (d, J=9.20 Hz, 1H), 7.13 (t, 2H), 6.07 (d, J=6.40 Hz, 1H), 3.89 (m, 5H), 2.80 (s, 6H), 2.29 (m, 3H), 1.74 (d, J=6.80 Hz, 3H).

Example 125

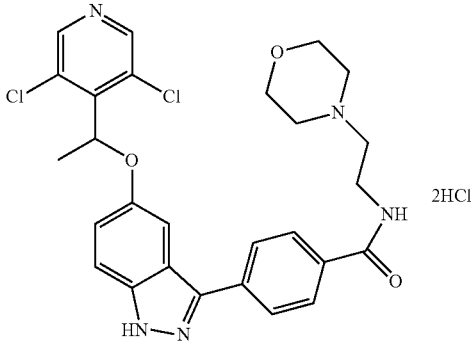 [SMILES: CC(Oc1ccc2[nH]nc(-c3ccc(C(=O)NCCN4CCOCC4)cc3)c2c1)c1c(Cl)cncc1Cl]

This example was prepared by the method as described in Example 111.
LCMS (ESI) m/z: 540.2 [M+1]⁺

Example 126
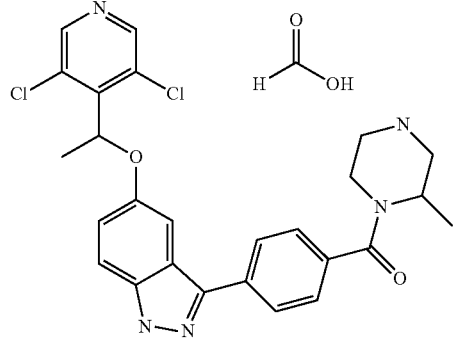
This example was prepared by the method as described in Example 111.
LCMS (ESI) m/z: 532.1 [M+23]$^+$
$^1$H NMR (400 MHz, DMSO-d$_6$): ppm 13.26 (s, 1H), 8.62 (s, 2H), 8.18 (s, 1H), 7.81 (d, J=8.0 Hz, 2H), 7.56 (d, J=8.0 Hz, 2H), 7.51 (d, J=9.2 Hz, 1H), 7.17 (s, 1H), 7.12 (dd, J$_1$=2 Hz, J$_2$=9.2 Hz 1H), 6.12-6.06 (m, 1H), 4.41-4.39 (m, 2H), 3.12-2.85 (m, 5H), 1.76 (d, J=6.4 Hz, 3H), 1.12-1.10 (m, 3H).
Scheme P
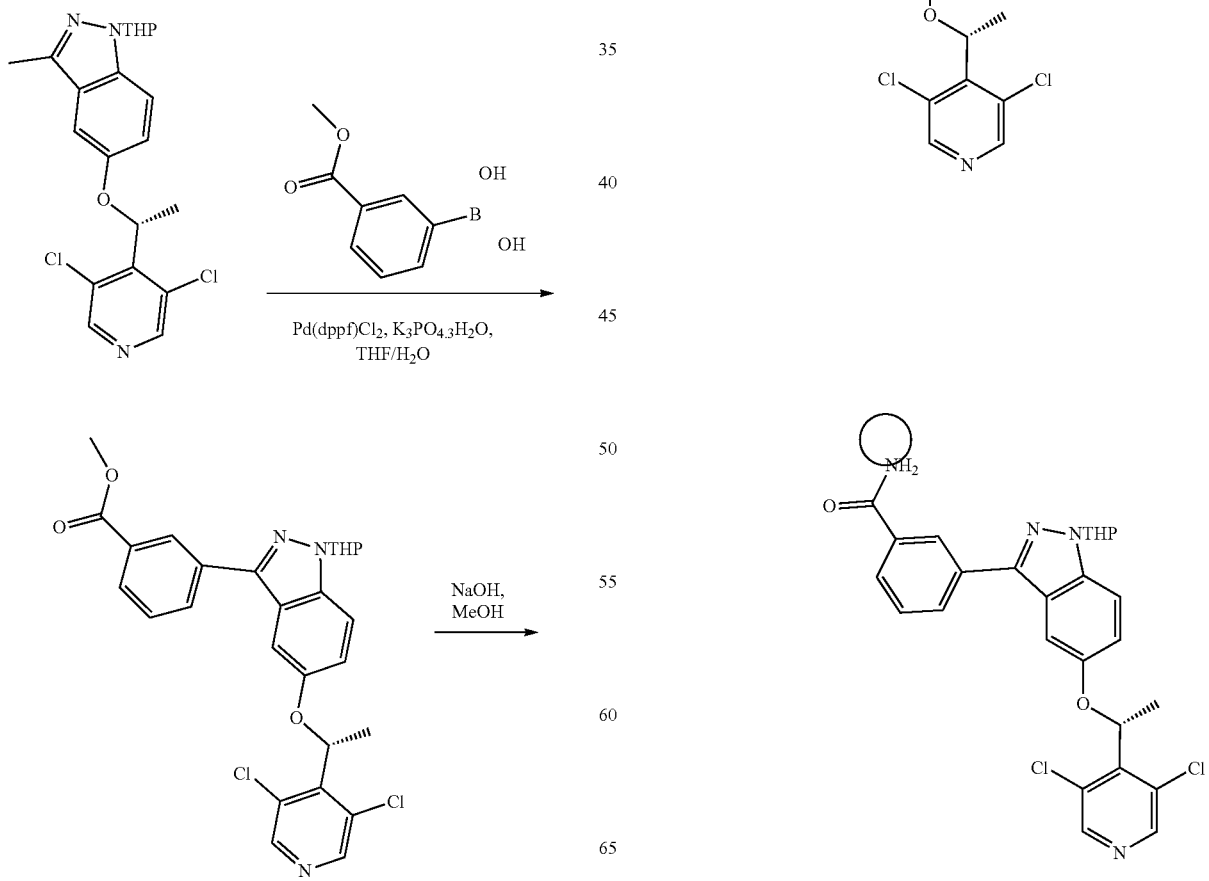
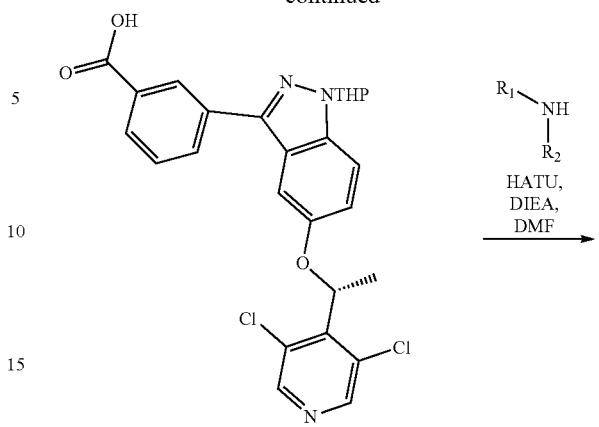

Example 127

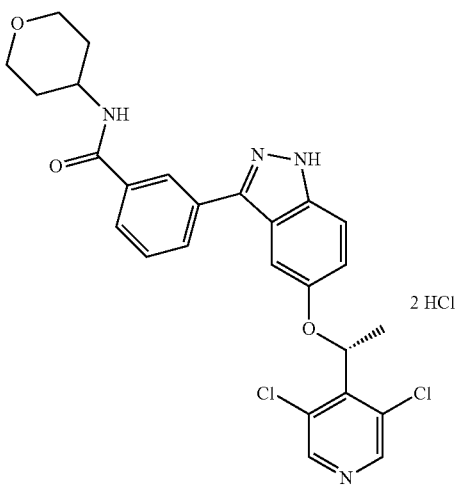 [SMILES: C[C@@H](Oc1ccc2[nH]nc(-c3cccc(C(=O)NC4CCOCC4)c3)c2c1)c1c(Cl)cncc1Cl]

2 HCl

Example 127A

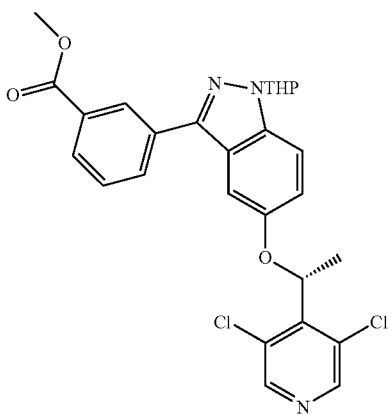

A suspension of Example 24H (600 mg, 1.16 mmol), 3-methoxycarbonyl-phenylboronic acid (229.23 mg, 1.27 mmol), Pd(dppf)Cl₂ (84.73 mg, 115.79 μmol) and potassium phosphate trihydrate (925.10 mg, 3.47 mmol) and triethylamine (555.53 mmol, 5.49 mmol) in THF/H₂O (4/2 mL) was stirred under nitrogen atmosphere at 100° C. for 2 hours. The reaction solution was added with water (50 mL) and extracted with ethyl acetate (50 mL×3), dried over anhydrous sodium sulfate and concentrated in vacuo. The residue was purified by column chromatography to give the title compound (600 mg, yield 93.35%), LCMS(ESI) m/z: 526.2 [M+1]⁺. ¹H NMR (CHLOROFORM-d, 400 MHz) ppm 8.51 (d, J=1.00 Hz, 1H), 8.40 (d, J=2.51 Hz, 2H), 7.95-8.07 (m, 2H), 7.47-7.58 (m, 2H), 7.24 (d, J=1.51 Hz, 1H), 7.15 (dd, J=2.01, 9.03 Hz, 1H), 6.08 (q, J=6.53 Hz, 1H), 5.69 (ddd, J=3.01, 6.02, 9.03 Hz, 1H), 4.00-4.07 (m, 1H), 3.97 (s, 3H), 3.73 (t, J=10.29 Hz, 1H), 2.59 (dd, J=3.26, 7.78 Hz, 1H), 2.06-2.23 (m, 2H), 1.71-1.84 (m, 5H).

Example 127B

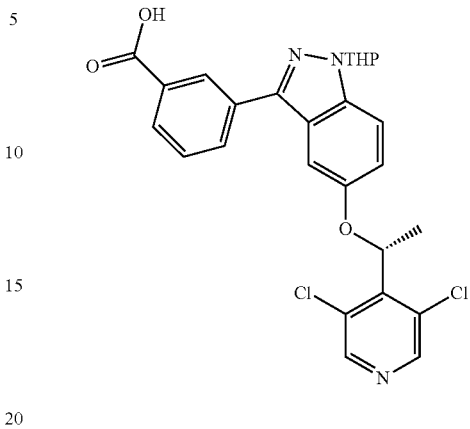

Lithium hydroxide monohydrate (51.34 mg, 1.35 mmol) was added in one batch to a solution of Example 1A (600 mg, 1.14 mmol) in methanol/tetrahydrofuran/water (6/6/4 mL) at 30° C., then the mixture was stirred at this temperature for 5 hours. The reaction solution was concentrated in vacuo, added with water (50 mL), adjusted to pH=6 with 2M dilute hydrochloric acid, extracted with ethyl acetate (50 mL×3). The organic phase was dried over anhydrous sodium sulfate and concentrated in vacuo to give the title compound (520 mg, yield 85.26%). ¹H NMR (CHLOROFORM-d, 400 MHz) ppm 8.44-8.56 (m, 1H), 8.03-8.19 (m, 1H), 7.48-7.62 (m, 1H), 7.12-7.23 (m, 1H), 6.08 (q, J=6.53 Hz, 1H), 5.66-5.75 (m, 1H), 4.03 (d, J=6.53 Hz, 1H), 3.74 (br. s., 1H), 2.53-2.67 (m, 1H), 2.06-2.23 (m, 2H), 1.59-1.86 (m, 6H).

Example 127C

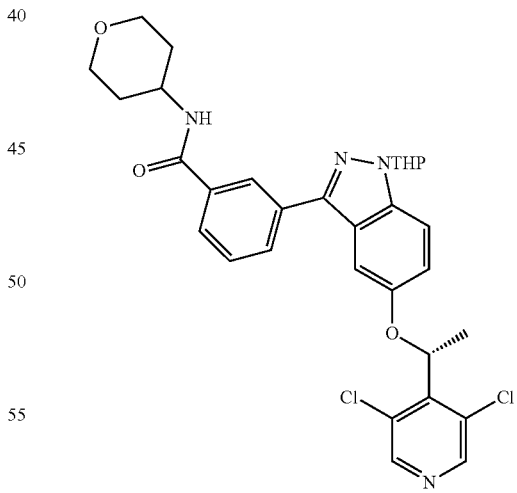

4-Amino tetrahydropyran hydrochloride (23.63 mg, 1.42 mmol) was added to a solution of Example 127A (80 mg, 156.13 mmol), HATU (89.05 mg, 234.20 mmol) and DIPEA (80.72 mg, 624.54 mmol) in DMF (5 mL) at 30° C. and the suspension was stirred at 30° C. for 2 hours. The mixture was added with water (50 mL) and extracted with ethyl acetate (50 mL×3), dried over anhydrous sodium sulfate and concentrated in vacuo. The residue was purified by preparative thin layer chromatography to give the title compound as a yellow oil (90 mg, yield 89.05%), LCMS(ESI) m/z: 595.1 [M+1]⁺.

Example 127D

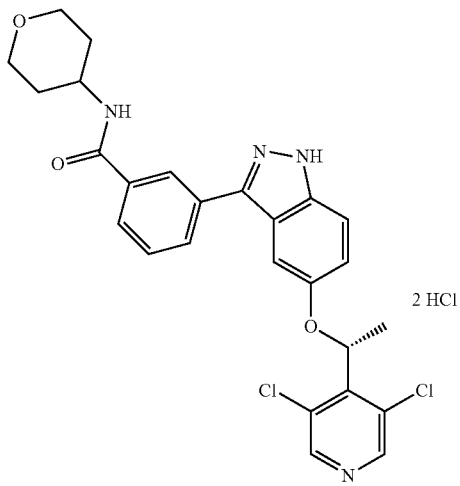 [SMILES: C[C@@H](Oc1ccc2[nH]nc(-c3cccc(C(=O)NC4CCOCC4)c3)c2c1)c1c(Cl)cncc1Cl]

Acetyl chloride (1 mL) was added dropwise to methanol (4 mL) at 0° C., and the mixture was stirred for 15 minutes, then Example 127C (90 mg, 151.13 μmol) was added to the solution. After the addition, the mixture was stirred at 40° C. for 2 hours, then concentrated in vacuo, and the residue was purified by preparative HPLC (hydrochloric acid system) to give the title compound (20 mg, yield 24.16%).

LCMS (ESI) m/z: 511.2 [M+1]⁺. $^1$H NMR (METHANOL-$d_4$, 400 MHz) ppm 8.49 (s, 2H), 8.22 (s, 1H), 7.88 (d, J=7.28 Hz, 2H), 7.59-7.67 (m, 1H), 7.54 (d, J=9.29 Hz, 1H), 7.27 (dd, J=2.01, 9.03 Hz, 1H), 7.16 (d, J=1.76 Hz, 1H), 6.15 (q, J=6.78 Hz, 1H), 4.11-4.27 (m, 1H), 4.02 (d, J=9.29 Hz, 2H), 3.56 (t, J=11.67 Hz, 2H), 1.97 (d, J=11.29 Hz, 2H), 1.66-1.84 (m, 5H).

Example 129

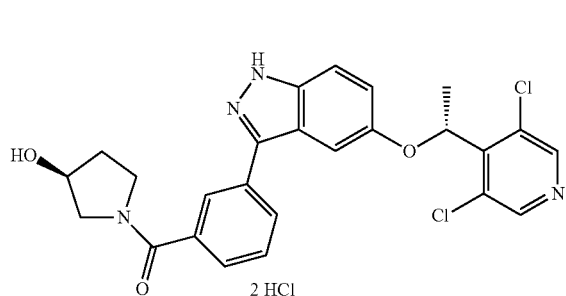 [SMILES: C[C@@H](Oc1ccc2[nH]nc(-c3cccc(C(=O)N4CC[C@H](O)C4)c3)c2c1)c1c(Cl)cncc1Cl]

This example was prepared by the method as described in Example 127. LCMS (ESI) m/z [M+H]⁺: 497.1 [M+1]⁺.

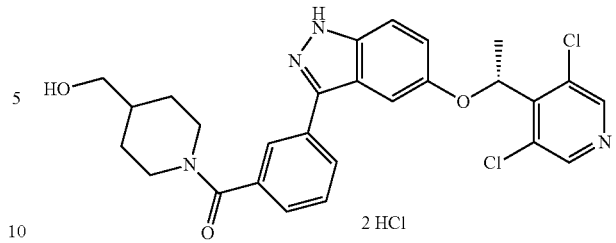

This example was prepared by the method as described in Example 127. LCMS(ESI) m/z [M+H]⁺: 525.3 [M+1]⁺.

Scheme Q

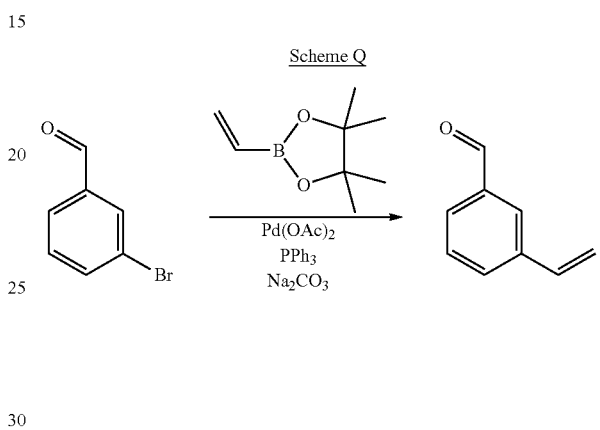

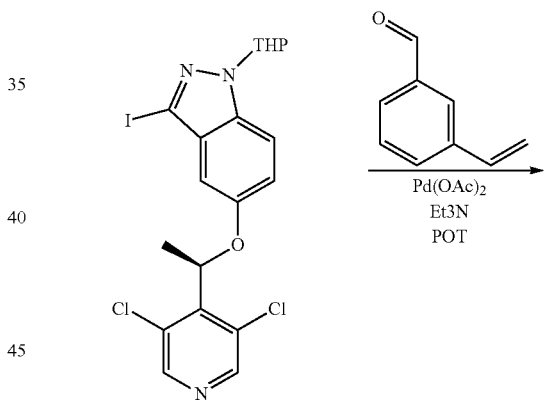

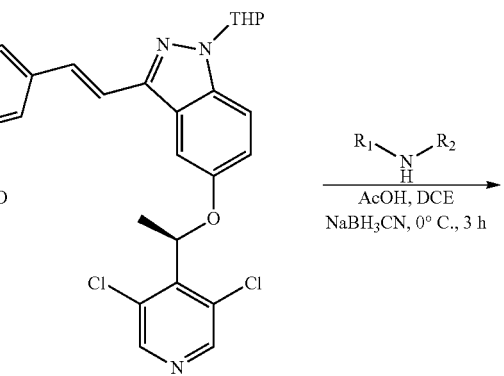

-continued

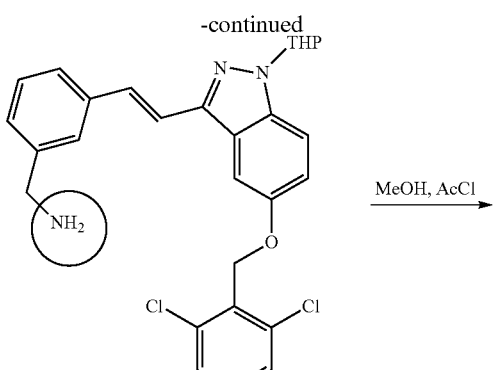

Example 132

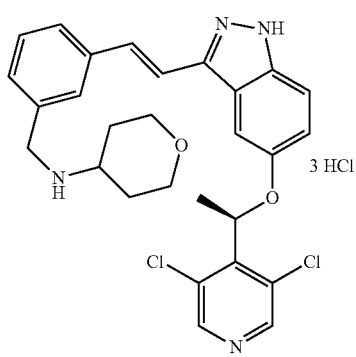 [SMILES: C[C@@H](Oc1ccc2[nH]nc(/C=C/c3cccc(CNC4CCOCC4)c3)c2c1)c1c(Cl)cncc1Cl]

Example 132A

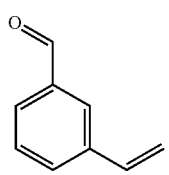

3-Bromobenzaldehyde (1 g, 5.40 mmol), pinacolato-4,4,5,5-tetramethyl-2-vinyl-1,3,2-borate (1.2 g, 8.10 μmol), Pd(OAc)₂ (121.24 mg, 0.54 mmol) and PPh₃ (283.27 mg, 1.08 mmol) and Na₂CO₃ (1.14 mg, 10.80 mmol) were dissolved in a mixture of water (3 mL) and DMF (9 mL), the mixture was reacted at 80° C. under nitrogen atmosphere for 12 hours. Thin layer chromatography (petroleum ether:ethyl acetate=2/1) indicated that the starting material was completely reacted. The reaction mixture was concentrated under reduced pressure and the residue was purified by silica gel column chromatography (petroleum ether/ethyl acetate=40/1 to 30/1) to give the title compound (as a yellowish oil, 540.00 mg, 3.40 μmol, yield 63.05%). ¹H NMR (400 MHz, METHANOL-d₄) 9.99-10.05 (m, 1H), 7.98 (s, 1H), 7.71-7.86 (m, 2H), 7.48-7.60 (m, 1H), 6.78-6.90 (m, 1H), 5.93 (d, J=17.57 Hz, 1H), 5.38 (d, J=11.04 Hz, 1H)

Example 132B

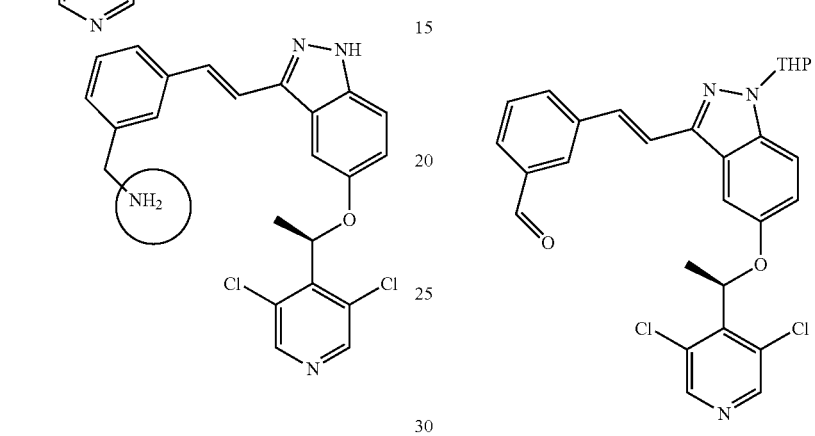

Example 24H (300.00 mg, 0.58 mmol), 132 A (76.52 mg, 578.96 mmol), Et₃N (175.75 mg, 1.74 mmol) and PPh₃ (283.27 mg, 1.08 mmol), Pd(OAc)₂ (13.00 mg, 57.90 mmol), tri-o-tolylphosphine (17.62 mg, 57.90 mmol) were dissolved in DMF (4 mL) and the mixture was reacted at 100° C. under nitrogen atmosphere for 12 hours. Thin-layer chromatography (petroleum ether:ethyl acetate=2/1) indicated that the starting material was completely reacted. The reaction mixture was quenched with 5 mL ice-water, stirred for 5 minutes and then extracted with ethyl acetate (10 mL×3), then layering. The organic phase was washed with brine, dried over anhydrous sodium sulfate, filtered, and the solvent was evaporated. The residue was purified by silica gel column chromatography (petroleum ether/ethyl acetate=15/1) to give the title compound (220.00 mg, 421.12 μmol, yield 72.74%). LCMS (ESI) m/z [M+H]⁺: 552.1.

Example 132C

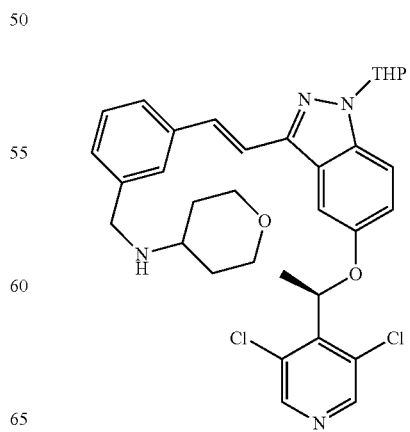

Acetic acid (0.80 mg, 13.4 μmol) was added dropwise to a mixed solution of Example 132B (70 mg, 133.99 μmol) and tetrahydropyran-4-amino (40.66 mg, 401.97 μmol) in 1,2-dichloroethane (1 mL), and the mixture was stirred at 20° C. for 30 minutes after the addition. Sodium cyanoborohydride (25.26 mg, 401.98 μmol) was slowly added and the mixture was stirred for 2 hours at 20° C. The reaction solution was quenched with water. The aqueous layer was extracted with dichloromethane (10 mL×3), and the organic layers were combined and washed with brine (10 mL×2), dried over anhydrous sodium sulfate, filtered and the filtrate was concentrated in vacuo. The residue was purified by thin layer chromatography (petroleum ether/ethyl acetate=1/1) to give the title compound (as a yellow oily liquid, 30 mg, 49.38 μmol, yield 36.85%). LCMS (ESI) m/z [M+H]+: 607.4

Example 132D

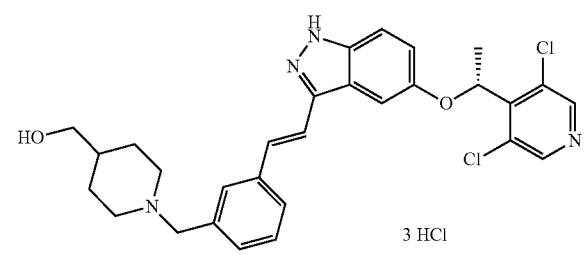 [SMILES: C[C@@H](Oc1ccc2[nH]nc(/C=C/c3cccc(CN4CCC(CO)CC4)c3)c2c1)c1c(Cl)cncc1Cl]

Example 132C (30.00 mg, 49.38 μmol) was dissolved in dry methanol (1 mL) and then this solution was added dropwise to a solution of acetyl chloride (1 mL) in dry methanol (4 mL) at 0° C. The reaction solution was warmed to 40° C. and stirred for 30 hours. Upon the completion of the reaction, the solvent was spun off to give the title compound (22 mg, 42.03 μmol, yield 85.11%). LCMS (ESI) m/z [M+H]+: 522.3

Example 134

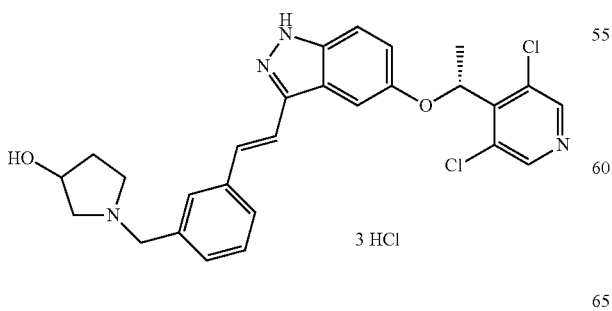

This example was prepared by the method as described in Example 132. LCMS (ESI) m/z [M+H]+: 509.1

Example 135

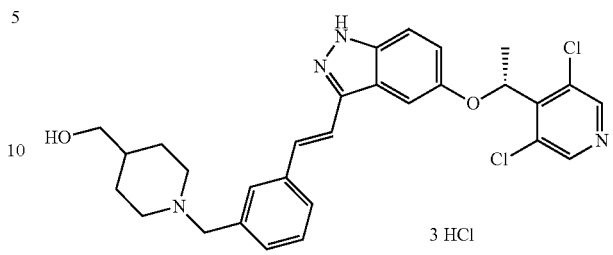

This example was prepared by the method as described in Example 132. LCMS (ESI) m/z [M+H]+: 537.5

Scheme R

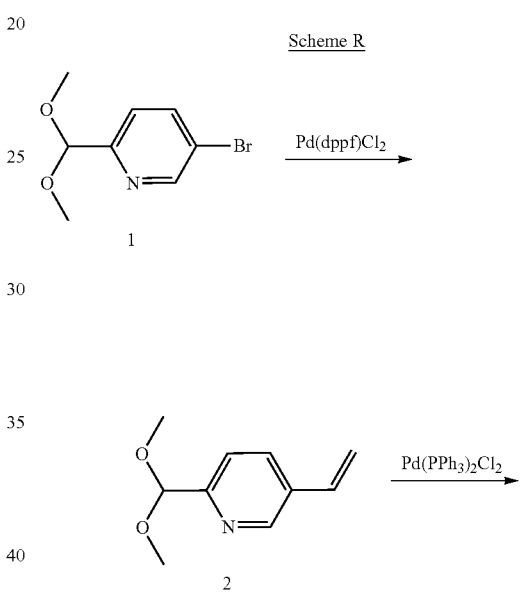

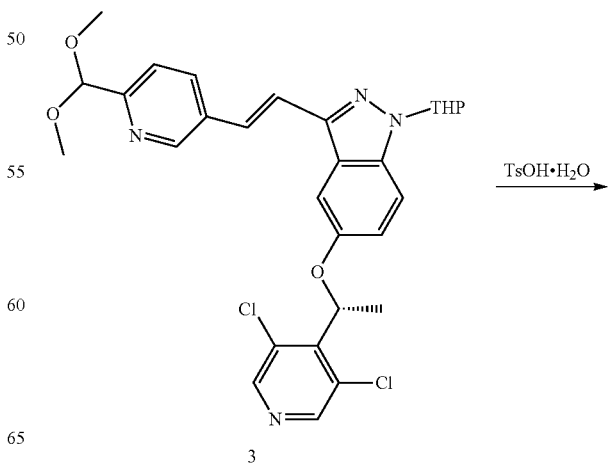

-continued

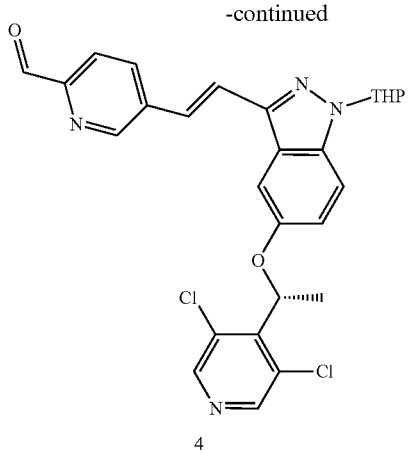

4

NaBH₃CN →

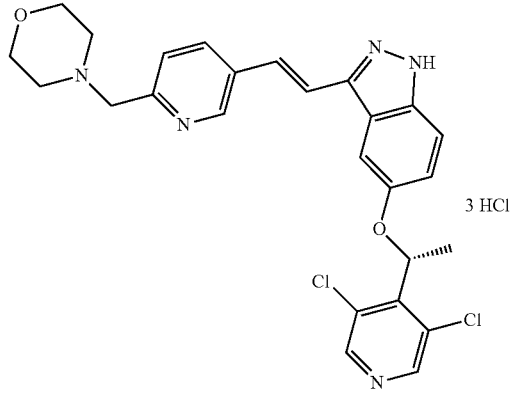 [SMILES: C[C@@H](Oc1ccc2[nH]nc(/C=C/c3ccc(CN4CCOCC4)nc3)c2c1)c1c(Cl)cncc1Cl]

Example 137

3 HCl

Example 137A

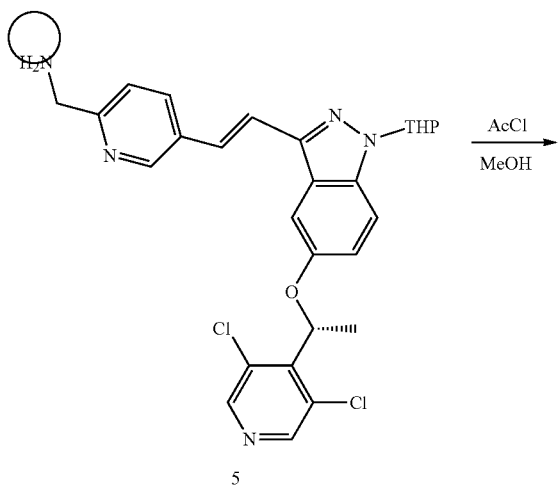

5

AcCl
MeOH
→

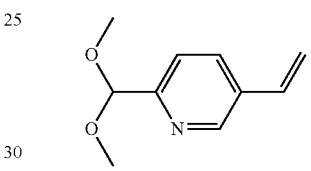

A suspension of bis-pinacol boronate (995.45 mg, 6.46 mmol), 5-bromo-2-(dimethoxymethyl)pyridine (1 g, 4.31 mmol), Pd(dppf)Cl₂ (315.29 mg, 0.43 mmol) and potassium carbonate (1.79 g, 12.93 mmol) in dioxane (15 mL) was heated at 100° C. for 16 hours under nitrogen atmosphere. The suspension was cooled, added with water (10 mL), extracted with ethyl acetate (3×10 mL), washed with brine, dried, filtered and the filtrate was concentrated in vacuo. The residue was purified by column chromatography to give the title compound as a yellow oil (700 mg, yield 87%). ¹H NMR (400 MHz, CHLOROFORM-d)=8.63 (d, J=1.8 Hz, 1H), 7.80 (dd, J=2.1, 8.2 Hz, 1H), 7.53 (d, J=8.3 Hz, 1H), 6.74 (dd, J=11.0, 17.6 Hz, 1H), 5.86 (d, J=17.8 Hz, 1H), 5.45-5.37 (m, 2H), 3.43 (s, 6H)

Example 137B

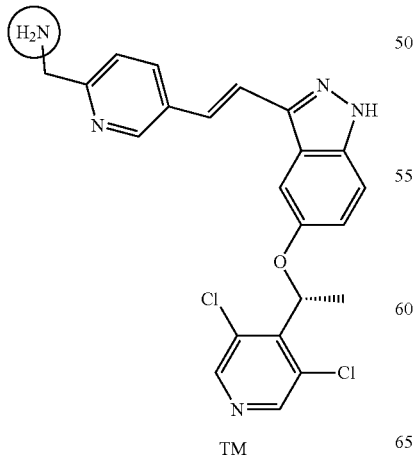

TM

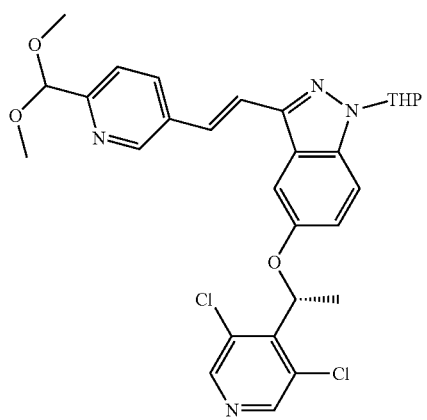

A suspension of Example 137A (850 mg, 4.74 mmol), 24H (2.46 g, 4.74 mmol), POT (144.27 mg, 474 mmol), palladium acetate (106.42 mg, 474 mmol) and DIEA (1.84 g, 14.2 mmol) in DMF (30 mL) was stirred at 100° C. for 16 hours under nitrogen atmosphere. The suspension was cooled, filtered and the filtrate was concentrated in vacuo. The residue was purified by preparative column chromatography to give the title compound as a yellow oil (1.4 g, yield 52%). LCMS (ESI) m/z [M+H]$^+$: 569.4. $^1$H NMR (400 MHz, CHLOROFORM-d) ppm 8.82-8.77 (m, 1H), 8.46 (s, 2H), 8.40-8.36 (m, 1H), 7.95 (dd, J=2.0, 8.3 Hz, 1H), 7.60 (d, J=8.0 Hz, 1H), 7.45 (d, J=16.8 Hz, 1H), 7.28-7.22 (m, 1H), 7.21-7.15 (m, 2H), 6.18-6.07 (m, 1H), 5.65 (ddd, J=2.5, 5.8, 9.0 Hz, 1H), 5.47-5.43 (m, 1H), 4.05 (t, J=8.9 Hz, 1H), 3.86-3.69 (m, 2H), 3.50-3.42 (m, 6H), 2.61-2.49 (m, 1H), 2.22-2.11 (m, 1H), 2.09-1.99 (m, 3H), 1.85 (d, J=6.5 Hz, 3H), 1.80-1.73 (m, 2H)

Example 137C

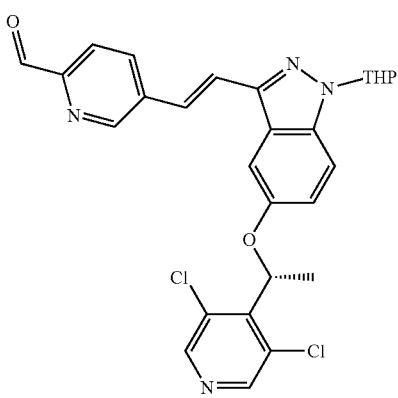

A mixed solution of Example 137B (1.4 g, 2.46 mmol) and p-benzenesulfonic acid monohydrate (234 mg, 1.23 mmol) in water (5 mL) and acetone (15 mL) was stirred at 50° C. for 3 hours. After cooled, the aqueous layer was extracted with dichloromethane (10 mL×3), and the organic layers were combined, washed with brine, dried over anhydrous sodium sulfate, filtered and the filtrate was concentrated in vacuo to give the title compound (1.2 g, yield 76%) which was used directly in next step. LCMS (ESI) m/z: 541.4 (M+1).

Example 137D

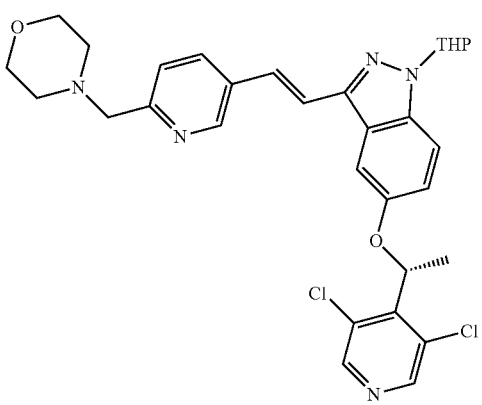

A mixed solution of Example 137C (100 mg, 191 µmol) and morpholine (50 mg, 573.15 µmol) in 1,2-dichloroethane (2 mL) was added with acetic acid (100 µL) until pH=5. After the addition, the mixture was stirred at 29° C. for 2 hours. Sodium cyanoborohydride (36 mg, 573.15 µmol) was slowly added and the mixture was stirred for 3 hours at 29° C. The reaction solution was quenched with water and the aqueous layer was extracted with dichloromethane (5 mL×3), the organic layers were combined, washed with brine, dried over anhydrous sodium sulfate, filtered and the filtrate was concentrated in vacuo to give the title compound as a dark oil (100 mg, crude). LCMS (ESI) m/z: 594.2 [M+1]$^+$.

Example 137E

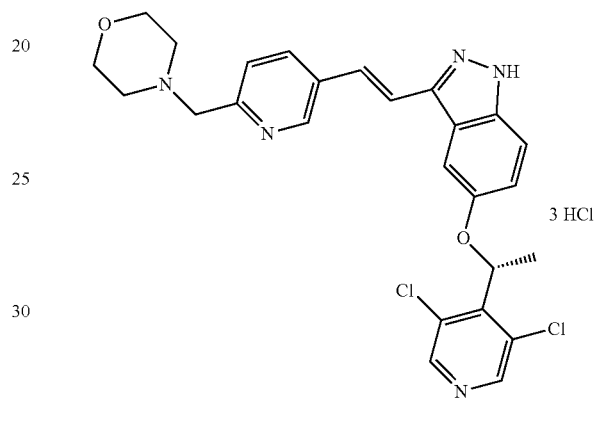

A mixed solution of methanol (1 mL)/acetyl chloride (0.25 ml) was added to a solution of Example 137D (100 mg, 148 µmol) in methanol (1 mL), and the mixture was heated to 40° C. and stirred for 3 hours, then cooled in vacuo to give the title compound (20.00 mg, yield 46%). LCMS (ESI) m/z 510.4 (M+1). $^1$H NMR (400 MHz, METHANOL-d$_4$) ppm 8.95 (d, J=1.8 Hz, 1H), 8.51 (s, 2H), 8.26 (dd, J=2.0, 8.3 Hz, 1H), 7.67 (d, J=8.0 Hz, 1H), 7.60 (d, J=16.8 Hz, 1H), 7.51 (d, J=9.3 Hz, 1H), 7.37 (s, 2H), 7.25 (dd, J=2.1, 9.2 Hz, 1H), 6.24 (q, J=6.7 Hz, 1H), 4.61 (s, 2H), 4.04-3.98 (m, 4H), 3.47 (t, J=4.5 Hz, 4H), 1.87 (d, J=6.5 Hz, 3H).

Example 138

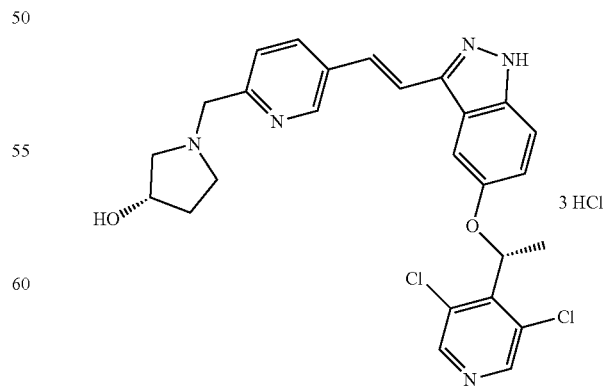

$^1$H NMR (400 MHz, METHANOL-d$_4$) ppm 9.06 (s, 1H), 8.60-8.49 (m, 3H), 7.98 (d, J=8.0 Hz, 1H), 7.71 (d, J=16.6

Hz, 1H), 7.57 (d, J=9.0 Hz, 1H), 7.46 (d, J=16.8 Hz, 1H), 7.39-7.28 (m, 2H), 6.25 (q, J=6.5 Hz, 1H), 4.84 (s, 2H), 4.66 (br. s., 1H), 3.70 (br. s., 4H), 2.39 (br. s., 1H), 2.18 (br. s., 1H), 1.86 (d, J=6.5 Hz, 3H).
Example 140
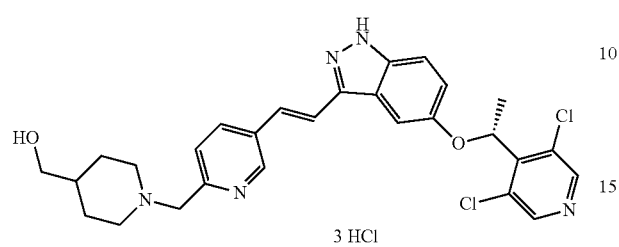
3 HCl
This example was prepared by the method as described in Example 137. LCMS (ESI) m/z: 538.4 (M+1).
Example 142
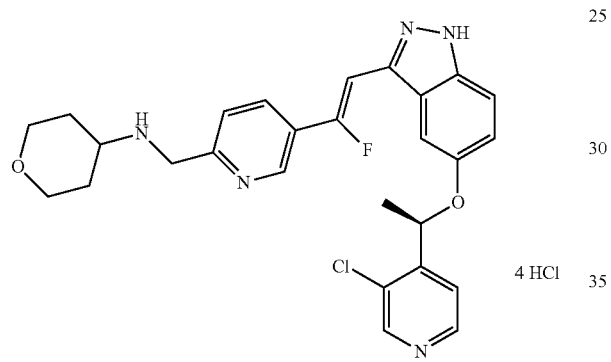
4 HCl
Scheme S
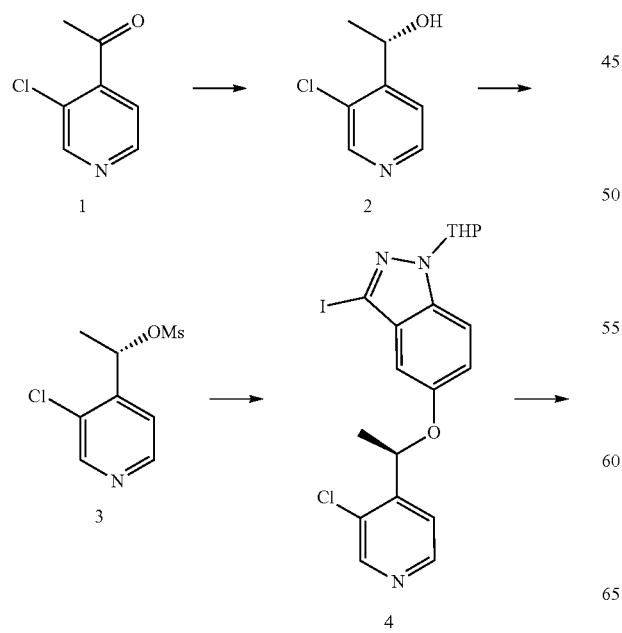
-continued
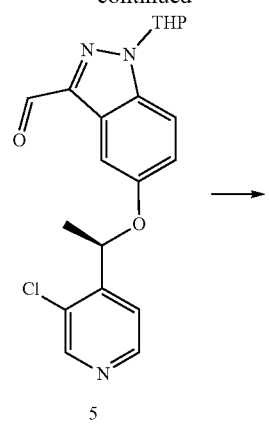
5
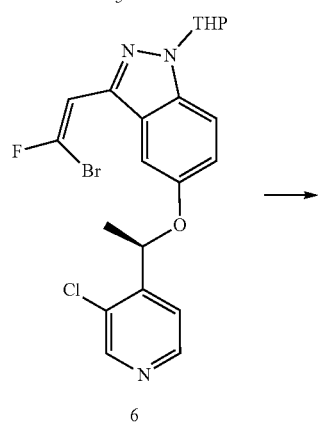
6
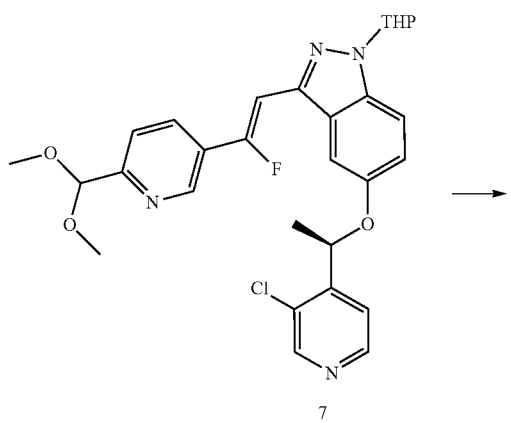
7
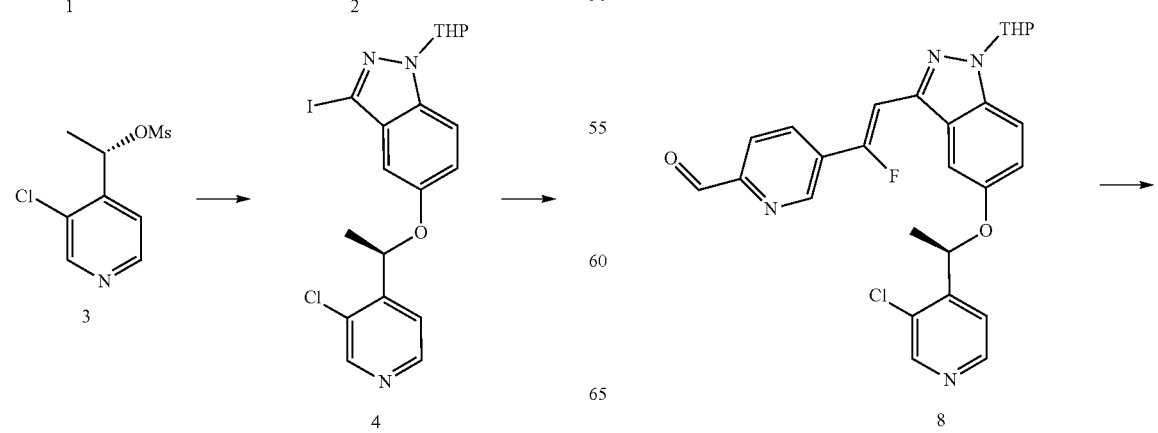
8

-continued

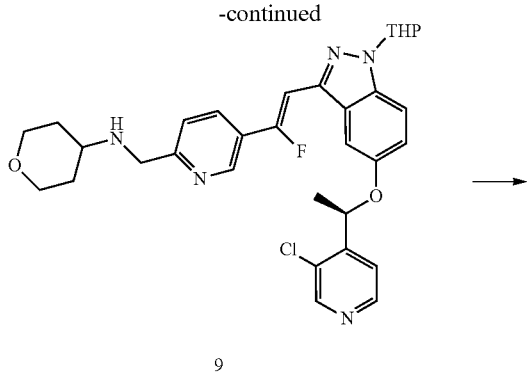

9

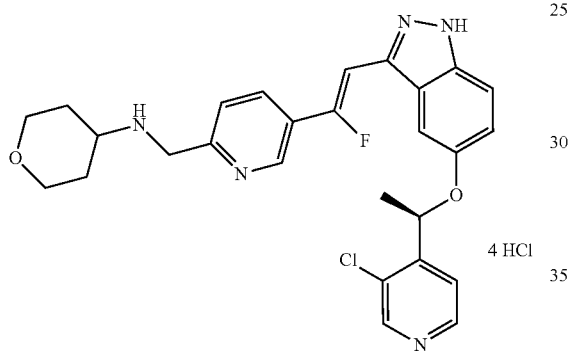

Example 142

Example 142A

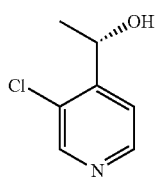

A solution of 1-(3-chloro-4-pyridine)ethanone (1 g, 6.43 mmol) in tetrahydrofuran (5 mL) was added dropwise to a solution of DIPCl (3.09 g, 9.65 mmol) in tetrahydrofuran (5 mL) at −20° C. and the mixture was stirred at this temperature for 1.5 hours, then heated to 0° C. and stirred for half an hour. The reaction was quenched with methanol (3 mL) and concentrated. The residue was added with water (15 mL), extracted with ethyl acetate (3×10 mL), washed with brine (10 mL), dried, filtered and the filtrate was concentrated in vacuo. The residue was purified by column chromatography to give the title compound as a yellow oil (650 mg, yield 61%).

LCMS (ESI) m/z: 158.5 [M+1]$^+$

Example 142B

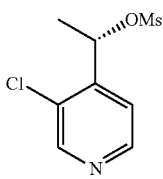

MsCl (1.42 g, 12.37 mmol) and triethylamine (1.25 g, 12.37 mmol) were added to a solution of Example 142A (650 mg, 4.12 mmol) in dichloromethane (6 mL) at 0° C., and the mixture was stirred at this temperature for 1 hour. The mixture was added with water (1 mL), basified with aqueous sodium bicarbonate solution to pH=7-8, then added with water (10 mL), and extracted with dichloromethane (2×8 mL). The organic phase was washed with brine (5 mL), dried, filtered and the filtrate was concentrated in vacuo. The residue was purified by column chromatography to give the title compound as a yellow oil.

LCMS (ESI) m/z: 236.7 [M+1]$^+$

Example 142

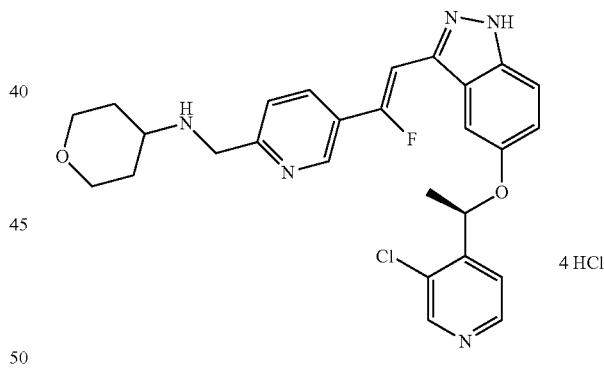

Example 142 was synthesized from Example 3 according to the same method described in Example 24 to give Example 142 (11.00 mg, yield 20%).

LCMS (ESI) m/z: 508.1 [M+1]$^+$

1H NMR (400 MHz, METHANOL-d4) Shift 9.05-9.18 (m, 1H), 8.78 (d, J=5.52 Hz, 1H), 8.24-8.32 (m, 2H), 7.66 (d, J=8.03 Hz, 1H), 7.57 (d, J=9.54 Hz, 1H), 7.41 (s, 1H), 7.32 (d, J=9.03 Hz, 1H), 7.03-7.18 (m, 1H), 6.05 (q, J=6.02 Hz, 1H), 4.54 (s, 2H), 4.09 (dd, J=4.02, 11.54 Hz, 2H), 3.45-3.65 (m, 3H), 2.16 (d, J=10.54 Hz, 2H), 1.74-1.89 (m, 5H)

Example 143
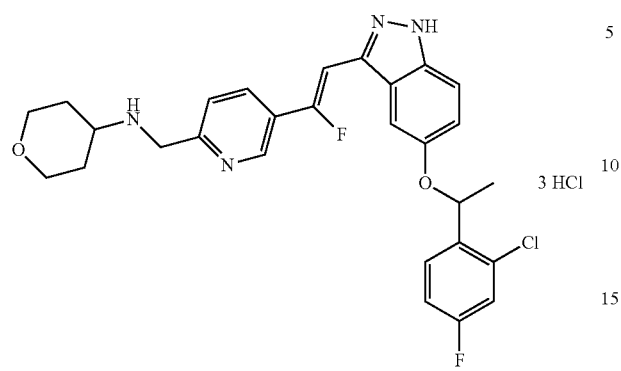
Scheme T
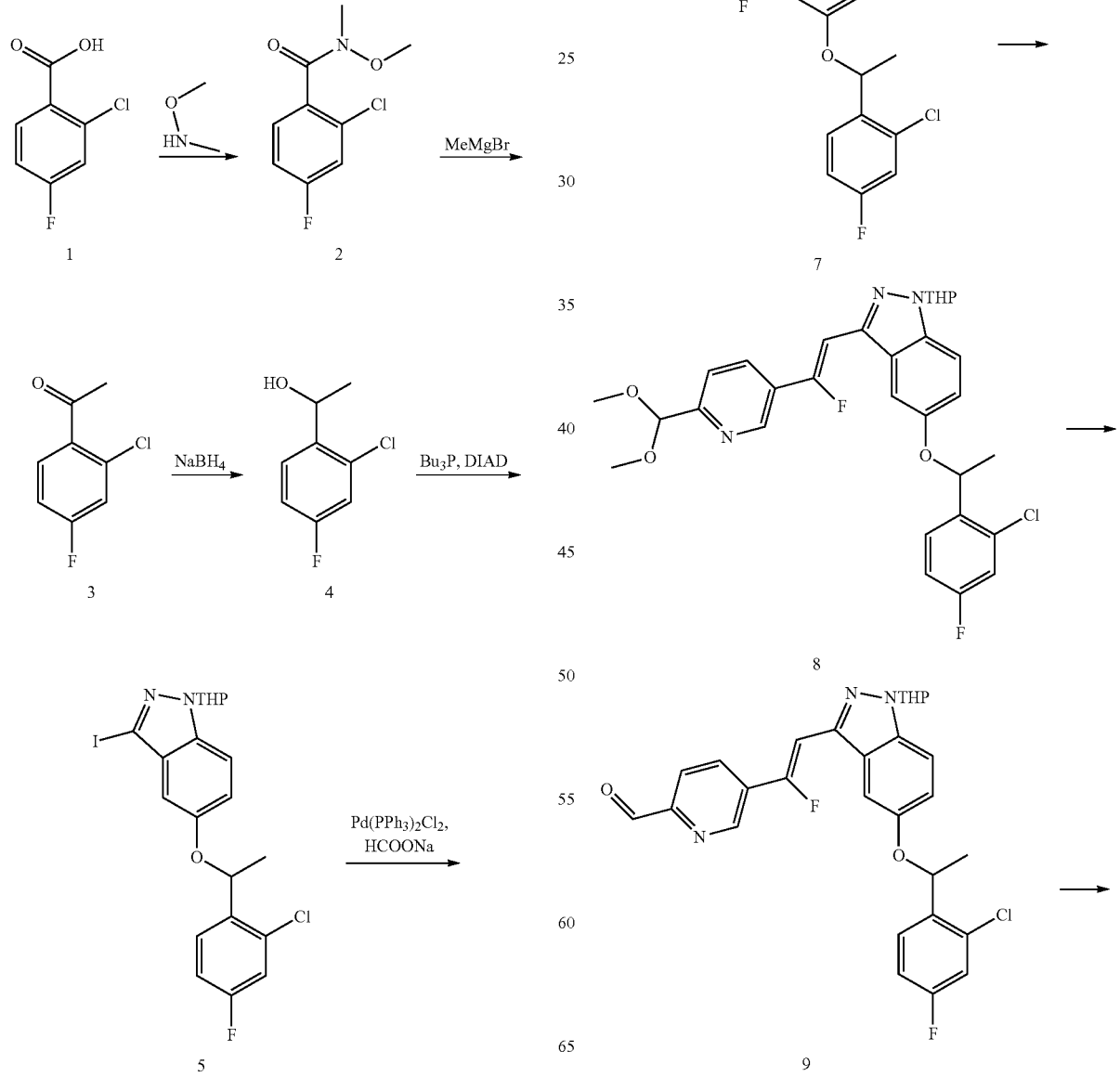

-continued

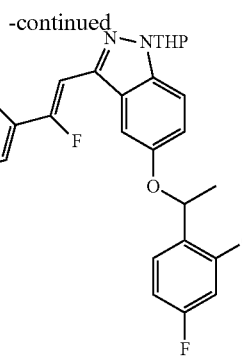

10

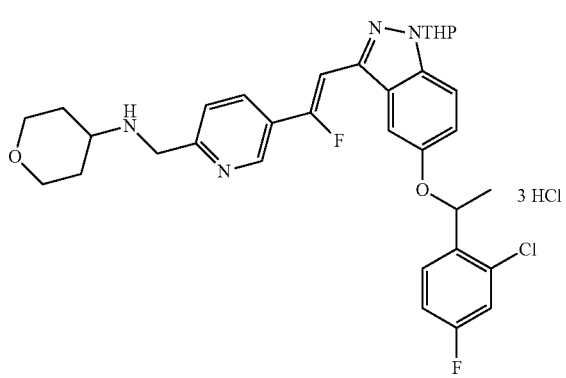

10

Example 143A

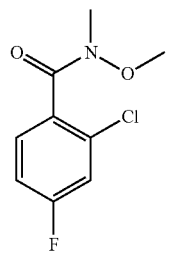

A solution of 2-chloro-4-fluorobenzoic acid (10.00 g, 57.29 mmol), 1-methoxy-1-methylamine hydrochloride (10.00 g, 57.29 mmol), 1-hydroxybenzotriazole (11.61 g, 85.94 mmol), 1-ethyl-(3-dimethylaminopropyl)carbodiimide hydrochloride (16.47 g, 85.94 mmol), triethylamine (14.49 g, 143.23 mmol) in DCM (200.00 mL) was stirred at 15° C. for 3 hours. The solution was added with water (300 mL), extracted with DCM (200 mL×3) and washed with brine (500 mL×2). The organic phases were combined and dried over anhydrous sodium sulfate, filtered and the filtrate was concentrated in vacuo. The residue was purified by column chromatography to give Example 143A as a colorless oil (12.30 g, yield 98.66%).

$^1$H NMR (400 MHz, CHLOROFORM-d) 7.35 (dd, J=6.02, 8.53 Hz, 1H), 7.17 (dd, J=2.51, 8.53 Hz, 1H), 7.04 (dt, J=2.26, 8.28 Hz, 1H), 3.27-3.58 (m, 6H).

Example 143B

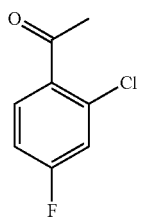

Methylmagnesium bromide (13.48 g, 113.04 mmol) was added dropwise to a solution of Example 144A (12.30 g, 56.52 mmol) in tetrahydrofuran (100.00 mL) at −78° C. over 30 minutes, and the mixture was stirred at 0° C. for 5 hours. The mixture was added with saturated aqueous ammonium chloride solution (100 mL), diluted with water (50 mL), extracted with ethyl acetate (200 mL×3) and washed with brine (400 mL×2). The organic phases were combined, dried over anhydrous sodium sulfate, filtered, the filtrate was concentrated in vacuo and the residue was purified by column chromatography to give Example 143B as a colorless oil (9.60 g, yield 98.42%).

$^1$H NMR (400 MHz, CHLOROFORM-d) 7.64 (dd, J=6.02, 8.53 Hz, 1H), 7.17 (dd, J=2.38, 8.41 Hz, 1H), 7.01-7.07 (m, 1H), 2.61-2.67 (m, 3H).

Example 143C

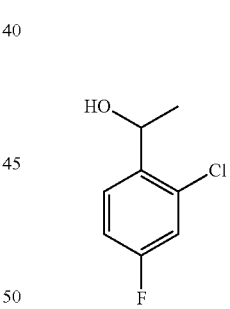

Sodium borohydride (5.26 g, 139.08 mmol) was added to a solution of Example 144B (9.60 g, 55.63 mmol) in MeOH (80.00 mL) at 0° C., and the mixture was stirred for 3 h at 15° C. The mixture was added with water (100 mL) at 0° C., extracted with DCM (100 mL×2), and washed with brine (200 mL×3). The organic phases were combined, dried over anhydrous sodium sulfate, filtered and the filtrate was concentrated in vacuo. The residue was purified by column chromatography to give Example 143C as a colorless oil (9.50 g, yield 97.81%).

Example 143

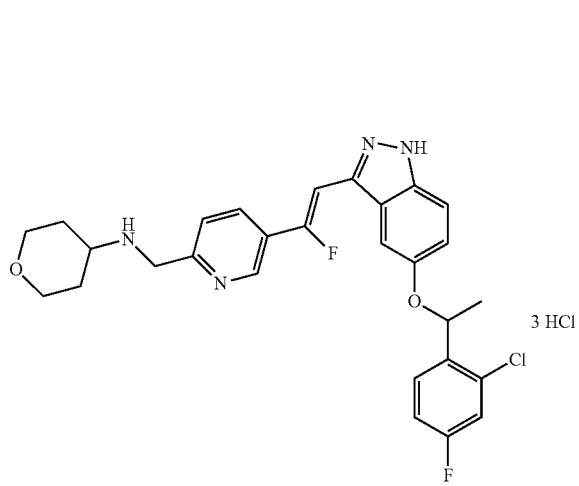 [SMILES: CC(Oc1ccc2[nH]nc(/C=C(\F)c3ccc(CNC4CCOCC4)nc3)c2c1)c1ccc(F)cc1Cl]

Example 143 was synthesized from Example 4 according to the same method described in Example 24 to give Example 143 (350.00 mg, yield 33.84%).

LCMS(ESI) m/z [M+H]+: 525.1 [M+1]+

$^1$H NMR (400 MHz, METHANOL-d4): 9.04 (d, J=1.76 Hz, 1H), 8.23 (dd, J=2.26, 8.28 Hz, 1H), 7.52-7.65 (m, 2H), 7.48 (d, J=9.03 Hz, 1H), 7.16-7.28 (m, 3H), 6.90-7.10 (m, 2H), 5.79 (q, J=6.36 Hz, 1H), 4.52 (s, 2H), 4.08 (dd, J=4.52, 11.80 Hz, 2H), 3.39-3.58 (m, 3H), 2.14 (dd, J=2.38, 12.42 Hz, 2H), 1.79 (dq, J=4.64, 12.26 Hz, 2H), 1.60-1.69 (m, 3H).

Example 144

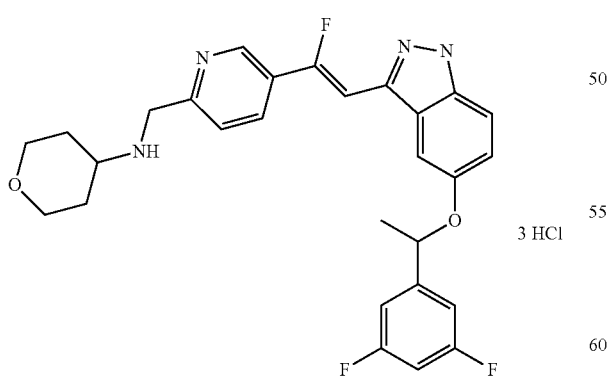

This example was prepared by the method as described in Example 144. LCMS (ESI) m/z: 509.1 [M+1]+

Example 145

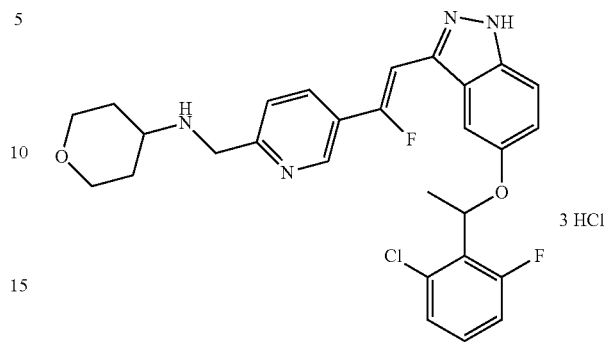

This example was prepared by the method as described in Example 144. LCMS (ESI) m/z: 525.1 [M+1]+

1H NMR (400 MHz, METHANOL-d$_4$) 9.07 (s, 1H), 8.25 (d, J=8.03 Hz, 1H), 7.63 (d, J=8.28 Hz, 1H), 7.44 (d, J=9.03 Hz, 1H), 7.37 (br. s., 1H), 7.22-7.31 (m, 2H), 7.17 (d, J=9.03 Hz, 1H), 6.90-7.09 (m, 2H), 6.01 (d, J=6.53 Hz, 1H), 4.53 (s, 2H), 4.10 (d, J=8.28 Hz, 2H), 3.43-3.58 (m, 3H), 2.16 (d, J=12.30 Hz, 2H), 1.81 (d, J=6.53 Hz, 5H).

Example 146

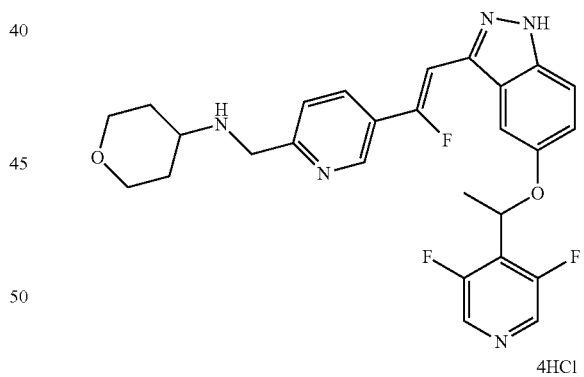

This example was prepared by the method as described in Example 144. LCMS (ESI) m/z: 510.4 [M+1]+

$^1$H NMR (400 MHz, METHANOL-d$_4$) 9.09-9.38 (m, 1H), 8.42-8.82 (m, 3H), 7.85-8.06 (m, 1H), 7.55-7.76 (m, 2H), 7.31-7.54 (m, 2H), 5.92-6.30 (m, 1H), 4.65 (br. s., 2H), 4.07 (d, J=7.78 Hz, 2H), 3.41-3.67 (m, 3H), 2.20 (d, J=9.79 Hz, 2H), 1.88 (br. s., 5H)

Example 147

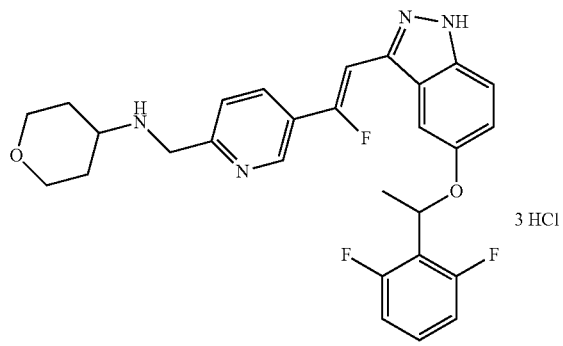 [SMILES: CC(Oc1ccc2[nH]nc(/C=C(\F)c3ccc(CNC4CCOCC4)nc3)c2c1)c1c(F)cccc1F]

3 HCl

This example was prepared by the method as described in Example 144.

LCMS(ESI) m/z: 509.5 [M+1]+.

$^1$H NMR (400 MHz, METHANOL-d4): 9.09 (d, J=1.25 Hz, 1H), 8.28 (d, J=6.78 Hz, 1H), 7.66 (d, J=8.03 Hz, 1H), 7.43-7.55 (m, 2H), 7.26-7.35 (m, 1H), 7.22 (dd, J=2.01, 9.03 Hz, 1H), 7.00-7.16 (m, 1H), 6.94 (t, J=8.53 Hz, 2H), 5.89 (q, J=6.53 Hz, 1H), 4.54 (s, 2H), 4.08 (dd, J=4.27, 11.54 Hz, 2H), 3.42-3.59 (m, 3H), 2.16 (d, J=11.04 Hz, 2H), 1.67-1.89 (m, 5H).

Example 148

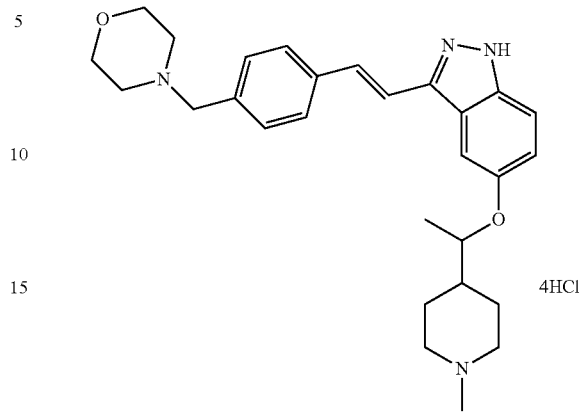

4HCl

This example was prepared by the method as described in Example 137. LCMS(ESI) m/z: 475.3 [M+1]+.

$^1$H NMR (400 MHz, METHANOL-d$_4$): 7.79-7.84 (m, 2H), 7.54-7.63 (m, 4H), 7.52 (d, J=7.53 Hz, 2H), 7.40-7.49 (m, 1H), 7.15 (d, J=9.03 Hz, 1H), 4.49 (t, J=5.77 Hz, 1H), 4.41 (s, 2H), 4.03-4.15 (m, 2H), 3.73-3.85 (m, 2H), 3.67 (br. s., 2H), 3.38-3.50 (m, 3H), 3.17-3.27 (m, 5H), 2.93-3.06 (m, 1H), 2.05-2.37 (m, 1H), 1.40 (br. s., 3H), 1.38 (br. s., 3H), 1.35-1.37 (m, 2H)

Example 149

4HCl

This example was prepared according to the method as described in Example 137. LCMS(ESI) m/z: 461.3 [M+1]+.

$^1$H NMR (400 MHz, METHANOL-d$_4$) ☐ 7.79-7.84 (m, 2H), 7.56-7.61 (m, 3H), 7.51-7.56 (m, 2H), 7.50 (d, J=9.29 Hz, 1H), 7.13-7.19 (m, 1H), 4.45-4.53 (m, 2H), 4.41 (s, 2H), 4.09 (d, J=13.30 Hz, 2H), 3.78 (t, J=12.80 Hz, 2H), 3.35-3.48 (m, 4H), 3.20-3.30 (m, 4H), 3.07 (t, J=13.05 Hz, 1H), 2.90 (s, 3H), 1.97 (s, 3H), 1.36-1.40 (m, 3H), 1.31 (br. s., 2H)

Example 150 (Reference Example)

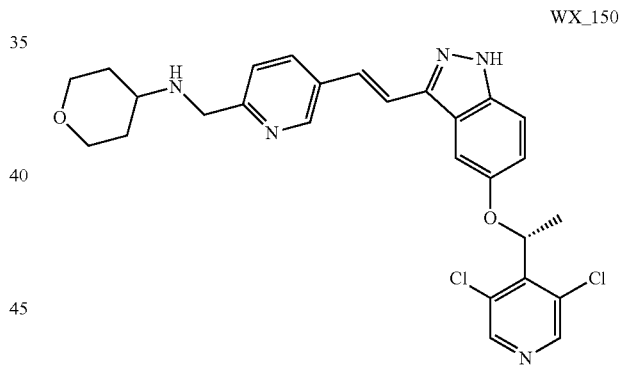

WX_150

This example was prepared according to the method as described in Example 137.

$^1$H NMR (400 MHz, METHANOL-d$_4$) ☐=8.95 (d, J=1.5 Hz, 1H), 8.52 (s, 2H), 8.33 (dd, J=2.0, 8.3 Hz, 1H), 7.72 (d, J=8.3 Hz, 1H), 7.62 (d, J=16.8 Hz, 1H), 7.53 (d, J=9.0 Hz, 1H), 7.38 (d, J=16.8 Hz, 1H), 7.33 (d, J=1.8 Hz, 1H), 7.27 (dd, J=2.0, 9.0 Hz, 1H), 6.25 (q, J=6.5 Hz, 1H), 4.55 (s, 2H), 4.10 (dd, J=4.3, 11.5 Hz, 2H), 3.61-3.42 (m, 4H), 2.22-2.12 (m, 2H), 1.91-1.76 (m, 5H)

Experimental Example 1: In Vitro Enzymatic Activity Test of the Compound of the Present Disclosure Experimental Purpose:

To measure enzyme activity by Z'-LYTE™ Detection Kinase Assay, and to evaluate the inhibitory effect of the compounds on FGFR1 using IC$_{50}$ value of the compounds as an indicator.

Experimental Materials:
  FGFR1 (Invitrogen# PV4105)
  Tyr4 (Invitrogen-PR5053U)
  ATP (Sigma-A7699)
  DMSO (Sigma cat #34869-100 ML)
  Reaction Buffer: 50 mM Hepes (pH 7.5), 10 mM MgCl$_2$, 1 mM EGTA, 0.01% Brij-35, 1 mM DTT, 2 mM MnCl$_2$
  384 Reaction plate (Corning Costar 3573)
  384 Compound plate (Greiner #781280)
Development Reagent B (Invitrogen# PR5193D)
Development Buffer (Invitrogen# PR4876B)
  Centrifuge (Eppendorf #5810R)
  Electronic sample pipette (Eppendorf)
  Multidrop Liquid Workstation (Thermo Scientific)
  Bravo Automatic Liquid Workstation (Agilent)
  Envision (Perkin Elmer)
Experimental Steps and Methods:
  A. Preparing Enzyme/Substrate Mix
  0.6 nM FGFR1, 2 uM Tyr4 peptide and 10 uM ATP in reaction buffer (50 mM Hepes, pH 7.5, 10 mM MgCl$_2$, 0.01% BRIJ-35, 1 mM EGTA, 4 mM MnCl$_2$, 2 mM DTT).
  B. Compound Loading:
  a. Diluting the compounds with DMSO to 10 mM, 3-fold dilution, 11 gradients, duplicate wells.
  b. Diluting the compound by 1:25 into middle plate at Bravo Automatic Liquid Station, then transferring 2.5 ul to the reaction plate to ensure the final DMSO concentration to be 1%.
  c. Transferring 5 ul of enzyme/substrate buffer into each well
  d. Using Multidrop Liquid Workstation to sequentially add ATP solution to each well
  e. Centrifuging at 1000 rpm for 1 minute
  f. Placing the reaction plate in an incubator at 23° C. to react for 60 min.
  C. Color Reaction Test
  a. Preparing a 1:128 mixture of Development Regent B and Development Buffer
  b. Adding 5 ul to each well and centrifuging at 1000 rpm for 1 minute
  c. Placing the reaction plate in a thermostat (23° C.) after centrifuging for 90 minutes, removing and reading on Envision (Perkin Elmer) Plate Reader
  D. Analyzing Data: Analyzing Data Using XLFIT (IDBS) and Calculating IC$_{50}$ Values for the Compounds.
  The experimental results are shown in Table 1:

TABLE 1

Test results of Z'-LYTE ™ Detection for IC$_{50}$

| Sample tested (Title compound) | FGFR1 |
|---|---|
| Example 1 | A |
| Example 2 | A |
| Example 3 | A |
| Example 4 | A |
| Example 5 | A |
| Example 6 | A |
| Example 9 | AA |
| Example 10 | AA |
| Example 11 | A |
| Example 12 | AA |
| Example 13 | A |
| Example 16 | AA |
| Example 17 | A |
| Example 18 | AAA |
| Example 18b | AAA |
| Example 21 | AAA |
| Example 22 | AA |
| Example 23 | AAA |
| Example 26 | AA |
| Example 27 | AAA |
| Example 29 | AAA |
| Example 30 | AAA |
| Example 31 | AAA |
| Example 32 | AAA |
| Example 33 | AAA |
| Example 34 | AAA |
| Example 36 | A |
| Example 37 | A |
| Example 38 | A |
| Example 41 | A |
| Example 43 | AAA |
| Example 44 | AAA |
| Example 45 | A |
| Example 47 | AAA |
| Example 48 | AAA |
| Example 49 | N/A |
| Example 50 | AAA |
| Example 51 | AAA |
| Example 52 | A |
| Example 53 | AA |
| Example 54 | AAA |
| Example 55 | A |
| Example 56 | A |
| Example 57 | A |
| Example 58 | A |
| Example 59 | A |
| Example 60 | A |
| Example 61 | A |
| Example 62 | A |
| Example 63 | AA |
| Example 64 | A |
| Example 65 | AAA |
| Example 66 | AAA |
| Example 67 | AAA |
| Example 68 | AAA |
| Example 69 | AAA |
| Example 70 | A |
| Example 71 | AA |
| Example 72 | AAA |
| Example 73 | AAA |
| Example 74 | AAA |
| Example 76 | AAA |
| Example 78 | AAA |
| Example 80 | A |
| Example 81 | AAA |
| Example 82 | A |
| Example 83 | A |
| Example 86 | A |
| Example 87 | A |
| Example 88 | AA |
| Example 89 | AAA |
| Example 90 | A |
| Example 91 | A |
| Example 93 | AA |
| Example 94 | A |
| Example 95 | A |
| Example 97 | AAA |
| Example 99 | A |
| Example 100 | AAA |
| Example 101 | AAA |
| Example 102 | AAA |
| Example 103 | AAA |
| Example 104 | A |
| Example 106 | AAA |
| Example 107 | A |
| Example 108 | A |
| Example 109 | AAA |
| Example 112 | A |
| Example 113 | A |
| Example 114 | A |
| Example 115 | AA |

TABLE 1-continued

Test results of Z'-LYTE ™ Detection for IC$_{50}$

| Sample tested (Title compound) | FGFR1 |
|---|---|
| Example 116 | A |
| Example 117 | A |
| Example 119 | A |
| Example 120 | A |
| Example 121 | A |
| Example 125 | A |
| Example 126 | A |
| Example 127 | A |
| Example 129 | A |
| Example 130 | A |
| Example 132 | AAA |
| Example 134 | AAA |
| Example 135 | AAA |
| Example 137 | AAA |
| Example 138 | AAA |
| Example 140 | AA |
| Example 142 | AA |
| Example 143 | A |
| Example 144 | AAA |
| Example 145 | A |
| Example 146 | AAA |
| Example 147 | A |
| Example 148 | A |
| Example 149 | A |

Note:
50 nM < A ≤ 1 uM, 10 nM < AA ≤ 50 nM, AAA ≤ 10 nM, N/A represents unmeasured.

Conclusion: The compounds of the present disclosure have a significant inhibitory effect on FGFR1.

Experimental Example 2: In Vitro Cytotoxic Activity of the Compounds of the Disclosure In Vitro Experimental Purpose:
To detect the change of intracellular ATP by CellTiter-Glo® Luminescent Cell Viability Assay, and to evaluate the inhibitory effect of the compounds on in vitro cell SNU-16 using IC$_{50}$ value of the compounds as an indicator.

Experimental Materials:
Cell line: SNU-16 cell strain
SNU-1 cell culture medium: RPMI 1640 (Invitrogen #22400105), 10% serum (Invitrogen #10099141), Penicillin-Streptomycin (Invitrogen Gibco #15140-122)
Trypsin (Invitrogen, #25200-072)
DPBS (Hyclone, # SH30028.01B)
384 cell plate (Greiner #781090)
384 Compound Plate (Greiner #781280)
CO$_2$ Incubator (Thermo #371)
Centrifuge (Eppendorf #5810R)
Vi-cell cytometer (Beckman Coulter)
Bravo Automatic Liquid Workstation (Agilent)
Envision (Perkin Elmer)

Experimental Steps and Methods:
E. Cell Vaccination (SNU-16 Cell)
a. Preheating medium, trypsin, DPBS in 37° C. water bath. Aspirating the cell culture media and washing with 10 mL DPBS;
b. Adding the preheated trypsin to the culture flask, rotating the culture flask to evenly cover the culture flask with trypsin, and placing the flask in a 5% CO$_2$ incubator to let it digest for 1-2 minutes at 37° C.;
c. Suspending cells in 10-15 mL medium for each T150 cells, centrifuging at 800 rpm for 5 minutes, re-suspending cells in 10 mL medium, drawing 1 mL cell suspension for Vi-cell counting;
d. Diluting SNU-16 with medium, adding the diluted cells to the 384 plate (Greiner. 781090) (50 μL/well, SNU-16 cell 750 cells/well) with multi-channel pipette. Placing the cell plate in a 37° C., 5% CO$_2$ incubator overnight.

F. Compound Loading:
g. Diluting the compound with DMSO to 10 mM, 3-fold dilution, 11 gradients, duplicate wells.
h. Transferring 2.4 ul of the compound to the middle plate added with 47.6 ul of cell culture media at Bravo Automatic Liquid Station. Then transferring 5 ul to the cell culture plate (55 ul) to ensure the final DMSO concentration to be 0.4%.
i. Placing the cell culture plate in 5% CO$_2$ incubator at 37° C. to continue cultivating for 3 days.

G. CTG Experiment:
d. Balancing Cell Titer Glo Reagent to room temperature
e. Taking 30 ul of Cell Titer Glo Reagent in a 1:2 ratio into each well and gently mixing for 2 minutes
f. Placing the cell culture plate in an incubator (23° C.) for 10 minutes, taking out and centrifuging at 1000 rpm for 1 minute
g. Reading on Envision (Perkin Elmer) Plate Reader.

H. Analyzing Data: Analyzing the Data Using XLFIT (IDBS) and Calculating IC$_{50}$ Values for the Compounds.

The experimental results are shown in Table 2:

TABLE 2

Test results of CellTiter-Glo ® Detection for IC$_{50}$

| Sample tested (Title compound) | SNU-16 |
|---|---|
| Example 1 | + |
| Example 16 | ++ |
| Example 17 | ++ |
| Example 19 | + |
| Example 21 | ++ |
| Example 29 | + |
| Example 32 | ++ |
| Example 33 | ++ |
| Example 34 | ++ |
| Example 38 | ++ |
| Example 39 | ++ |
| Example 41 | ++ |
| Example 42 | ++ |
| Example 45 | ++ |
| Example 47 | ++ |
| Example 53 | ++ |
| Example 62 | ++ |
| Example 70 | ++ |
| Example 76 | ++ |

Note:
10 nM < + ≤ 1 uM, ++ ≤ 10 nM.

Conclusion: The compounds of the present disclosure have a significant inhibitory effect on SNU-16.

Experimental Example 3: Tumor Growth Inhibition (TGI) Analysis

The evolutionary growth potential of tumors was evaluated by the relationship between tumor volume and time. The long axis (L) and short axis (W) of the subcutaneous tumor were measured twice a week by the caliper and the tumor volume (TV) was calculated by the formula ((L×W$^2$)/2). TGI was calculated from the difference between the median tumor volume in the solvent group mice and the median tumor volume in the drug group mice, expressed as a percentage counting for the median tumor volume in the solvent control group, calculated by the following formula:

% TGI=((median tumor volume(control)−median tumor volume(dosing group))/median tumor volume(control group))×100

The original statistical analysis was done by repeating the analysis of variance, followed by Scheffe psot hoc experimental method for multiple comparisons, with solvent alone (0.5% methylcellulose+0.2% Tween in water) as negative control.

| | FGFR1/2 Highly Expressed Patient-derived Liver Tumor Transplantation Model | TGI % (last administration) |
|---|---|---|
| Example 16 | 15 mg/kg, BID | 84.5 |
| Example 18 | 5 mg/kg, BID | 85 |
| Example 54 | 10 mg/kg, BID | 85.4 |
| Example 63 | 15 mg/kg, BID | 86 |

The experimental results are shown in Table 3:

The compound of the disclosure has excellent in vitro FGFR1 kinase inhibitory activity and SNU-16 cell inhibitory activity and can be used as a small molecule tyrosine kinase inhibitor; and it can inhibit cell proliferation and angiogenesis, having excellent antitumor activity, and having excellent results for the treatment of various mammals (including humans).

Experimental Example 4

The introduction of fluoroalkene instead of alkene into the molecule can obviously improve the metabolic stability of the compound in vivo and increase the bioavailability of the compound, as shown by the comparison of WX_018 and WX_150

Experimental Procedure: A clear solution of the test compound in 20% DMSO/60% PEG400/20% water at 1 mg/ml was injected via the caudal vein into female Balb/c nude mice (fasted overnight, 7-9 weeks of age) with a dose of 1 mg/kg. The test compound suspended in 0.5% Methocel/0.2% Tween 80 at 1 mg/ml was administered by intragastric administration to female Balb/c nude mice (fasted overnight, 7-9 weeks of age) with a dose of 10 mg/kg. About 30 µL of blood collected from the jugular vein or caudal vein at 0.0833, 0.25, 0.5, 1.0, 2.0, 4.0, 8.0 and 24 h after administration in both groups of animals, were placed in anticoagulation tube with EDTA-K2 and the plasma was centrifuged. Plasma concentrations were determined by LC-MS/MS and related pharmacokinetic parameters were calculated using the non-compartmental model linear logarithmic trapezoidal method using WinNonlin™ Version 6.3 (Pharsight, Mountain View, Calif.) pharmacokinetic software.

Experimental data analysis: After a single intravenous injection of 1.0 mg/kg WX_018 to female Balb/c nude mice, the plasma clearance (CL) was 53.0±1.69 mL/min/kg and the steady state apparent volume of distribution (Vdss) was 5.45±0.491 L/kg, the elimination half-life (T1/2) and the area under the plasma concentration curve (AUC0-last) from 0 to the last quantifiable time point were 1.57±0.0286 h and 567±19.4 nM·h, respectively.

After a single intragastric administration of 10 mg/kg WX_018 to female Balb/c nude mice, the bioavailability thereof was 30.1%, $AUC_{0-last}$ was 1649±40.1 nM·h and the peak concentration ($C_{max}$) was 479±62.9 nM, and the peak time appeared 2.00 h after administration. After a single intravenous injection of 1.0 mg/kg WX_015 to female Balb/c nude mice, the plasma clearance (CL) was 83.5±18.5 mL/min/kg and the steady state apparent volume of distribution (Vdss) was 5.31±0.268 L/kg, the elimination half-life (T1/2) and the area under the plasma concentration curve (AUC 0-last) from 0 to the last quantifiable time point were 0.971±0.461 h and 386±88.3 nM·h, respectively.

After a single intragastric administration of 10 mg/kg WX_015 to female Balb/c nude mice, the bioavailability thereof was 11.4%, the $AUC_{0-last}$ was 439±202 nM·h and the peak concentration ($C_{max}$) was 134±68.3 nM, and the peak time appeared 1.50±0.866 h after administration.

In addition, the introduction of a fluorine on the alkene has many advantages, such as: 1) the structure of fluoroalkene itself is a novel design, synthesis of which requires great skill; 2) it can significantly improve the physical and chemical properties of the compound, improve its solubility on the biofilm, vary the compound's acidity and alkalinity, improve the affinity of the compound and organic tissues, and promote the speed of absorption in the body; 3) at the same time it can increase the stability of the compound, improve the metabolic stability of the compound in vivo and increase exposure quantity, potentially improve in vivo efficacy, and reducing the dose at the same efficacy.

Experimental Example 5

Compared with compound B1 of formula (I) as a chain, compound B1 of formula (I) as a ring can significantly increase the metabolic stability of the compound in vivo and increase the bioavailability of the compound, as shown by the comparison of WX_077 and WX_063

Experimental Procedure: A clear solution of the test compound in 20% DMSO/60% PEG400/20% water at 0.4 mg/ml was administered by intragastric administration to female Balb/c nude mice (fasted overnight, 7-9 weeks of age) with a dose of 2 mg/kg. About 30 µL of blood was collected from the jugular vein or caudal vein at 0.25, 0.5, 1.0, 2.0, 4.0, 8.0 and 24 h after administration in both groups of animals, placed in anticoagulation tube with EDTA-K2 and the plasma was centrifuged. Plasma concentrations were determined by LC-MS/MS and related pharmacokinetic parameters were calculated using the non-compartmental model linear logarithmic trapezoidal method using WinNonlin™ Version 6.3 (Pharsight, Mountain View, Calif.) pharmacokinetic software.

Experimental data analysis: After a single intragastric administration of 2 mg/kg WX_077 to female Balb/c nude mice, the $AUC_{0-last}$ was 72.1±19.8 nM·h and the peak concentration ($C_{max}$) was 41.7±6.45 nM, and the peak time appeared 0.25 h after administration.

After a single intragastric administration of 2 mg/kg WX_063 to female Balb/c nude mice, the $AUC_{0-last}$ was 221±71.3 nM·h and the peak concentration ($C_{max}$) was 214±39.7 nM, and the peak time appeared 0.25 h after administration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are to be regarded as a departure from the disclosure, and all such modifications are intended to be included within the scope of the disclosure.

What is claimed is:

1. A compound represented by formula (I) or formula (II), a pharmaceutically acceptable salt or a tautomer thereof, (I)
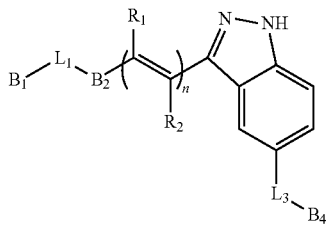
(II)
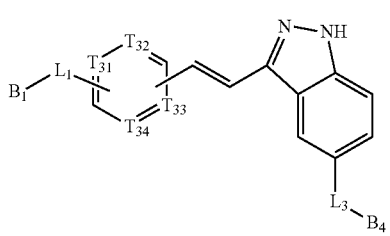
wherein, one of $R_1$ and $R_2$ is selected from the group consisting of F, Cl, Br, I, CN, OH and $NH_2$, the other is selected from the group consisting of H, F, Cl, Br, I, CN, OH and $NH_2$;
$B_1$ is selected from the group consisting of
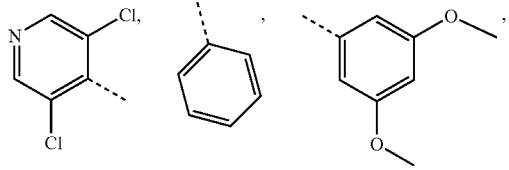
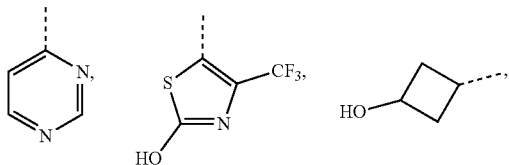
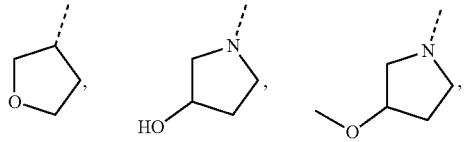
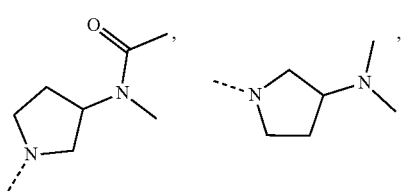
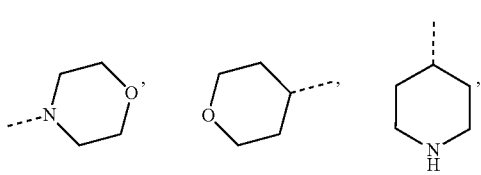
-continued
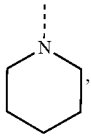
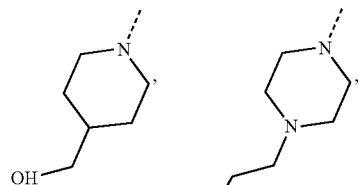
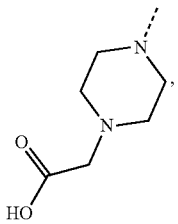
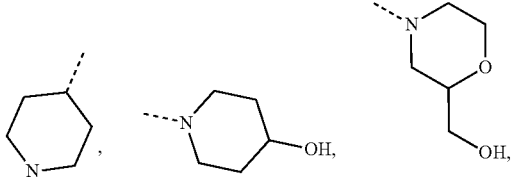
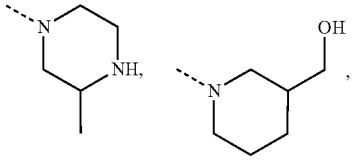
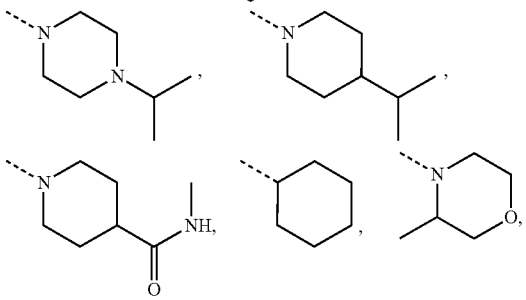
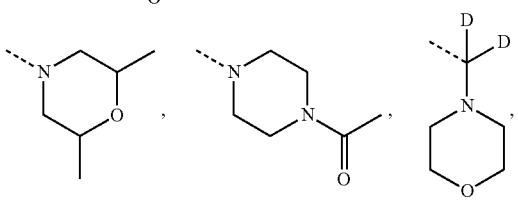
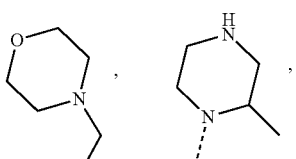
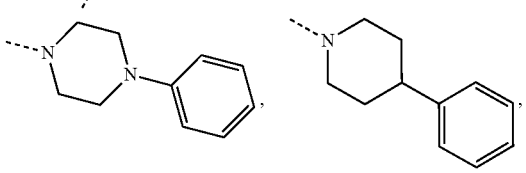

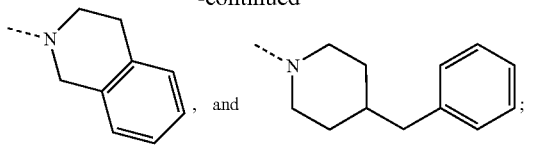, and

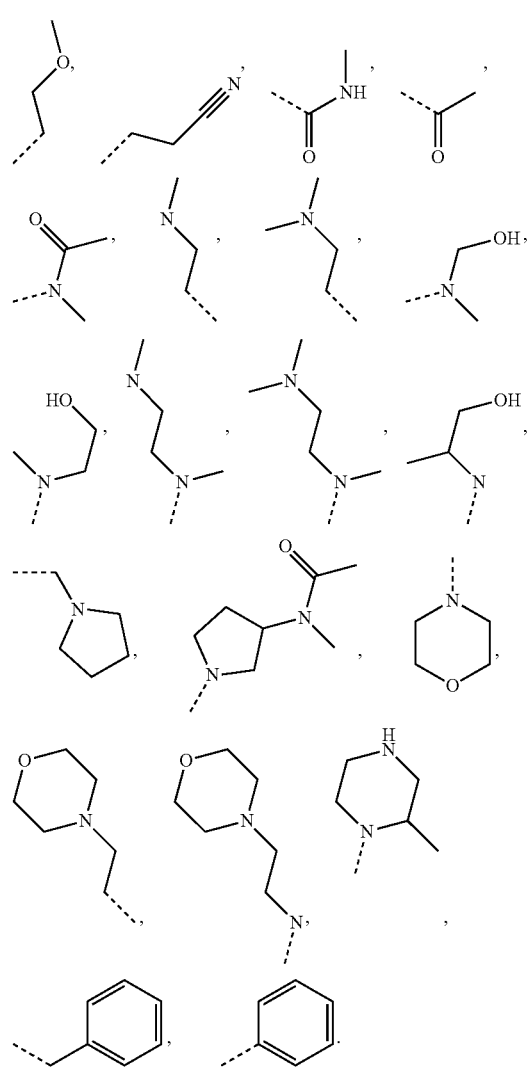

$L_1$ and $L_3$ are each independently selected from the group consisting of —$(CRR)_{0-3}$—, —$(CRR)_{0-3}$—N(R)—$(CRR)_{0-3}$— and —$(CRR)_{0-3}$—O—$(CRR)_{0-3}$—;

$B_2$ is selected from a 5- to 10-membered aryl or heteroaryl which is optionally substituted with R;

$B_4$ is selected from a 5- to 6-membered aryl or heteroaryl and a 5- to 6-membered cycloalkyl or heterocycloalkyl, each of which is optionally substituted with R;

$T_{31-34}$ are each independently selected from N or C(R);

optionally, any two of $T_{31-34}$ are connected to the same atom or atom group to form a 3-6 membered ring;

n is 1;

R is selected from the group consisting of H, F, Cl, Br, I, CN, SH, $NH_2$, CHO, COOH, C(=O)$NH_2$, S(=O)$NH_2$, S(=O)$_2NH_2$, or selected from a $C_{1-12}$ alkyl or heteroalkyl, a $C_{3-12}$ cyclocarbyl or heterocyclocarbyl, and a $C_{1-12}$ alkyl or heteroalkyl substituted with a $C_{3-12}$ cyclocarbyl or heterocyclocarbyl; and the $C_{1-12}$ alkyl or heteroalkyl and the $C_{3-12}$ cyclocarbyl or heterocyclocarbyl is optionally substituted with R';

R' is selected from the group consisting of F, Cl, Br, I, CN, OH, SH, $NH_2$, CHO, COOH, C(=O)$NH_2$, S(=O)$NH_2$, S(=O)$_2NH_2$, =NH, =O, =S, or selected from the group optionally substituted with R" consisting of NHC(=O)$CH_3$, a $C_{1-12}$ alkyl, a $C_{1-12}$ alkylamino, N,N-di($C_{1-12}$ alkyl)amino, a $C_{1-12}$ alkoxy, a $C_{1-12}$ alkanoyl, a $C_{1-12}$ alkoxycarbonyl, a $C_{1-12}$ alkylsulfonyl, a $C_{1-12}$ alkylsulfinyl, a 3- to 12-membered cycloalkyl, a 3- to 12-membered cycloalkylamino, a 3- to 12-membered heterocycloalkylamino, a 3- to 12-membered cycloalkyloxy, a 3- to 12-membered cycloalkylcarbonyl, a 3- to 12-membered cycloalkyloxycarbonyl, a 3- to 12-membered cycloalkylsulfonyl, a 3- to 12-cycloalkylsulfinyl, a 5- to 12-membered aryl or heteroaryl, a 5 to 12-membered aralkyl or heteroaralkyl;

R" is selected from the group consisting of F, Cl, Br, I, CN, OH, N($CH_3$)$_2$, NH($CH_3$), $NH_2$, CHO, COOH, C(=O)$NH_2$, S(=O)$NH_2$, S(=O)$_2NH_2$, =NH, =O, =S, trihalomethyl, dihalomethyl, monohalomethyl, aminomethyl, hydroxymethyl, methyl, methoxy, formyl, methoxycarbonyl, methanesulfonyl, methylsulfinyl;

"hetero" represents a heteroatom or a heteroatom group selected from the group consisting of —C(=O)N(R)—, —N(R)—, —C(=NR)—, —S(=O)$_2$N(R)—, —S(=O)N(R)—, —O—, —S—, =O, =S, —C(=O)O—, —C(=O)—, —C(=S)—, —S(=O)—, —S(=O)$_2$— and/or —N(R)C(=O)N(R)—;

in each of the above cases, the number of R, R', R", heteroatoms or heteroatom groups is independently selected from 0, 1, 2 or 3.

2. The compound, the pharmaceutically acceptable salt or the tautomer thereof according to claim 1, wherein R is selected from the group consisting of H, F, Cl, Br, I, $NH_2$, CN, hydroxymethyl, hydroxyethyl, carboxypropyl, carboxymethyl, methoxy, ethoxy, propoxy, methyl, ethyl, propyl, isopropyl, monohalomethyl, dihalomethyl, trihalomethyl, methylamino, dimethylamino, 3. The compound, the pharmaceutically acceptable salt or the tautomer thereof according to claim 1, wherein any two of $T_{31-34}$ are connected together to the same atom or atom group to form a benzene ring.

4. The compound, the pharmaceutically acceptable salt or the tautomer thereof according to claim 1, wherein $L_1$ and $L_3$ are each independently selected from the group consisting of a single bond, NH,

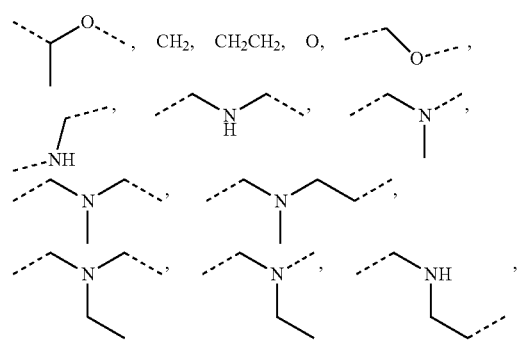

-continued

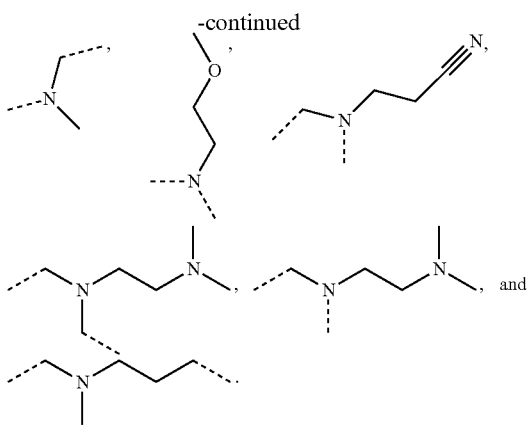

5. The compound, the pharmaceutically acceptable salt or the tautomer thereof according to claim 1, wherein $B_2$ is selected from the group consisting of

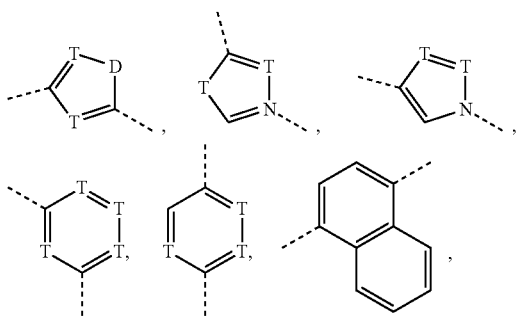

wherein, T is selected from N or C(R);
D is selected from the group consisting of —C(R)(R)—, —C(=O)N(R)—, —N(R)—, —C(=NR)—, —S(=O)$_2$N(R)—, —S(=O)N(R)—, —O—, —S—, —C(=O)O—, —C(=O)—, C(=S)—, —S(=O)—, —S(=O)$_2$— or —N(R)C(=O)N(R)—.

6. The compound, the pharmaceutically acceptable salt or the tautomer thereof according to claim 5, wherein $B_2$ is selected from the group consisting of

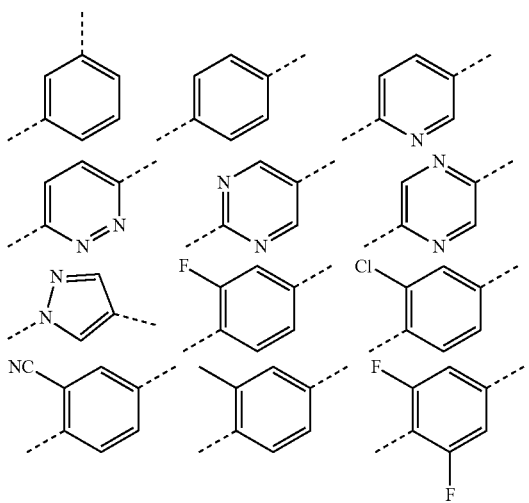

-continued

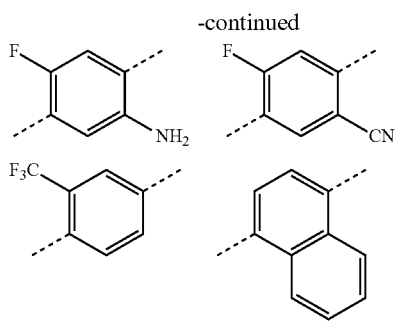

7. The compound, the pharmaceutically acceptable salt or the tautomer thereof according to claim 1, wherein $B_4$ is selected from the group consisting of phenyl, pyridyl, imidazolyl, furyl, thiazolyl, piperidinyl, piperazinyl or morpholinyl, and each of which is optionally substituted with 1, 2 or 3 R.

8. The compound, the pharmaceutically acceptable salt or the tautomer thereof according to claim 1, wherein the structure unit

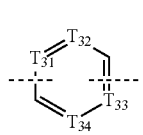

is selected from the group consisting of

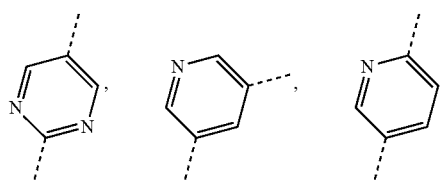

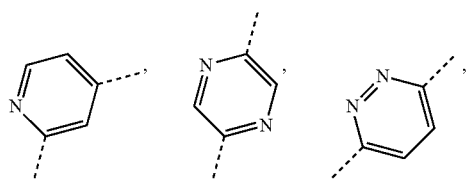

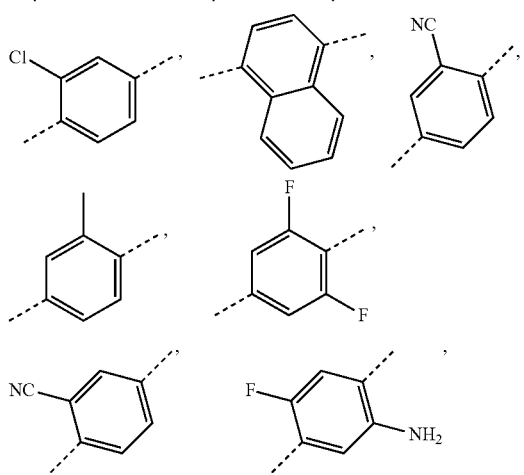

213
-continued
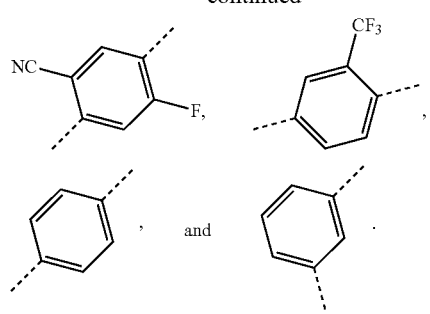
9. The compound, the pharmaceutically acceptable salt or the tautomer thereof according to claim 1, which is selected from the group consisting of
214
-continued
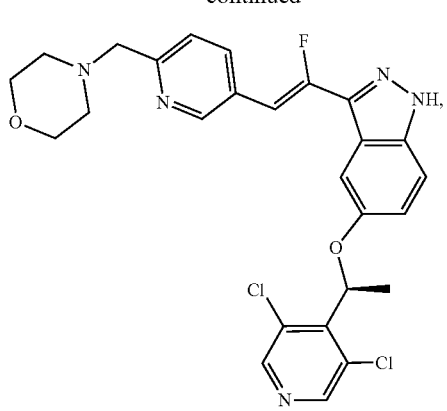

-continued
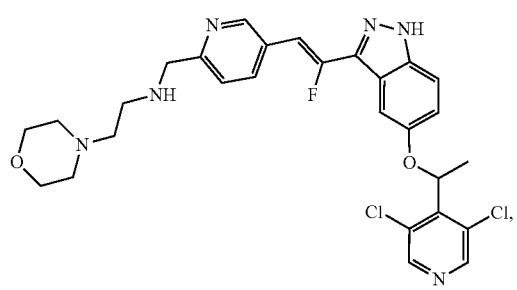
WX_011
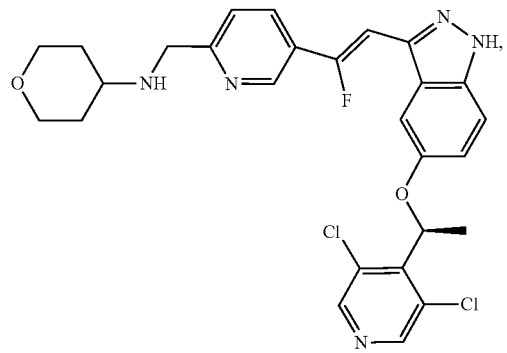
WX_017
WX_012
WX_018
WX_013
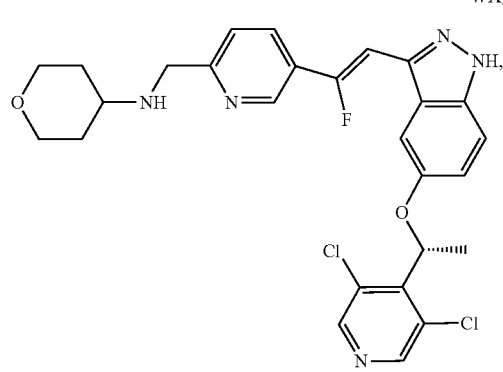
WX_018b
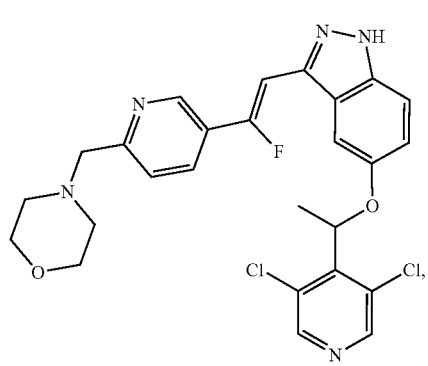
WX_016
WX_021

WX_022
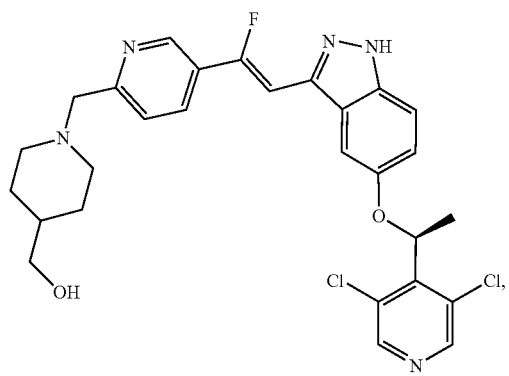
WX_023
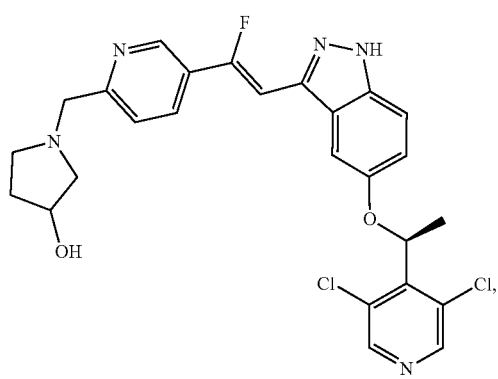
WX_026
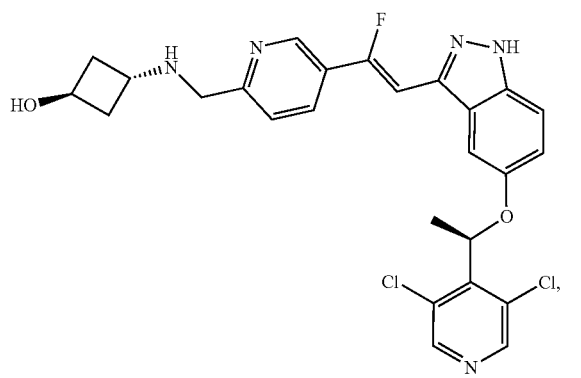
WX_027
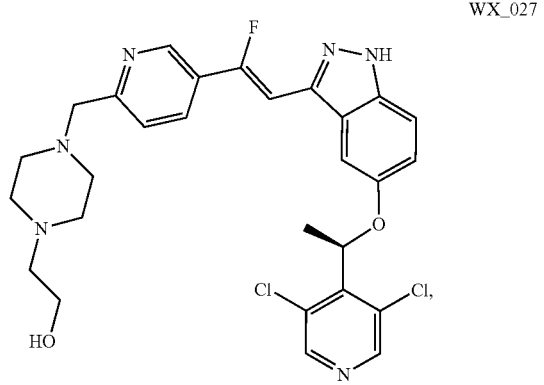
WX_029
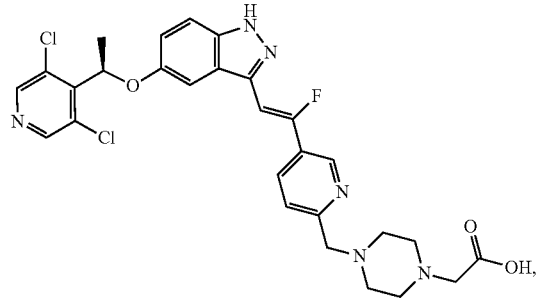
WX_030
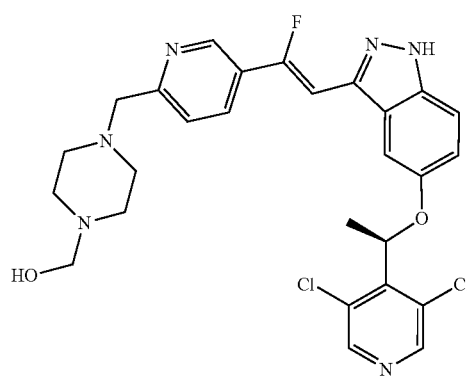
WX_031
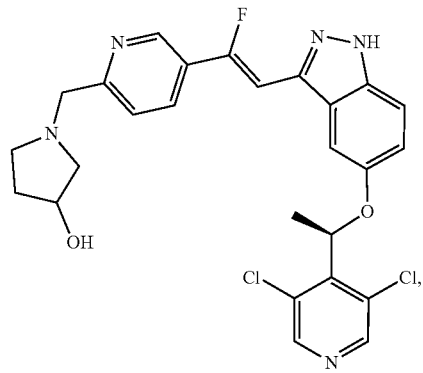
WX_032
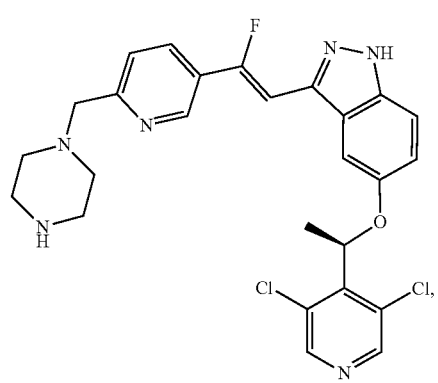

-continued
WX_033
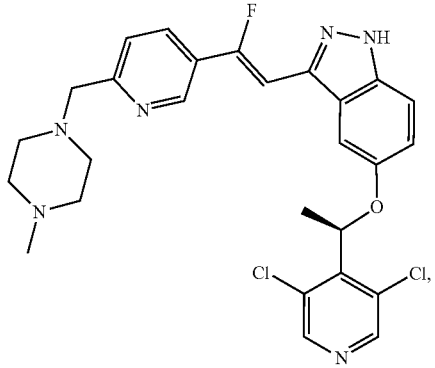
WX_034
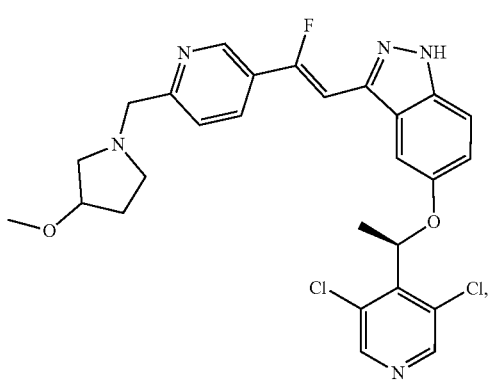
WX_036
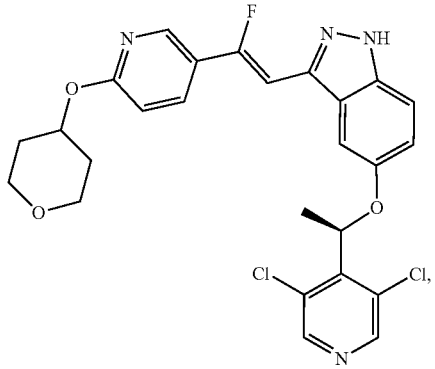
WX_037
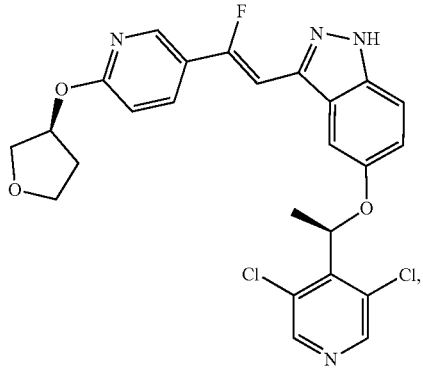
-continued
WX_038
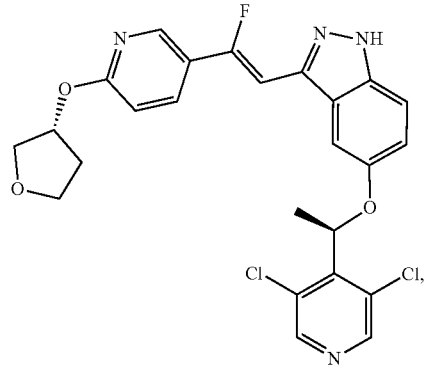
WX_041
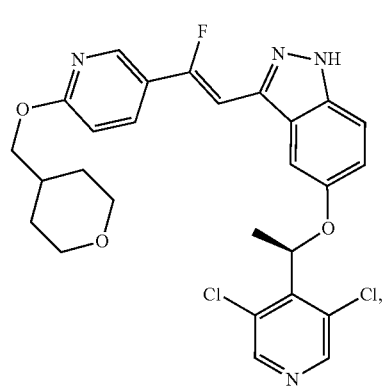
WX_043
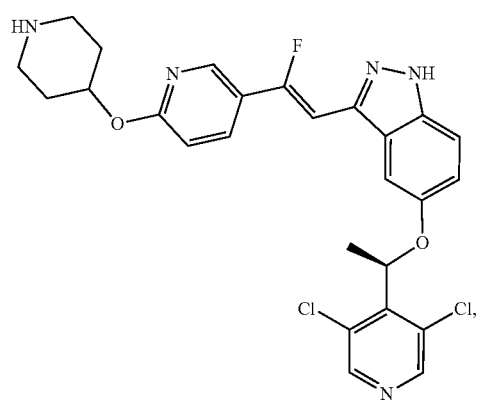
WX_044
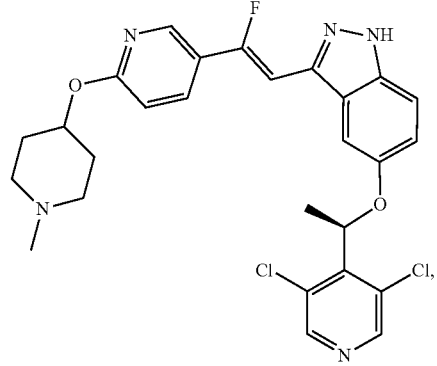

221
-continued
WX_045
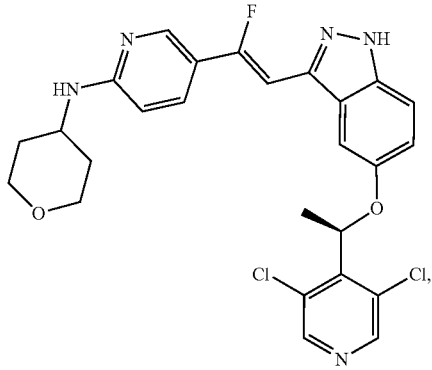
WX_047
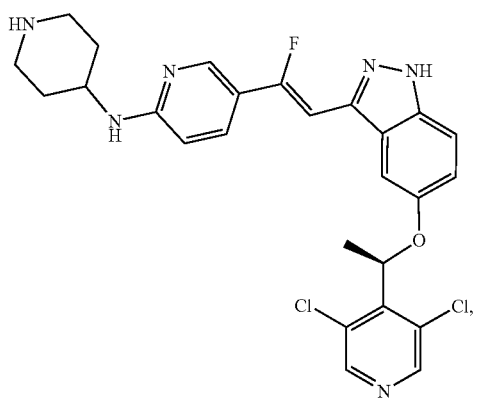
WX_048
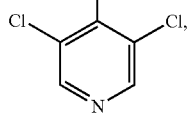
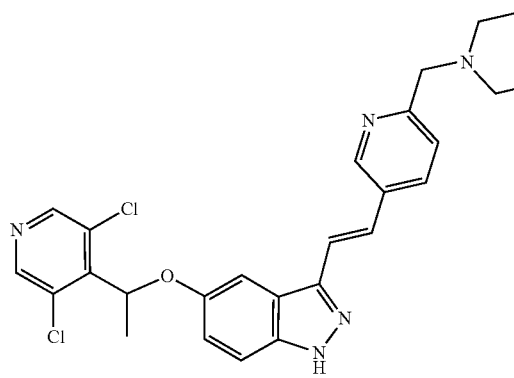
WX_049
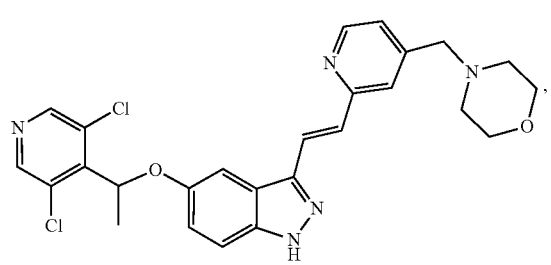
222
-continued
WX_050
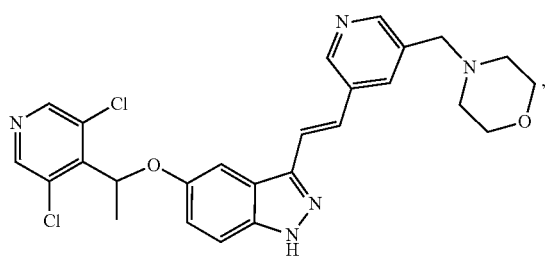
WX_051
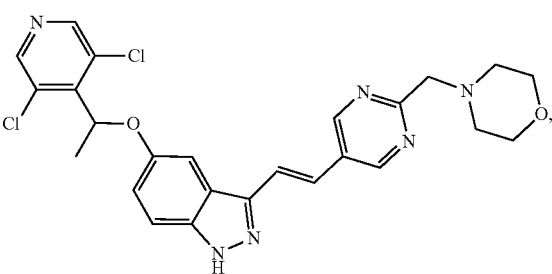
WX_052
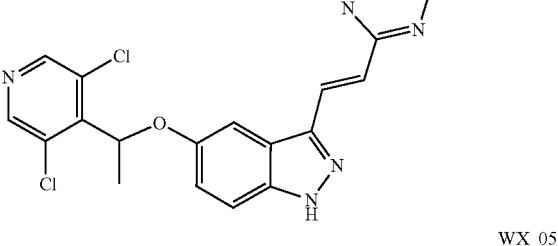
WX_053
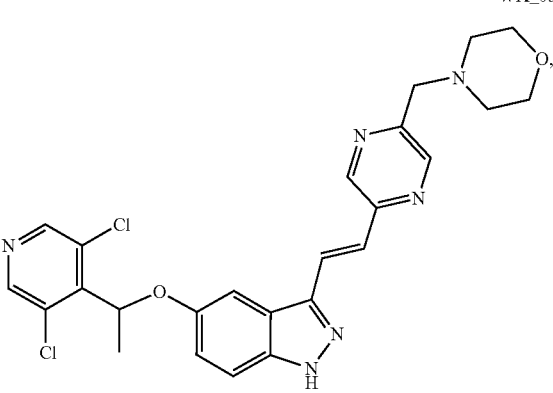
WX_054
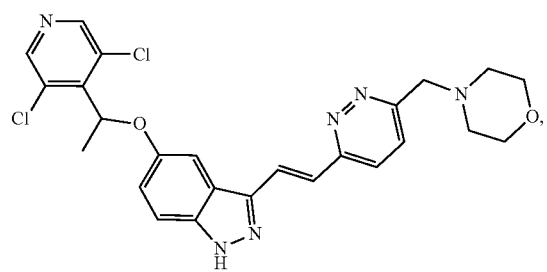

-continued

WX_055

WX_056

WX_057

WX_058

WX_059

WX_060

WX_061

WX_062

WX_063

WX_064

-continued
WX_065
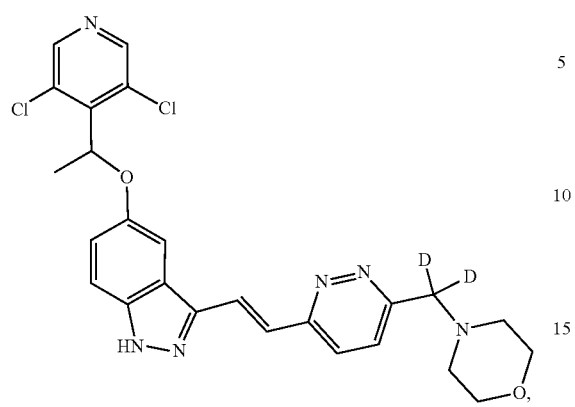
WX_066
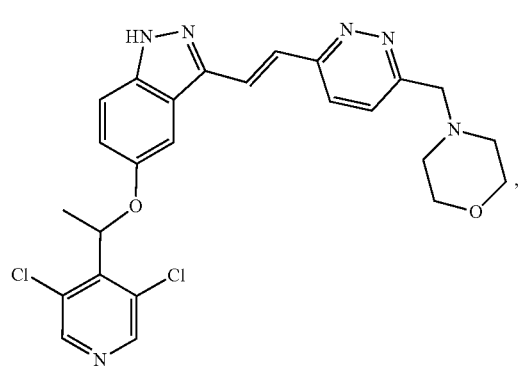
WX_067
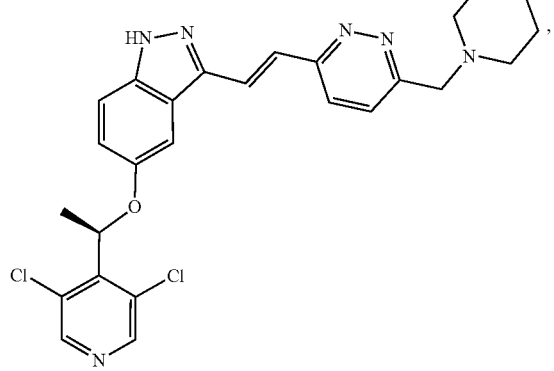
WX_068
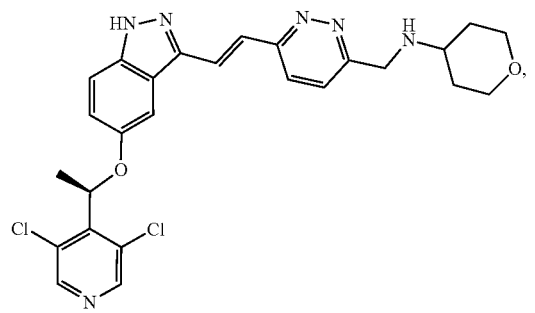
-continued
WX_069
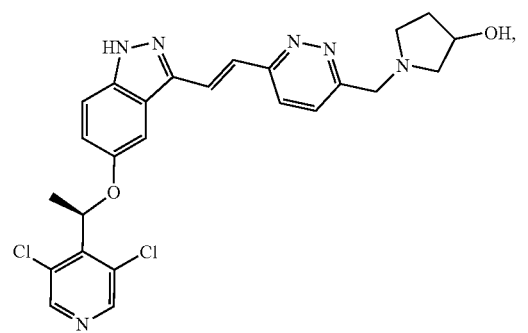
WX_071
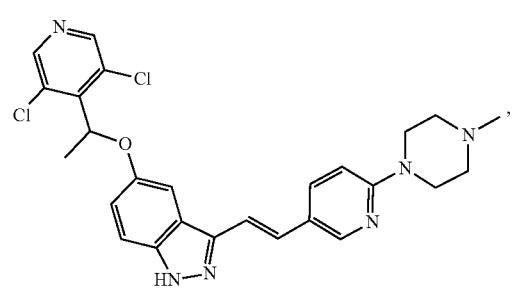
WX_072
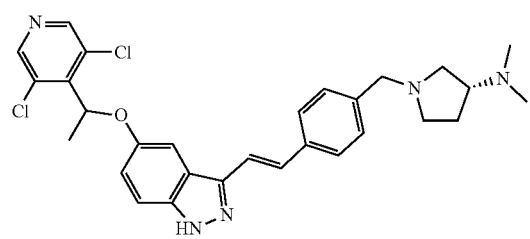
WX_073
WX_074
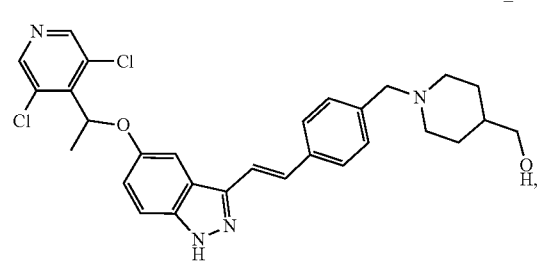

227
-continued
WX_076
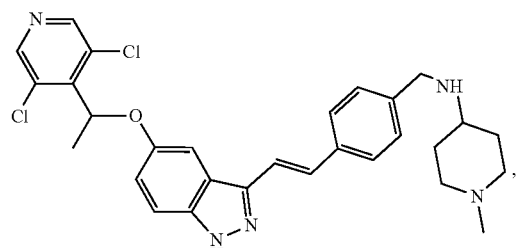
WX_078
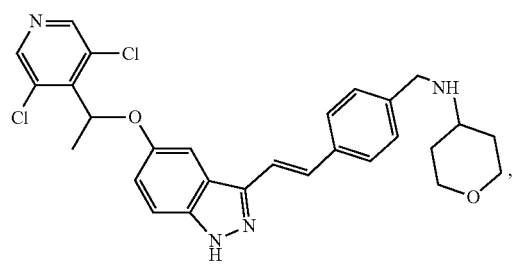
WX_080
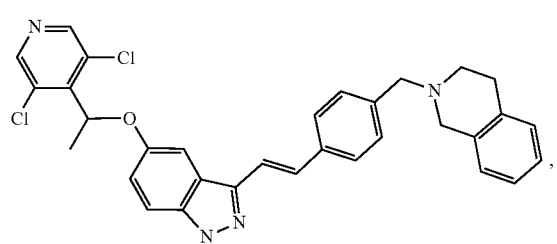
WX_081
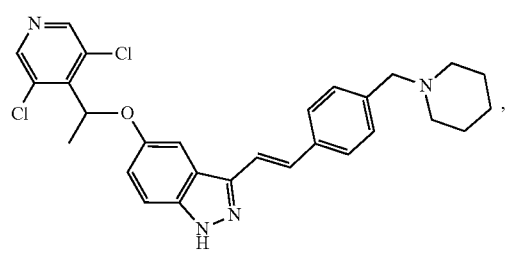
WX_082
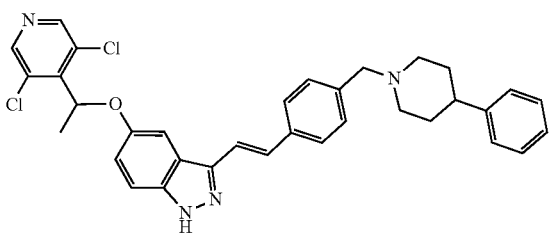
WX_083
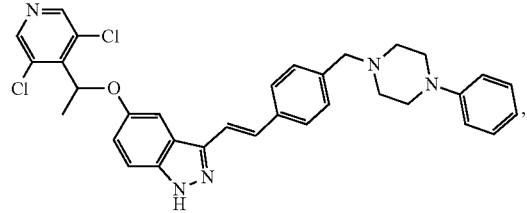
228
-continued
WX_086
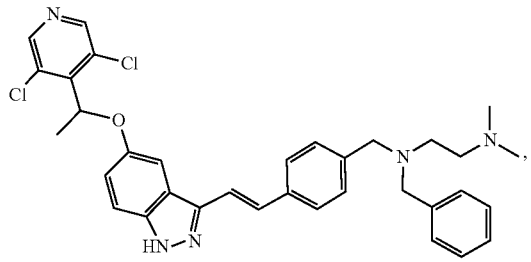
WX_087
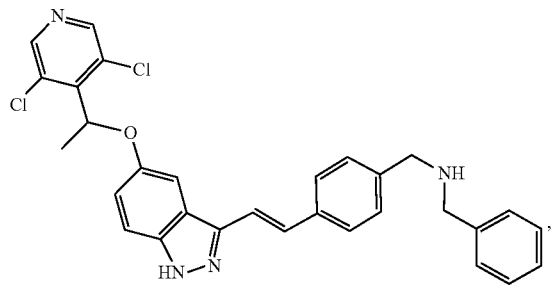
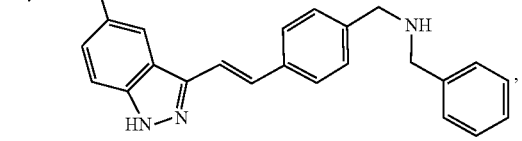
WX_088
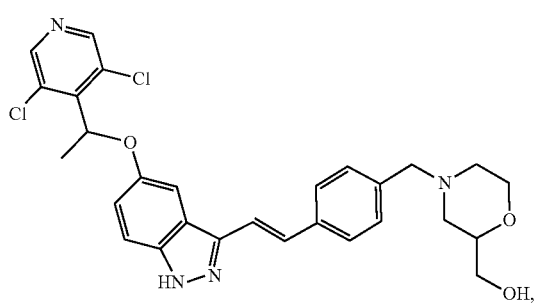
WX_089
WX_090
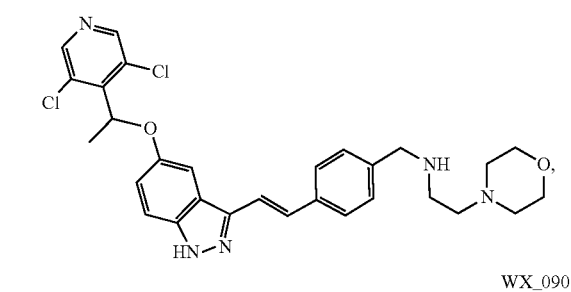

WX_091
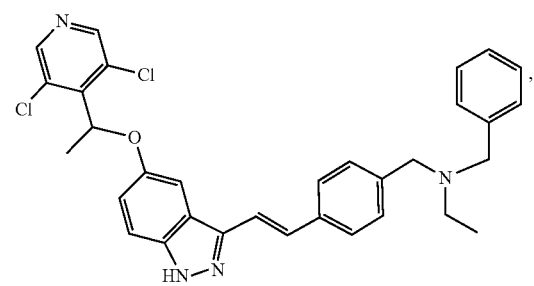
WX_093
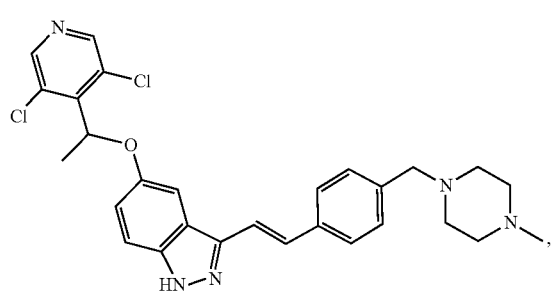
WX_094
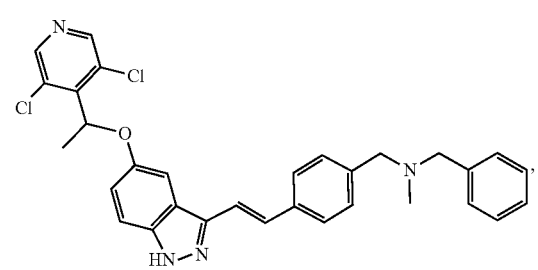
WX_095
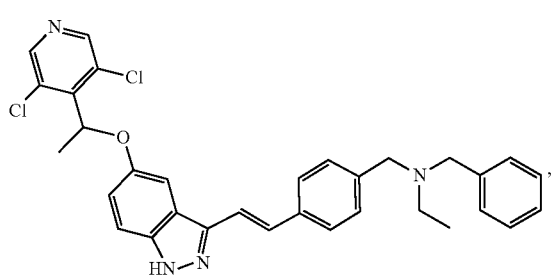
WX_097
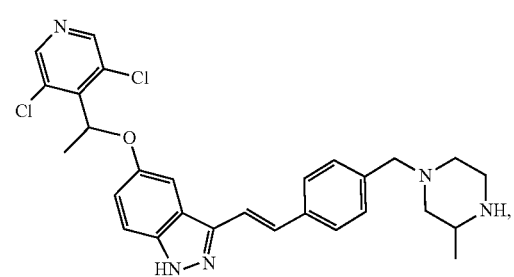
WX_099
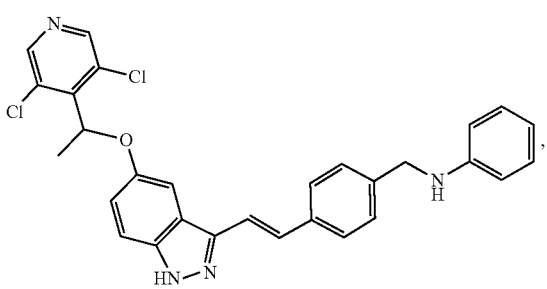
WX_100
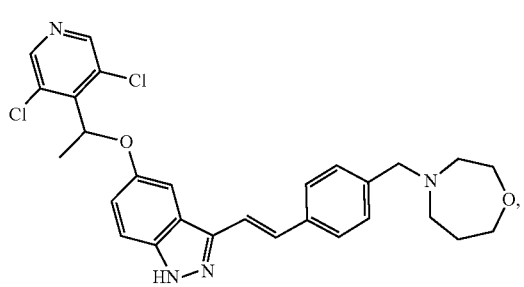
WX_101
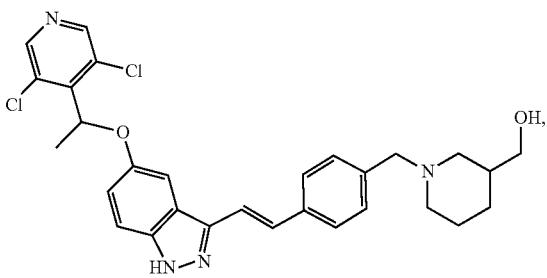
WX_102
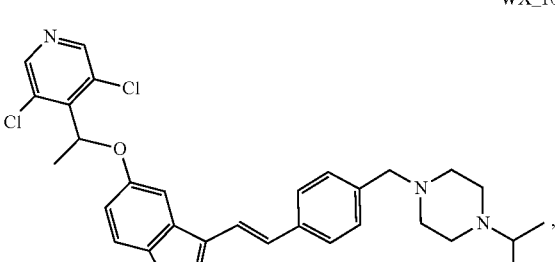
WX_103
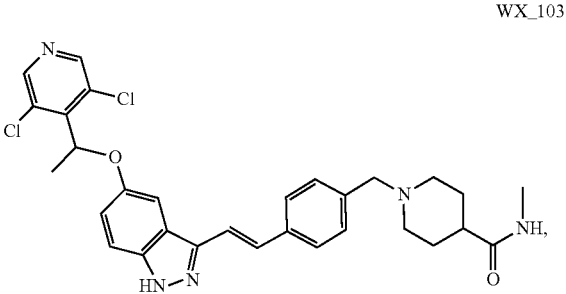

231
-continued
WX_104
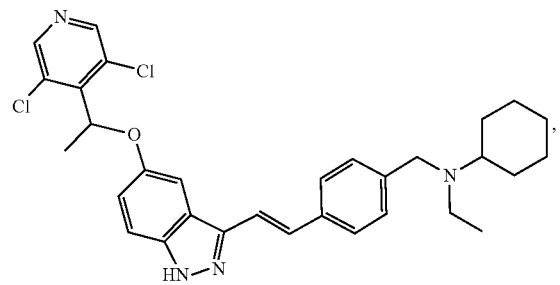
WX_106
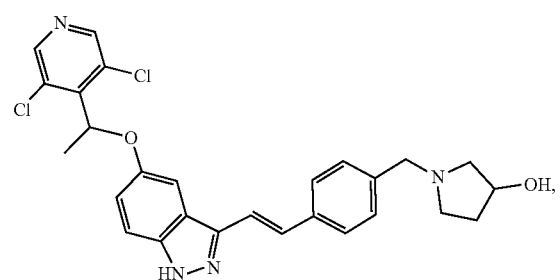
WX_107
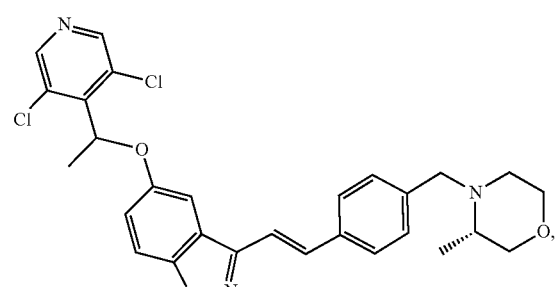
WX_108
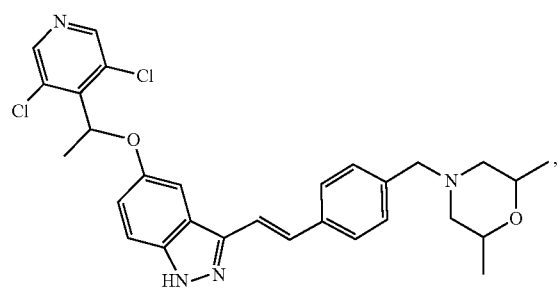
WX_109
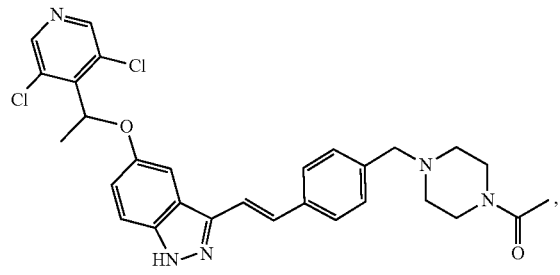
232
-continued
WX_132
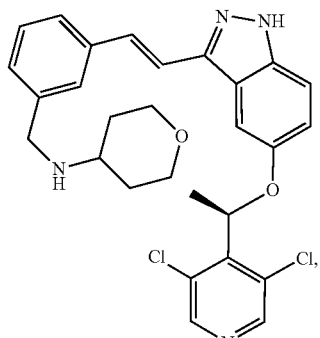
WX_134
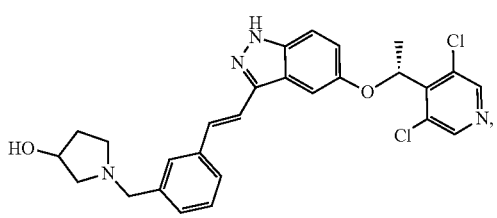
WX_135
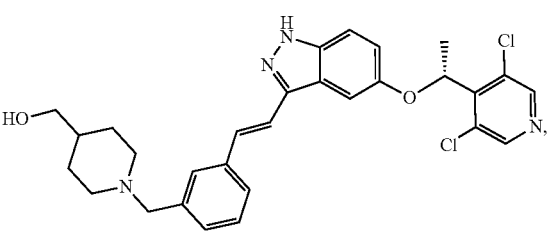
WX_137
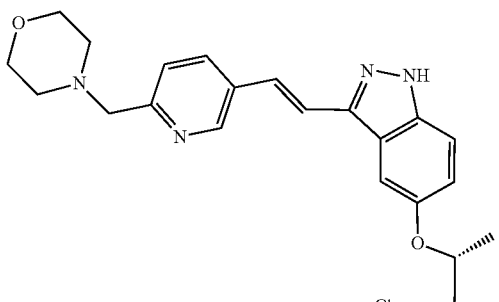
WX_138
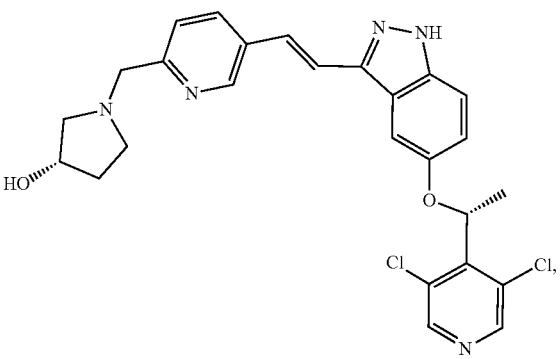

233
-continued
WX_140
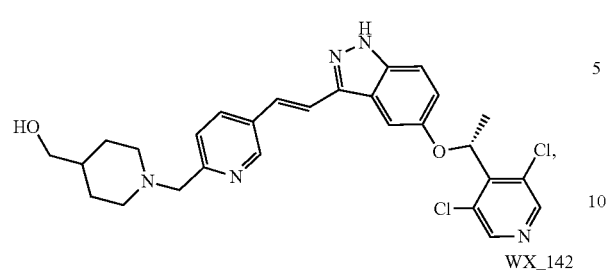
WX_142
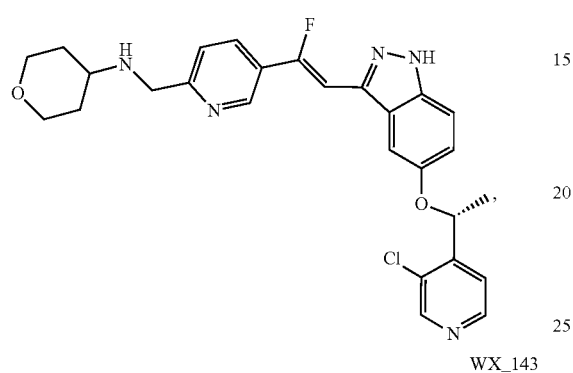
WX_143
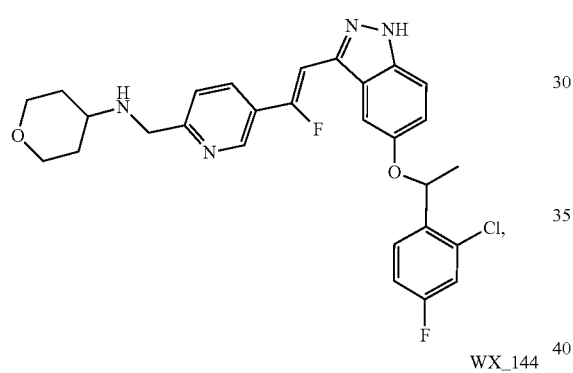
WX_144
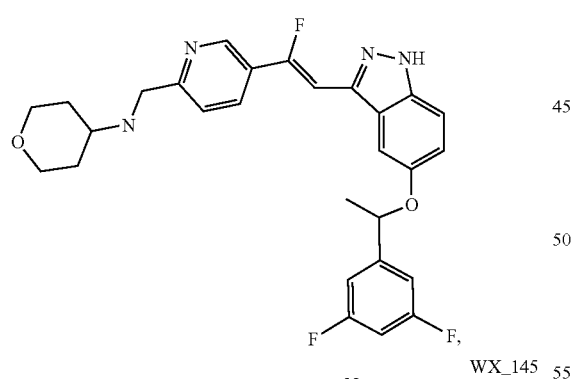
WX_145
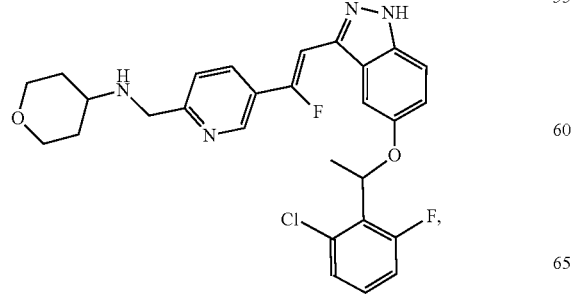
234
-continued
WX_146
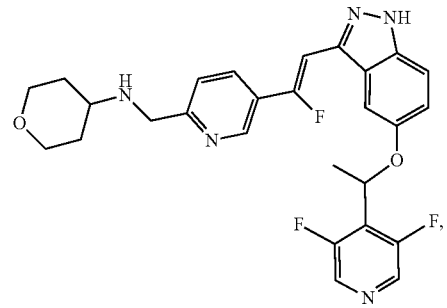
WX_147
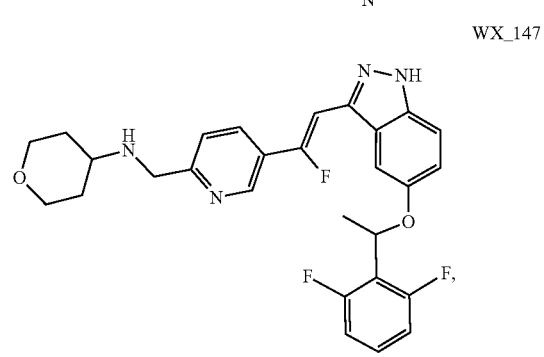
WX_148
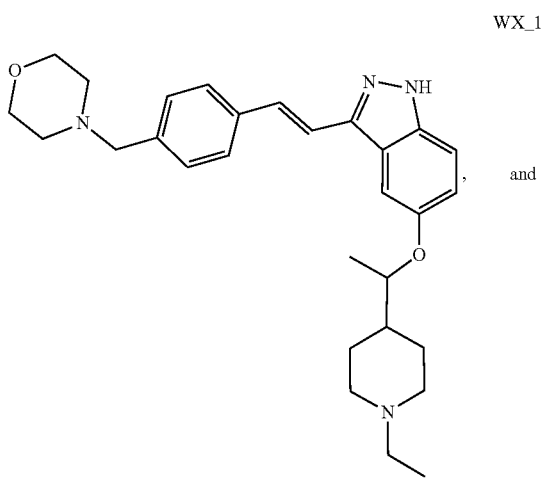
and
WX_149
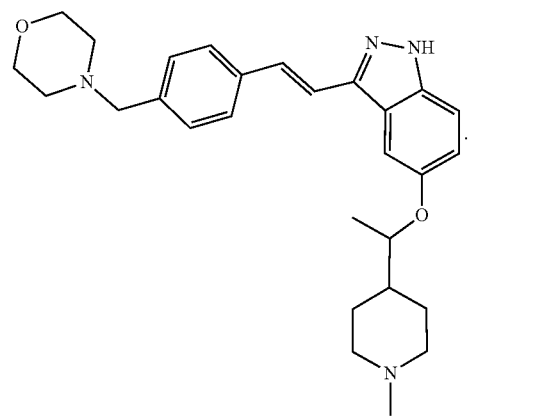

10. A process for preparing the compound represented by formula (I) according to claim 1, comprising:

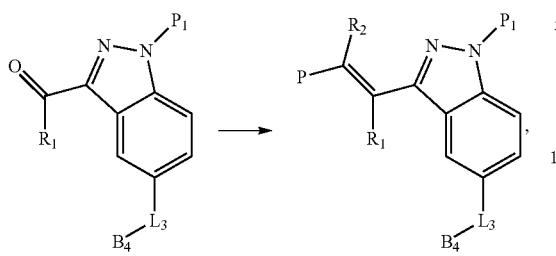

wherein, P is selected from a halogen, OH, NH$_2$ and CN;
$P_1$ is an amino protecting group;
one of $R_1$ and $R_2$ is selected from the group consisting of F, Cl, Br, I, CN, OH and NH$_2$ the other is selected from the group consisting of H, F, Cl, Br, I, CN, OH and NH$_2$;
$L_3$ is selected from the group consisting of —(CRR)$_{0-3}$—, —(CRR)$_{0-3}$—N(R)—(CRR)$_{0-3}$— and —(CRR)$_{0-3}$—O—(CRR)$_{0-3}$—;
$B_4$ is selected from a 5- to 6-membered aryl or heteroaryl and a 5- to 6-membered cycloalkyl or heterocycloalkyl, each of which is optionally substituted with R;
R is selected from the group consisting of H, F, Cl, Br, I, CN, SH, NH$_2$, CHO, COOH, C(=O)NH$_2$, S(=O)NH$_2$, S(=O)$_2$NH$_2$, or selected from a C$_{1-12}$ alkyl or heteroalkyl, a C$_{3-12}$ cyclocarbyl or heterocyclocarbyl, and a C$_{1-12}$ alkyl or heteroalkyl substituted with a C$_{3-12}$ cyclocarbyl or heterocyclocarbyl; and the C$_{1-12}$ alkyl or heteroalkyl and the C$_{3-12}$ cyclocarbyl or heterocyclocarbyl is optionally substituted with R';
R' is selected from the group consisting of F, Cl, Br, I, CN, OH, SH, NH$_2$, CHO, COOH, C(=O)NH$_2$, S(=O)NH$_2$, S(=O)$_2$NH$_2$, =NH, =O, =S, or selected from the group optionally substituted with R" consisting of NHC(=O)CH$_3$, a C$_{1-12}$ alkyl, a C$_{1-12}$ alkylamino, N,N-di(C$_{1-12}$ alkyl)amino, a C$_{1-12}$ alkoxy, a C$_{1-12}$ alkanoyl, a C$_{1-12}$ alkoxycarbonyl, a C$_{1-12}$ alkylsulfonyl, a C$_{1-12}$ alkylsulfinyl, a 3- to 12-membered cycloalkyl, a 3- to 12-membered cycloalkylamino, a 3- to 12-membered heterocycloalkylamino, a 3- to 12-membered cycloalkyloxy, a 3- to 12-membered cycloalkylcarbonyl, a 3- to 12-membered cycloalkyloxycarbonyl, a 3- to 12-membered cycloalkylsulfonyl, a 3- to 12-membered cycloalkylsulfinyl, a 5- to 12-membered aryl or heteroaryl, a 5- to 12-membered aralkyl or heteroaralkyl;
R" is selected from the group consisting of F, Cl, Br, I, CN, OH, N(CH$_3$)$_2$, NH(CH$_3$), NH$_2$, CHO, COOH, C(=O)NH$_2$, S(=O)NH$_2$, S(=O)$_2$NH$_2$, =NH, =O, =S, trihalomethyl, dihalomethyl, monohalomethyl, aminomethyl, hydroxymethyl, methyl, methoxy, formyl, methoxycarbonyl, methanesulfonyl, methylsulfinyl;
"hetero" represents a heteroatom or a heteroatom group selected from the group consisting of —C(=O)N(R)—, —N(R)—, —C(=NR)—, —S(=O)$_2$N(R)—, —S(=O)N(R)—, —O—, —S—, =O, =S, —C(=O)O—, —C(=O)—, —C(=S)—, —S(=O)—, —S(=O)$_2$— and/or —N(R)C(=O)N(R)—;
in each of the above cases, the number of R, R', R", heteroatoms or heteroatom groups is independently selected from 0, 1, 2 or 3.

11. The process for preparing the compound represented by formula (I) according to claim 10, comprising:

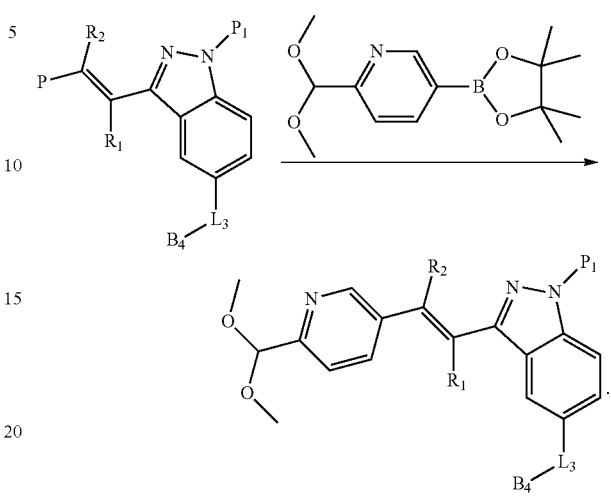

12. A pharmaceutical composition comprising a therapeutically effective amount of the compound, the pharmaceutically acceptable salt or the tautomer thereof according to claim 1, and a pharmaceutically acceptable carrier.

13. A method for treating cancers in a subject in need thereof, comprising administering an effective amount of the compound, the pharmaceutically acceptable salt or the tautomer thereof according to claim 1 to the subject.

14. A method for treating cancers in a subject in need thereof, comprising administering an effective amount of the pharmaceutical composition according to claim 12 to the subject.

15. The compound, the pharmaceutically acceptable salt or the tautomer thereof according to claim 7, wherein $B_4$ is selected from the group consisting of

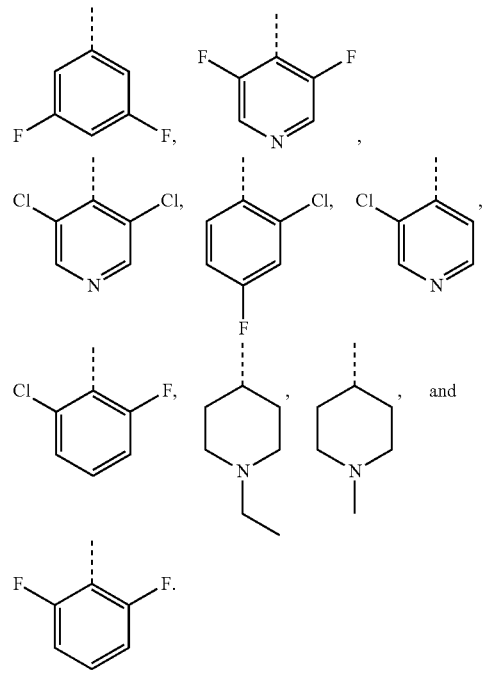

16. The process according to claim 10, wherein $P_1$ is THP.

* * * * *